(12) United States Patent
Wu et al.

(10) Patent No.: US 7,495,016 B2
(45) Date of Patent: Feb. 24, 2009

(54) PYRROLIDONES WITH ANTI-HIV ACTIVITY

(75) Inventors: Baogen Wu, San Diego, CA (US); Yun He, San Diego, CA (US); Truc Ngoc Nguyen, Vista, CA (US); Kelli L. Kuhen, Carlsbad, CA (US); David Archer Ellis, San Diego, CA (US); Tao Jiang, San Diego, CA (US); Xiaohui He, San Diego, CA (US); Kunyong Yang, San Diego, CA (US); Badry Bursulaya, San Diego, CA (US)

(73) Assignee: IRM LLC, Hamilton (BM)

( * ) Notice: Subject to any disclaimer, the term of this patent is extended or adjusted under 35 U.S.C. 154(b) by 766 days.

(21) Appl. No.: 10/690,873

(22) Filed: Oct. 21, 2003

(65) Prior Publication Data

US 2004/0157859 A1 Aug. 12, 2004

Related U.S. Application Data

(60) Provisional application No. 60/422,619, filed on Oct. 30, 2002, provisional application No. 60/420,480, filed on Oct. 21, 2002.

(51) Int. Cl.
*A61K 31/443* (2006.01)
*A61K 31/402* (2006.01)
*C07D 401/04* (2006.01)
*C07D 207/08* (2006.01)

(52) U.S. Cl. ............ 514/340; 514/422; 514/423; 546/276.4; 548/518; 548/530

(58) Field of Classification Search ............ 548/518, 548/530; 546/276.4; 514/340, 422, 423
See application file for complete search history.

(56) References Cited

U.S. PATENT DOCUMENTS

| 4,012,495 A | 3/1977 | Schmiechen et al. |
| 4,193,926 A | 3/1980 | Schmiechen et al. |
| 5,547,979 A | 8/1996 | Christensen, IV et al. |
| 5,783,591 A | 7/1998 | Klose et al. |
| 5,998,453 A | 12/1999 | Klose et al. |

FOREIGN PATENT DOCUMENTS

| WO | WO-93/07141 | * | 4/1993 |
| WO | WO 93/07141 A1 | | 4/1993 |
| WO | WO 03/032981 A1 | | 4/2003 |

OTHER PUBLICATIONS

Bacher, Edmond et al, "N-Arylrolipram Derivatives as Potent and Selective PDE4 inhibitors," Bioorganic & Med. Chem. Letters, 1998 pp. 3229-3234 vol. 8.*
Keller, Thomas H. et al, "Synthesis and Structure-Activity Relationship of N-Arylrolipram Derivatives as Inhibitors of PDE4 Isozymes," Chem. Pharm. Bull. 2001 pp. 1009-1017, vol. 49(8).*
Huff, et al., "HIV Protease: A Novel Chemotherapeutic Targe for AIDS," J. Med. Chem. vol. 34(8), 1991, pp. 2305-2314.*
Menendez-Arias, Luis, "Targeting HIV: antiretroviral therapy and development of drug resistance," Trends in Pharmaceutical Sciences, vol. 23(8), Aug. 2002.*
Bacher, Edmond, et al.; "N-Arylrolipram Derivatives as Potent and Selective PDE4 Inhibitors"; *Bioorganic & Medicinal Chemistry Letters* 1998 pp. 3229-3234 vol. 8.
Keller, Thomas H., et al.; "Synthesis and Structure-Activity Relationship of N-Arylrolipram Derivatives as Inhibitors of PDE4 Isozymes"; *Chem. Pharm. Bull.* 2001 pp. 1009-1017 vol. 49 No. 8.
Aebischer, et al., "Synthesis of N-Arylrolipram Derivatives—Potent and Selective Phosphodiesterase-IV Inhibitors—By Copper Catalyzed Lactam-Aryl Halide Coupling", *Heterocycles*, vol. 48, No. 11, pp. 2225-2229, 1998.

* cited by examiner

*Primary Examiner*—Kamal A Saeed
*Assistant Examiner*—Janet L Coppins
(74) *Attorney, Agent, or Firm*—Emily Tongo Wu; Genomics Institute of the Novartis Research Foundation

(57) ABSTRACT

The present invention relates to inhibition of viruses, e.g., HIV using pyrrolidones and compounds related to pyrrolidones. The invention further relates to methods for identifying and using agents, including small molecule chemical compositions that inhibit HIV in a cell; as well as to methods of prophylaxis, and therapy related to HIV infection and related disease states such as AIDS.

26 Claims, 101 Drawing Sheets

FIG. 1A

| Compound Number | Structure | Physical Data<br>¹H NMR 400 MHz and/or MS (m/z) |
|---|---|---|
| 1 | 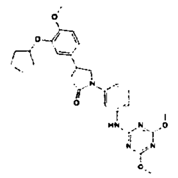 | MS m/z: 506.2 (M + 1). |
| 2 | 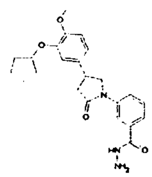 | MS m/z: 410.2(M + 1'). |
| 3 | 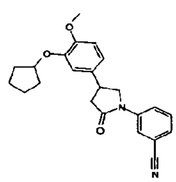 | ¹H NMR (CDCl₃): δ 7.97 (1H, s), 7.93 (1H, d, J = 8.1 Hz), 7.46 (1H, d, J = 8.1 Hz), 7.44 (1H, d, J = 8 Hz), 6.81 (3H, m), 4.76 (1H, brs), 4.16 (1H, t, J = 11.8 Hz), 3.84 (3H, s), 3.84 (1H, t, J = 11.8 Hz) 3.66 (1H, m) 3.03 (1H, q, J = 8.4 Hz), 2.81 (1H, q, J = 8.4 Hz), 1.60-1.89 (8H, m) ppm. MS m/z: 377.2 (M + 1). |
| 4 | 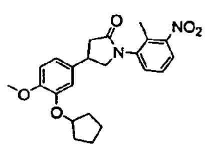 | MS m/z: 411.1(M + 1). |
| 5 | 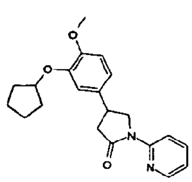 | ¹H NMR (CDCl₃): δ 8.41 (1H, d, J =8.0 Hz); 8.35 (1H, m); 7.78 (1H, m); 7.04 (1H, m); 6.81 (2H, dd, J = 2.3 Hz); 4.67 (1H, brs), 4.52 (1H, dd, J = 8.0 Hz, 10.6 Hz); 4.03 (1H, dd, J = 8.0 Hz, 10.6 Hz); 3.83 (3H, s); 3.61 (1H, m); 3.03 (1H, dd. J = 8.5 Hz, 16.8 Hz), 2.83 (1H, dd, J = 8.5 Hz, 16.8 Hz); 1.89 (8H, m) ppm. MS m/z: 353.1 (M + 1). |
| 6 | 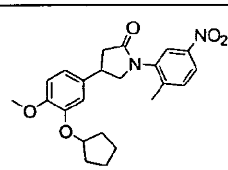 | MS m/z: 411.1(M + 1). |

FIG. 1B
| Compound Number | Structure | Physical Data<br>¹H NMR 400 MHz and/or MS (m/z) |
|---|---|---|
| 7 | 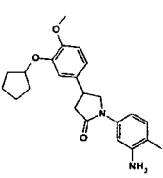 | MS m/z: 381.2 (M + 1). |
| 8 | 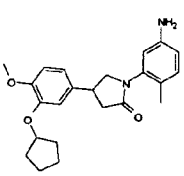 | MS m/z: 381.2 (M + 1). |
| 9 | 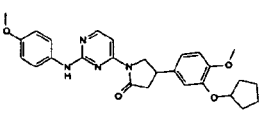 | MS m/z: 475.2 (M + 1). |
| 10 | 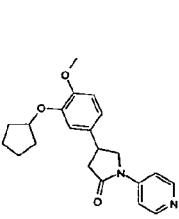 | ¹HNMR (CDCl₃): δ 8.68 (2H, brs), 7.67 (2H, brs), 6.84 (1H, d, J = 8.1 Hz), 6.80 (1H, d, J = 8.0 Hz), 6.78 (1H, s), 4.76 (1H, m), 4.17 (1H, t, J = 8.4 Hz), 3.83 (3H, s), 3.80 (1H, t, J = 8.3 Hz), 3.64 (1H, m), 3.02 (1H, q, J = 8.6 Hz), 2.80 (1H, q, J = 8.5 Hz), 1.82-1.91 (6H, m), 1.60-1.62 (2H, brs). MS m/z: 353.1 (M + 1). |
| 11 | 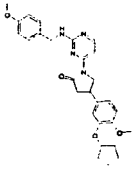 | MS m/z: 489.2 (M + 1). |
| 12 | 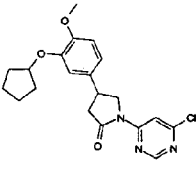 | MS m/z: 388.1 (M + 1). |
| 13 | 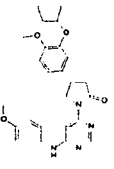 | MS m/z: 475.2 (M + 1). |

FIG. 1C

| Compound Number | Structure | Physical Data<br>¹H NMR 400 MHz and/or MS (m/z) |
|---|---|---|
| 14 | 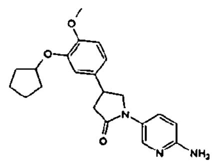 | MS m/z: 368.1 (M + 1). |
| 15 | 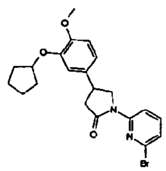 | MS m/z: 431.0 (M + 1). |
| 16 | 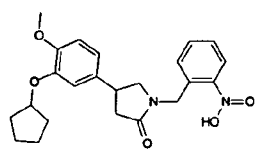 | MS m/z: 411.1 (M + 1). |
| 17 | 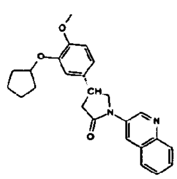 | MS m/z: 403.2 (M + 1). |
| 18 | 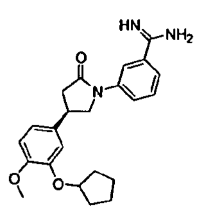 | ¹H NMR (DMSO-d₆): 8.99 (s, 1H), 8.30 (s, 1H), 8.15 (d, 1H, J = 8.3 Hz), 7.96 (s, 1H), ), 7.61 (t, 1H, J = 8.0), 7.53 (d, 1H, J = 7.7 Hz), 7.08 (s, 1H), 6.99-6.86 (m, 2H), ), 4.79 (brs, 1H), 4.21 (t, 1H, J = 8.8 Hz), 3.87 (t, 1H, J = 9.2 Hz), 3.71 (s, 3H), 3.68-3.63 (m, 1H), 2.89 (dd, 1H, J = 8.5, 16.7 Hz), 2.77 (dd, 1H, J = 9.6, 16.7 Hz), 1.86 (brs, 2H), 1.69 (brs, 2H), 1.54 (brs, 2H). MS m/z 494.2 (M + 1). |
| 19 | 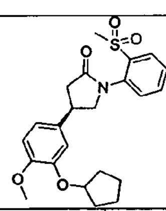 | MS m/z 430.1 (M + 1). |
| 20 | 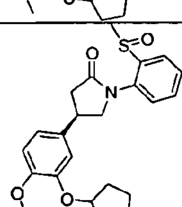 | MS m/z 414.1 (M + 1). |

FIG. 1D
| Compound Number | Structure | Physical Data <br> ¹H NMR 400 MHz and/or MS (m/z) |
|---|---|---|
| 21 | 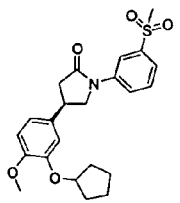 | ¹H NMR (CDCl₃): 8.12 (d, 1H, J = 7.8 Hz), 7.73-7.69 (m, 1H), 7.60-7.56(m, 1H), 7.34 (brs, 1H), 6.99-6.85 (m, 3H), 4.80 (brs, 1H), 4.26 (brs, 1H), 3.84-3.75 (m, 4H), 3.66 (brs, 1H), 3.22 (s, 3H), 2.98-2.92 (m, 1H), 2.77 (dd, 1H, J = 9.7, 16.9 Hz), 1.90-1.77 (m, 6H), 1.63-1.60 (m, 2H). |
| 22 | 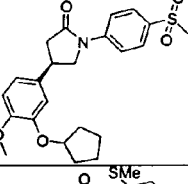 | MS m/z 430.1 (M + 1). |
| 23 | 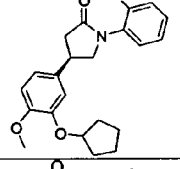 | MS m/z 398.1 (M + 1). |
| 24 | 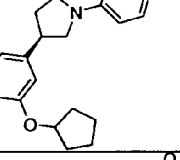 | MS m/z 398.1 (M + 1). |
| 25 | 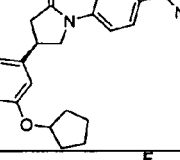 | MS m/z 395.1 (M + 1). |
| 26 | 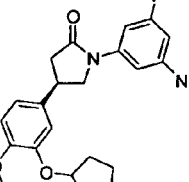 | MS m/z 385.2 (M + 1). |
| 27 | 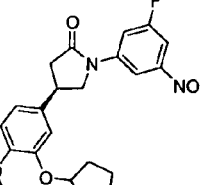 | MS m/z 415.1 (M + 1). |
| 28 | 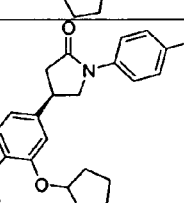 | MS m/z 370.1 (M + 1). |

FIG. 1E
| Compound Number | Structure | Physical Data <br> $^1$H NMR 400 MHz and/or MS (m/z) |
|---|---|---|
| 29 | 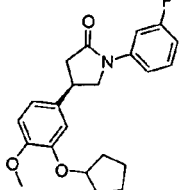 | MS m/z 370.1 (M + 1). |
| 30 | 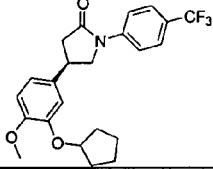 | MS m/z 420.2 (M + 1). |
| 31 | 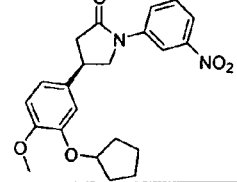 | MS m/z 415.1 (M + 1). |
| 32 | 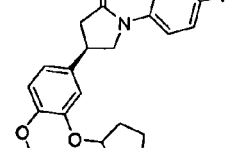 | MS m/z 370.1 (M + 1) |
| 33 | 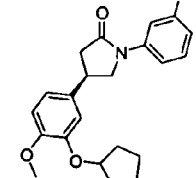 | MS m/z 370.1 (M + 1). |
| 34 | 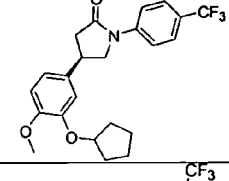 | MS m/z 420.2 (M + 1). |
| 35 | 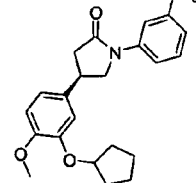 | MS m/z 420.2 (M + 1). |
| 36 | 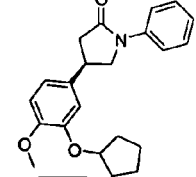 | MS m/z 352.1 (M + 1). |

FIG. 1F
| Compound Number | Structure | Physical Data<br>¹H NMR 400 MHz and/or MS (m/z) |
|---|---|---|
| 37 | 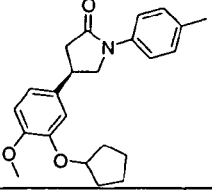 | MS m/z 366.2 (M + 1). |
| 38 | 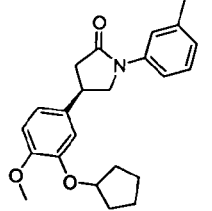 | MS m/z 366.2 (M + 1). |
| 39 | 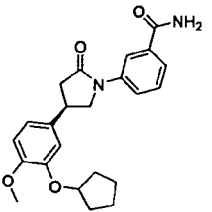 | ¹H NMR (CDCl₃): 8.01 (brs, 1H), 7.90 (dd, 1H, J = 1.5, 8.1 Hz), ), 7.58 (d, 1H, J = 7.7 Hz), 7.46 (t, 1H, J = 8.0 Hz), 6.86-6.80 (m, 3H), ), 6.24 (brs, 1H), 5.68 (brs, 1H), 4.79-4.75 (m, 1H), 4.21 (dd, 1H, J = 8.3, 9.4 Hz), 3.90 (dd, 1H, J = 7.6, 9.4 Hz), 3.84 (s, 3H), 3.69-3.61 (m, 1H), 3.01 (dd, 1H, J = 8.7, 17.0 Hz), 2.79 (dd, 1H, J = 8.9, 17.0 Hz), 1.96-1.82 (m, 6H), 1.65-1.59 (m, 2H),. |
| 40 | 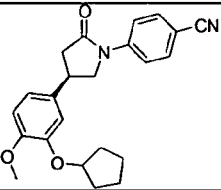 | MS m/z 377.1 (M + 1). |
| 41 | 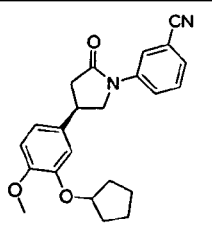 | ¹H NMR (CDCl₃): 7.97-7.95 (m, 2H), 7.50-7.42 (m, 2H), 6.86-6.78 (m, 3H), 4.77 (brs, 1H), 4.17 (dd, 1H, J = 8.1, 9.3 Hz), 3.85-3.81 (m, 4H), 3.66 (t, 1H, J = 8.1 Hz), 3.02 (dd, 1H, J = 8.7, 17.2 Hz), 2.80 (dd, 1H, J = 8.9, 17.2 Hz), 1.63-1.60 (m, 2H), 1.92-1.83 (m, 6H). MS m/z 377.1 (M + 1). |
| 42 | 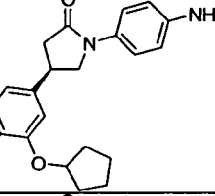 | MS m/z 367.1 (M + 1). |
| 43 | 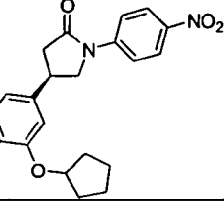 | MS m/z 397.1 (M + 1). |

FIG. 1G
| Compound Number | Structure | Physical Data<br>¹H NMR 400 MHz and/or MS (m/z) |
|---|---|---|
| 44 | 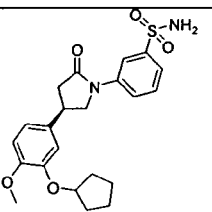 | MS m/z 431.20 (M + 1). |
| 45 | 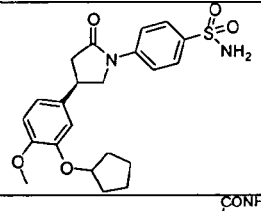 | MS m/z 431.20 (M + 1). |
| 46 | 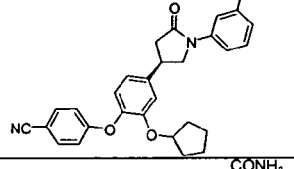 | MS m/z 482.2 (M + 1). |
| 47 | 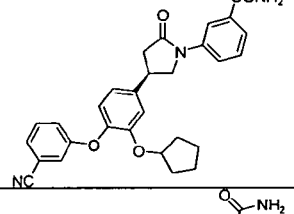 | MS m/z 482.2 (M + 1). |
| 48 | 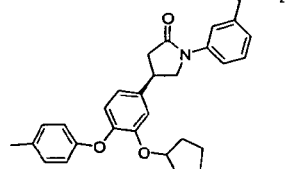 | MS m/z 403.1 (M + 1). |
| 49 | 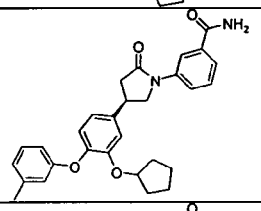 | MS m/z 403.1 (M + 1). |
| 50 | 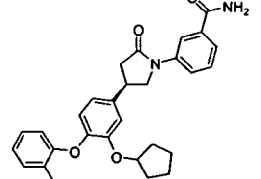 | MS m/z 403.1 (M + 1). |
| 51 | 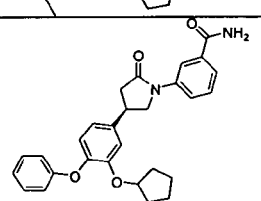 | MS m/z 389.1 (M + 1). |

FIG. 1H

| Compound Number | Structure | Physical Data<br>¹H NMR 400 MHz and/or MS (m/z) |
|---|---|---|
| 52 | 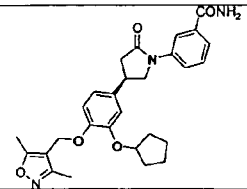 | MS m/z 490.20 (M + 1). |
| 53 | 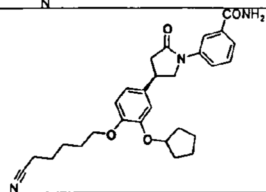 | MS m/z 476.2 (M + 1). |
| 54 | 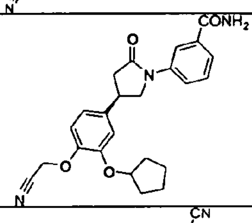 | MS m/z 420.2 (M + 1). |
| 55 | 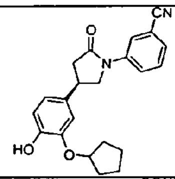 | MS m/z 363.20 (M + 1). |
| 56 | 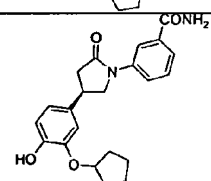 | MS m/z 381.2 (M + 1). |
| 57 | 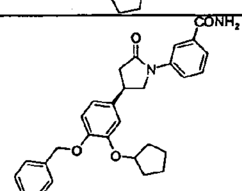 | MS m/z 471.2 (M + 1). |
| 58 | 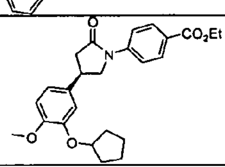 | MS m/z 424.2 (M + 1). |
| 59 | 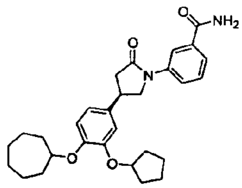 | 1H NMR (CDCl3): 8.08 (s, 1H), 7.93 (d, 1H, J = 14.5 Hz), 7.58 (d, 1H, J = 7.6 Hz), 7.46 (t, 1H, J = 7.9 Hz), 6.86 (d, 1H, J = 8.0 Hz), 6.79-6.76 (m, 2H), 6.24 (brs, 1H), 5.68 (brs, 1H), 4.77 (brs, 1H), 4.32-4.26 (m, 1H), 4.21 (t, 1H, J = 8.9 Hz), 3.90 (t, 1H, J = 7.8 Hz), 3.68-3.60 (m, 1H), 3.01 (dd, 1H, J = 8.7, 17.0 Hz), 2.79 (dd, 1H, J = 9.0, 17.0 Hz), 2.03-1.96 (m, 2H), 1.87-1.58 (m, 16H), 1.58-1.39 (m, 2H). |

FIG. 1I
| Compound Number | Structure | Physical Data<br>$^1$H NMR 400 MHz and/or MS (m/z) |
|---|---|---|
| 60 | 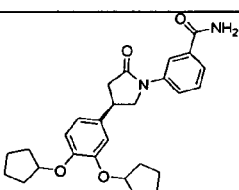 | MS m/z 449.2 (M + 1). |
| 61 | 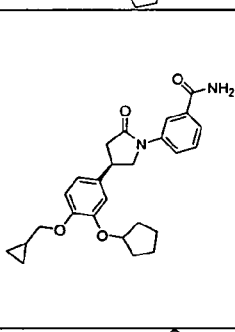 | 1H NMR (CDCl3): 8.08, (s, 1H), 7.88 (d, 1H, J = 8.0 Hz), 7.59 (d, 1H, J = 7.6 Hz), 7.46 (t, 1H, J = 8.0 Hz), 6.88 (d, 1H, J = 8.0 Hz), 6.80-6.77 (m, 2H), 6.27 (brs, 1H), 5.62 (brs, 1H), 4.79 (brs, 1H), 4.21 (t, 1H, J = 8.7 Hz), 3.90 (t, 1H, J = 7.8), 3.82 (d, 2H, J = 6.8), 3.69-3.60 (m, 1H), 3.01 (dd, 1H, J = 8.7, 17.0 Hz), 2.79 (dd, 1H, J = 9.0, 17.0 Hz), 1.87-1.84 (m, 6H), 1.55-1.68 (m, 2H), 1.29-1.25 (m, 3H), 0.60 (dd, 2H, J = 5.9, 12.8 Hz), 0.33 (dd, 2H, J = 4.6, 10.3 Hz). |
| 62 | 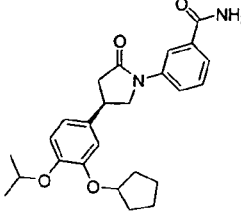 | MS m/z 423.2 (M + 1). |
| 63 | 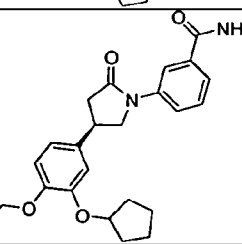 | MS m/z 409.2 (M + 1). |
| 64 | 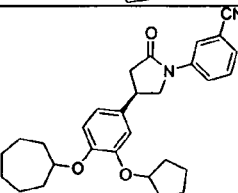 | MS m/z 459.3 (M + 1). |
| 65 | 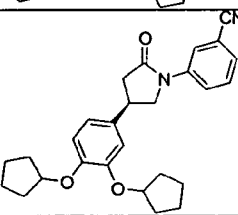 | MS m/z 431.2 (M + 1). |
| 66 | 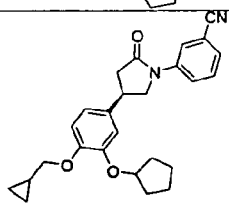 | MS m/z 417.2 (M + 1). |

FIG. 1J

| Compound Number | Structure | Physical Data<br>¹H NMR 400 MHz and/or MS (m/z) |
|---|---|---|
| 67 | 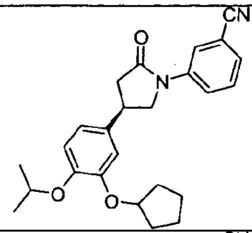 | MS m/z 405.2 (M + 1). |
| 68 | 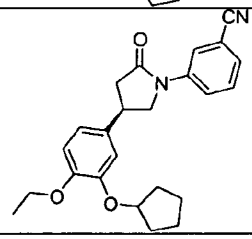 | MS m/z 391.20 (M + 1). |
| 69 | 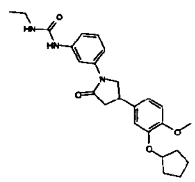 | MS m/z: 438.2 (M + 1). |
| 70 | 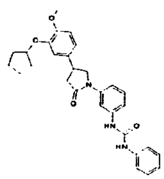 | MS m/z: 486.2 (M + 1). |
| 71 | 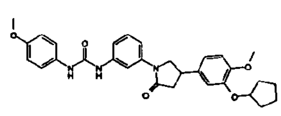 | MS m/z: 516.2 (M + 1). |
| 72 | 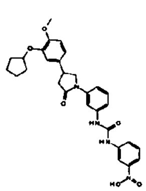 | ¹H NMR (CDCl₃): δ 8.39 (1H, brs), 8.10 (1H, brs), 7.80 (1H, s), 7.79 (1H, d, J = 7.2 Hz), 7.72 (1H, d, J = 7.2 Hz), 7.63 (1H, s), 7.34 (1H, t, J = 6.8 Hz), 7.11 (1H, t, J = 6.9 Hz), 6.91-6.96 (2H, m), 6.83-6.85 (3H, m), 4.80 (1H, brs), 4.13 (1H, t, J = 8.1 Hz), 3.88 (1H, t, J = 8.1 Hz), 3.85 (3H, s), 3.70 (1H, m), 3.04 (1H, q, J = 8.2 Hz), 2.88 (1H, q, J = 8.2 Hz), 1.96 (8H, m) ppm. MS m/z: 531.2 (M + 1). |
| 73 | 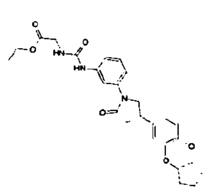 | MS m/z: 496.2 (M + 1). |

FIG. 1K
| Compound Number | Structure | Physical Data<br>$^1$H NMR 400 MHz and/or MS (m/z) |
|---|---|---|
| 74 | 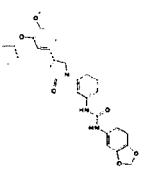 | MS m/z: 530.2 (M + 1). |
| 75 | 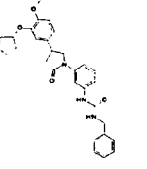 | MS m/z: 500.2 (M + 1). |
| 76 | 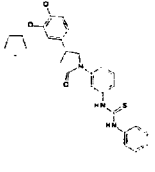 | MS m/z: 502.2 (M + 1). |
| 77 | 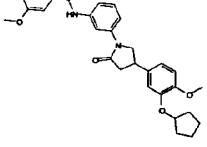 | MS m/z: 501.2 (M + 1). |
| 78 | 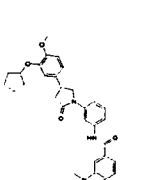 | $^1$H NMR (CDCl$_3$): δ 8.05 (1H, brs), 7.91 (1H, brs), 7.41 (1H, m), 7.10-7.28 (5H, m), 7.13 (1H, m), 6.79-6.83 (3H, m), 4.77 (1H, m), 4.21 (1H, t, J = 8.1 Hz), 3.83 (1H, t, J = 8.1 Hz), 3.61 (1H, m), 2.98 (3H, s), 2.96 (1H, q, J = 8.2 Hz), 2.75 (1H, q, J = 8.1 Hz), 1.91-1.99 (8H, m) ppm. MS m/z: 514.2 (M + 1). |
| 79 | 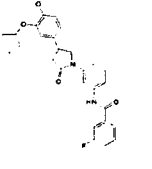 | MS m/z: 489.2 (M + 1). |
| 80 | 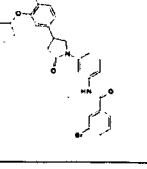 | MS m/z: 549.1 (M + 1). |

FIG. 1L

| Compound Number | Structure | Physical Data<br>¹H NMR 400 MHz and/or MS (m/z) |
|---|---|---|
| 81 | 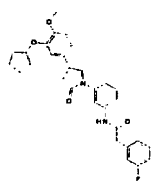 | MS m/z: 503.2 (M + 1). |
| 82 | 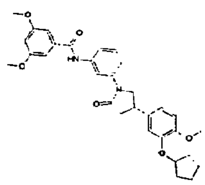 | MS m/z: 531.2 (M + 1). |
| 83 | 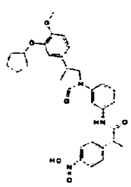 | MS m/z: 544.2 (M + 1). |
| 84 | 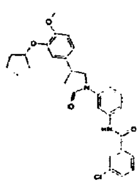 | MS m/z: 505.2 (M + 1). |
| 85 | 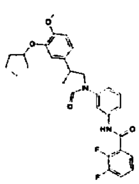 | MS m/z: 507.2 (M + 1). |
| 86 | 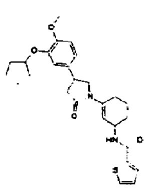 | MS m/z: 477.1 (M + 1). |
| 87 | 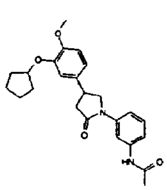 | MS m/z: 409.2 (M + 1). |

FIG. 1M

| Compound Number | Structure | Physical Data<br>¹H NMR 400 MHz and/or MS (m/z) |
|---|---|---|
| 88 | 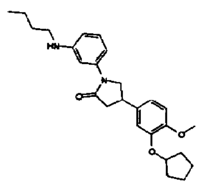 | MS m/z: 423.2 (M + 1). |
| 89 | 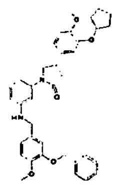 | MS m/z: 593.2 (M + 1). |
| 90 | 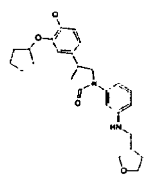 | MS m/z: 451.2 (M + 1). |
| 91 | 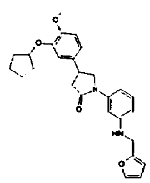 | MS m/z: 447.2 (M + 1). |
| 92 | 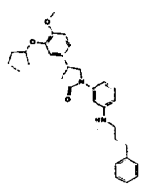 | MS m/z: 485.2 (M + 1). |
| 93 | 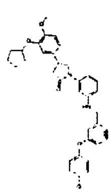 | MS m/z: 581.2 (M + 1). |
| 94 | 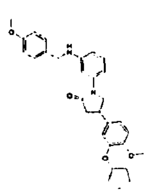 | MS m/z: 487.2 (M + 1). |

FIG. 1N

| Compound Number | Structure | Physical Data<br>¹H NMR 400 MHz and/or MS (m/z) |
|---|---|---|
| 95 | 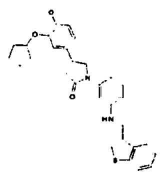 | MS m/z: 513.2 (M + 1). |
| 96 | 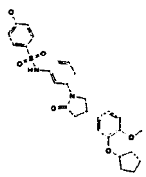 | MS m/z: 537.1 (M + 1). |
| 97 | 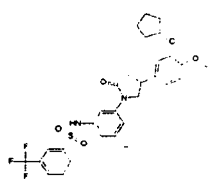 | MS m/z: 575.1 (M + 1). |
| 98 | 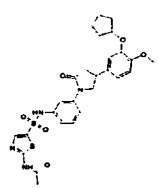 | MS m/z: 585.1 (M + 1). |
| 99 | 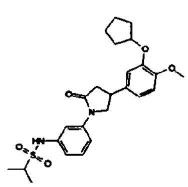 | MS m/z: 473.2 (M + 1). |
| 100 | 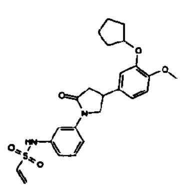 | MS m/z: 457.1 (M + 1). |
| 101 | 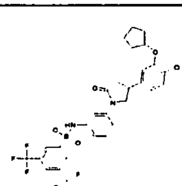 | MS m/z: 642.1 (M + 1). |

FIG. 10

| Compound Number | Structure | Physical Data<br>¹H NMR 400 MHz and/or MS (m/z) |
|---|---|---|
| 102 | 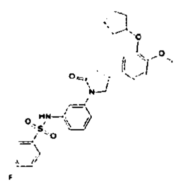 | MS m/z: 524.1 (M + 1). |
| 103 | 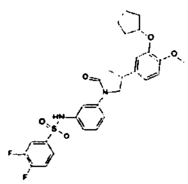 | MS m/z: 543.1 (M + 1). |
| 104 | 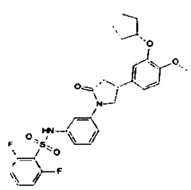 | MS m/z: 543.1 (M + 1). |
| 105 | 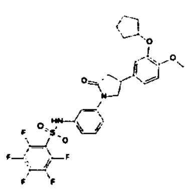 | MS m/z: 597.1 (M + 1). |
| 106 | 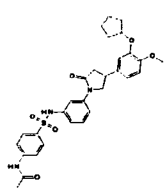 | MS m/z: 564.2 (M + 1). |
| 107 | 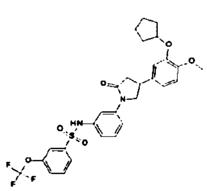 | MS m/z: 691.1 (M + 1). |
| 108 | 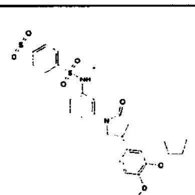 | MS m/z: 585.1 (M + 1). |

FIG. 1P

| Compound Number | Structure | Physical Data<br>¹H NMR 400 MHz and/or MS (m/z) |
|---|---|---|
| 109 | 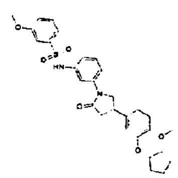 | ¹H NMR (CDCl₃): δ 7.70 (1H, brs), 7.37 (1H, d, J = 7.8 Hz), 7.19-7.29 (4H, m), 7.00 (2H, t, J = 7.6 Hz); 6.83 (1H, d, J = 8 Hz), 6.79 (1H, s), 6.79 (1H, d, J = 8 Hz), 4.76 (1H, brs), 4.11 (1H, t, J = 8.4 Hz), 3.83 (3H, s), 3.78 (1H, t, J = 8.4 Hz), 3.60 (1H, m), 3.02 (1H, q, J = 8.1 Hz), 2.85 (1H, q, J = 8.1 Hz), 1.61-1.88 (8H, m) ppm. MS m/z: 537.1 (M + 1). |
| 110 | 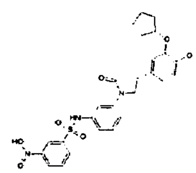 | MS m/z: 552.1 (M + 1). |
| 111 | 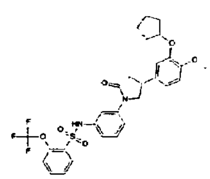 | MS m/z: 591.1 (M + 1). |
| 112 | 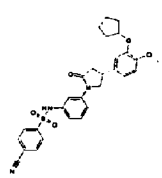 | MS m/z: 532.1 (M + 1). |
| 113 | 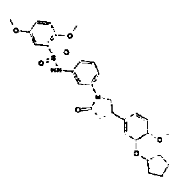 | MS m/z: 567.2 (M + 1). |
| 114 | 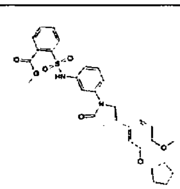 | MS m/z: 565.2 (M + 1). |
| 115 | 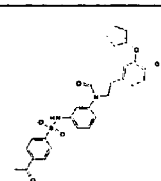 | MS m/z: 549.1 (M + 1). |

FIG. 1Q

| Compound Number | Structure | Physical Data<br>¹H NMR 400 MHz and/or MS (m/z) |
|---|---|---|
| 116 | 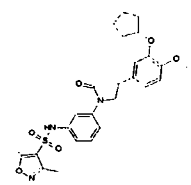 | MS m/z: 526.1(M + 1). |
| 117 | 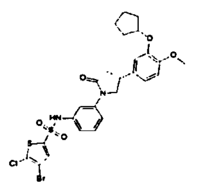 | MS m/z: 625.0 (M + 1). |
| 118 | 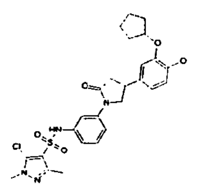 | MS m/z: 559.1(M + 1). |
| 119 | 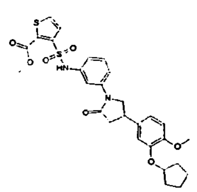 | MS m/z: 571.1 (M + 1). |
| 120 | 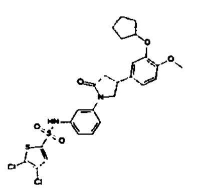 | MS m/z: 581.0 (M + 1). |
| 121 | 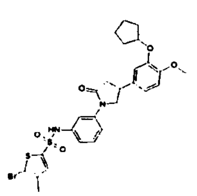 | MS m/z: 668.9(M + 1). |
| 122 | 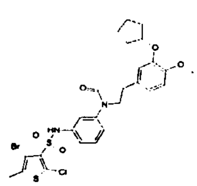 | MS m/z: 658.9 (M + 1). |

FIG. 1R

| Compound Number | Structure | Physical Data<br>¹H NMR 400 MHz and/or MS (m/z) |
|---|---|---|
| 123 | 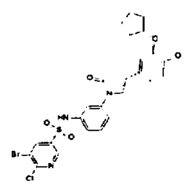 | MS m/z: 620.0 (M + 1). |
| 124 | 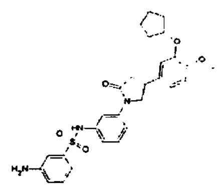 | MS m/z: 522.2 (M + 1). |
| 125 | 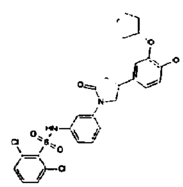 | MS m/z: 575.1 (M + 1). |
| 126 | 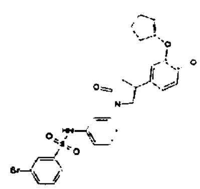 | MS m/z: 585.1 (M + 1). |
| 127 | 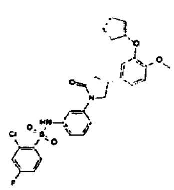 | MS m/z: 559.1 (M + 1). |
| 128 | 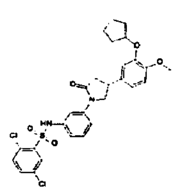 | MS m/z: 575.1 (M + 1). |
| 129 | 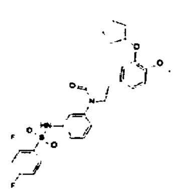 | MS m/z: 543.1 (M + 1). |

FIG. 1S

| Compound Number | Structure | Physical Data<br>¹H NMR 400 MHz and/or MS (m/z) |
|---|---|---|
| 130 | 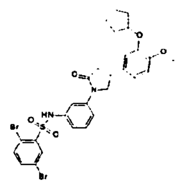 | MS m/z: 663.0 (M + 1). |
| 131 | 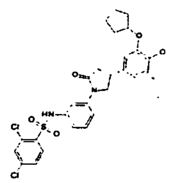 | MS m/z: 575.1 (M + 1). |
| 132 | 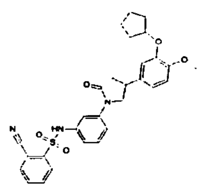 | MS m/z: 532.2 (M + 1). |
| 133 | 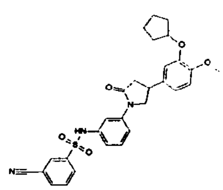 | MS m/z: 532.2 (M + 1). |
| 134 | 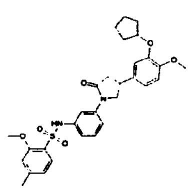 | MS m/z: 551.2 (M + 1). |
| 135 | 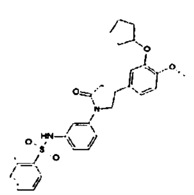 | MS m/z: 521.2 (M + 1). |
| 136 | 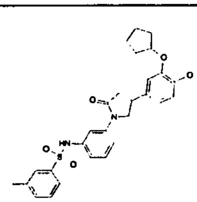 | MS m/z: 521.2 (M + 1). |

FIG. 1T

| Compound Number | Structure | Physical Data<br>¹H NMR 400 MHz and/or MS (m/z) |
|---|---|---|
| 137 | 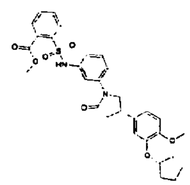 | MS m/z: 565.2 (M + 1). |
| 138 | 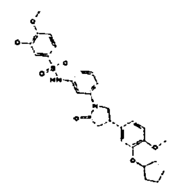 | MS m/z: 567.2 (M + 1). |
| 139 | 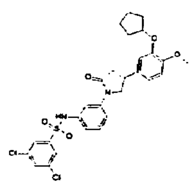 | MS m/z: 575.1 (M + 1). |
| 140 | 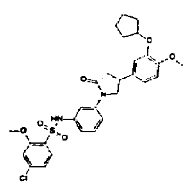 | MS m/z: 571.1 (M + 1). |
| 141 | 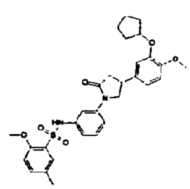 | MS m/z: 551.2 (M + 1). |
| 142 | 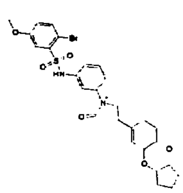 | MS m/z: 615.1 (M + 1). |
| 143 | 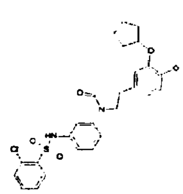 | MS m/z: 541.1 (M + 1). |

FIG. 1U

| Compound Number | Structure | Physical Data<br>$^1$H NMR 400 MHz and/or MS (m/z) |
|---|---|---|
| 144 | 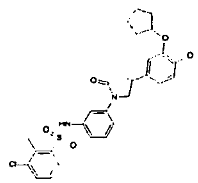 | MS m/z: 555.1 (M + 1). |
| 145 | 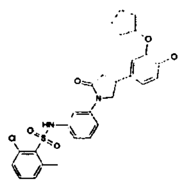 | MS m/z: 555.1 (M + 1). |
| 146 | 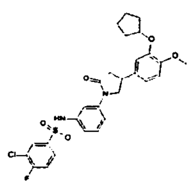 | MS m/z: 559.1 (M + 1). |
| 147 | 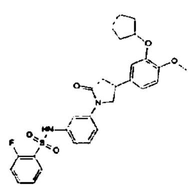 | MS m/z: 525.1 (M + 1). |
| 148 | 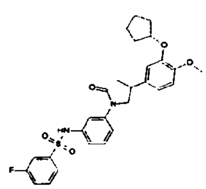 | MS m/z: 525.1 (M + 1). |
| 149 | 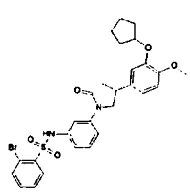 | MS m/z: 585.1 (M + 1). |
| 150 | 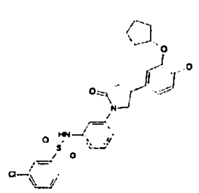 | MS m/z: 541.1 (M + 1). |

FIG. 1V

| Compound Number | Structure | Physical Data <br> ¹H NMR 400 MHz and/or MS (m/z) |
|---|---|---|
| 151 | 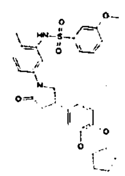 | MS m/z: 537.1(M + 1). |
| 152 | 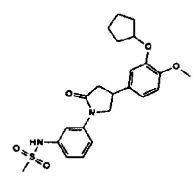 | MS m/z: 445.1(M + 1). |
| 153 | 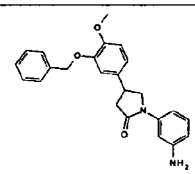 | MS m/z 389.1 (M + 1). |
| 154 | 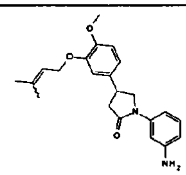 | MS m/z 367.2 (M + 1). |
| 155 | 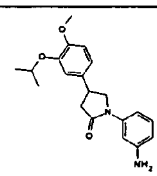 | MS m/z 340.2 (M + 1). |
| 156 | 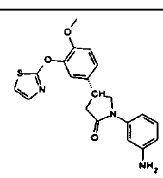 | MS m/z 382.1 (M + 1). |
| 157 | 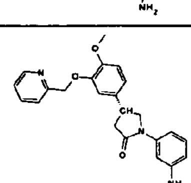 | MS m/z 390.1 (M + 1). |
| 158 | 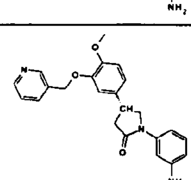 | MS m/z 390.1 (M + 1). |

FIG. 1W

| Compound Number | Structure | Physical Data<br>¹H NMR 400 MHz and/or MS (m/z) |
|---|---|---|
| 159 | 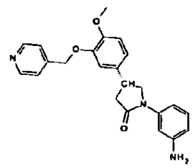 | MS m/z 390.1 (M + 1). |
| 160 | 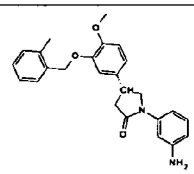 | MS m/z 403.2 (M + 1). |
| 161 | 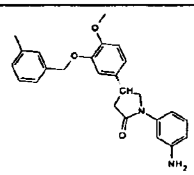 | MS m/z 403.2 (M + 1). |
| 162 | 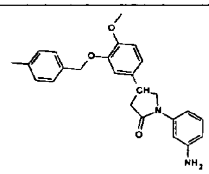 | MS m/z 403.2 (M + 1). |
| 163 | 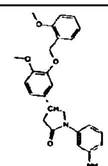 | MS m/z 419.2 (M + 1). |
| 164 | 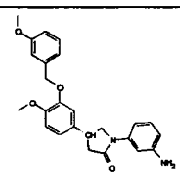 | MS m/z 419.2 (M + 1). |
| 165 | 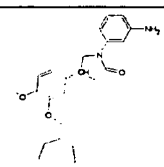 | MS m/z 395.2 (M + 1). |
| 166 | 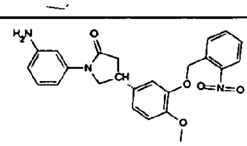 | MS m/z 434.1 (M + 1). |
| 167 | 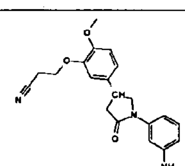 | MS m/z 352.1 (M + 1). |

FIG. 1X

| Compound Number | Structure | Physical Data<br>¹H NMR 400 MHz and/or MS (m/z) |
|---|---|---|
| 168 | 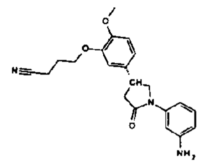 | MS m/z 366.1 (M + 1). |
| 169 | 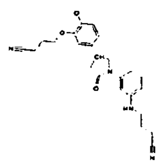 | MS m/z 433.2 (M + 1). |
| 170 | 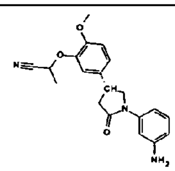 | MS m/z 352.1 (M + 1). |
| 171 | 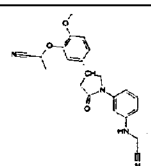 | MS m/z 405.2 (M + 1). |
| 172 | 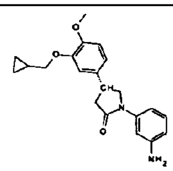 | MS m/z 353.2 (M + 1). |
| 173 | 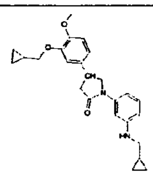 | MS m/z 407.2 (M + 1). |
| 174 | 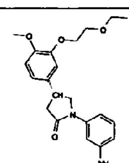 | MS m/z 371.2 (M + 1). |
| 175 | 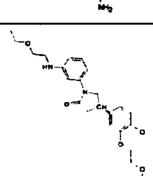 | MS m/z 443.2 (M + 1). |
| 176 | 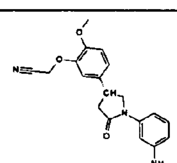 | MS m/z 338.1 (M + 1). |

FIG. 1Y

| Compound Number | Structure | Physical Data<br>¹H NMR 400 MHz and/or MS (m/z) |
|---|---|---|
| 177 | 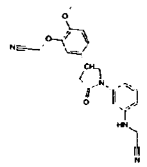 | MS m/z 377.1 (M + 1). |
| 178 | 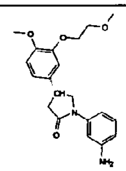 | MS m/z 356.1 (M + 1). |
| 179 | 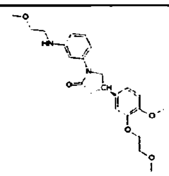 | MS m/z 415.2 (M + 1). |
| 180 | 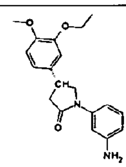 | MS m/z 327.1 (M + 1). |
| 181 | 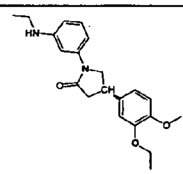 | MS m/z 355.2 (M + 1). |
| 182 | 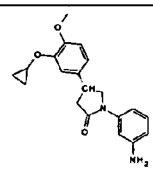 | MS m/z 407.2 (M + 1). |
| 183 | 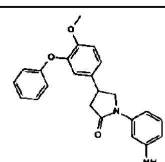 | MS m/z 375.1 (M + 1). |
| 184 | 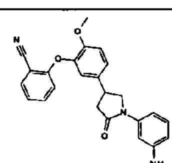 | MS m/z 400.1 (M + 1). |
| 185 | 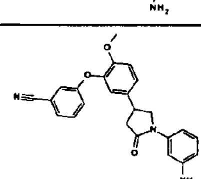 | MS m/z 400.1 (M + 1). |

FIG. 1Z
| Compound Number | Structure | Physical Data<br>¹H NMR 400 MHz and/or MS (m/z) |
|---|---|---|
| 186 | 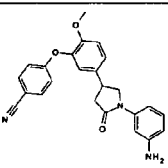 | MS m/z 400.1 (M + 1). |
| 187 | 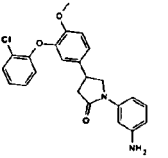 | MS m/z 409.1 (M + 1). |
| 188 | 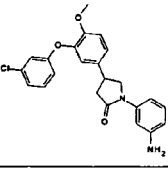 | MS m/z 409.1 (M + 1). |
| 189 | 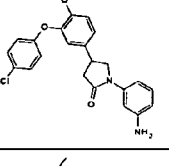 | MS m/z 409.1 (M + 1). |
| 190 | 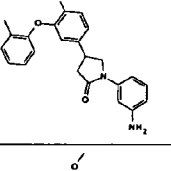 | MS m/z 389.1 (M + 1). |
| 191 | 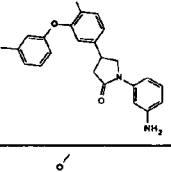 | MS m/z 389.1 (M + 1). |
| 192 | 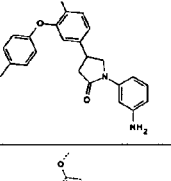 | MS m/z 389.1 (M + 1). |
| 193 | 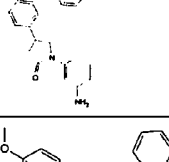 | MS m/z 405.1 (M + 1). |
| 194 | 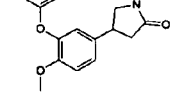 | MS m/z 405.1 (M + 1). |

FIG. 1BA

| Compound Number | Structure | Physical Data<br>¹H NMR 400 MHz and/or MS (m/z) |
|---|---|---|
| 195 | 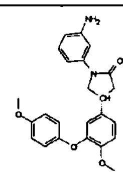 | MS m/z 405.1 (M + 1). |
| 196 | 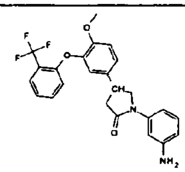 | MS m/z 443.1 (M + 1). |
| 197 | 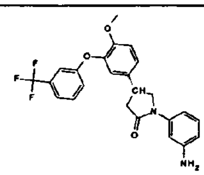 | MS m/z 443.1 (M + 1). |
| 198 | 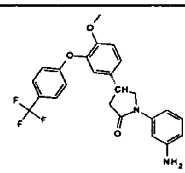 | MS m/z 443.1 (M + 1). |
| 199 | 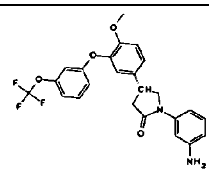 | MS m/z 459.1 (M + 1). |
| 200 | 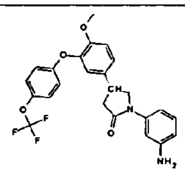 | MS m/z 459.1 (M + 1). |
| 201 | 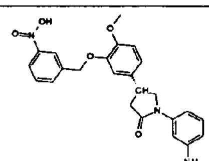 | MS m/z 434.1 (M + 1). |
| 202 | 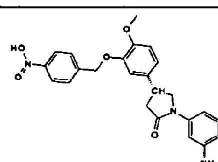 | MS m/z 434.1 (M + 1). |
| 203 | 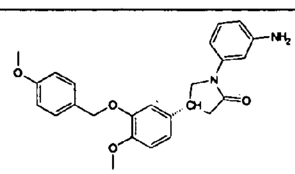 | MS m/z 419.2 (M + 1). |

FIG. 1BB

| Compound Number | Structure | Physical Data<br>¹H NMR 400 MHz and/or MS (m/z) |
|---|---|---|
| 204 | 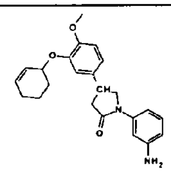 | MS m/z 379.2 (M + 1). |
| 205 | 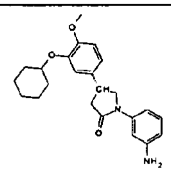 | MS m/z 381.2 (M + 1). |
| 206 | 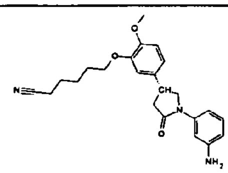 | MS m/z 394.2 (M + 1). |
| 207 | 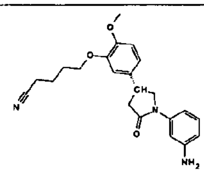 | MS m/z 380.2 (M + 1). |
| 208 | 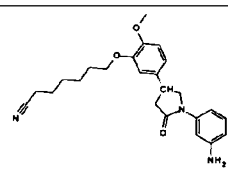 | MS m/z 408.2 (M + 1). |
| 209 | 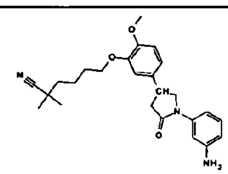 | MS m/z 422.2 (M + 1). |
| 210 | 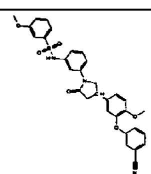 | MS m/z 570.1 (M + 1). |
| 211 | 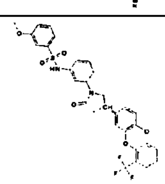 | MS m/z 613.1 (M + 1). |
| 213 | 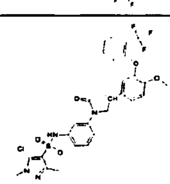 | MS m/z 635.1 (M + 1). |

FIG. 1BC

| Compound Number | Structure | Physical Data<br>¹H NMR 400 MHz and/or MS (m/z) |
|---|---|---|
| 214 | 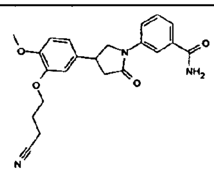 | MS m/z 394.1 (M + 1). |
| 215 | 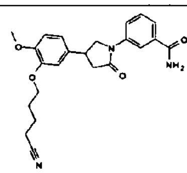 | MS m/z 408.1 (M + 1). |
| 216 | 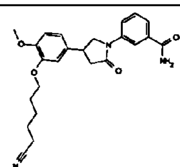 | MS m/z 422.2 (M + 1). |
| 217 | 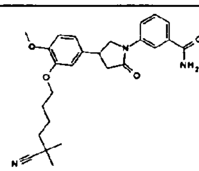 | MS m/z 450.2 (M + 1). |
| 218 | 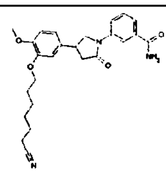 | MS m/z 436.2 (M + 1). |
| 219 | 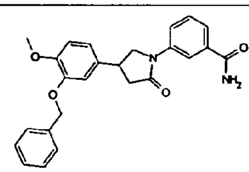 | MS m/z 417.1 (M + 1). |
| 220 | 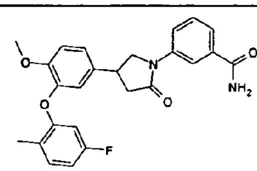 | MS m/z 435.1 (M + 1). |
| 221 | 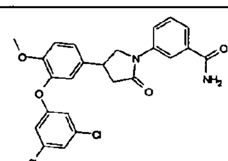 | MS m/z 470.1 (M + 1). |
| 222 | 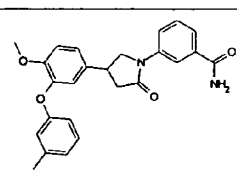 | MS m/z 416.1 (M + 1). |

FIG. 1BD

| Compound Number | Structure | Physical Data<br>¹H NMR 400 MHz and/or MS (m/z) |
|---|---|---|
| 223 | 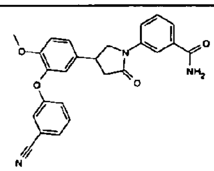 | MS m/z 428.1 (M + 1). |
| 224 | 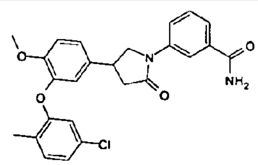 | MS m/z 451.1 (M + 1). |
| 225 | 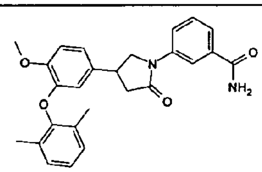 | MS m/z 431.2 (M + 1). |
| 226 | 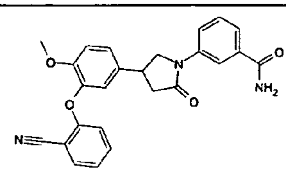 | MS m/z 428.1 (M + 1). |
| 227 | 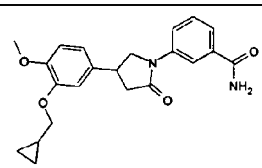 | MS m/z 381.2 (M + 1). |
| 228 | 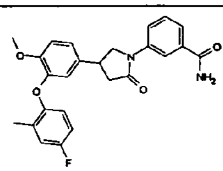 | MS m/z 434.2 (M + 1). |
| 229 | 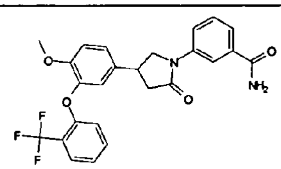 | MS m/z 471.1 (M + 1). |
| 230 | 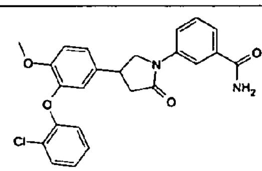 | MS m/z 437.1 (M + 1). |
| 231 | 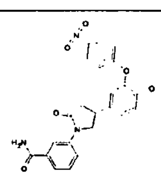 | MS m/z 448.1 (M + 1). |

FIG. 1BE

| Compound Number | Structure | Physical Data $^1$H NMR 400 MHz and/or MS (m/z) |
|---|---|---|
| 232 | 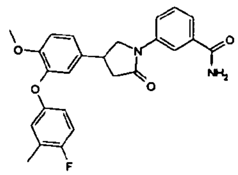 | MS m/z 434.1 (M + 1). |
| 233 | 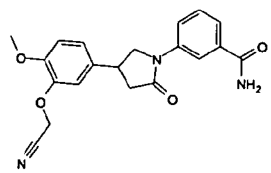 | MS m/z 366.1 (M + 1). |
| 234 | 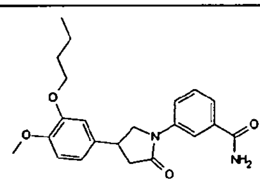 | MS m/z 383.2 (M + 1). |
| 235 | 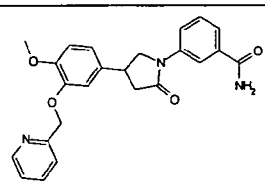 | MS m/z 418.2 (M + 1). |
| 236 | 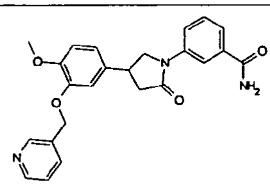 | MS m/z 418.2 (M + 1). |
| 237 | 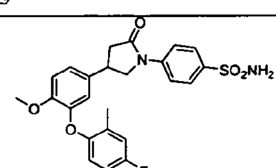 | MS m/z 471.1 (M + 1). |
| 238 | 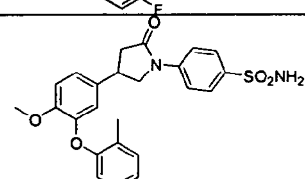 | MS m/z 453.1 (M + 1). |
| 239 | 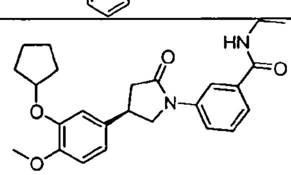 | MS m/z 423.1 (M + 1) |

FIG. 1BF
| Compound Number | Structure | Physical Data<br>¹H NMR 400 MHz and/or MS (m/z) |
|---|---|---|
| 240 | 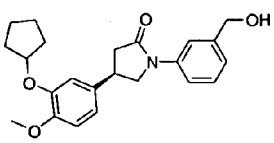 | MS m/z 382.1 (M + 1) |
| 241 | 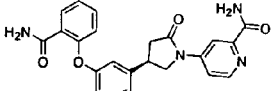 | MS m/z 447.1 (M + 1) |
| 242 | 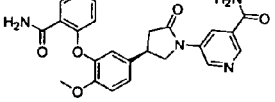 | MS m/z 447.1 (M + 1) |
| 243 | 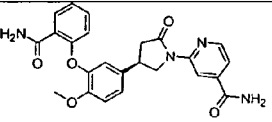 | MS m/z 447.1 (M + 1) |
| 244 | 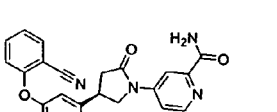 | MS m/z 429.1 (M + 1). |
| 245 | 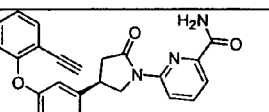 | ¹H NMR 400 MHz (CDCl₃) δ 8.60 (d, 1H), 7.97 (d, 1H), 7.89 (t, 1H), 7.62 (dd, 1H), 7.55 (b, 1H), 7.40 (td, 1H), 7.16 (dd, 1H), 7.09 (m, 2H), 7.02 (d, 1H), 6.76 (d, 1H), 4.54 (dd, 1H), 4.04 (dd, 1H), 3.78 (s, 3H), 3.67 (m, 1H), 3.08 (dd, 1H), 2.84 (dd, 1H); MS m/z 429.1 (M + 1). |
| 246 | 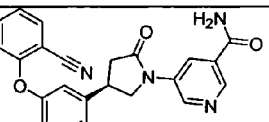 | MS m/z 429.1 (M + 1). |
| 247 | 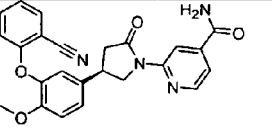 | MS m/z 429.1 (M + 1). |
| 248 | 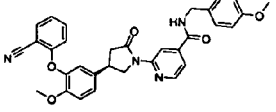 | MS m/z 549.2 (M + 1) |

FIG. 1BG

| Compound Number | Structure | Physical Data<br>¹H NMR 400 MHz and/or MS (m/z) |
|---|---|---|
| 249 | 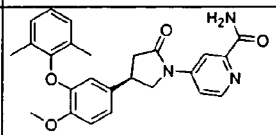 | MS m/z 432.1 (M + 1) |
| 250 | 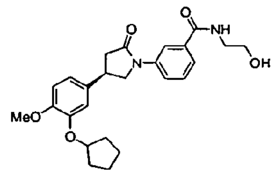 | MS m/z 439.5 (M + 1). |
| 251 | 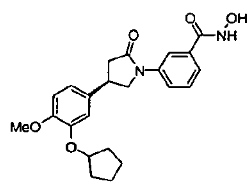 | MS m/z 411.1 (M + 1). |
| 252 | 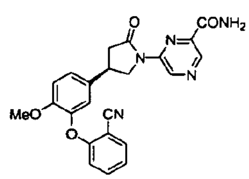 | ¹H NMR 400 MHz (CDCl₃) δ 8.89 (s, 1H), 7.89 (s, 1H), 7.64 (dd, 1H), 7.43 (ddd, 1H), 7.18-7.00 (m, 4H), 6.67 (d, 1H), 4.48 (dd, 1H), 3.94 (dd, 1H), 3.78 (s, 3H), 3.68 (m, 1H), 3.08 (dd, 1H), 2.84 (dd, 1H); MS m/z 430.1 (M + 1). |
| 253 | 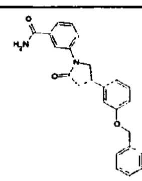 | MS m/z 387.1 1). |
| 254 | 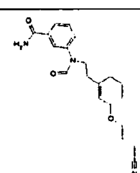 | MS m/z 364 (M + 1). |

FIG. 1BH
| Compound Number | Structure | Physical Data<br>¹H NMR 400 MHz and/or MS (m/z) |
|---|---|---|
| 255 | 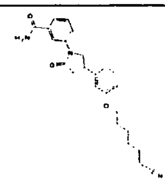 | MS m/z 406.2). |
| 256 | 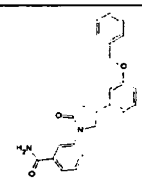 | MS m/z 401.2 (M + 1). |
| 257 | 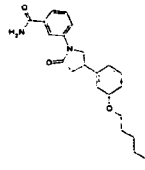 | MS m/z 378.1 (M+1). |
| 258 | 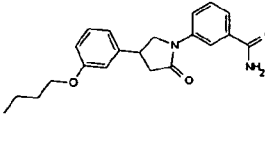 | MS m/z 353.2 (M + 1). |
| 259 | 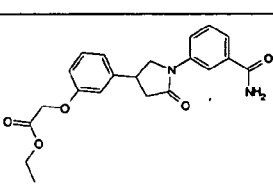 | MS m/z 383.2 (M + 1). |
| 260 | 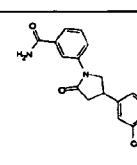 | MS m/z 351.1 (M + 1). |

FIG. 1BI

| Compound Number | Structure | Physical Data<br>¹H NMR 400 MHz and/or MS (m/z) |
|---|---|---|
| 261 | 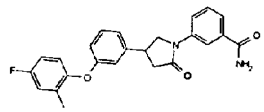 | MS m/z 405.1 (M + 1). |
| 262 | 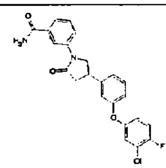 | MS m/z 425.1 (M + 1). |
| 263 | 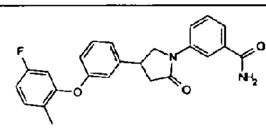 | MS m/z 405.1 (M + 1). |
| 264 | 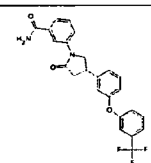 | MS m/z 441.1 (M + 1). |
| 265 | 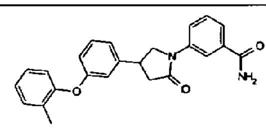 | MS m/z 387.1 (M + 1). |
| 266 | 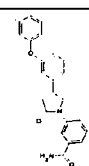 | MS m/z 387.1 (M + 1). |
| 267 | 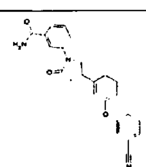 | MS m/z 398.1 (M + 1). |

FIG. 1BJ
| Compound Number | Structure | Physical Data <br> $^1$H NMR 400 MHz and/or MS (m/z) |
|---|---|---|
| 268 | 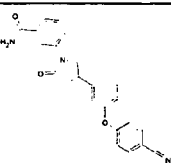 | MS m/z 398.1 (M + 1). |
| 269 | 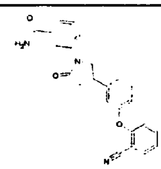 | MS m/z 398.1 (M + 1). |
| 270 | 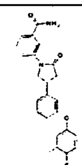 | MS m/z 405.1 (M + 1). |
| 271 | 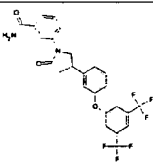 | MS m/z 509.1 (M + 1). |
| 272 | 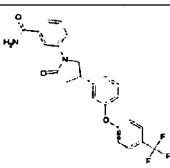 | MS m/z 441.1 (M + 1). |
| 273 | 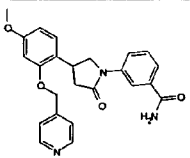 | MS m/z 418.1 (M + 1). |
| 274 | 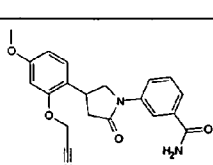 | MS m/z 366.1 (M + 1). |

FIG. 1BK

| Compound Number | Structure | Physical Data<br>¹H NMR 400 MHz and/or MS (m/z) |
|---|---|---|
| 275 | 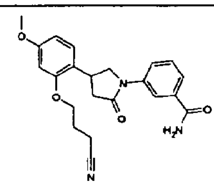 | MS m/z 394.1 (M + 1). |
| 276 | 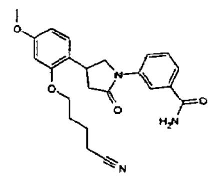 | MS m/z 408.4 (M + 1). |
| 277 | 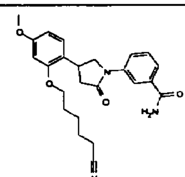 | MS m/z 422.2 (M + 1). |
| 278 | 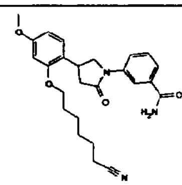 | MS m/z 436.2 (M + 1). |
| 279 | 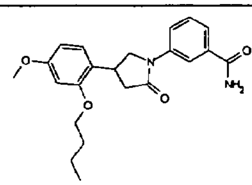 | MS m/z 383.2 (M + 1). |
| 280 | 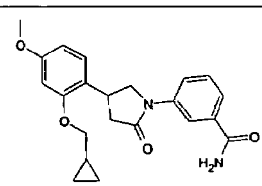 | MS m/z 381.1 (M + 1). |

FIG. 1BL
| Compound Number | Structure | Physical Data<br>¹H NMR 400 MHz and/or MS (m/z) |
|---|---|---|
| 281 | 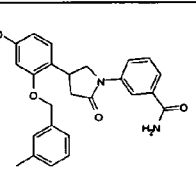 | MS m/z 431.1 (M + 1). |
| 282 | 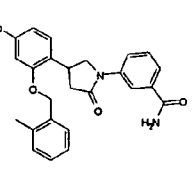 | MS m/z 431.1 (M + 1). |
| 283 | 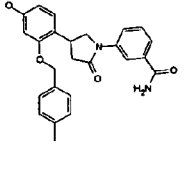 | MS m/z 431.1 (M + 1). |
| 284 | 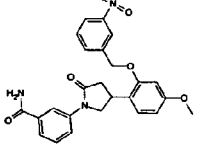 | MS m/z 462.1 (M + 1). |
| 285 | 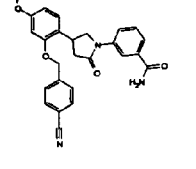 | MS m/z 442.1 (M + 1). |
| 286 | 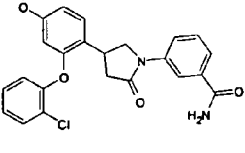 | MS m/z 437.1 (M + 1). |
| 287 | 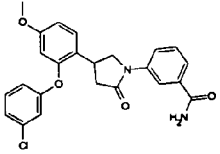 | MS m/z 437.1 (M + 1). |

FIG. 1BM
| Compound Number | Structure | Physical Data<br>¹H NMR 400 MHz and/or MS (m/z) |
|---|---|---|
| 288 | 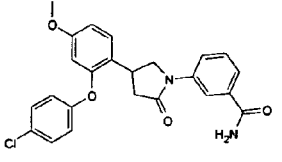 | MS m/z 437.1 (M + 1). |
| 289 | 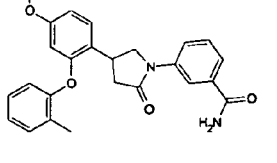 | MS m/z 417.1 (M + 1). |
| 290 | 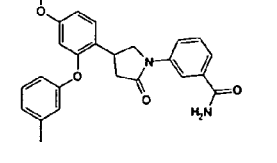 | MS m/z 417.1 (M + 1). |
| 291 | 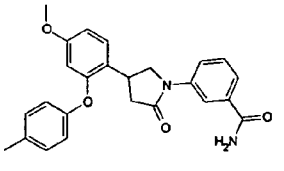 | MS m/z 417.1 (M + 1). |
| 292 | 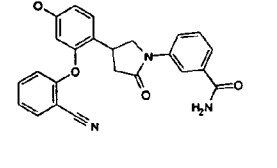 | MS m/z 428.1 (M + 1). |
| 293 | 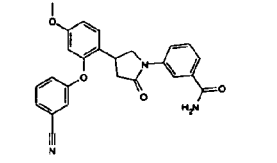 | MS m/z 428.1 (M + 1). |
| 294 | 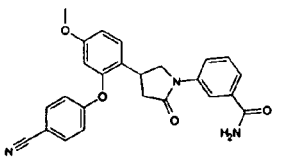 | MS m/z 428.1 (M + 1). |

FIG. 1BN

| Compound Number | Structure | Physical Data<br>¹H NMR 400 MHz and/or MS (m/z) |
|---|---|---|
| 295 | 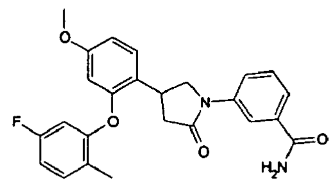 | MS m/z 435.1 (M + 1). |
| 296 | 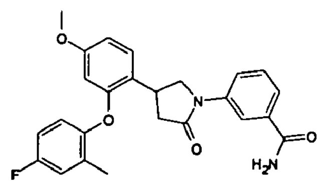 | MS m/z 435.1 (M + 1). |
| 297 | 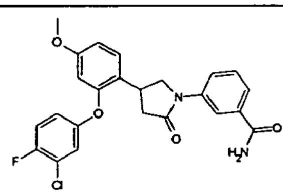 | MS m/z 455.1 (M + 1). |
| 298 | 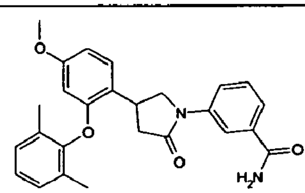 | MS m/z 431.1 (M + 1). |
| 299 | 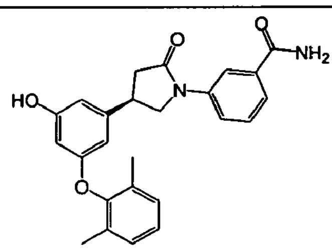 | MS m/z 417.1 (M + 1). |

FIG. 1BO
| Compound Number | Structure | Physical Data<br>¹H NMR 400 MHz and/or MS (m/z) |
|---|---|---|
| 300 | 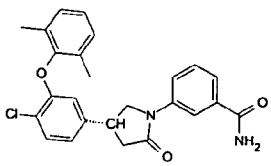 | MS m/z: 435.1(M + 1). |
| 301 | 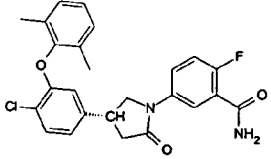 | MS m/z: 453.1(M + 1). |
| 302 | 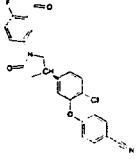 | MS m/z: 450.1(M + 1). |
| 303 | 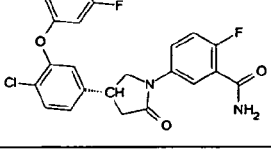 | MS m/z: 457.1(M + 1). |
| 304 | 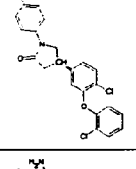 | MS m/z: 459.1(M + 1). |
| 305 | 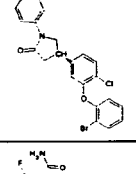 | MS m/z: 503.0(M + 1). |
| 306 | 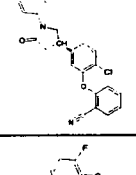 | MS m/z: 450.1(M + 1). |
| 307 | 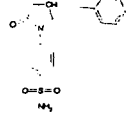 | MS m/z: 435.1(M + 1). |

FIG. 1BP

| Compound Number | Structure | Physical Data<br>¹H NMR 400 MHz and/or MS (m/z) |
|---|---|---|
| 308 | 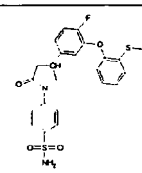 | MS m/z: 473.1 (M + 1). |
| 309 | 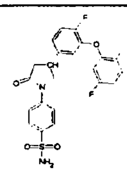 | MS m/z: 459.1 (M + 1). |
| 310 | 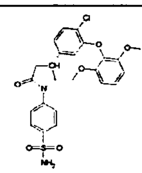 | MS m/z: 503.1 (M + 1). |
| 311 | 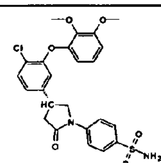 | MS m/z: 503.1 (M + 1). |
| 312 | 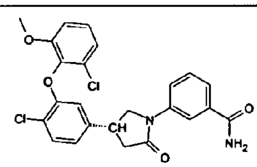 | MS m/z: 471.0 (M + 1). |
| 313 | 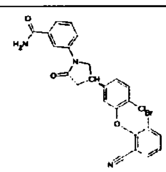 | MS m/z: 510.0 (M + 1). |
| 314 | 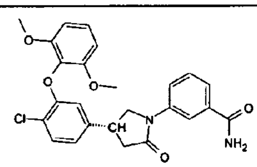 | MS m/z: 467.1 (M + 1). |
| 315 | 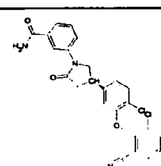 | MS m/z: 466.0 (M + 1). |
| 316 | 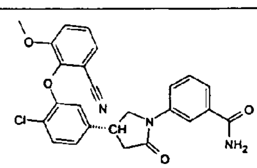 | MS m/z: 462.1 (M + 1). |

FIG. 1BQ

| Compound Number | Structure | Physical Data<br>¹H NMR 400 MHz and/or MS (m/z) |
|---|---|---|
| 317 | 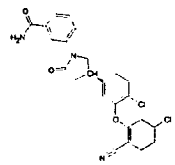 | MS m/z: 466.0 (M + 1). |
| 318 | 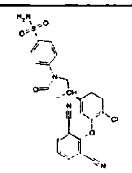 | MS m/z: 493.0 (M + 1). |
| 319 | 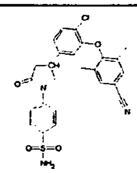 | MS m/z: 496.1 (M + 1). |
| 320 | 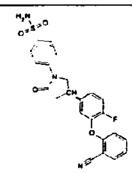 | MS m/z: 452.1 (M + 1). |
| 321 | 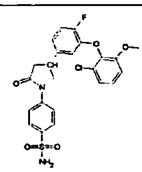 | MS m/z: 491.1 (M + 1). |
| 322 | 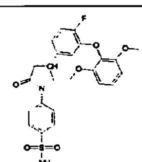 | MS m/z: 487.1 (M + 1). |
| 323 | 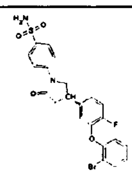 | MS m/z: 505.0 (M + 1). |
| 324 | 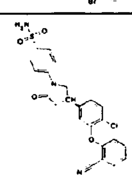 | MS m/z: 468.0 (M + 1). |
| 325 | 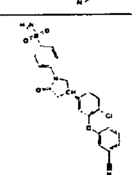 | MS m/z: 468.0 (M + 1). |

FIG. 1BR

| Compound Number | Structure | Physical Data<br>¹H NMR 400 MHz and/or MS (m/z) |
|---|---|---|
| 326 | 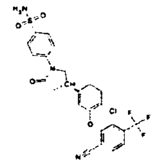 | MS m/z: 536.0 (M + 1). |
| 327 | 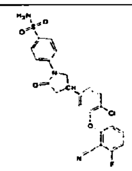 | MS m/z: 486.0 (M + 1). |
| 328 | 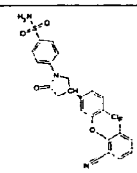 | MS m/z: 486.0 (M + 1). |
| 329 | 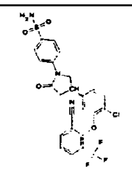 | MS m/z: 536.0 (M + 1). |
| 330 | 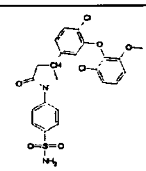 | MS m/z: 567.0 (M + 1). |
| 331 | 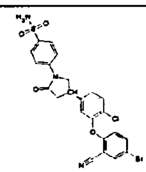 | MS m/z: 545.9 (M + 1). |
| 332 | 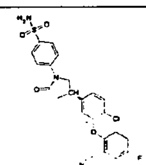 | MS m/z: 486.0 (M + 1). |
| 333 | 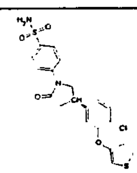 | MS m/z: 449.0 (M + 1). |
| 334 | 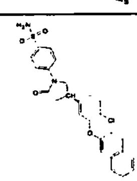 | MS m/z: 493.1 (M + 1). |

FIG. 1BS

| Compound Number | Structure | Physical Data<br>¹H NMR 400 MHz and/or MS (m/z) |
|---|---|---|
| 335 | 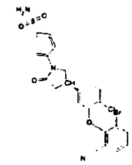 | MS m/z: 545.9 (M + 1). |
| 336 | 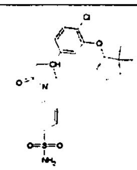 | MS m/z: 463.1 (M + 1). |
| 337 | 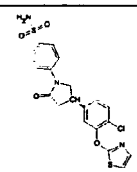 | MS m/z: 450.0 (M + 1). |
| 338 | 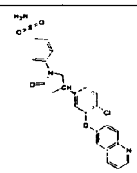 | MS m/z: 494.1 (M + 1). |
| 339 | 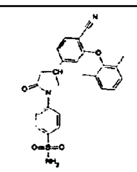 | MS m/z: 462.1 (M + 1). |
| 340 | 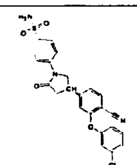 | MS m/z: 468.0 (M + 1). |
| 341 | 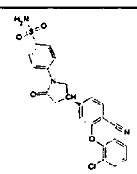 | MS m/z: 468.0 (M + 1). |
| 342 | 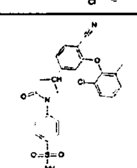 | MS m/z: 482.1 (M + 1). |
| 343 | 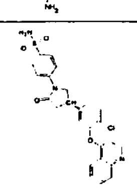 | MS m/z: 494.1 (M + 1). |

FIG. 1BT

| Compound Number | Structure | Physical Data $^1$H NMR 400 MHz and/or MS (m/z) |
|---|---|---|
| 344 | 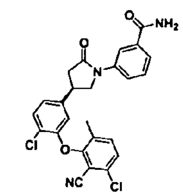 | MS m/z 480.0 (M + 1). |
| 345 | 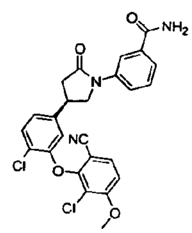 | MS m/z 496.0 (M + 1). |
| 346 | 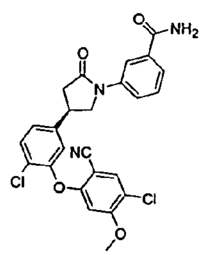 | MS m/z 496.0 (M + 1). |
| 347 | 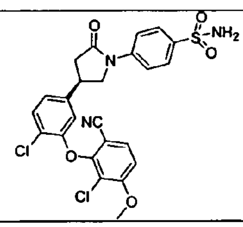 | MS m/z 532.0 (M + 1). |
| 348 | 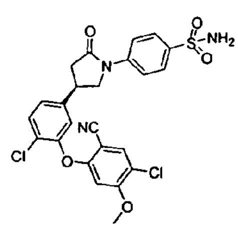 | MS m/z 532.2 (M + 1). |
| 349 | 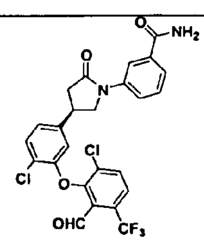 | MS m/z 536.95 (M + 1). |

FIG. 1BU

| Compound Number | Structure | Physical Data<br>¹H NMR 400 MHz and/or MS (m/z) |
|---|---|---|
| 350 | 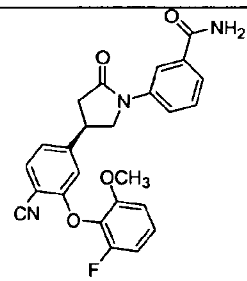 | ¹H NMR (CDCl₃): 7.88, (t, 1H), 7.88 (d, 1H, J = 8.0 Hz), 7.59 (d, 1H, J = 7.6 Hz), 7.46 (t, 1H, J = 8.0 Hz), 6.88 (d, 1H, J = 8.0 Hz), 6.80-6.77 (m, 2H), 6.27 (brs, 1H), 5.62 (brs, 1H), 4.79 (brs, 1H), 4.21 (t, 1H, J = 8.7 Hz), 3.90 (t, 1H, J = 7.8), 3.82 (d, 2H, J = 6.8), 3.69-3.60 (m, 1H), 3.01 (dd, 1H, J = 8.7, 17.0 Hz), 2.79 (dd, 1H, J = 9.0, 17.0 Hz), 1.87-1.84 (m, 6H), 1.55-1.68 (m, 2H), 1.29-1.25 (m, 3H), 0.60 (dd, 2H, J = 5.9, 12.8 Hz), 0.33 (dd, 2H, J = 4.6, 10.3 Hz). MS m/z 446.1 (M + 1). |
| 351 | 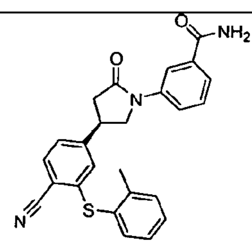 | MS m/z 428.10 (M + 1). |
| 352 | 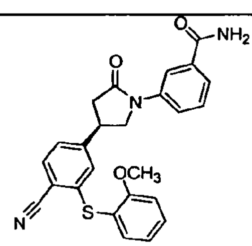 | MS m/z 444.10 (M + 1). |
| 353 | 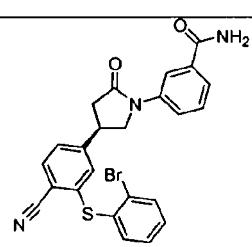 | MS m/z 492.0 (M + 1). |

FIG. 1BV
| Compound Number | Structure | Physical Data<br>¹H NMR 400 MHz and/or MS (m/z) |
|---|---|---|
| 354 | 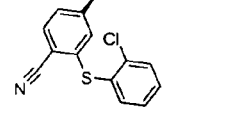 | MS m/z 448.0 (M + 1). |
| 355 | 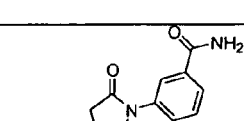 | MS m/z 442.10 (M + 1). |
| 356 | 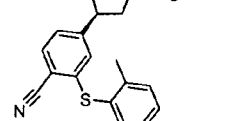 | MS m/z 446.10 (M + 1). |
| 357 | 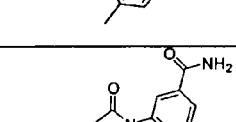 | MS m/z 432.05 (M + 1). |
| 358 | 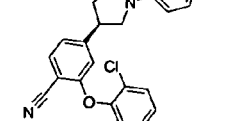 | MS m/z 432.10 (M + 1). |
| 359 | 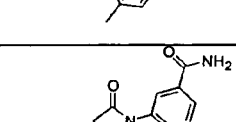 | MS m/z 423.1 (M + 1). |

FIG. 1BW

| Compound Number | Structure | Physical Data<br>¹H NMR 400 MHz and/or MS (m/z) |
|---|---|---|
| 360 | 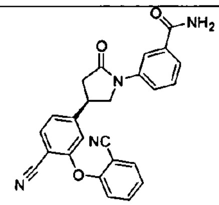 | MS m/z 423.1 (M + 1). |
| 361 | 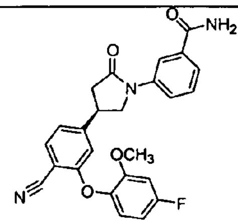 | MS m/z 446.1 (M + 1). |
| 362 | 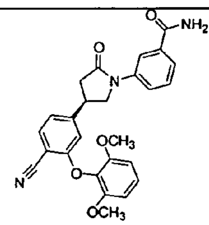 | MS m/z 458.10 (M + 1). |
| 363 | 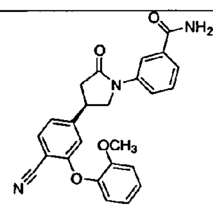 | MS m/z 428.10 (M + 1). |
| 364 | 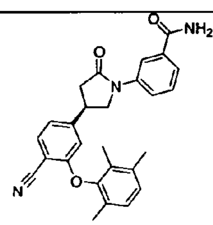 | 953-118B-19<br>¹H NMR (CDCl₃): 7.97 (t, 1H, J = 1.6 Hz), 7.81-7.79 (m, 1H), 7.66 (d, 1H, J = 8.0 Hz), 7.59-7.57 (m, 1H), 7.46 (t, 1H, J = 8.0 Hz), 7.00-6.97 (m, 3H), 6.33 (brs, 1H), 7.30 (d, 1H, J = 1.6 Hz), 6.16 (brs, 1H), 4.18 (dd, 1H, J = 8.0, 9.6 Hz), 3.77 (dd, 1H, J = 6.8, 10 Hz), 3.60-3.56 (m, 1H), 2.96 (dd, 1H, J = 8.8, 17.2 Hz), 2.62 (dd, 1H, J = 8.0, 17.2 Hz). MS m/z 440.10 (M + 1). |
| 365 | 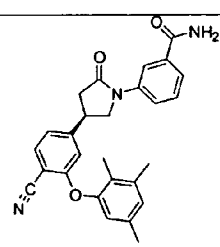 | MS m/z 440.10 (M + 1). |

FIG. 1BX
| Compound Number | Structure | Physical Data<br>¹H NMR 400 MHz and/or MS (m/z) |
|---|---|---|
| 366 | 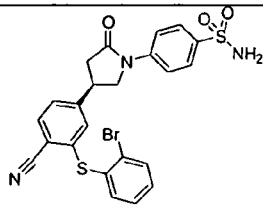 | MS m/z 528.0 (M + 1). |
| 367 | 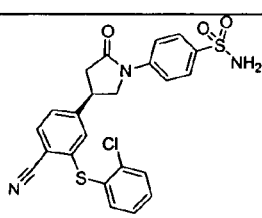 | MS m/z 484.05 (M + 1). |
| 368 | 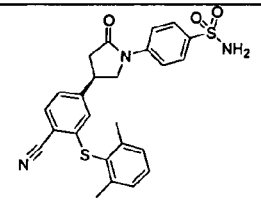 | MS m/z 478.10 (M + 1). |
| 369 | 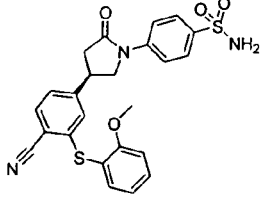 | MS m/z 480.10 (M + 1). |
| 370 | 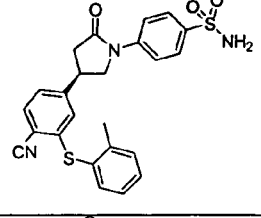 | MS m/z 464.10 (M + 1). |
| 371 | 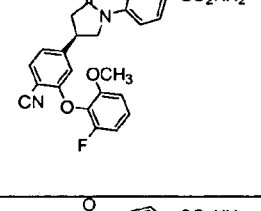 | MS m/z 482.0 (M + 1). |
| 372 | 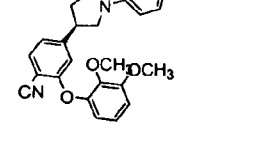 | MS m/z 494.1 (M + 1). |

FIG. 1BY
| Compound Number | Structure | Physical Data<br>¹H NMR 400 MHz and/or MS (m/z) |
|---|---|---|
| 373 | 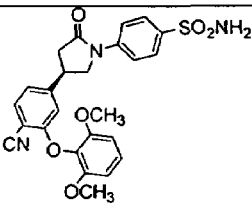 | MS m/z 494.1 (M + 1). |
| 374 | 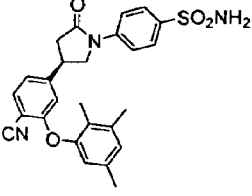 | MS m/z 476.1 (M + 1). |
| 375 | 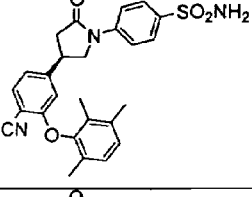 | MS m/z 476.1 (M + 1). |
| 376 | 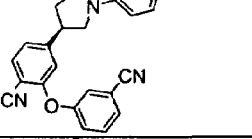 | MS m/z 459.0 (M + 1). |
| 377 | 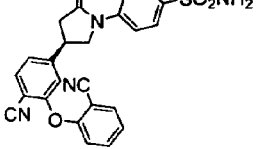 | MS m/z 459.0 (M + 1). |
| 378 | 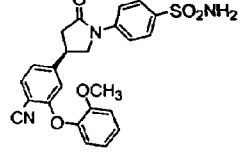 | MS m/z 464.1 (M + 1). |
| 379 | 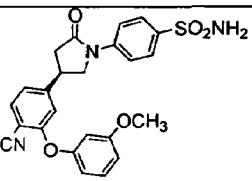 | MS m/z 464.1 (M + 1). |
| 380 | 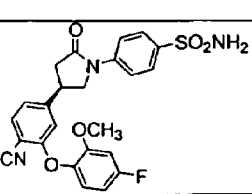 | MS m/z 482.1 (M + 1). |

FIG. 1BZ
| Compound Number | Structure | Physical Data <br> ¹H NMR 400 MHz and/or MS (m/z) |
|---|---|---|
| 381 | 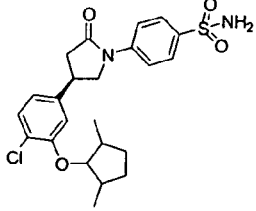 | MS m/z 463.10 (M + 1). |
| 382 | 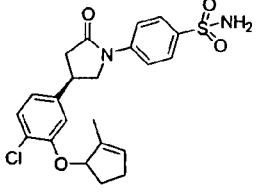 | MS m/z 447.1 (M + 1). |
| 383 | 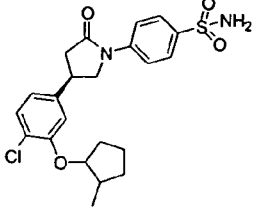 | MS m/z 449.10 (M + 1). |
| 384 | 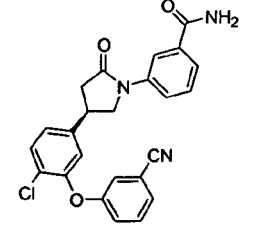 | 953-79A <br> ¹H NMR (Acetone-d6): 7.97-7.96 (m, 1H), 7.93-7.91 (m, 1H), 7.59-7.57 (m, 1H), 7.52-7.47 (m, 2H), 7.42-7.40 (m, 1H), 7.35-7.31 (m, 4H), 7.23-7.21 (m, 2H), 6.51 (brs, 1H), 4.23 (dd, 1H, J = 8.0, 9.6 Hz), 3.91 (dd, 1H, J = 8.0, 9.6 Hz), 3.80-3.76 (m, 1H), 2.86 (dd, 1H, J = 8.8, 16.8 Hz), 2.69 (dd, 1H, J = 9.6, 16.8 Hz). |
| 385 | 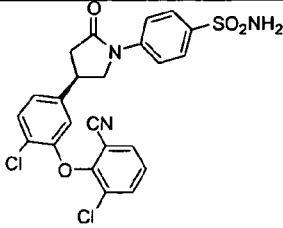 | 953-77B <br> 1H NMR (Acetone-d6): 7.99 (dd, 1H, J = 1.6, 8.0 Hz), 7.98-7.91 (m, 5H), 7.69 (d, 1H, J = 8.4 Hz), 7.63 (t, 1H, J = 8.0 Hz), 7.37 (dd, 1H, J = 2.0, 8.0 Hz), 6.96 (d, 1H, J = 2.0 Hz), 6.96 (d, 1H, J = 2.0 Hz), 6.64-6.63 (m, 2H), 4.37 (dd, 1H, J = 8.0, 9.6 Hz), 3.97 (dd, 1H, J = 7.2, 9.6 Hz), 3.92-3.84 (m, 1H), 3.02 (dd, 1H, J = 8.8, 16.8 Hz), 2.75 (dd, 1H, J = 8.4, 16.8 Hz). LCMS m/z: 466.3 (M+H). |

FIG. 1CA

| Compound Number | Structure | Physical Data<br>¹H NMR 400 MHz and/or MS (m/z) |
|---|---|---|
| 386 | 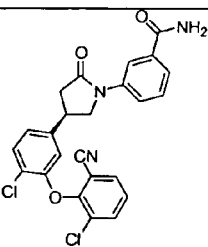 | 953-77A<br>¹H NMR (Acetone-d6): 8.02 (t, 1H, J = 1.6 Hz), 7.97-7.94 (m, 1H), 7.92 (dd, 1H, J = 1.2, 8.0 Hz), 7.88 (dd, 1H, J = 1.6, 7.6 Hz), 7.70-6.68 (m, 1H), 7.60 (d, 1H, J = 8.0 Hz), 7.53 (t, 1H, J = 8.0 Hz), 7.48 (brs, 1H), 7.44 (t, 1H, J = 8.0 Hz), 7.29 (dd, 1H, J = 2.0, 8.0 Hz), 6.91 (d, 1H, J = 1.6 Hz), 6.64 (brs, 1H), 4.25 (dd, 1H, J = 8.0, 9.6 Hz), 3.87 (dd, 1H, J = 7.2, 9.6 Hz), 3.81-3.73 (m, 1H), 2.89 (dd, 1H, J = 8.4, 16.8 Hz), 2.64 (dd, 1H, J = 8.4, 16.4 Hz). |
| 387 | 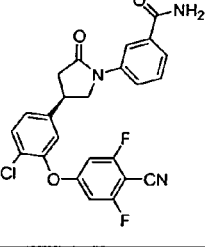 | MS m/z 468.10 (M + 1). |
| 388 | 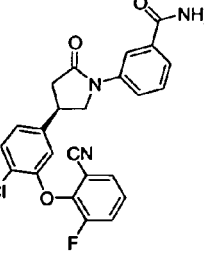 | 953-70F<br>¹H NMR (CDCl₃): 8.02 (t, 1H, J = 2.0 Hz), 7.97-7.94 (m, 1H), 7.60 (d, 1H, J = 8.0 Hz), 7.50-7.40 (m, 4H), 7.32-7.29 (m, 1H), 7.04 (dd, 1H, J = 2.0, 8.0 Hz), 6.68 (s, 1H), 6.40 (brs, 1H), 6.08 (brs, 1H), 4.21 (dd, 1H, J = 8.0, 9.6 Hz), 3.83 (dd, 1H, J = 6.8, 10.0 Hz), 3.67-3.60 (m, 1H), 3.00 (dd, 1H, J = 8.8, 17.2 Hz), 2.69 (dd, 1H, J = 8.4, 17.2 Hz). LCMS m/z: 450.1 (M+H). |
| 389 | 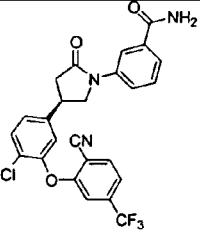 | 953-70E<br>¹H NMR (CDCl₃): 8.07 (t, 1H, J = 2.0 Hz), 7.89-7.84 (m, 1H), 7.83 (d, 1H, J = 8.4 Hz), 7.61-7.59 (m, 1H), 7.55 (d, 1H, J = 8.4 Hz), 7.48 (t, 1H, J = 8.0 Hz), 7.43 (dd, 1H, J = 0.8, 8.0 Hz), 7.27-7.23 (m, 1H), 7.16 (d, 1H, J = 2.0 Hz), 6.85 (s, 1H), 6.35 (brs, 1H), 6.21 (brs, 1H), 4.30 (dd, 1H, J = 8.0, 9.6 Hz), 3.95 (dd, 1H, J = 7.2, 9.6 Hz), 3.81-3.75 (m, 1H), 3.10 (dd, 1H, J = 8.8, 17.2 Hz), 2.80 (dd, 1H, J = |

FIG. 1CB
| Compound Number | Structure | Physical Data $^1$H NMR 400 MHz and/or MS (m/z) |
|---|---|---|
| | | 8.4, 17.2 Hz). LCMS *m/z*: 500.1 (M+H). |
| 390 | 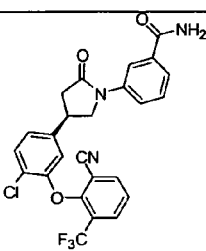 | 953-70D<br>$^1$H NMR (CDCl$_3$): 8.02 (s, 1H), 7.97 (dd, 1H, J = 0.8, 8.0 Hz), 7.82 (d, 1H, J = 6.4 Hz), 7.75 (d, 1H, J = 8.0 Hz), 7.61 (d, 1H, J = 7.6 Hz), 7.50 -7.42 (m, 3H), 7.06 (dd, 1H, J = 1.6, 8.0 Hz), 6.58 (d, 1H, J = 2.0 Hz), 6.42 (brs, 1H), 6.33 (brs, 1H), 4.21 (dd, 1H, J = 8.0, 9.6 Hz), 3.82 (dd, 1H, J = 6.8, 9.6 Hz), 3.67-3.59 (m, 1H), 3.00 (dd, 1H, J = 8.4, 17.2 Hz), 2.68 (dd, 1H, J = 7.6, 17.2 Hz). LCMS *m/z*: 500.1(M+H). |
| 391 | 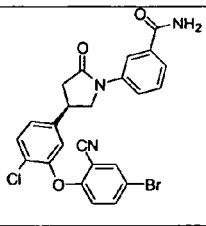 | MS *m/z* 510.0 (M + 1). |
| 392 | 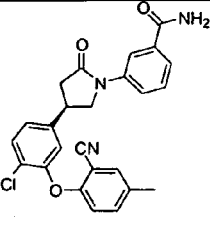 | MS *m/z* 446.10 (M + 1). |
| 393 | 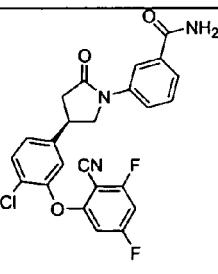 | MS *m/z* 468.10(M + 1). |

FIG. 1CC
| Compound Number | Structure | Physical Data <br> ¹H NMR 400 MHz and/or MS (m/z) |
|---|---|---|
| 394 | 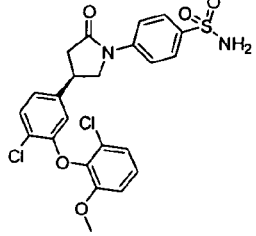 | MS m/z 507.2 (M + 1). |
| 395 | 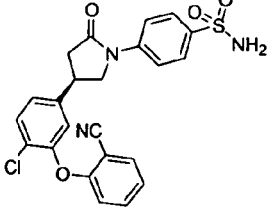 | MS m/z 468.2 (M + 1). |
| 396 | 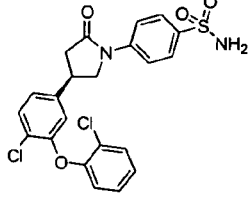 | MS m/z 477.15 (M + 1). |
| 397 | 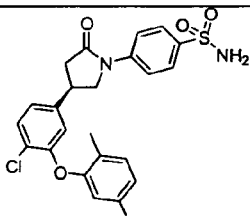 | MS m/z 475.2 (M + 1). |
| 398 | 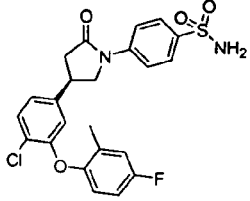 | MS m/z 475.2 (M + 1). |
| 399 | 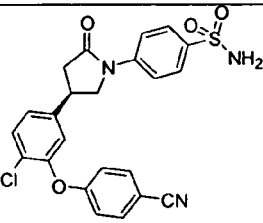 | MS m/z 468.2 (M + 1). |

FIG. 1CD
| Compound Number | Structure | Physical Data $^1$H NMR 400 MHz and/or MS (m/z) |
|---|---|---|
| 400 | 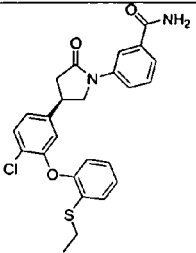 | MS m/z 467.2 (M + 1). |
| 401 | 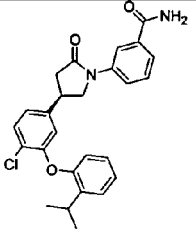 | MS m/z 449.3 (M + 1). |
| 402 | 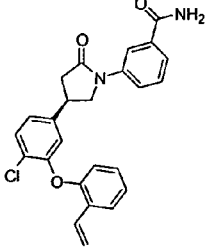 | MS m/z 433.2 (M + 1). |
| 403 | 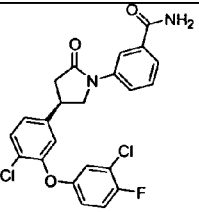 | MS m/z 459.2 (M + 1). |
| 404 | 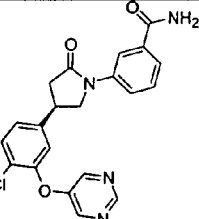 | MS m/z 409.2 (M + 1). |
| 405 | 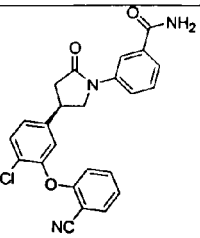 | MS m/z 432.3 (M + 1). |

FIG. 1CE
| Compound Number | Structure | Physical Data<br>¹H NMR 400 MHz and/or MS (m/z) |
|---|---|---|
| 406 | 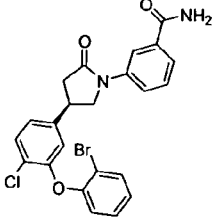 | MS m/z 485.2 (M + 1). |
| 407 | 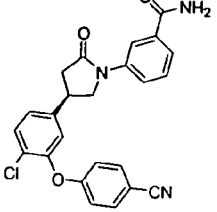 | 953-14D<br>¹H NMR (Acetone-d6): 8.09 (t, 1H, J = 2.0 Hz), 8.06-8.04 (m, 1H), 7.81-7.78 (m, 1H), 7.72-7.67 (m, 1H), 7.64 (d, 1H, J = 8.4 Hz), 7.50 (brs, 1H), 7.49 -7.44 (m, 3H), 7.13-7.09 (m, 2H), 6.70 (brs, 1H), 4.36 (dd, 1H, J = 8.0, 9.6 Hz), 4.04 (dd, 1H, J = 8.0, 9.2 Hz), 3.96-3.88 (m, 1H), 3.00 (dd, 1H, J = 8.4, 16.8 Hz), 2.81 (dd, 1H, J = 9.6, 16.4 Hz). LCMS m/z: 432.2(M+H). |
| 408 | 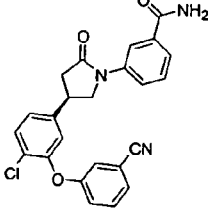 | MS m/z 432.2 (M + 1). |
| 409 | 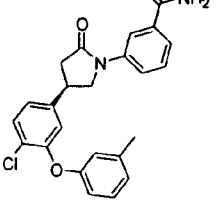 | 953-14A<br>¹H NMR (CDCl₃): 8.00 (t, 1H, J = 2.0 Hz), 7.87-7.85 (m, 1H), 7.58-7.56 (m, 1H), 7.47-7.42 (m, 2H), 7.24 -7.21 (m, 1H), 7.01 (dd, 1H, J = 2.0, 8.0 Hz), 6.95-6.93 (m, 1H), 6.89 (d, 1H, J = 2.0 Hz), 6.80 (s, 1H), 6.74 (dd, 1H, J = 2.4, 8.0 Hz), 6.22 (brs, 1H), 5.77 (brs, 1H), 4.21 (dd, 1H, J = 8.0, 9.6 Hz), 3.85 (dd, 1H, J = 6.4, 9.6 Hz), 3.68-3.60 (m, 1H), 2.99 (dd, 1H, J = 8.4, 16.8 Hz), 2.71 (dd, 1H, J = 8.4, 16.8 Hz), 2.33 (s, 3H). LCMS m/z: 421.25 (M+H). |

FIG. 1CF
| Compound Number | Structure | Physical Data<br>$^1$H NMR 400 MHz and/or MS (m/z) |
|---|---|---|
| 410 | 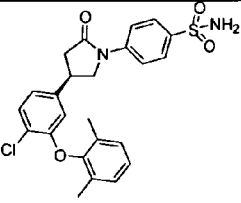 | MS m/z 471.2 (M + 1). |
| 411 | 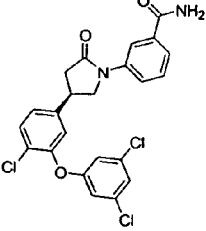 | $^1$H NMR (CDCl$_3$): 8.03-8.02 (m, 1H), 7.88-7.85 (m, 1H), 7.59-7.57 (m, 1H), 7.49-7.46 (m, 2H), 7.19 -7.17 (m, 1H), 7.05-7.02 (m, 2H), 6.79 (d, 1H, J = 2.4 Hz), 6.69 (d, 1H, J = 2.0 Hz), 6.13 (brs, 1H), 5.60 (brs, 1H), 4.24 (dd, 1H, J = 8.4, 10 Hz), 3.87 (dd, 1H, J = 6.8, 9.6 Hz), 3.70-3.64 (m, 1H), 3.02 (dd, 1H, J = 8.8, 17.2 Hz), 2.73 (dd, 1H, J = 8.8, 17.2 Hz). LCMS m/z: 475.10 (M+H). |
| 412 | 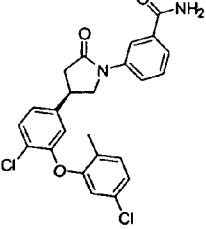 | 690-170H<br>$^1$H NMR (CDCl$_3$): 8.18 (t, 1H, J = 2.0 Hz), 7.78-7.75 (m, 1H), 7.66 (d, 2H, J = 1.6 Hz), 7.53-7.45 (m, 2H), 7.32 (d, 1H, J = 8.0 Hz), 7.15 (t, 1H, J = 1.6 Hz), 6.97 (d, 1H, J = 2.4 Hz), 6.80 (d, 1H, J = 1.6 Hz), 6.18 (brs, 1H), 5.64 (brs, 1H), 4.26 (dd, 1H, J = 8.0, 9.6 Hz), 3.92 (dd, 1H, J = 7.2, 9.6 Hz), 3.74-3.65 (m, 1H), 3.06 (dd, 1H, J = 8.8, 17.2 Hz), 2.79 (dd, 1H, J = 8.8, 17.2 Hz), 1.25 (s, 3H). LCMS m/z: 445.2 (M+H). |
| 413 | 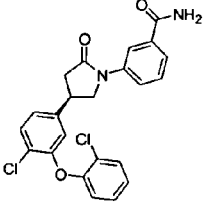 | MS m/z 441.2 (M + 1). |
| 414 | 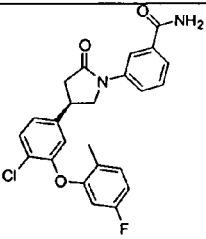 | MS m/z 439.2 (M + 1). |

FIG. 1CG
| Compound Number | Structure | Physical Data<br>¹H NMR 400 MHz and/or MS (m/z) |
|---|---|---|
| 415 | 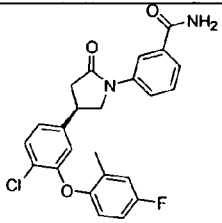 | MS m/z 439.2 (M + 1). |
| 416 | 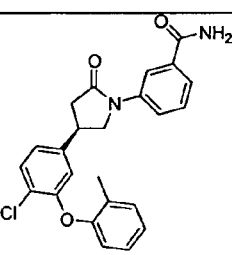 | 690-170B-1<br>¹H NMR (CDCl₃): 8.00 (t, 1H, J = 1.6 Hz), 7.85-7.82 (m, 1H), 7.59-7.57 (m, 1H), 7.47-7.43 (m, 2H), 7.18 -7.14 (m, 1H), 7.10-7.06 (m, 1H), 6.96 (dd, 1H, J = 2.0, 8.0 Hz), 6.80 (dd, 1H, J = 0.8, 8.0 Hz), 6.69 (d, 1H, J = 2.0 Hz), 6.20 (brs, 1H), 5.65 (brs, 1H), 4.19 (dd, 1H, J = 8.4, 10.0 Hz), 3.82 (dd, 1H, J = 7.2, 9.6 Hz), 3.64-3.56 (m, 1H), 2.97 (dd, 1H, J = 8.4, 16.8 Hz), 2.69 (dd, 1H, J = 8.4, 16.8 Hz), 2.26 (s, 3H). LCMS m/z: 421.2 (M+H). |
| 417 | 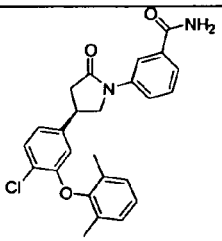 | 690-170A-1<br>¹H NMR (CDCl₃): 7.97 (t, 1H, J = 1.6 Hz), 7.80-7.78 (m, 1H), 7.58-7.56 (m, 1H), 7.47-7.43 (m, 2H), 7.13 -7.05 (m, 3H), 6.86 (dd, 1H, J = 4.0, 8.0 Hz), 6.27 (d, 1H, J = 2.0 Hz), 6.23 (brs, 1H), 5.73 (brs, 1H), 4.14 (dd, 1H, J = 8.0, 9.6 Hz), 3.74 (dd, 1H, J = 6.8, 9.6 Hz), 3.56-3.48 (m, 1H), 2.92 (dd, 1H, J = 8.8, 17.2 Hz), 2.61 (dd, 1H, J = 8.0, 16.8 Hz), 2.12 (s, 6H). LCMS m/z: 435.2 (M+H). |
| 418 | 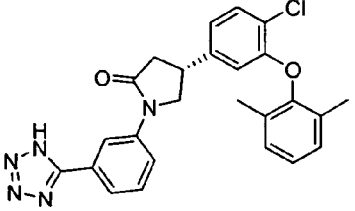 | MS m/z 460.2 (M + 1). |

FIG. 1CH
| Compound Number | Structure | Physical Data $^1$H NMR 400 MHz and/or MS (m/z) |
|---|---|---|
| 419 | 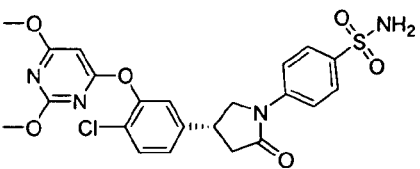 | MS m/z 460.2 (M + 1). |
| 420 | 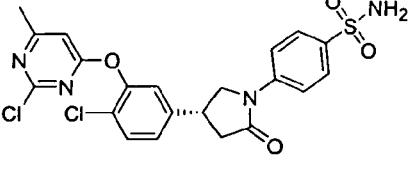 | MS m/z 493.1 (M + 1). |
| 421 | 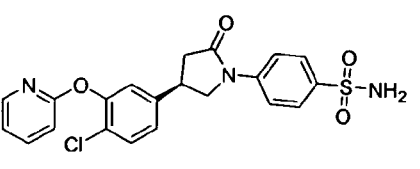 | MS m/z 444.3 (M + 1). |
| 422 | 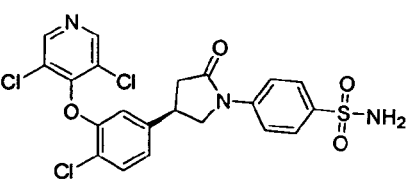 | MS m/z 512.3 (M + 1). |
| 423 | 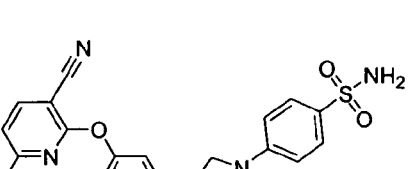 | MS m/z 483.1 (M + 1). |

FIG. 1CI
| Compound Number | Structure | Physical Data $^1$H NMR 400 MHz and/or MS (m/z) |
|---|---|---|
| 424 | 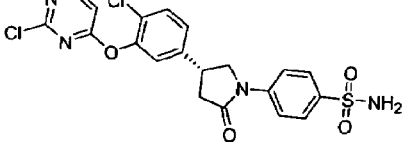 | MS m/z 479.1 (M + 1). |
| 425 | 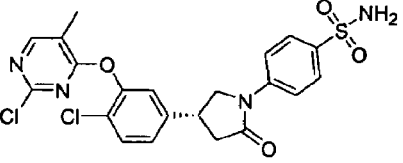 | MS m/z 493.1 (M + 1). |
| 426 | 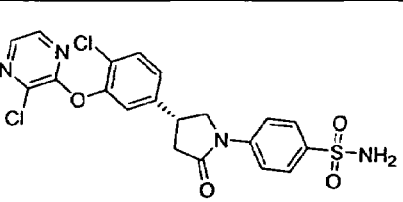 | MS m/z 479.1 (M + 1). |
| 427 | 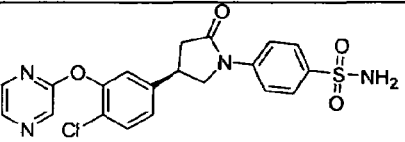 | MS m/z 445.1 (M + 1). |

FIG. 1CJ
| Compound Number | Structure | Physical Data<br>¹H NMR 400 MHz and/or MS (m/z) |
|---|---|---|
| 428 | 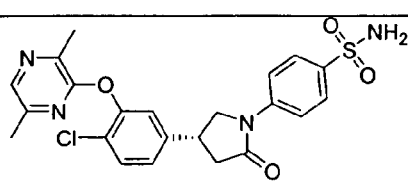 | MS m/z 473.4 (M + 1). |
| 429 | 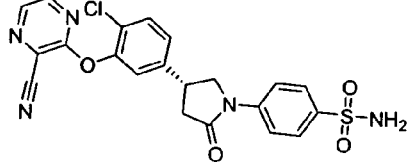 | MS m/z 470.1 (M + 1). |
| 430 | 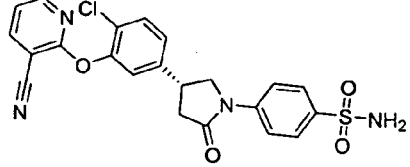 | MS m/z 469.4 (M + 1). |
| 431 | 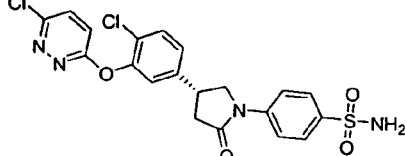 | MS m/z 479.1 (M + 1). |

FIG. 1CK
| Compound Number | Structure | Physical Data<br>¹H NMR 400 MHz and/or MS (m/z) |
|---|---|---|
| 432 | 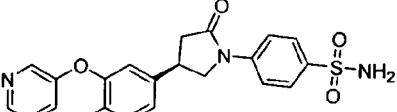 | MS m/z 444.1 (M + 1). |
| 433 | 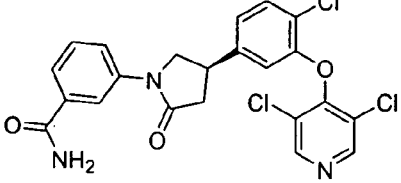 | MS m/z 476.2 (M + 1). |
| 434 | 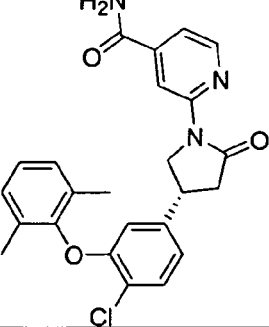 | ¹H NMR 400 MHz (CDCl₃) δ 8.63 (s, 1H), 8.48 (d, 1H), 7.56 (d, 1H), 7.43 (d, 1H), 7.11 (b, 1H), 7.08 (m, 3H), 6.95 (b, 1H), 6.85 (dd, 1H), 6.25 (d, 1H), 4.43 (dd, 1H), 3.94 (dd, 1H), 3.51 (m, 1H), 2.99 (dd, 1H), 2.69 (dd, 1H) 2.10 (s, 6H); MS m/z 436.1 (M + 1). |
| 435 | 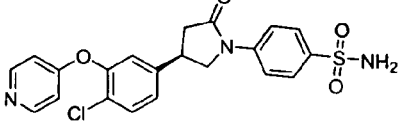 | MS m/z 444.1 (M + 1). |

FIG. 1CL
| Compound Number | Structure | Physical Data<br>¹H NMR 400 MHz and/or MS (m/z) |
|---|---|---|
| 436 | 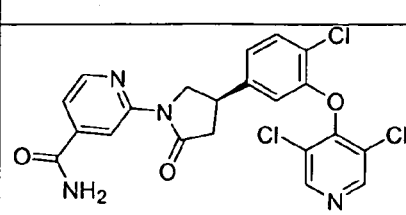 | MS m/z 477.0 (M + 1). |
| 437 | 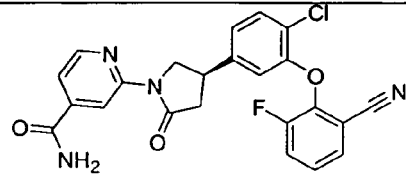 | MS m/z 451.0 (M + 1). |
| 438 | 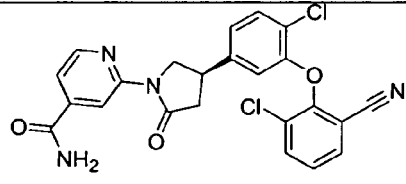 | ¹H NMR 400 MHz (CDCl₃) δ 8.63 (s, 1H), 8.44 (d, 1H), 7.70 (d, 1H), 7.62 (d, 1H), 7.53 (d, 1H), 7.47 (d, 1H), 7.33 (t, 1H), 7.02 (dd, 1H), 6.60 (b, 1H), 6.43 (dd, 1H), 5.92 (b, 1H), 4.48 (dd, 1H), 3.98 (dd, 1H), 3.57 (m, 1H), 3.01 (dd, 1H), 2.71 (dd, 1H); MS m/z 467.0 (M + 1). |
| 439 | 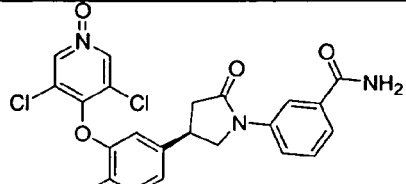 | ¹H NMR 400 MHz (MeOD) δ 8.61 (s, 2H), 8.02 (s, 1H), 7.88 (dd, 1H), 7.70 (d, 1H), 7.57 (d, 1H), 7.52 (t, 1H), 7.23 (dd, 1H), 6.89 (d, 1H), 4.28 (dd, 1H), 3.93 (dd, 1H), 3.77 (m, 1H), 3.00 (dd, 1H), 2.73 (dd, 1H); MS m/z 492.1 (M + 1). |

FIG. 1CM
| Compound Number | Structure | Physical Data<br>$^1$H NMR 400 MHz and/or MS (m/z) |
|---|---|---|
| 440 | 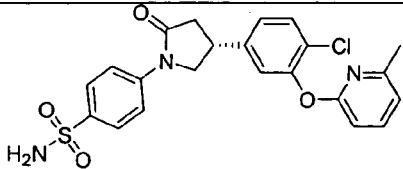 | MS m/z 458.2 (M + 1) |
| 441 | 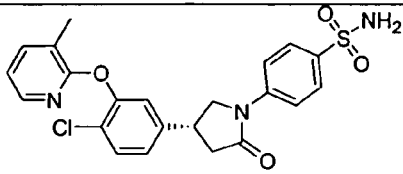 | MS m/z 458.2 (M + 1) |
| 442 | 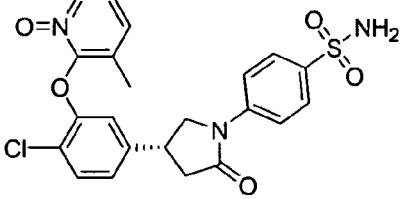 | $^1$H NMR 400 MHz (MeOD) δ 8.06 (s, 1H), 7.79 (d, 2H), 7.68 (d, 2H), 7.43 (d, 1H), 7.41( d, 1H), 7.21 (t, 1H), 7.06 (dd, 1H), 6.47 (d, 1H), 4.13 (dd, 1H), 3.80 (dd, 1H), 3.60 (m, 1H), 2.87 (dd, 1H), 2.57 (dd, 1H), 2.19 (s, 3H); MS m/z 474.2 (M + 1) |
| 443 | 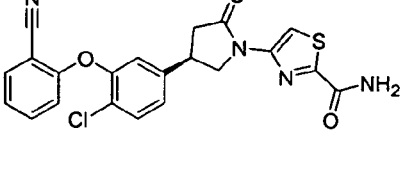 | $^1$H NMR 400 MHz (MeOD) δ 8.07 (s, 1H), 7.79 (d, 1H), 7.58-7.62 (m, 2H), 7.37 (dd, 1H), 7.26 (t, 1H), 6.78 (d, 1H), 4.62 (dd, 1H), 4.15 (dd, 1H), 3.90 (m, 1H), 3.07 (dd, 1H), 2.85 (dd, 1H); MS m/z 439.1 (M + 1) |

FIG. 1CN

| Compound Number | Structure | Physical Data <br> ¹H NMR 400 MHz and/or MS (m/z) |
|---|---|---|
| 444 | (structure) | ¹H NMR 400 MHz (MeOD) δ 7.91 (s, 1H), 7.79 (d, 1H), 7.58-7.62 (m, 2H), 7.37 (dd, 1H), 7.26 (t, 1H), 6.78 (d, 1H), 4.64 (dd, 1H), 4.15 (dd, 1H), 3.95 (m, 1H), 3.13 (dd, 1H), 2.93 (dd, 1H); MS m/z 439.1 (M + 1) |
| 445 | (structure) | ¹H NMR 400 MHz (MeOD) δ 8.61 (s, 1H), 8.48 (d, 1H), 7.56 (d, 1H), 7.40 (d, 1H), 7.12 (t, 1H), 6.95 (dd, 1H), 6.67 (d, 2H), 6.40 (d, 1H), 4.43 (dd, 1H), 3.98 (dd, 1H), 3.73 (s, 6H), 3.65 (m, 1H), 3.09 (dd, 1H), 2.59 (dd, 1H); MS m/z 468.0 (M + 1) |
| 446 | (structure) | ¹H NMR 400 MHz (MeOD) δ 8.66 (s, 1H), 8.45 (d, 1H), 7.53 (d, 1H), 7.51 (d, 1H), 7.49 (d, 1H), 7.28 (t, 1H), 7.20 (d, 1H), 7.15 (t, 1H), 6.92 (dd, 1H), 6.88 (dd, 1H), 4.49 (dd, 1H), 4.05 (dd, 1H), 3.75 (m, 1H), 3.09 (dd, 1H), 2.85 (dd, 1H); MS m/z 442.0 (M + 1) |
| 447 | (structure) | MS m/z 480.1 (M + 1) |

FIG. 1CO

| Compound Number | Structure | Physical Data<br>¹H NMR 400 MHz and/or MS (m/z) |
|---|---|---|
| 448 | 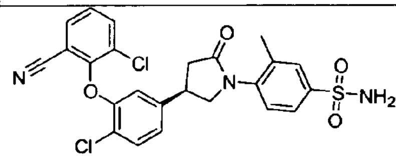 | ¹H NMR 400 MHz (acetone-d₆) δ 7.98 (dd, 1H), 7.93 (dd, 1H), 7.77 (d, 1H), 7.71(dd, 1H), 7.57-7.63 (m, 2H), 7.34 (d, 1H), 7.31 (dd, 1H), 6.88 (d, 1H), 6.58 (b, 2H), 4.12 (dd, 1H), 3.89 (m, 1H), 3.83 (dd, 1H), 2.85 (dd, 1H), 2.61 (dd, 1H), 2.24 (s, 3H); MS m/z 516.0 (M + 1) |
| 449 | 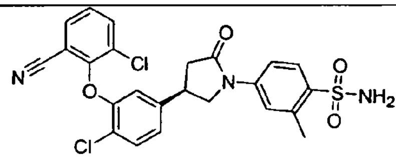 | MS m/z 516.0 (M + 1) |
| 450 | 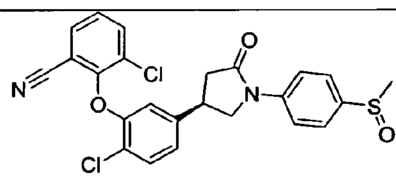 | MS m/z 485.0 (M + 1) |
| 451 | 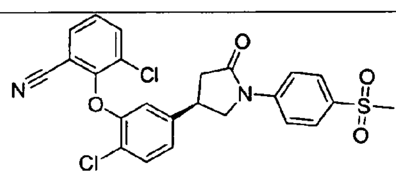 | MS m/z 501.0 (M + 1) |

FIG. 1CP
| Compound Number | Structure | Physical Data<br>¹H NMR 400 MHz and/or MS (m/z) |
|---|---|---|
| 452 | 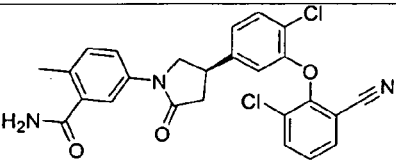 | MS m/z 480.1 (M + 1) |
| 453 | 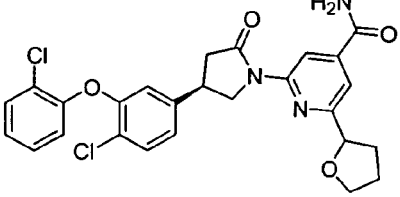 | ¹H NMR 400 MHz (MeOD) δ 8.52 (s, 1H), 7.61 (s, 1H), 7.53 (d, 1H), 7.49 (d, 1H), 7.28 (t, 1H), 7.20 (m, 1H), 7.15 (t, 1H), 6.92 (dd, 1H), 6.87 (m, 1H), 4.78 (dd, 1H), 4.28 (dd, 1H), 3.94 (dd, 1H), 3.70-3.90 (m, 2H), 3.50 (m, 1H), 2.87 (dd, 1H), 2.56 (dd, 2H), 2.19 (m, 1H), 1.81 (m, 3H); MS m/z 512.1 (M + 1) |
| 454 | 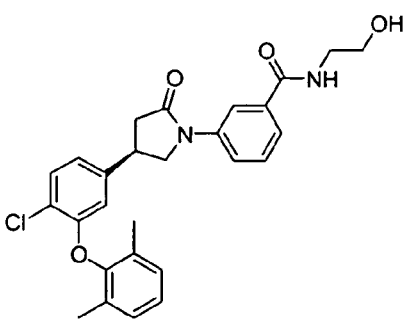 | MS m/z 479.1 (M + 1). |
| 455 | 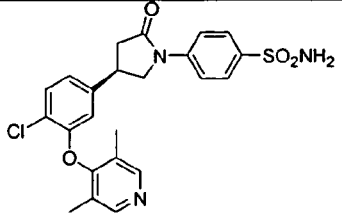 | ¹H NMR 400 MHz (CDCl₃) δ 8.36 (s, 2H), 7.97 (d, 2H), 7.61 (d, 2H), 7.49 (d, 1H), 6.97 (dd, 1H), 6.24 (d, 1H), 4.15 (dd, 1H), 3.71 (dd, 1H), 3.60 (m, 1H), 3.03 (dd, 1H), 2.58 (dd, 1H), 2.14 (s, 6H); MS m/z 472.0 (M + 1). |

FIG. 1CQ
| Compound Number | Structure | Physical Data $^1$H NMR 400 MHz and/or MS (m/z) |
|---|---|---|
| 456 | 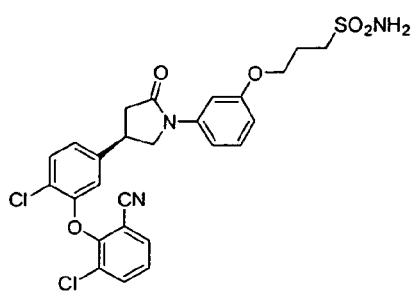 | $^1$H NMR 400 MHz (CDCl$_3$) δ 7.72 (dd, 1H), 7.62 (dd, 1H), 7.47 (d, 1H), 7.32 (m, 2H), 7.25 (t, 1H), 7.01 (dd, 1H), 6.94 (dd, 1H), 6.70 (dd, 1H), 6.23 (d, 1H), 4.13 (m, 3H), 3.74 (dd, 1H), 3.57 (m, 1H), 3.33 (t, 2H), 2.96 (dd, 1H), 2.65 (dd, 1H), 2.33 (m, 2H); MS m/z 559.9 (M + 1). |
| 457 | 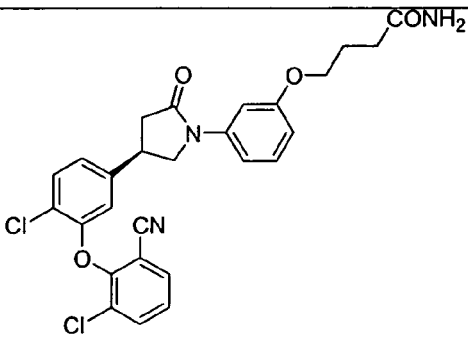 | MS m/z 524.0 (M + 1). |
| 458 | 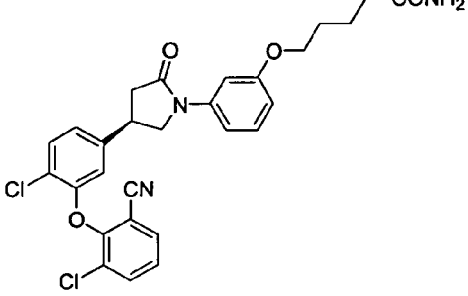 | MS m/z 538.0 (M + 1). |
| 459 | | |

FIG. 1CR
| Compound Number | Structure | Physical Data<br>$^1$H NMR 400 MHz and/or MS (m/z) |
|---|---|---|
| 460 | 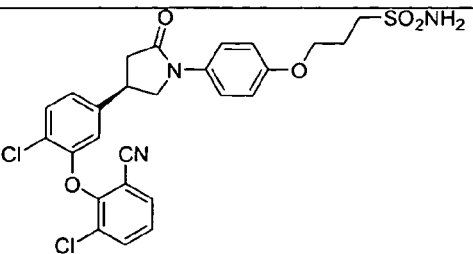 | MS m/z 560.0 (M + 1). |
| 461 | 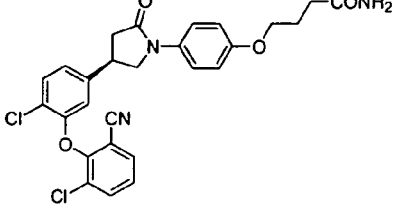 | MS m/z 524.0 (M + 1). |
| 462 | 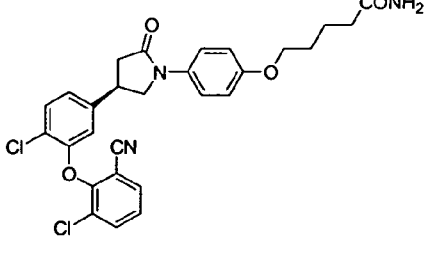 | MS m/z 538.0 (M + 1). |
| 463 | 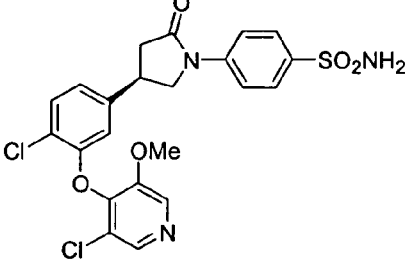 | $^1$H NMR 400 MHz (CDCl$_3$) δ 8.36 (s, 1H), 8.26 (s, 1H), 7.95 (d, 2H), 7.67 (d, 2H), 7.46 (d, 1H), 7.02 (dd, 1H), 6.40 (d, 1H), 4.23 (dd, 1H), 3.83 (s, 3H), 3.78 (dd, 1H), 3.64 (m, 1H), 3.08 (dd, 1H), 2.60 (dd, 1H); MS m/z 507.9 (M + 1). |

FIG. 1CS
| Compound Number | Structure | Physical Data <br> ¹H NMR 400 MHz and/or MS (m/z) |
|---|---|---|
| 464 | 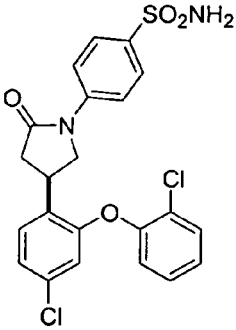 | ¹H NMR 400 MHz (Acetone-d₆) δ 7.86 (dd, 2H), 7.81 (dd, 2H), 7.56 (dd, 1H), 7.51 (d, 1H), 7.37 (m, 1H), 7.25 (m, 1H), 7.20 (dd, 1H), 7.15 (dd, 1H), 6.64 (d, 1H), 6.45 (bs, 2H), 4.36 (m, 1H), 4.13-4.04 (m, 2H), 3.03-2.69 (m, 2H); MS m/z 476.7 (M + 1). |
| 465 | 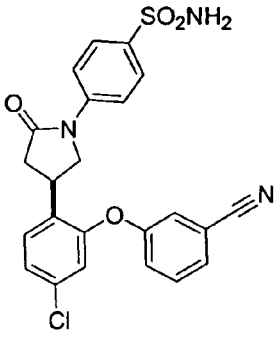 | ¹H NMR 400 MHz (CDCl₃) δ 7.83 (dd, 2H), 7.67 (dd, 2H), 7.41-7.37 (m, 2H), 7.25 (d, 1H), 7.16-7.12 (m, 3H), 6.84 (d, 1H), 4.72 (bs, 2H), 4.15 (dd, 1H), 3.83-3.81 (m, 2H), 2.95 (dd, 1H), 2.80 (dd, 1H); MS m/z 467.8 (M + 1). |
| 466 | 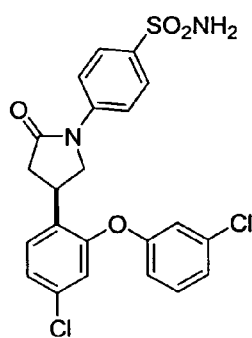 | ¹H NMR 400 MHz (CDCl₃) δ 7.83 (dd, 2H), 7.69 (dd, 2H), 7.22-7.18 (m, 2H), 7.10-7.07 (m, 2H), 6.89 (d, 1H), 6.84 (d, 1H), 6.80 (dd, 1H), 4.68 (s, 2H), 4.16 (dd, 1H), 3.90-3.81 (m, 2H), 2.94 (dd, 1H), 2.82 (dd, 1H); MS m/z 477.1 (M + 1). |
| 467 | 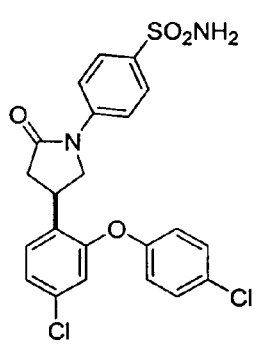 | ¹H NMR 400 MHz (CDCl₃) δ 7.90 (dd, 2H), 7.75 (dd, 2H), 7.32 (dd, 2H), 7.26 (d, 1H), 7.13 (d, 1H), 6.91 (dd, 2H), 6.85 (d, 1H), 4.80 (s, 2H), 4.24 (dd, 1H), 3.98 (m, 1H), 3.90 (dd, 1H), 3.02 (dd, 1H), 2.88 (dd, 1H); MS m/z 477.1 (M + 1). |

FIG. 1CT
| Compound Number | Structure | Physical Data<br>¹H NMR 400 MHz and/or MS (m/z) |
|---|---|---|
| 468 | 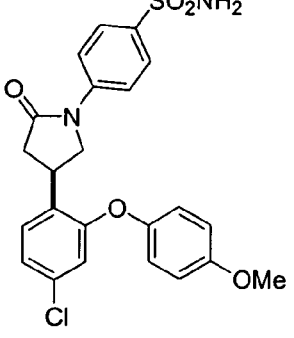 | ¹H NMR 400 MHz (CDCl₃) δ 7.82 (dd, 2H), 7.69 (dd, 2H), 7.15 (d, 1H), 6.96 (dd, 1H), 6.86-6.76 (m, 4H), 6.67 (d, 1H), 4.84 (s, 2H), 4.20 (dd, 1H), 3.98 (m, 1H), 3.88 (dd, 1H), 3.74 (s, 3H), 2.95 (dd, 1H), 2.90 (dd, 1H); MS m/z 473.1 (M + 1). |
| 469 | 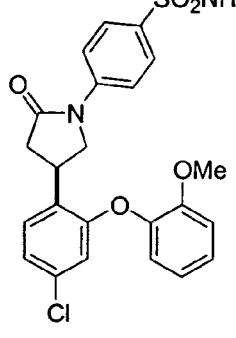 | ¹H NMR 400 MHz (CDCl₃) δ 7.83 (dd, 2H), 7.73 (dd, 2H), 7.14-7.12 (m, 2H), 6.95-6.91 (m, 4H), 6.55 (d, 1H), 4.68 (s, 2H), 4.23 (dd, 1H), 4.06-4.00 (m, 2H), 3.68 (s, 3H), 3.00-2.96 (m, 2H); MS m/z 473.1 (M + 1). |
| 470 | 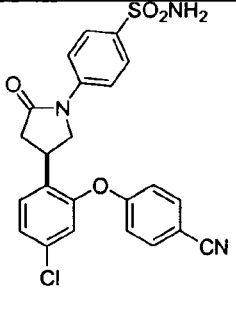 | MS m/z 468.1 (M + 1). |
| 471 | 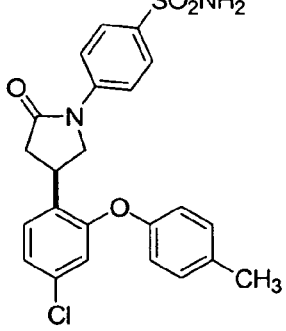 | MS m/z 457.1 (M + 1). |

FIG. 1CU
| Compound Number | Structure | Physical Data <br> ¹H NMR 400 MHz and/or MS (m/z) |
|---|---|---|
| 472 | 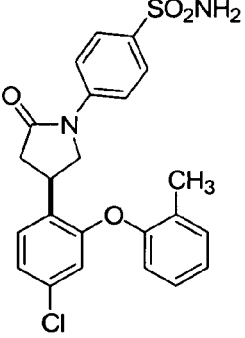 | MS m/z 457.1 (M + 1). |
| 473 | 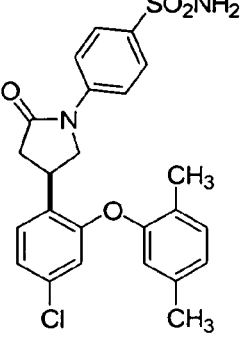 | MS m/z 471.1 (M + 1). |
| 474 | 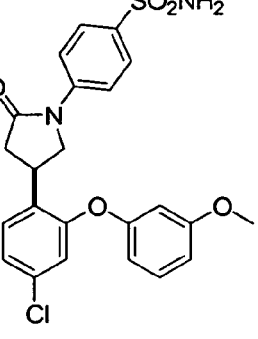 | ¹H NMR 400 MHz (CDCl₃) δ 8.01 (dd, 2H), 7.87 (dd, 2H), 7.38-7.35 (m, 2H), 7.20 (dd, 1H), 7.02 (d, 1H), 6.81 (d, 1H), 6.70-6.62 (m, 2H), 4.82 (s, 2H), 4.34 (dd, 1H), 4.10-4.02 (m, 2H), 3.90 (s, 3H), 3.10 (dd, 1H), 3.03 (dd, 1H); MS m/z 473.1 (M + 1). |
| 475 | 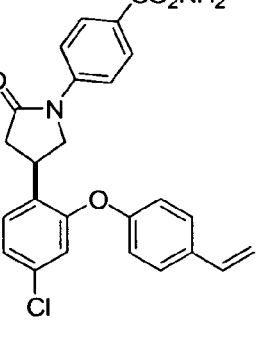 | MS m/z 469.4 (M + 1). |

FIG. 1CV
| Compound Number | Structure | Physical Data<br>¹H NMR 400 MHz and/or MS (m/z) |
|---|---|---|
| 476 | 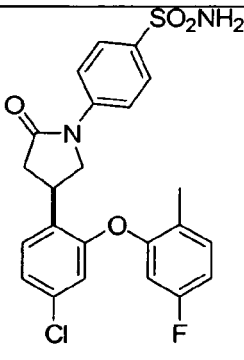 | ¹H NMR 400 MHz (CDCl₃) δ 7.84 (dd, 2H), 7.71 (dd, 2H), 7.20-7.10 (m, 2H), 7.03 (dd, 1H), 6.77 (dd, 1H), 6.63 (d, 1H), 6.50 (dd, 1H), 4.71 (s, 2H), 4.19 (dd, 1H), 3.96-3.88 (m, 2H), 2.96 (dd, 1H), 2.87 (dd, 1H), 2.14 (s, 3H); MS m/z 475.3 (M + 1). |
| 477 | 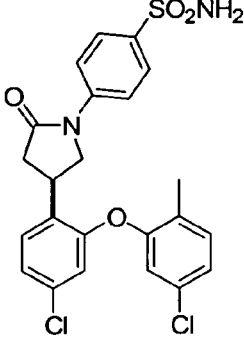 | ¹H NMR 400 MHz (CDCl₃) δ 7.84 (dd, 2H), 7.70 (dd, 2H), 7.20 (dd, 1H), 7.14 (d, 1H), 7.03 (dd, 2H), 6.75 (d, 1H), 6.60 (d, 1H), 4.73 (s, 2H), 4.19 (dd, 1H), 3.95-3.88 (m, 2H), 2.98 (dd, 1H), 2.86 (dd, 1H), 2.12 (s, 3H); MS m/z 491.3 (M + 1). |
| 478 | 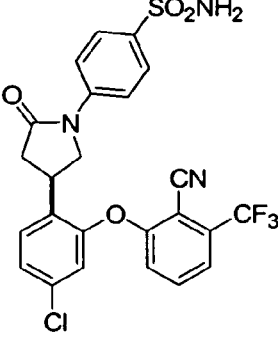 | MS m/z 536.2 (M + 1). |
| 479 | 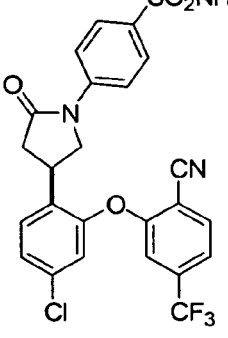 | MS m/z 536.2 (M + 1). |

FIG. 1CW

| Compound Number | Structure | Physical Data<br>¹H NMR 400 MHz and/or MS (m/z) |
|---|---|---|
| 480 | (structure with SO₂NH₂, pyrrolidinone, chlorophenyl-O-phenyl with CN and F₃C substituents) | MS m/z 536.2 (M + 1). |
| 481 | (structure with SO₂NH₂, pyrrolidinone, chlorophenyl-O-phenyl with CN and Cl substituents) | MS m/z 502.2 (M + 1). |
| 482 | (structure with SO₂NH₂, pyrrolidinone, chlorophenyl-O-phenyl with two CH₃ substituents) | MS m/z 471.2 (M + 1). |
| 483 | (structure with SO₂NH₂, pyrrolidinone, chlorophenyl-O-phenyl with OMe and methyl substituents) | ¹H NMR 400 MHz (CDCl₃) δ 7.83 (dd, 2H), 7.73 (dd, 2H), 7.12 (d, 1H), 6.93 (dd, 2H), 6.82 (d, 1H), 6.76 (d, 1H), 6.54 (d, 1H), 4.68 (s, 2H), 4.22 (dd, 1H), 4.05-3.95 (m, 2H), 3.57 (s, 3H), 3.00-2.96 (m, 2H), 2.23 (s, 3H); MS m/z 487.1 (M + 1). |

FIG. 1CX
| Compound Number | Structure | Physical Data<br>¹H NMR 400 MHz and/or MS (m/z) |
|---|---|---|
| 484 | 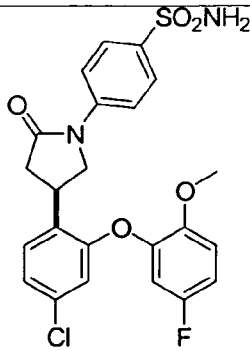 | ¹H NMR 400 MHz (CDCl₃) δ 7.84 (dd, 2H), 7.43 (dd, 2H), 7.15 (d, 1H), 6.99 (dd, 1H), 6.86-6.84 (m, 2H), 6.71 (dd, 1H), 6.60 (d, 1H), 4.68 (s, 2H), 4.21 (dd, 1H), 3.98-3.96 (m, 2H), 3.66 (s, 3H), 2.96-2.94 (m, 2H); MS m/z 491.1 (M + 1). |
| 485 | 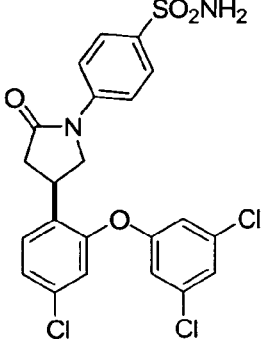 | ¹H NMR 400 MHz (CDCl₃) δ 7.84 (dd, 2H), 7.70 (dd, 2H), 7.24 (d, 1H), 7.15 (dd, 1H), 7.06 (dd, 1H), 6.88 (d, 1H), 6.77 (d, 2H), 4.67 (s, 2H), 4.14 (dd, 1H), 3.85-3.80 (m, 2H), 2.93 (dd, 1H), 2.78 (dd, 1H); MS m/z 511.0 (M + 1). |
| 486 | 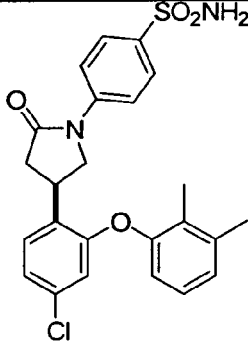 | ¹H NMR 400 MHz (CDCl₃) δ 7.90 (dd, 2H), 7.79 (dd, 2H), 7.25 (dd, 1H), 7.10 (dd, 1H), 7.04-7.01 (m, 2H), 6.72 (d, 1H), 6.60 (d, 1H), 4.75 (s, 2H), 4.29 (dd, 1H), 4.10-4.00 (m, 2H), 3.04 (dd, 1H), 3.00 (dd, 1H), 2.32 (s, 3H), 2.11 (s, 3H); MS m/z 471.0 (M + 1). |
| 487 | 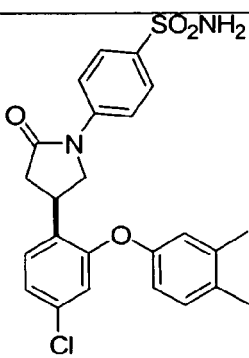 | MS m/z 471.0 (M + 1). |

FIG. 1CY
| Compound Number | Structure | Physical Data<br>¹H NMR 400 MHz and/or MS (m/z) |
|---|---|---|
| 488 | 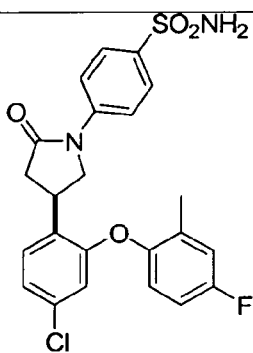 | ¹H NMR 400 MHz (CDCl₃) δ 7.85 (dd, 2H), 7.72 (dd, 2H), 7.18 (dd, 1H), 6.98-6.95 (m, 2H), 6.85 (m, 1H), 6.79 (m, 1H), 6.48 (d, 1H), 4.71 (s, 2H), 4.23 (dd, 1H), 4.05 (m, 1H), 3.92 (dd, 1H), 2.99 (dd, 1H), 2.88 (dd, 1H), 2.11 (s, 3H); MS m/z 475.0 (M + 1). |
| 489 | 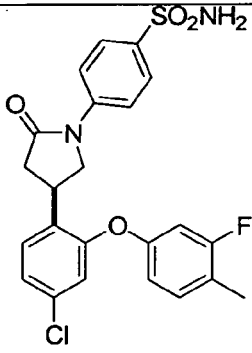 | ¹H NMR 400 MHz (CDCl₃) δ 7.90 (dd, 2H), 7.77 (dd, 2H), 7.26 (d, 1H), 7.15-7.10 (m, 2H), 6.87 (d, 1H), 6.87-6.64 (m, 2H), 4.81 (s, 2h), 4.23 (dd, 1H), 4.01 (m, 1H), 3.91 (dd, 1H), 3.02 (dd, 1H), 2.90 (dd, 1H), 2.24 (s, 3H); MS m/z 475.0 (M + 1). |
| 490 | 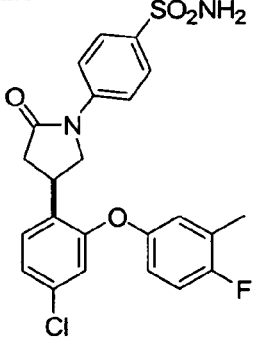 | ¹H NMR 400 MHz (CDCl₃) δ 7.84 (dd, 2H), 7.71 (dd, 2H), 7.18 (d, 1H), 7.01 (dd, 1H), 6.93 (t, 1H), 6.75-6.70 (m, 3H), 4.71 (s, 2H), 4.19 (dd, 1H), 4.01-3.95 (m, 1H), 3.87 (dd, 1H), 2.97 (dd, 1H), 2.86 (dd, 1H), 2.19 (s, 3h); MS m/z 475.0 (M + 1). |
| 491 | 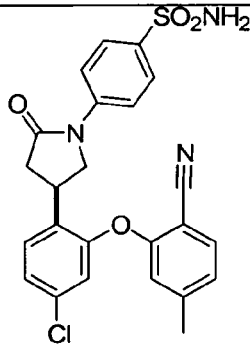 | ¹H NMR 400 MHz (CDCl₃) δ 7.88 (dd, 2H), 7.80 (dd, 2H), 7.49 (d, 1H), 7.40 (dd, 1H), 7.28 (d, 1H), 7.15 (dd, 1H), 6.92 (d, 1H), 6.77 (d, 1H), 4.78 (s, 2H), 4.33 (dd, 1H), 4.00-3.99 (m, 2H), 2.99 (dd, 1H), 2.93 (dd, 1H), 2.38 (s, 3H); MS m/z 482.0 (M + 1). |

FIG. 1CZ
| Compound Number | Structure | Physical Data<br>¹H NMR 400 MHz and/or MS (m/z) |
|---|---|---|
| 492 | 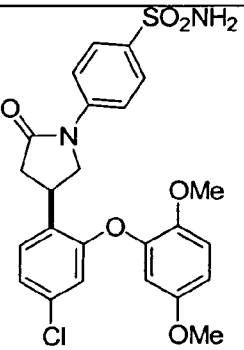 | ¹H NMR 400 MHz (CDCl₃) δ 7.75 (dd, 2H), 7.64 (dd, 2H), 7.02 (d, 1H), 6.85 (dd, 1H) 6.75 (d, 1H), 6.55 (dd, 1H), 6.50 (d, 1H), 6.43 (d, 1H), 4.54 (s, 2H), 4.12 (dd, 1H), 3.93-3.87 (m, 2H), 3.60 (s, 3H), 3.53 (s, 3H), 2.88-2.86 (m, 2H); MS m/z 503.1 (M + 1). |
| 493 | 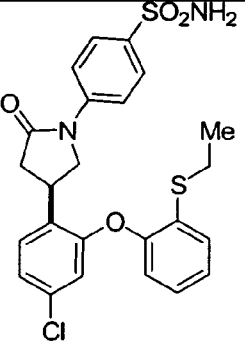 | ¹H NMR 400 MHz (CDCl₃) δ 8.06 (dd, 2H), 7.99 (dd, 2H), 7.60 (dd, 1H), 7.42-7.15 (m, 3H), 7.20 (dd, 1H), 7.15 (d, 1H), 6.82 (d, 1H), 4.87 (s, 2H), 4.50 (dd, 1H), 4.26-4.21 (m, 2H), 3.20 (m, 2H), 3.05 (q, 2H), 1.43 (t, 3H); MS m/z 503.1 (M + 1). |
| 494 | 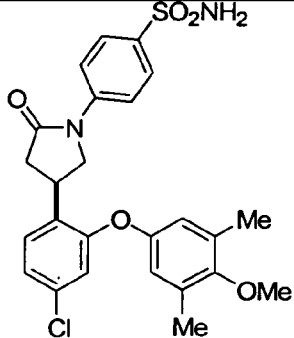 | ¹H NMR 400 MHz (CDCl₃) δ 7.81 (dd, 2H), 7.68 (dd, 2H), 7.15 (d, 1H), 6.99 (dd, 1H), 6.74 (d, 1H), 6.53 (d, 2h), 4.85 (s, 2H), 4.17 (dd, 1h), 3.91-3.83 (m, 2H), 3.63 (s, 3H), 2.95 (dd, 1H), 2.91 (dd, 1H), 2.18 (s, 6H); MS m/z 501.1 (M + 1). |
| 495 | 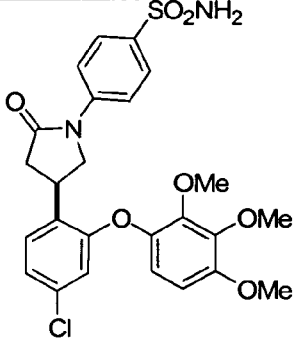 | MS m/z 533.1 (M + 1). |

FIG. 1DA
| Compound Number | Structure | Physical Data<br>¹H NMR 400 MHz and/or MS (m/z) |
|---|---|---|
| 496 | 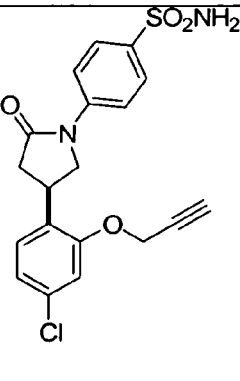 | ¹H NMR 400 MHz (CDCl₃) δ 7.87 (dd, 2H), 7.77 (dd, 2H), 7.10 (d, 1H), 6.97-6.94 (m, 2H), 4.70-4.69 (m, 4H), 4.18 (dd, 1H), 3.89-3.79 (m, 2H), 2.94 (dd, 1H), 2.84 (dd, 1H), 2.49 (t, 1H); MS m/z 405.0 (M + 1). |
| 497 | 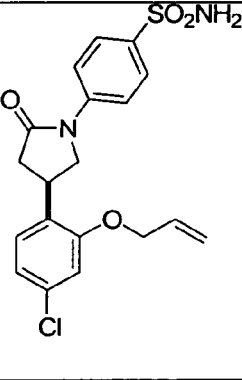 | ¹H NMR 400 MHz (CDCl₃) δ 7.84 (dd, 2H), 7.54 (dd, 2h), 7.05 (d, 1H), 6.87 (dd, 1H), 6.82 (d, 1H), 5.99-5.87 (m, 1H), 5.31-5.19 (m, 2H), 4.67 (s, 2H), 4.49-4.47 (m, 2H), 4.14 (dd, 1H), 3.87-3.81 (m, 2H), 2.89 (dd, 1H), 2.84 (dd, 1H); MS m/z 407.0 (M + 1). |
| 498 | 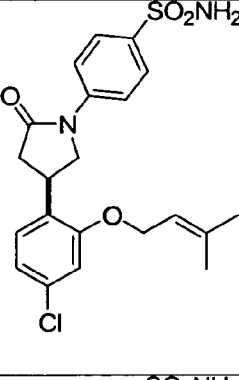 | ¹H NMR 400 MHz (CDCl₃) δ 7.83 (dd, 2H), 7.72 (dd, 2H), 7.04 (d, 1H), 6.86-6.82 (m, 2H), 5.30 (m, 1H), 4.94 (s, 2H), 4.45-4.42 (m, 2H), 4.13 (dd, 1H), 3.82-3.78 (m, 2H), 2.89-2.80 (m, 2H), 1.65 (s, 3H), 1.62 (s, 3H); MS m/z 435.1 (M + 1). |
| 499 | 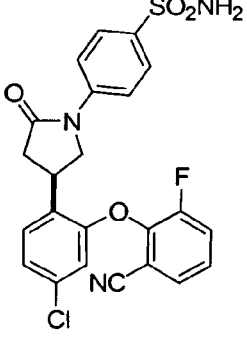 | ¹H NMR 400 MHz (CDCl₃) δ 8.07 (dd, 2H), 8.00 (dd, 2H), 7.70-7.60 (m, 2H), 7.55 (m, 1H), 7.42 (m, 1H), 7.29 (dd, 1H), 6.66 (d, 1H), 4.87 (s, 2H), 4.53 (dd, 1H), 4.33 (m, 1H), 4.24 (dd, 1H), 3.30-3.20 (m, 2H); MS m/z 486.0 (M + 1). |

FIG. 1DB
| Compound Number | Structure | Physical Data $^1$H NMR 400 MHz and/or MS (m/z) |
|---|---|---|
| 500 | 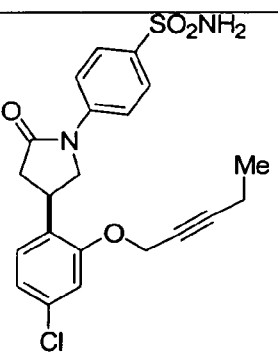 | $^1$H NMR 400 MHz (CDCl$_3$) δ 7.83 (dd, 2H), 7.43 (dd, 2H), 7.06 (d, 1H), 6.96 (d, 1H), 6.90 (dd, 1H), 4.83 (s, 2H), 4.63 (t, 2H), 4.16 (dd, 1H), 3.88-3.78 (m, 2H), 2.90-2.84 (m, 2H), 2.16-2.10 (m, 2H), 1.04 (t, 3H); MS m/z 433.0 (M + 1). |
| 501 | 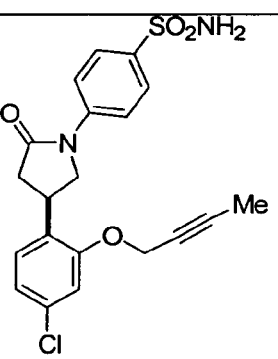 | $^1$H NMR 400 MHz (CDCl$_3$) δ 7.85 (dd, 2H), 7.75 (dd, 2H), 7.06 (d, 1H), 6.94 (d, 1H), 6.90 (dd, 1H), 4.78 (s, 2H), 4.62-4.61 (m, 2H), 4.16 (dd, 1H), 3.86-3.77 (m, 2H), 2.88 (dd, 1H), 2.83 (dd, 1H), 1.76 (t, 3H); MS m/z 419.0 (M + 1). |
| 502 | 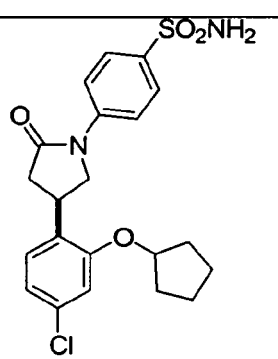 | $^1$H NMR 400 MHz (CDCl$_3$) δ 7.79 (dd, 2H), 7.70 (dd, 2H), 6.96 (d, 1H), 6.77-6.75 (m, 2H), 4.70-4.64 (m, 3H), 4.04 (dd, 1H), 3.77 (dd, 1H), 3.70 (m, 1H), 2.81 (dd, 1H), 2.79 (dd, 1H), 1.85-1.45 (m, 8H); MS m/z 435.0 (M + 1). |
| 503 | 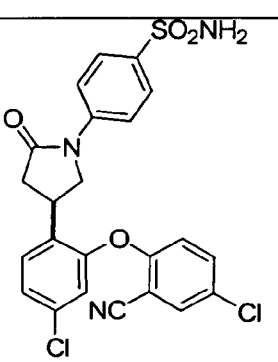 | $^1$H NMR 400 MHz (CDCl$_3$) δ 7.88 (dd, 2H), 7.77 (dd, 2H), 7.48 (t, 1H), 7.33-7.28 (m, 2H), 7.23 (d, 1H), 6.90 (d, 1H), 6.85 (dd, 1H), 4.79 (s, 2H), 4.31 (m, 1H), 3.96-3.92 (m, 2H), 2.99 (dd, 1H), 2.87 (dd, 1H); MS m/z 502.0 (M + 1). |

FIG. 1DC
| Compound Number | Structure | Physical Data<br>¹H NMR 400 MHz and/or MS (m/z) |
|---|---|---|
| 504 | 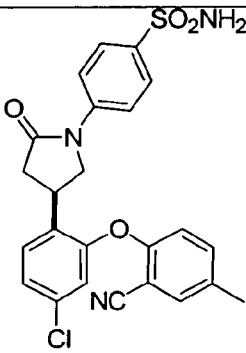 | ¹H NMR 400 MHz (CDCl₃) δ 7.88 (dd, 2H), 7.77 (dd, 2H), 7.66 (d, 1H), 7.54 (dd, 1H), 7.31 (d, 1H), 7.21 (dd, 1H), 6.92 (d, 1H), 6.83 (d, 1H), 4.82 (s, 2H), 4.30 (m, 1H), 4.00-3.92 (m, 2H), 3.00 (dd, 1H), 2.86 (dd, 1H); MS m/z 502.0 (M + 1). |
| 505 | 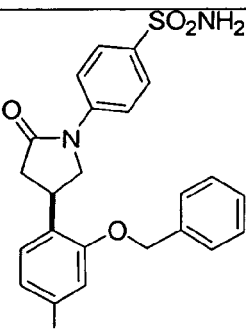 | ¹H NMR 400 MHz (CDCl₃) δ 7.91 (dd, 2H), 7.82 (dd, 2H), 7.51 (d, 1H), 7.40 (dd, 1H), 7.30 (d, 1H), 7.17 (dd, 1H), 6.93 (d, 1H), 6.78 (d, 1H), 4.79 (s, 2H), 4.34 (m, 1H), 4.04-3.98 (m, 2H), 3.03 (dd, 1H), 2.93 (dd, 1H); MS m/z 482.1 (M + 1). |
| 506 | 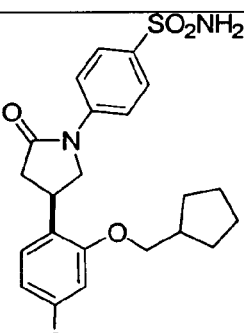 | ¹H NMR 400 MHz (CDCl₃) δ 7.88 (dd, 2H), 7.71 (dd, 2H), 7.35-7.33 (m, 5H), 7.14 (d, 1H), 7.01-6.98 (m, 2H), 5.08-5.05 (m, 2H), 4.74 (s, 2H), 4.17 (dd, 1H), 3.91 (m, 1H), 3.87 (dd, 1H), 2.95 (dd, 1H), 2.90 (dd, 1H); MS m/z 457.0 (M + 1). |
| 507 | 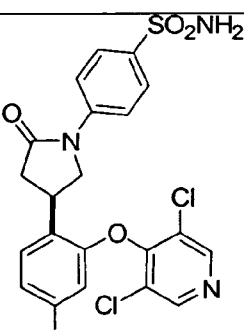 | ¹H NMR 400 MHz (CDCl₃) δ 7.93 (dd, 2H), 7.83 (dd, 2H), 7.10 (d, 1H), 6.93-6.89 (m, 2H), 4.77 (s, 2H), 4.19 (dd, 1H), 3.96-3.84 (m, 4H), 2.98-2.94 (m, 2H), 2.32 (m, 1H), 1.80 (m, 2H), 1.56 (m, 4H), 1.31 (m, 2H); MS m/z 449.1 (M + 1). |

FIG. 1DD
| Compound Number | Structure | Physical Data<br>¹H NMR 400 MHz and/or MS (m/z) |
|---|---|---|
| 508 | 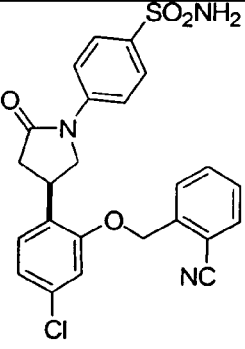 | MS m/z 512.0 (M + 1). |
| 509 | 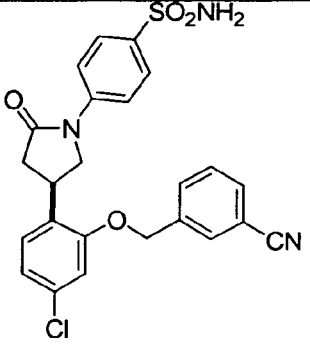 | MS m/z 482.0 (M + 1). |
| 510 | 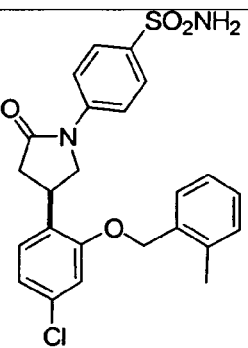 | ¹H NMR 400 MHz (CDCl₃) δ 7.90 (dd, 2H), 7.69 (dd, 2H), 7.59-7.57 (m, 2H), 7.50-7.47 (m, 2H), 7.16 (d, 1H), 7.01-6.97 (m, 2H), 5.08-5.01 (m, 2H), 4.88 (s, 2H), 4.17 (dd, 1H), 3.90-3.84 (m, 2H), 3.01 (dd, 1H), 2.81 (dd, 1H); MS m/z 482.1 (M + 1). |
| 511 | 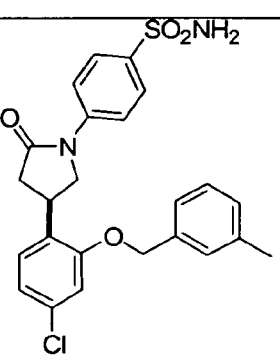 | MS m/z 470.1 (M + 1). |

FIG. 1DE
| Compound Number | Structure | Physical Data<br>$^1$H NMR 400 MHz and/or MS (m/z) |
|---|---|---|
| 512 | 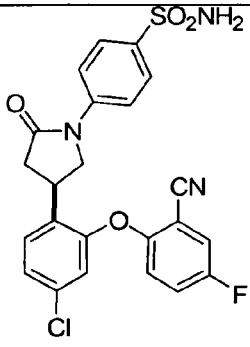 | MS m/z 470.1 (M + 1). |
| 513 | 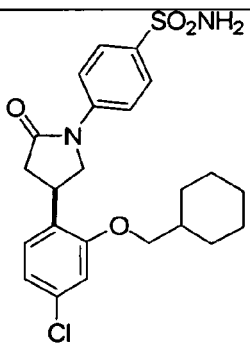 | MS m/z 486.0 (M + 1). |
| 514 | 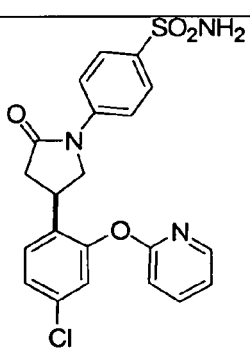 | MS m/z 463.1 (M + 1). |
| 515 | 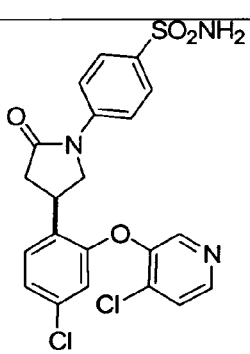 | MS m/z 443.0 (M + 1). |

FIG. 1DF
| Compound Number | Structure | Physical Data<br>$^1$H NMR 400 MHz and/or MS (m/z) |
|---|---|---|
| 516 | 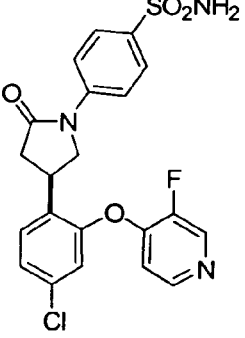 | MS m/z 478.0 (M + 1). |
| 517 | 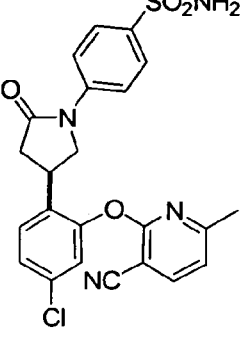 | $^1$H NMR 400 MHz (Acetone-d$_6$) δ 8.45 (d, 1H), 8.24 (d, 1H), 7.77-7.74 (m, 4H), 7.61 (d, 1H), 7.30 (dd, 1H), 7.18 (d, 1H), 6.94 (dd, 1H), 6.42 (s, 2H), 4.23 (m, 1H), 4.00-3.96 (m, 2H), 2.87 (dd, 1H), 2.75 (dd, 1H); MS m/z 462.0 (M + 1). |
| 518 | 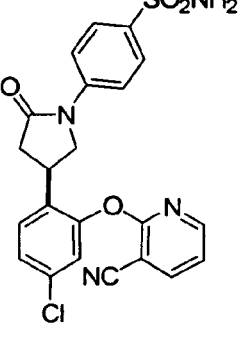 | MS m/z 483.0 (M + 1). |
| 519 | 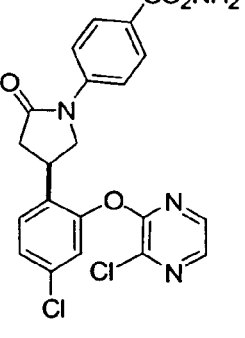 | $^1$H NMR 400 MHz (CDCl$_3$) δ 8.27 (dd, 1H), 7.98 (dd, 1H), 7.84 (dd, 2H), 7.71 (dd, 2H), 7.28-7.24 (m, 2H), 7.16 (d, 1H), 7.13 (dd, 1H), 4.69 (s, 2H), 4.18 (dd, 1H), 3.88 (dd, 1H), 3.81 (m, 1H), 2.90 (dd, 1H), 2.78 (dd, 1H); MS m/z 469.0 (M + 1). |

FIG. 1DG
| Compound Number | Structure | Physical Data $^1$H NMR 400 MHz and/or MS (m/z) |
|---|---|---|
| 520 | 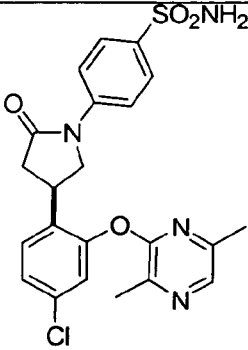 | MS m/z 479.0 (M + 1). |
| 521 | 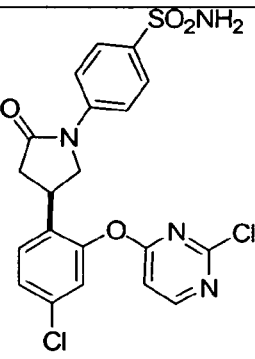 | MS m/z 473.1 (M + 1). |
| 522 | 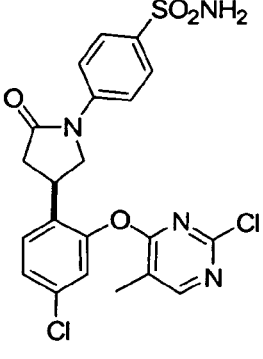 | $^1$H NMR 400 MHz (Acetone-d$_6$) δ 8.63 (d, 1H), 7.91-7.87 (m, 4H), 7.76 (d, 1H), 7.48 (m, 2H), 7.25 (d, 1H), 6.57 (s, 2H), 4.31 (dd, 1H), 4.07 (dd, 1H), 4.02 (m, 1H), 2.99 (dd, 1H), 2.83 (dd, 1H); MS m/z 479.0 (M + 1). |
| 523 | 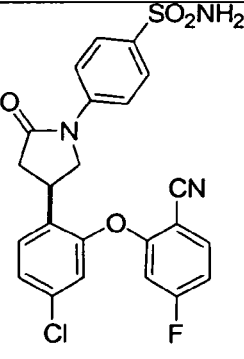 | $^1$H NMR 400 MHz (Acetone-d$_6$) δ 8.35 (s, 1H), 7.79 (m, 4H), 7.64 (d, 1H), 7.38-7.35 (m, 2H), 6.47 (s, 2H), 4.20 (dd, 1H), 3.99 (dd, 1H), 3.92 (m, 1H), 2.89 (dd, 1H), 2.76 (dd, 1H), 2.29 (s, 3H); MS m/z 493.0 (M + 1). |

FIG. 1DH
| Compound Number | Structure | Physical Data $^1$H NMR 400 MHz and/or MS (m/z) |
|---|---|---|
| 524 | 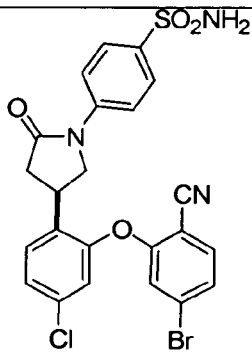 | MS m/z 486.0 (M + 1). |
| 525 | 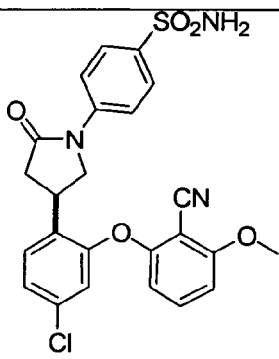 | MS m/z 546.0 (M + 1). |
| 526 | 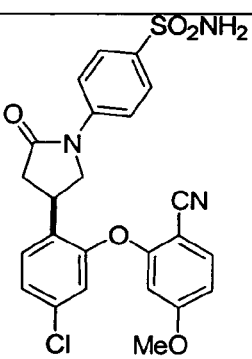 | MS m/z 498.0 (M + 1). |
| 527 | 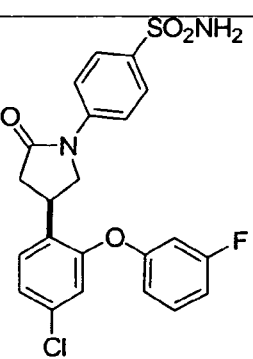 | MS m/z 498.0 (M + 1). |

FIG. 1DI
| Compound Number | Structure | Physical Data<br>¹H NMR 400 MHz and/or MS (m/z) |
|---|---|---|
| 528 | 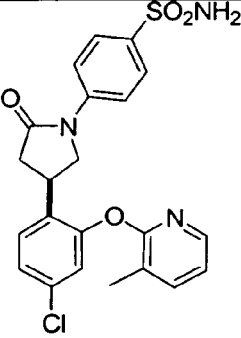 | MS m/z 461.0 (M + 1). |
| 529 | 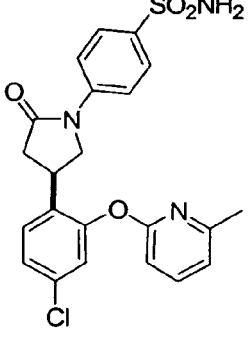 | MS m/z 458.0 (M + 1). |
| 530 | 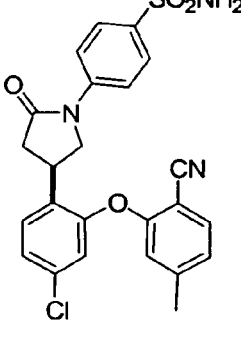 | ¹H NMR 400 MHz (Acetone-d₆) δ 7.98 (dd, 1H), 7.90 (m, 4H), 7.72 (dd, 1H), 7.66 (d, 1H), 7.37 (dd, 1H), 7.25 (d, 1H), 7.09 (dd, 1H), 6.60 (s, 2H), 4.29 (dd, 1H), 4.12 (dd, 1H), 4.09 (m, 1H), 3.00 (dd, 1H), 2.90 (dd, 1H), 2.42 (s, 3H); MS m/z 458.0 (M + 1). |
| 531 | 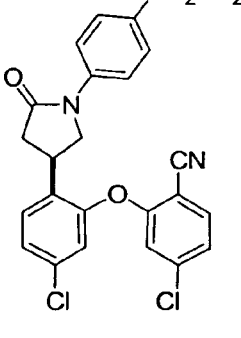 | MS m/z 482.0 (M + 1). |

FIG. 1DJ

| Compound Number | Structure | Physical Data $^1$H NMR 400 MHz and/or MS (m/z) |
|---|---|---|
| 532 | (structure) | MS m/z 501.9 (M + 1). |
| 533 | (structure) | MS m/z 507.0 (M + 1). |
| 534 | (structure) | $^1$H NMR 400 MHz (CDCl$_3$) δ 7.83 (dd, 2H), 7.63 (dd, 2H), 7.49 (d, 1H), 7.43-7.40 (m, 2H), 7.10 (d, 1H), 6.94-6.91 (m, 2H), 5.13-5.06 (m, 2H), 4.80 (s, 2H), 4.06 (dd, 1H), 3.85-3.80 (m, 2H), 2.95 (dd, 1H), 2.75 (dd, 1H); MS m/z 516.0 (M + 1). |
| 535 | (structure) | MS m/z 471.0 (M + 1). |

FIG. 1DK
| Compound Number | Structure | Physical Data<br>¹H NMR 400 MHz and/or MS (m/z) |
|---|---|---|
| 536 | 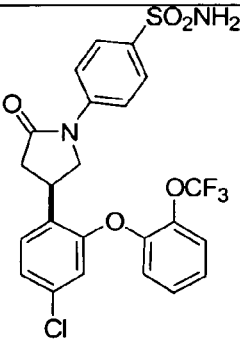 | MS m/z 526.9 (M + 1). |
| 537 | 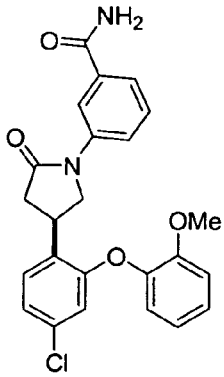 | MS m/z 527.0 (M + 1). |
| 538 | 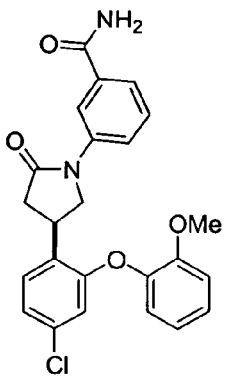 | ¹H NMR 400 MHz (CDCl₃) δ (8.02 (t, 1H), 7.81 (dd, 1H), 7.51 (d, 1H), 7.39 (t, 1H), 7.19-7.11 (m, 2H), 6.99-6.87 (m, 4H), 6.55 (d, 1H), 6.16 (bs, 1H), 5.79 (bs, 1H), 4.25 (dd, 1H), 4.09-3.55 (m, 2H), 3.69 (s, 3H), 2.97 (d, 2H); MS m/z 437.1 (M + 1). |

FIG. 1DL
| Compound Number | Structure | Physical Data<br>¹H NMR 400 MHz and/or MS (m/z) |
|---|---|---|
| 539 | 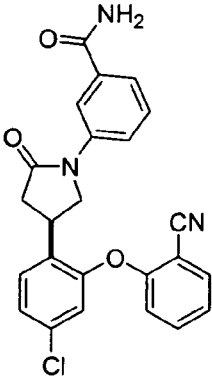 | MS m/z 432.0 (M + 1). |
| 540 | 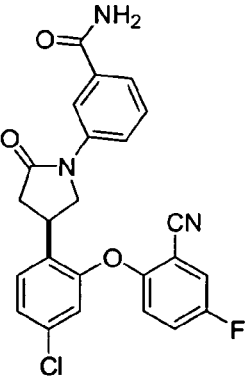 | MS m/z 450.0 (M + 1). |
| 541 | 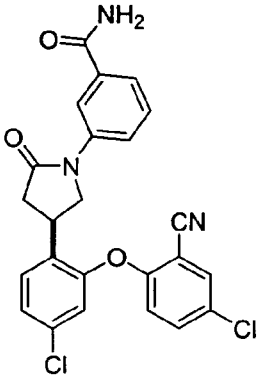 | ¹H NMR 400 MHz (CDCl₃) δ 8.01 (dd, 1H), 7.87 (s, 1H), 7.69 (s, 1H), 7.65 (d, 1H), 7.57 (dd, 1H), 7.47 (t, 1H), 7.35 (d, 1H), 7.23 (dd, 1H), 7.01 (d, 1H), 6.87 (d, 1H), 6.55 (brs, 1H), 5.70 (brs, 1H), 4.39 (dd, 1H), 4.05 (dd, 1H), 3.95 (m, 1H), 3.05 (dd, 1H), 2.89 (dd, 1H); MS m/z 466.0 (M + 1). |

FIG. 1DM
| Compound Number | Structure | Physical Data $^1$H NMR 400 MHz and/or MS (m/z) |
|---|---|---|
| 542 | 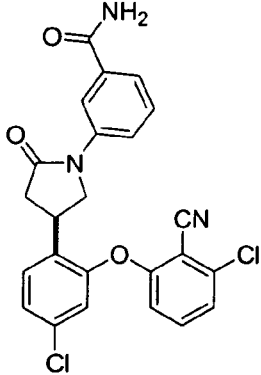 | MS m/z 466.0 (M + 1). |
| 543 | 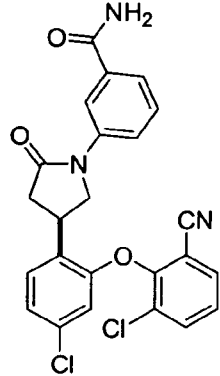 | $^1$H NMR 400 MHz (CDCl$_3$) δ 7.98 (brs, 1H), 7.81 (brs, 1H), 7.71 (d, 1H), 7.61 (d, 2H), 7.39 (t, 1H), 7.29 (t, 1H), 7.21 (d, 1H), 7.03 (dd, 1H), 6.52 (brs, 1H), 6.25 (dd, 1H), 5.95 (brs, 1H), 4.45-3.39 (m, 3H), 3.05 (d, 2H); MS m/z 466.0 (M + 1). |
| 544 | 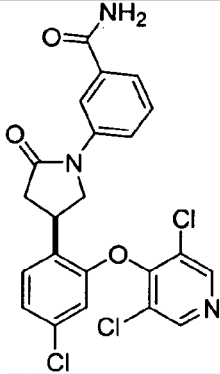 | $^1$H NMR 400 MHz (CDCl$_3$) δ 8.39 (s, 2H), 7.87 (t, 1H), 7.62 (dd, 1H), 7.35 (dd, 1H), 7.25 (t, 1H), 7.08 (d, 1H), 6.87 (dd, 1H), 6.11 (d, 1H), 6.01 (brs, 1H), 5.45 (brs, 1H), 4.15 (dd, 1H), 3.99-3.85 (m, 2H), 2.89 (dd, 1H), 2.78 (dd, 1H); MS m/z 466.0 (M + 1). |
| 545 | 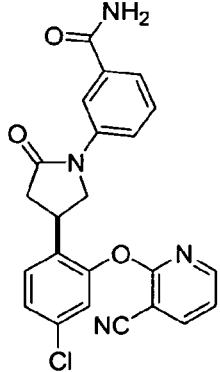 | $^1$H NMR 400 MHz (DMSO-$d_6$) δ 8.43-8.39 (m, 2H), 7.98-7.94 (m, 2H), 7.86 (dd, 1H), 7.65-7.62 (m, 2H), 7.49 (d, 1H), 7.44-7.39 (m, 3H), 7.33 (dd, 1H), 4.08 (dd, 1H), 3.95 (dd, 1H), 3.80 (m, 1H), 2.81 (dd, 1H), 2.69 (dd, 1H); MS m/z 433.1 (M + 1). |

FIG. 1DN
| Compound Number | Structure | Physical Data $^1$H NMR 400 MHz and/or MS (m/z) |
|---|---|---|
| 546 | 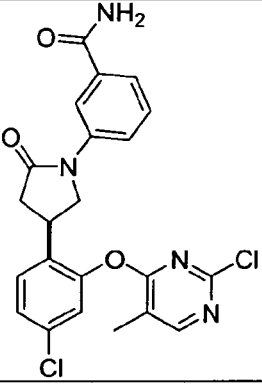 | MS m/z 457.0 (M + 1). |
| 547 | 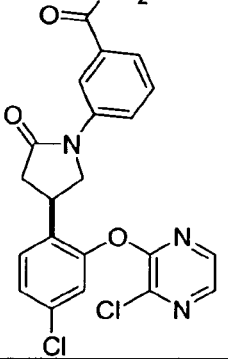 | MS m/z 443.0 (M + 1). |
| 548 | 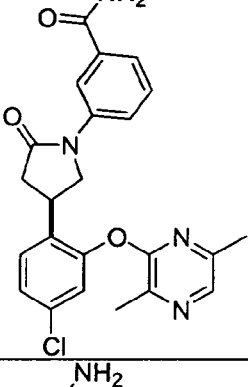 | MS m/z 437.1 (M + 1). |
| 549 | 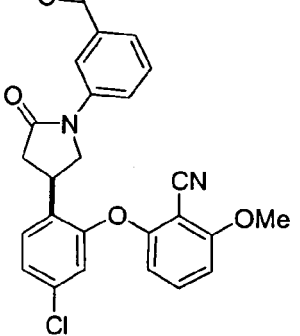 | $^1$H NMR 400 MHz (CDCl$_3$) δ 8.15 (dd, 1H), 7.79 (t, 1H), 7.72 (d, 1H), 7.53 (t, 1H), 7.45 (t, 1H), 7.33 (d, 1H), 7.21 (dd, 1H), 6.95 (d, 1H), 6.82 (brs, 1H), 6.76 (d, 1H), 6.58 (d, 1H), 5.75 (brs, 1H), 4.45 (dd, 1H), 4.09 (dd, 1H), 3.97 (s, 3H), 3.91 (m, 1H), 3.03-2.87 (m, 2H); MS m/z 462.1 (M + 1). |

FIG. 1DO
| Compound Number | Structure | Physical Data<br>¹H NMR 400 MHz and/or MS (m/z) |
|---|---|---|
| 550 | 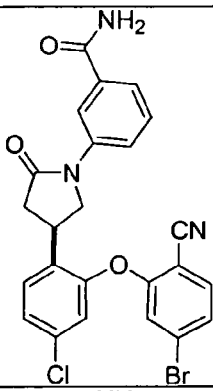 | ¹H NMR 400 MHz (CDCl₃) δ 8.11 (dd, 1H), 7.96 (t, 1H), 7.75 (dd, 1H), 7.65 (d, 1H), 7.59-7.47 (m, 2H), 7.43 (d, 1H), 7.34 (dd, 1H), 7.21 (d, 1H), 7.05 (d, 1H), 6.67 (brs, 1H), 5.85 (brs, 1H), 4.47 (dd, 1H), 4.11 (dd, 1H), 3.99 (m, 1H), 3.07 (dd, 1H), 2.99 (dd, 1H); MS *m/z* 510.0 (M + 1). |
| 551 | 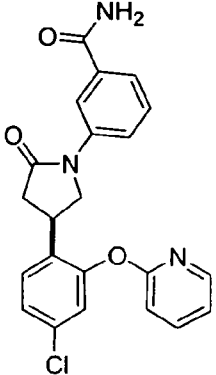 | MS *m/z* 408.05 (M + 1). |
| 552 | 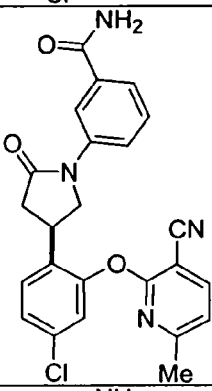 | ¹H NMR 400 MHz (CDCl₃) δ 8.01 (d, 1H), 7.91-7.86 (m, 2H), 7.65 (d, 1H), 7.46 (t, 1H), 7.31 (d, 1H), 7.27 (dd, 1H), 7.19 (d, 1H), 7.01 (d, 1H), 6.75 (brs, 1H), 6.93 (brs, 1H), 4.36 (dd, 1H), 4.01 (dd, 1H), 3.85 (m, 1H), 3.02-2.82 (m, 2H), 2.45 (s, 3H); MS *m/z* 447.1 (M + 1). |
| 553 | 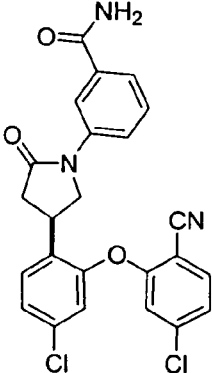 | MS *m/z* 446.0 (M + 1). |

FIG. 1DP

| Compound Number | Structure | Physical Data $^1$H NMR 400 MHz and/or MS (m/z) |
|---|---|---|
| 554 | 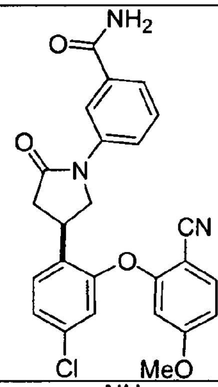 | MS m/z 462.1 (M + 1). |
| 555 | 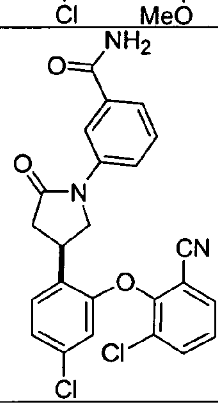 | MS m/z 466.0 (M + 1). |
| 556 | 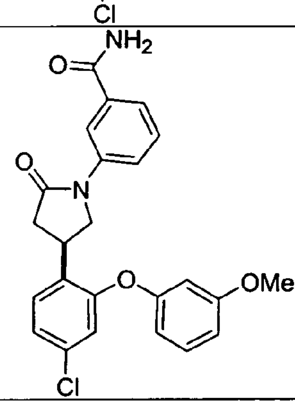 | MS m/z 437.0 (M + 1). |
| 557 | 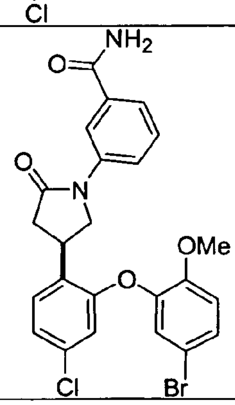 | MS m/z 514.9 (M + 1). |

FIG. 1DQ
| Compound Number | Structure | Physical Data<br>¹H NMR 400 MHz and/or MS (m/z) |
|---|---|---|
| 558 | 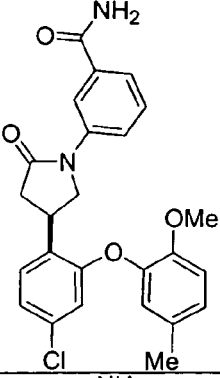 | MS m/z 451.0 (M + 1). |
| 559 | 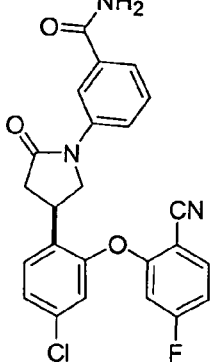 | ¹H NMR 400 MHz (CDCl₃) δ 8.07 (d, 1H), 7.84 (s, 1H), 7.75-7.65 (m, 2H), 7.45 (t, 1H), 7.35 (d, 1H), 7.28 (dd, 1H), 7.03-6.93 (m, 2H), 6.75 (brs, 1H), 6.69 (dd, 1H), 6.26 (brs, 1H), 4.43 (dd, 1H), 4.02 (dd, 1H), 3.89 (m, 1H), 2.97 (dd, 1H), 2.89 (dd, 1H); MS m/z 450.0 (M + 1). |
| 560 | 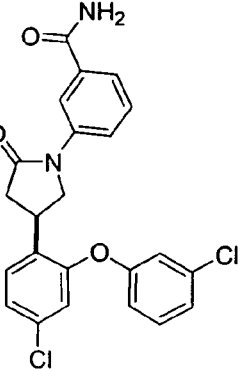 | MS m/z 441.0 (M + 1). |
| 561 | 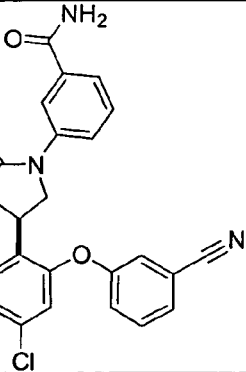 | MS m/z 432.0 (M + 1). |

FIG. 1DR
| Compound Number | Structure | Physical Data $^1$H NMR 400 MHz and/or MS (m/z) |
|---|---|---|
| 562 | 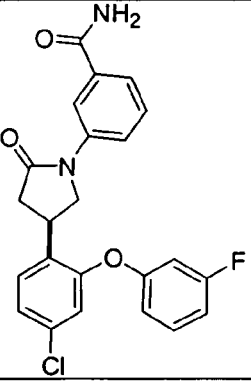 | MS m/z 425.0 (M + 1). |
| 563 | 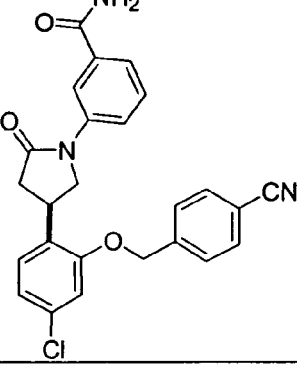 | MS m/z 446.0 (M + 1). |
| 564 | 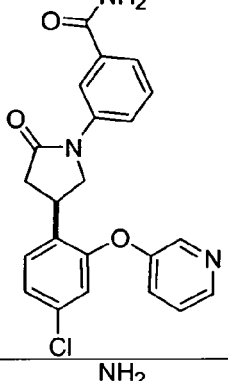 | MS m/z 408.0 (M + 1). |
| 565 | 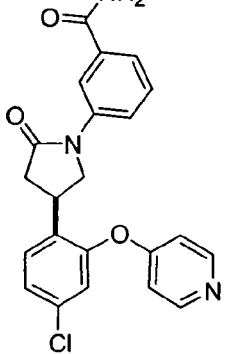 | MS m/z 408.0 (M + 1). |

FIG. 1DS
| Compound Number | Structure | Physical Data $^1$H NMR 400 MHz and/or MS (m/z) |
|---|---|---|
| 566 | 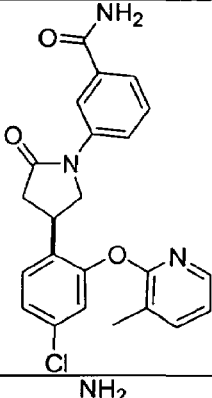 | MS m/z 422.0 (M + 1). |
| 567 | 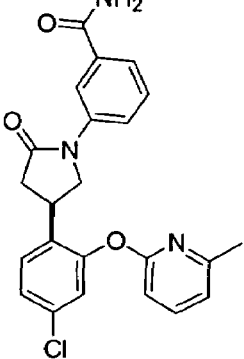 | MS m/z 422.0 (M + 1). |
| 568 | 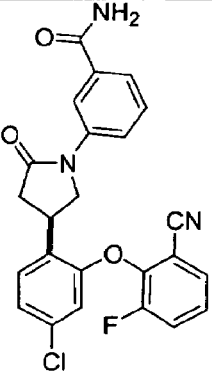 | MS m/z 450.0 (M + 1). |
| 569 | 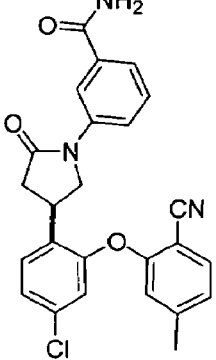 | MS m/z 446.0 (M + 1). |

FIG. 1DT
| Compound Number | Structure | Physical Data<br>¹H NMR 400 MHz and/or MS (m/z) |
|---|---|---|
| 570 | 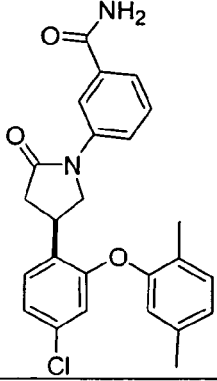 | MS m/z 435.0 (M + 1). |
| 571 | 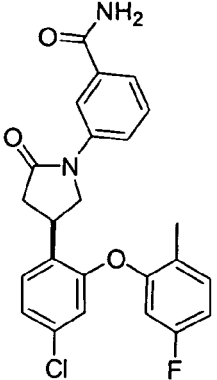 | MS m/z 439.0 (M + 1). |
| 572 | 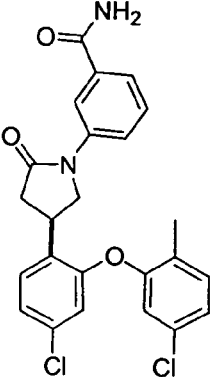 | MS m/z 455.0 (M + 1). |
| 573 | 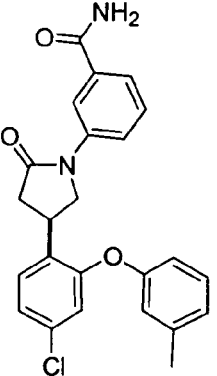 | MS m/z 421.0 (M + 1). |

FIG. 1DU
| Compound Number | Structure | Physical Data<br>¹H NMR 400 MHz and/or MS (m/z) |
|---|---|---|
| 574 | 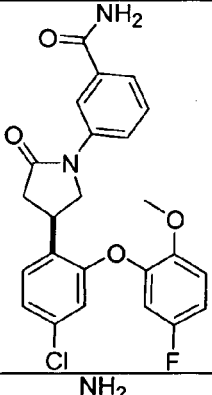 | ¹H NMR 400 MHz (Acetone-$d_6$) δ 8.12 (t, 1H), 8.07 (dd, 1H), 7.69 (dd, 1H), 7.49 (m, 2H), 7.21 (dd, 1H), 7.15 (dd, 1H), 7.08-7.05 (m, 2H), 6.68 (d, 1H), 4.39 (dd, 1H), 4.20-4.16 (m, 2H), 3.80 (s, 3H), 3.00-2.84 (m, 2H); MS m/z 455.0 (M + 1). |
| 575 | 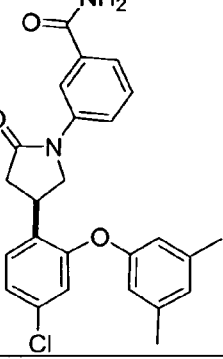 | MS m/z 435.0 (M + 1). |
| 576 | 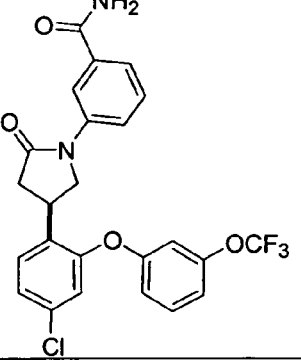 | MS m/z 491.0 (M + 1). |
| 577 | 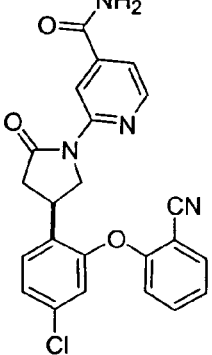 | ¹H NMR 400 MHz (CDCl₃) δ 8.62 (d, 1H), 8.39 (dd, 1H), 7.62 (dd, 1H), 7.46 (m, 1H), 7.42 (dd, 1H), 7.27 (d, 1H), 7.17 (dd, 1H), 7.14 (dd, 1H), 6.86 (d, 1H), 6.82 (d, 1H), 6.58 (bs, 1H), 6.05 (bs, 1H), 4.45 (dd, 1H), 4.12 (dd, 1H), 3.92 (m, 1H), 3.03 (dd, 1H), 2.79 (dd, 1H); MS m/z 433.1 (M + 1). |

FIG. 1DV
| Compound Number | Structure | Physical Data<br>¹H NMR 400 MHz and/or MS (m/z) |
|---|---|---|
| 578 | 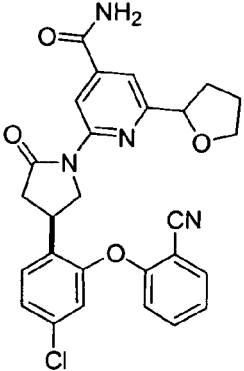 | MS m/z 503.1 (M + 1). |
| 579 | 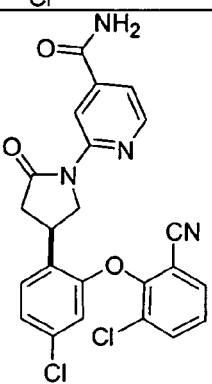 | MS m/z 467.0 (M + 1). |
| 580 | 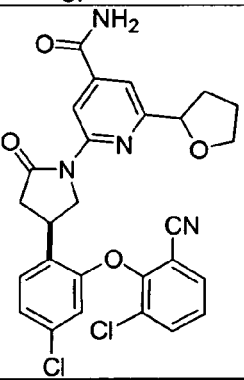 | MS m/z 537.1 (M + 1). |
| 581 | 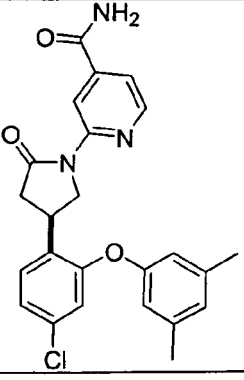 | MS m/z 436.1 (M + 1). |

FIG. 1DW

| Compound Number | Structure | Physical Data<br>¹H NMR 400 MHz and/or MS (m/z) |
|---|---|---|
| 582 | 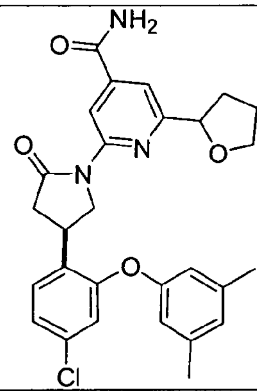 | MS m/z 506.1 (M + 1). |
| 583 | 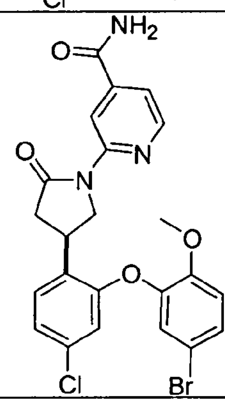 | MS m/z 516.0 (M + 1). |
| 584 | 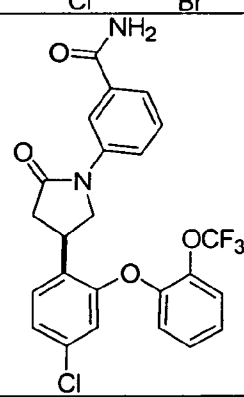 | MS m/z 491.1 (M + 1). |

PYRROLIDONES WITH ANTI-HIV ACTIVITY

CROSS-REFERENCE TO RELATED APPLICATIONS

This is a non-provisional filing of U.S. Provisional Patent Application No. 60/420,480 filed on Oct. 21, 2002 and U.S. Provisional Patent Application No. 60/422,619 filed on Oct. 30, 2002, the disclosure of each of which is incorporated herein by reference in its entirety for all purposes.

FIELD OF THE INVENTION

The present invention relates to inhibition of a virus, e.g., HIV, using pyrrolidone-based compounds. The compounds of the invention are of use to combat infection by mutant, drug-sensitive, drug-resistant, and multi-drug resistant strains of HIV. The invention further relates to methods for using pyrrolidones of the invention to inhibit HIV and to treat HIV-related diseases.

BACKGROUND OF THE INVENTION

The Human Immunodeficiency Virus (HIV) infects millions of people globally. Cases are reported from nearly every country amounting to 40 million adults and children living with HIV/AIDS worldwide. In 2001, 5 million people were newly infected with HIV, and there were 3 million adult and child deaths due to HIV/AIDS. A full third of those people living with AIDS are aged 15-24. (World Health Organization, 2001).

HIV/AIDS treatments exist, however, the drugs currently used in treatment modalities exhibit numerous side effects, require prolonged treatment that often induces drug resistance, and do not result in complete eradication of the virus from the body.

The disease AIDS is the end result of an HIV-1 or HIV-2 virus following its own complex life cycle. The virion life cycle begins with the virion attaching itself to the host human T-4 lymphocyte immune cell through the bonding of a glycoprotein on the surface of the virion's protective coat with the CD4 glycoprotein on the lymphocyte cell.

Once attached, the virion sheds its glycoprotein coat, penetrates into the membrane of the host cell, and uncoats its RNA. The virion enzyme, reverse transcriptase, directs the process of transcribing the RNA into single-stranded DNA. The viral RNA is degraded and a second DNA strand is created. The now double-stranded DNA is integrated into the human cell's genes and those genes are used for virus reproduction.

At this point, RNA polymerase transcribes the integrated DNA into viral RNA. The viral RNA is translated into the precursor gag-pol fusion polyprotein. The polyprotein is then cleaved by the HIV protease to yield the mature viral proteins. Thus, HIV protease is responsible for regulating a cascade of cleavage events that lead to the virus particle's maturing into a virus that is capable of full infectivity.

The typical human immune system response, killing the invading virion, is taxed because the virus infects and kills the immune system's T cells. In addition, viral reverse transcriptase, the enzyme used in making a new virion particle, is not very specific, and causes transcription mistakes that result in continually changed glycoproteins on the surface of the viral protective coat. This lack of specificity decreases the immune system's effectiveness because antibodies specifically produced against one glycoprotein may be useless against another, hence reducing the number of antibodies available to fight the virus. The virus continues to reproduce while the immune response system continues to weaken. Eventually, the HIV largely holds free reign over the body's immune system, allowing opportunistic infections to set in and, without the administration of antiviral agents, immunomodulators, or both, death may result.

There are at least three critical points in the virus's life cycle which have been identified as possible targets for antiviral drugs: (1) the initial attachment of the virion to the T-4 lymphocyte or macrophage site; (2) the transcription of viral RNA to viral DNA (reverse transcriptase, RT); and (3) the processing of gag-pol protein by HIV protease.

Inhibition of the virus at the second critical point, the viral RNA to viral DNA transcription process, has provided a number of the current therapies used in treading AIDS. This transcription must occur for the virion to reproduce because the virion's genes are encoded in RNA and the host cell reads only DNA. By introducing drugs that block the reverse transcriptase from completing the formation of viral DNA, HIV-1, replication can be stopped.

A number of compounds that interfere with viral replication have been developed to treat AIDS. For example, nucleoside analogs, such as 3'-azido-3'-deoxythymidine (AZT), 2',3'-dideoxycytidine (ddC), 2',3'-dideoxythymidinene (d4T), 2',3'-dideoxyinosine (ddI), and 2',3'-dideoxy-3'-thiacytidine (3TC) have been shown to be relatively effective in halting HIV replication at the reverse transcriptase (RT) stage.

Even with the current success of reverse transcriptase inhibitors, it has been found that HIV patients can become resistant to a single inhibitor. Thus, it is desirable to develop additional inhibitors to further combat HIV infection and inhibit the replication of drug resistant strains of HIV.

SUMMARY OF THE INVENTION

It has now been discovered that pyrrolidones having novel structures effectively inhibit the replication of HIV, including drug resistant strains of the virus. Selected pyrrolidones of the invention are potent reverse transcriptase inhibitors. Accordingly, the present invention provides pharmaceutical compositions, and prophylactic and therapeutic treatments, diagnostic and prognostic methods and kits, and pharmaceutical screening methods that take advantage of the anti-HIV activity of the pyrrolidones.

Because the pyrrolidones of the invention inhibit HIV replication, the prophylactic or therapeutic administration of the pyrrolidones is a treatment for HIV infection. Prophylactic treatments are especially useful for persons at high risk of HIV infection. Thus, the present invention provides methods of inhibiting HIV replication in a person by administering to the person a pharmaceutically effective amount of a pyrrolidone. This invention also provides pharmaceutical compositions comprising one or more pyrrolidones in a pharmaceutically acceptable carrier. The compounds of the invention can be administered orally, parentally (including subcutaneous injection, intravenous, intramuscular, intrasternal or infusion techniques), by inhalation spray, topically, by absorption through a mucous membrane, or rectally, in dosage unit formulations containing conventional non-toxic pharmaceutically acceptable carriers, adjuvants or vehicles.

Methods of inhibiting HIV replication described above can be applied to cells being cultured in vitro, as well.

In another aspect, the present invention provides a composition including at least one pyrrolidone and a second therapeutic agent or agents. In an exemplary embodiment, the second therapeutic agent is used to prevent or treat HIV infection. In another embodiment, the second therapeutic agent is used to treat an opportunistic infection associated with HIV infection. The second therapeutic is, for example, a protease inhibitor, a non-nucleoside reverse transcriptase inhibitor, a nucleoside reverse transcriptase inhibitor, an anti-retroviral nucleoside, an entry inhibitor, or any other antiviral agent effective to inhibit or treat HIV infection. In another embodiment, the second therapeutic agent is selected from the group consisting of zidovudine, didanosine, stavudine, interferon, lamivudine, adefovir, nevirapine, delaviridine, loviride, saquinavir, indinavir, and AZT. In another embodiment, the second therapeutic agent is an antibiotic or acyclovir. In still a further embodiment, the second agent is selected from immunomodulators, and entry inhibitors.

In another aspect, the present invention provides methods of treating or preventing HIV infection in a human comprising administering a pyrrolidone of the invention to a subject. As discussed above, the pyrrolidone is optionally combined with one or more additional therapeutic agents.

The invention also provides pyrrolidones that are of use for inhibiting the replication of drug resistant, including multi-drug resistant, HIV mutants. The compounds of the invention have low cytotoxicity and display high potency against HIV and drug resistant strains of HIV. The compounds have been shown to inhibit replication of clinically observed drug resistant strains of HIV.

In another aspect, the present invention provides methods of inhibiting HIV infection in a CD4$^+$ culture comprising the step of contacting the cell with a pyrrolidone of the invention, either alone or in combination with a second therapeutic agent or a combination of other therapeutic agents. In one embodiment, the therapeutic agent or agents are used to treat or prevent HIV infection.

Other aspects, objects and advantages of the invention will be apparent from the detailed description that follows.

BRIEF DESCRIPTION OF THE DRAWINGS

FIG. 1 is a table displaying exemplary compounds of the invention.

DETAILED DESCRIPTION OF THE INVENTION AND PREFERRED EMBODIMENTS

The present invention provides new compositions and methods for preventing or ameliorating viral, e.g., HIV infection, killing virally infected cells, e.g., HIV infected cells and generally, inhibiting viral, preferably HIV, replication. The present invention is, in part, based on the surprising discovery that the pyrrolidones of the invention effectively inhibit HIV infection, kill HIV infected cells and/or prevent HIV infection in the individual. Moreover, the compounds of the invention inhibit the replication of drug resistant strains of HIV.

The present invention provides compounds and pharmaceutical compositions that include those compounds. Moreover, the invention also provides methods of inhibiting HIV infection or replication by administering at least one compound of the invention to a patient in need of such treatment.

Definitions

"Reactive functional group," as used herein refers to groups including, but not limited to, olefins, acetylenes, alcohols, phenols, ethers, oxides, halides, aldehydes, ketones, carboxylic acids, esters, amides, cyanates, isocyanates, thiocyanates, isothiocyanates, amines, hydrazines, hydrazones, hydrazides, diazo, diazonium, nitro, nitriles, mercaptans, sulfides, disulfides, sulfoxides, sulfones, sulfonic acids, sulfinic acids, acetals, ketals, anhydrides, sulfates, sulfenic acids isonitriles, amidines, imides, imidates, nitrones, hydroxylamines, oximes, hydroxamic acids thiohydroxamic acids, allenes, ortho esters, sulfites, enamines, ynamines, ureas, pseudoureas, semicarbazides, carbodiimides, carbamates, imines, azides, azo compounds, azoxy compounds, and nitroso compounds. Reactive functional groups also include those used to prepare bioconjugates, e.g., N-hydroxysuccinimide esters, maleimides and the like. Methods to prepare each of these functional groups are well known in the art and their application to or modification for a particular purpose is within the ability of one of skill in the art (see, for example, Sandler and Karo, eds. ORGANIC FUNCTIONAL GROUP PREPARATIONS, Academic Press, San Diego, 1989).

"Non-covalent protein binding groups" are moieties that interact with an intact or denatured polypeptide in an associative manner. The interaction may be either reversible or irreversible in a biological milieu. The incorporation of a "non-covalent protein binding group" into a pyrrolidone of the invention provides the compound with the ability to interact with a polypeptide in a non-covalent manner. Exemplary non-covalent interactions include hydrophobic-hydrophobic and electrostatic interactions. Exemplary "non-covalent protein binding groups" include anionic groups, e.g., phosphate, thiophosphate, phosphonate, carboxylate, boronate, sulfate, sulfone, thiosulfate, and thiosulfonate.

As used herein, "linking member" refers to a covalent chemical bond that includes at least one heteroatom. Exemplary linking members include —C(O)NH—, —C(O)O—, —NH—, —S—, —O—, and the like.

The term "targeting group" is intended to mean a moiety that is: (1) able to actively direct the entity to which it is attached (e.g., a pyrrolidone) to a target region, e.g., an HIV infected cell; or (2) is preferentially passively absorbed by or entrained within a target tissue. The targeting group can be a small molecule, which is intended to include both non-peptides and peptides. The targeting group can also be a macromolecule, which includes, but is not limited to, saccharides, lectins, receptors, ligand for receptors, proteins such as BSA, antibodies, poly(ethers), dendrimers, poly(amino acids) and so forth.

The term "cleavable group" is intended to mean a moiety that allows for release of a pyrrolidone from a conjugate by cleaving a bond linking the pyrrolidone (or pyrrolidone linker arm construct) to the remainder of the conjugate. Such cleavage is either chemical in nature, or enzymatically mediated. Exemplary enzymatically cleavable groups include natural amino acids or peptide sequences that end with a natural amino acid.

In addition to enzymatically cleavable sites, it is within the scope of the present invention to include one or more sites that are cleaved by the action of an agent other than an enzyme. Exemplary non-enzymatic cleavage agents include, but are not limited to, acids, bases, light (e.g., nitrobenzyl derivatives, phenacyl groups, benzoin esters), and heat. Many cleaveable groups are known in the art. See, for example, Jung et al., *Biochem. Biophys. Acta*, 761: 152-162 (1983); Joshi et al., *J. Biol. Chem.*, 265: 14518-14525 (1990); Zarling et al., *J. Immunol.*, 124: 913-920 (1980); Bouizar et al., *Eur. J. Biochem.*, 155: 141-147 (1986); Park et al., *J. Biol. Chem.*, 261: 205-210 (1986); Browning et al., *J. Immunol.*, 143: 1859-1867 (1989). Moreover a broad range of cleavable, bifunctional (both homo- and hetero-bifunctional) spacer arms are commercially available from suppliers such as Pierce.

The symbol , whether utilized as a bond or displayed perpendicular to a bond indicates the point at which the displayed moiety is attached to the remainder of the molecule, solid support, etc.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are encompassed within the scope of the present invention.

The compounds of the invention may be prepared as a single isomer (e.g., enantiomer, cis-trans, positional, diastereomer) or as a mixture of isomers. In a preferred embodiment, the compounds are prepared as substantially a single isomer. Methods of preparing substantially isomerically pure compounds are known in the art. For example, enantiomerically enriched mixtures and pure enantiomeric compounds can be prepared by using synthetic intermediates that are enantiomerically pure in combination with reactions that either leave the stereochemistry at a chiral center unchanged or result in its complete inversion. Alternatively, the final product or intermediates along the synthetic route can be resolved into a single stereoisomer. Techniques for inverting or leaving unchanged a particular stereocenter, and those for resolving mixtures of stereoisomers are well known in the art and it is well within the ability of one of skill in the art to choose and appropriate method for a particular situation. See, generally, Furniss et al. (eds.), VOGEL'S ENCYCLOPEDIA OF PRACTICAL ORGANIC CHEMISTRY 5$^{TH}$ ED., Longman Scientific and Technical Ltd., Essex, 1991, pp. 809-816; and Heller, *Acc. Chem. Res.* 23: 128 (1990).

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 (125I) or carbon-14 ($^{14}$C). All isotopic variations of the compounds of the present invention, whether radioactive or not, are intended to be encompassed within the scope of the present invention.

Where substituent groups are specified by their conventional chemical formulae, written from left to right, they equally encompass the chemically identical substituents, which would result from writing the structure from right to left, e.g., —CH$_2$O— is intended to also recite —OCH$_2$—.

The term "alkyl," by itself or as part of another substituent means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. C$_1$-C$_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups that are limited to hydrocarbon groups are termed "homoalkyl".

The term "alkylene" by itself or as part of another substituent means a divalent radical derived from an alkane, as exemplified, but not limited, by —CH$_2$CH$_2$CH$_2$CH$_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, and —CH=CH—N(CH$_3$)—CH$_3$. Up to two heteroatoms may be consecutive, such as, for example, —CH$_2$—NH—OCH$_3$ and —CH$_2$—O—Si(CH$_3$)$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R° C(O)$_2$—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring or multiple rings (preferably from 1 to 3 rings), which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom.

Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, tetrazolyl, benzo[b] furanyl, benzo[b]thienyl, 2,3-dihydrobenzo[1,4]dioxin-6-yl, benzo[1,3]dioxol-5-yl and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") is meant to include both substituted and unsubstituted forms of the indicated radical.

Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: —OR', =O, =NR', =N—OR', —NR'R", —SR', -halogen, —SiR'R" R''', —OC(O)R', —C(O)R', —$CO_2$R', —CONR'R", —OC(O)NR'R", —NR'C(O)R', —NR'—C(O)NR"R''', —NR"C(O)$_2$R', —NR—C(NR'R" R''')=NR'''', —NR—C(NR'R")=NR''', —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R''' and R'''' each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R''' and R'''' groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for the alkyl radical, substituents for the aryl and heteroaryl groups are generically referred to as "aryl group substituents." The substituents are selected from, for example: halogen, —OR', =O, =NR', =N—OR', —NR'R", —SR', -halogen, —SiR'R" R''', —OC(O)R', —C(O)R', —$CO_2$R', —CONR'R", —OC(O)NR'R", —NR"C(O)R', —NR'—C(O)NR"R''', —NR"C(O)$_2$R', —NR—C(NR'R" R''')=NR'''', —NR—C(NR'R")=NR''', —S(O)R', —S(O)$_2$R', —S(O)$_2$NR'R", —NRSO$_2$R', —CN and —NO$_2$, —R', —$N_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R''' and R'''' are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R''' and R'''' groups when more than one of these groups is present. In the schemes that follow, the symbol X represents "R" as described above.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'- or a single bond, and q is an integer of from 0 to 3

Alternatively, two of the substituents on adjacent atoms of the aryl or heteroaryl ring may optionally be replaced with a substituent of the formula -A-($CH_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R''')$_d$—, where s and d are independently integers of from 0 to 3, and X is —O—, —NR'—, —S—, —S(O)—, —S(O)$_2$—, or —S(O)$_2$NR'—. The substituents R, R', R" and R''' are preferably independently selected from hydrogen or substituted or unsubstituted ($C_1$-$C_6$)alkyl.

As used herein, the term "heteroatom" is meant to include oxygen (O), nitrogen (N), sulfur (S) and silicon (Si).

"Protecting group," as used herein refers to a portion of a substrate that is substantially stable under a particular reaction condition, but which is cleaved from the substrate under a different reaction condition. A protecting group can also be selected such that it participates in the direct oxidation of the aromatic ring component of the compounds of the invention. For examples of useful protecting groups, see, for example, Greene et al., *Protective Groups in Organic Synthesis*, John Wiley & Sons, New York, 1991.

As used herein, "pharmaceutically acceptable salt" refers to a salt that retains the desired biological activity of the parent compound and does not impart any undesired toxicological effects. Examples of such salts include, but are not limited to, (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, pamoic acid, alginic acid, polyglutamic acid, naphthalenesulfonic acids, naphthalenedisulfonic acids, polygalacturonic acid; (b) salts with polyvalent metal cations such as zinc, calcium, bismuth, barium, magnesium, aluminum, copper, cobalt, nickel, cadmium, and the like; or (c) salts formed with an organic cation formed from N,N'-dibenzylethylenediamine or ethylenediamine; or (d) combinations of (a) and (b) or (c), e.g., a zinc tannate salt; and the like. The preferred acid addition salts are the trifluoroacetate salt and the acetate salt.

A "disorder associated with HIV infection" or "disease associated with HIV infection" refers to a disease state which is marked by HIV infection. Such disorders associated with HIV infection include, but are not limited to, AIDS, Kaposi's sarcoma, opportunistic infections such as those caused by *Pneumocystis carinii* and *Mycobacterium tuberculosis*; oral lesions, including thrush, hairy leukoplakia, and aphthous ulcers; generalized lymphadenopathy, shingles, thrombocytopenia, aseptic meningitis, and neurologic disease such as toxoplasmosis, cryptococcosis, CMV infection, primary CNS lymphoma, and HIV-associated dementia, peripheral neuropathies, seizures, and myopathy.

As used herein, "reverse transcriptase (RT) activity" means the ability to effect reverse transcription of retroviral RNA to proviral DNA. One means by which RT activity can be determined is by measuring viral replication. One measure of HIV-1 viral replication is the p24 core antigen enzyme immunoassay, for example, using the assay commercially available from Coulter Corporation/Immunotech, Inc. (Westbrooke, Mich.). Another means by which RT activity is analyzed is by assay of recombinant HIV-1 reverse transcriptase (rRT) activity, for example, using the Quan-T-RT assay system commercially available from Amersham (Arlington Heights, Ill.) and described in Bosworth, et al., *Nature*, 1989, 341:167-168.

As used herein, "HIV reverse transcriptase inhibitor" is intended to refer to both nucleoside and non-nucleoside inhibitors of HIV reverse transcriptase (RT). Examples of nucleoside RT inhibitors include, but are not limited to, AZT, ddC, ddI, d4T, and 3TC. Examples of non-nucleoside RT inhibitors include, but are no limited to, delavirdine (Pharmacia and Upjohn U90152S), efavirenz (DuPont), nevirapine (Boehringer Ingelheim), Ro 18,893 (Roche), trovirdine (Lilly), MKC-442 (Triangle), HBY 097 (Hoechst), ACT (Korean Research Institute), UC-781 (Rega Institute), UC-782 (Rega Institute), RD4-2025 (Tosoh Co. Ltd.), and MEN 10979 (Menarini Farmaceutici).

As used herein, "HIV protease inhibitor" is intended to refer to compounds that inhibit HIV protease. Examples include, but are not limited, saquinavir (Roche, Ro31-8959), ritonavir (Abbott, ABT-538), indinavir (Merck, MK-639), amprenavir (Vertex/Glaxo Wellcome), nelfinavir (Agouron, AG-1343), palinavir (Boehringer Ingelheim), BMS-232623 (Bristol-Myers Squibb), GS3333 (Gilead Sciences), KNI-413 (Japan Energy), KNI-272 (Japan Energy), LG-71350 (LG Chemical), CGP-61755 (Ciba-Geigy), PD 173606 (Parke Davis), PD 177298 (Parke Davis), PD 178390 (Parke Davis), PD 178392 (Parke Davis), U-140690 (Pharmacia and Upjohn), and ABT-378. Additional examples include the cyclic protease inhibitors disclosed in WO93/07128, WO 94/19329, WO 94/22840, and PCT Application Number US96/03426.

As used herein, a compound that "inhibits replication of human immunodeficiency virus (HIV)" means a compound that, when contacted with HIV, for example, via HIV-infected cells, effects a reduction in the amount of HIV as compared with untreated control. Inhibition of replication of HIV can be measured by various means known in the art, for example, the p24 assay.

By "therapeutically effective dose" herein is meant a dose that produces effects for which it is administered. The exact dose will depend on the purpose of the treatment, and is ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); and Pickar, *Dosage Calculations* (1999)).

"Mutant HIV" means a strain of HIV having one or more mutated or altered amino acids as compared with wild type.

"Multi-Drug Resistant HIV" means one or more HIV strain that is resistant to treatment with one or more chemotherapeutic agent.

Compounds

In a first aspect, the invention provides pyrrolidones and related compounds.

An exemplary compound of the invention has the formula:

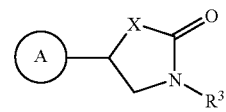

in which A represents a ring system that is selected from substituted or unsubstituted aryl and substituted or unsubstituted heteroaryl. The symbol $R^3$ represents substituted or unsubstituted aryl and substituted or unsubstituted heteroaryl. X is substituted or unsubstituted carbon or substituted or unsubstituted nitrogen.

Other exemplary compounds of the invention have the formulae:

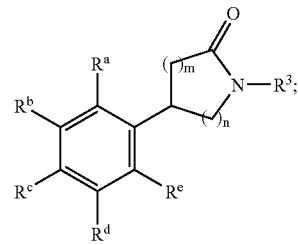

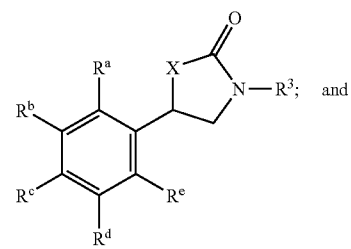

-continued

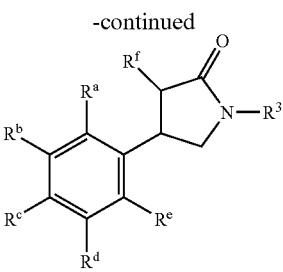

In the formulae above, the symbols m and n represent integers that are independently selected from 0, 1 and 2. X is substantially as described above.

The symbols $R^a$, $R^b$, $R^c$, $R^d$, $R^e$ and $R^f$ represent members independently selected from H, substituted or unsubstituted alkyl, substituted or unsubstituted cycloalkyl, substituted or unsubstituted heteroalkyl, substituted or unsubstituted aryl, substituted or unsubstituted heteroaryl, or another "alkyl substituent" as defined hereinabove. The symbol $R^3$ represents substituted or unsubstituted aryl and substituted or unsubstituted heteroaryl.

Further detail regarding the identities of the "R" groups set forth above, is provided in the succeeding paragraphs.

In another exemplary embodiment, the invention provides a compound according to Formula I:

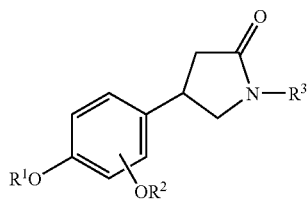

(I)

in which the symbols $R^1$ and $R^2$ independently represent H, substituted or unsubstituted alkyl, substituted or unsubstituted cycloalkyl, substituted or unsubstituted heteroalkyl, substituted or unsubstituted aryl, substituted or unsubstituted heterocycloalkyl or substituted or unsubstituted heteroaryl. The symbol $R^3$ represents substituted or unsubstituted aryl and substituted or unsubstituted heteroaryl. Exemplary heteroaryl moieties include substituted or unsubstituted pyridyl, substituted or unsubstituted pyrimidyl and substituted or unsubstituted pyrazinyl.

In an exemplary embodiment, $R^1$ is methyl and $R^2$ is substituted or unsubstituted cyclopentyl, substituted or unsubstituted phenyl or substituted or unsubstituted benzyl.

In a further embodiment, the invention provides compounds in which $R^1$ is a member independently selected from substituted or unsubstituted $C_1$-$C_3$ alkyl. The symbol $R^2$ represents substituted or unsubstituted phenyl or substituted or unsubstituted $C_4$-$C_6$ cycloalkyl. $R^3$ is unsubstituted phenyl or phenyl substituted with $S(O)_2NR^{3a}R^{3b}$, $S(O)_nR^3$, $NR^{3a}R^{3b}$, $C(O)NR^{3a}R^{3b}$ or $OR^{3a}$. The symbols $R^{3a}$ and $R^{3b}$ independently represent H or substituted or unsubstituted $C_1$-$C_6$ alkyl. The index "n" represents 0, 1 or 2.

Exemplary substituted phenyl groups include:

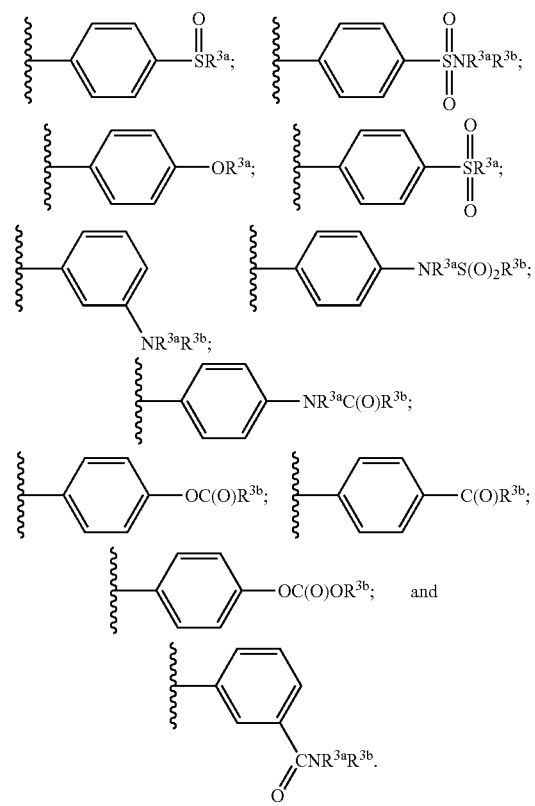

In another exemplary embodiment, at least one of $R^1$—$R^7$ is a moiety that increases the water-solubility of the parent compound. Exemplary moieties of use for increasing a compound's water solubility include ethers and polyethers, e.g., a member selected from ethylene glycol, and ethylene glycol oligomers, having a molecular weight of from about 60 daltons to about 10,000 daltons, and more preferably of from about 100 daltons to about 1,000 daltons.

Representative polyether-based substituents include, but are not limited to, the following structures:

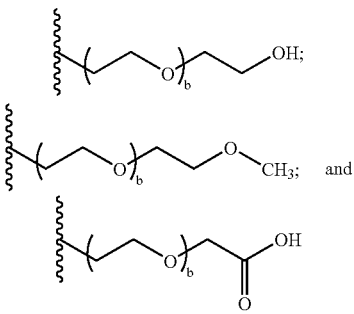

in which b is preferably a number from 1 to 100, inclusive. Other functionalized polyethers are known to those of skill in the art, and many are commercially available from, for example, Shearwater Polymers, Inc. (Alabama).

In another exemplary embodiment, at least one of $R^1$-$R^7$ is a linker moiety that includes a reactive functional group for conjugating the compound to another molecule or to a surface. The linkers of use in the compounds of the invention can also include a cleaveable group. In an exemplary embodiment, the cleaveable group is interposed between the pyrrolidone core and a targeting agent or macromolecular backbone. Representative useful reactive groups are discussed in greater detail in succeeding sections. Additional information on useful reactive groups is known to those of skill in the art. See, for example, Hermanson, BIOCONJUGATE TECHNIQUES, Academic Press, San Diego, 1996.

Reactive Functional Groups

As discussed above, the pyrrolidone core of the compounds of the invention are optionally tethered to other species by means of bonds formed between a reactive functional group on the pyrrolidone or a linker attached to the pyrrolidone, and a reactive functional group of complementary reactivity on the other species. For clarity of illustration the succeeding discussion focuses on the conjugation of representative pyrrolidone of the invention to polymers, including poly(ethers) and dendrimers, and to targeting agents useful for translocating the pyrrolidone -targeting agent conjugate across a membrane. The focus exemplifies selected embodiments of the invention from which others are readily inferred by one of skill in the art. No limitation of the invention is implied, by focusing the discussion on the representative embodiments.

Exemplary pyrrolidones of the invention bear a reactive functional group, which is generally located on the pyrrolidone ring or on a substituted or unsubstituted alkyl or heteroalkyl chain attached to the ring, allowing their facile attachment to another species. A convenient location for the reactive group is the terminal position of an alkyl or heteroalkyl substituent of the pyrrolidone core.

Reactive groups and classes of reactions useful in practicing the present invention are generally those that are well known in the art of bioconjugate chemistry. Currently favored classes of reactions available with reactive analogues are those proceeding under relatively mild conditions. These include, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982.

Exemplary reaction types include the reaction of carboxyl groups and various derivatives thereof including, but not limited to, N-hydroxysuccinimide esters, N-hydroxybenzotriazole esters, acid halides, acyl imidazoles, thioesters, p-nitrophenyl esters, alkyl, alkenyl, alkynyl and aromatic esters. Hydroxyl groups can be converted to esters, ethers, aldehydes, etc. Haloalkyl groups are converted to new species by reaction with, for example, an amine, a carboxylate anion, thiol anion, carbanion, or an alkoxide ion. Dienophile (e.g., maleimide) groups participate in Diels-Alder. Aldehyde or ketone groups can be converted to imines, hydrazones, semicarbazones or oximes, or reacted via such mechanisms as Grignard addition or alkyllithium addition. Sulfonyl halides react readily with amines, for example, to form sulfonamides. Amine or sulfhydryl groups are, for example, acylated, alkylated or oxidized. Alkenes can be converted to an array of new species using cycloadditions, acylation, Michael addition, etc. Epoxides react readily with amines and hydroxyl compounds.

Exemplary combinations of reactive functional groups found on a ligand of the invention and on a targeting moiety (or polymer or linker) are set forth in Table 1.

TABLE 1

| Chemical Functionality 1 | Chemical Functionality 2 | Linkage |
|---|---|---|
| Hydroxy | Carboxy | Ester |
|  | Hydroxy | Carbonate |
|  | Amine | Carbamate |
|  | $SO_3$ | Sulfate |
|  | $PO_3$ | Phosphate |
|  | Carboxy | Acyloxyalkyl |
|  | Ketone | Ketal |
|  | Aldehyde | Acetal |
|  | Hydroxy | Anhydride |
| Mercapto | Mercapto | Disulfide |
|  | Carboxy | Acyloxyalkyl Thioether |
|  | Carboxy | Thioester |
|  | Carboxy | Amino amide |
|  | Mercapto | Thioester |
|  | Carboxy | Acyloxyalkyl ester |
|  | Carboxy | Acyloxyalkyl amide |
|  | Amino | Acyloxyalkoxy carbonyl |
|  | Carboxy | Anhydride |
|  | Carboxy | N-acylamide |
|  | Hydroxy | Ester |
|  | Hydroxy | Hydroxymethyl ketone ester |
|  | Hydroxy | Alkoxycarbonyl oxyalkyl |
| Amino | Carboxy | Acyloxyalkylamine |
|  | Carboxy | Acyloxyalkylamide |
|  | Amino | Urea |
|  | Carboxy | Amide |
|  | Carboxy | Acyloxyalkoxycarbonyl |
|  | Amide | N-Mannich base |
|  | Carboxy | Acyloxyalkyl carbamate |
| Phosphate oxygen ester | Hydroxy | Phosphate |
|  | Amine | Phosphoramidate |
|  | Mercapto | Thiophosphate ester |
| Ketone | Carboxy | Enol ester |
| Sulfonamide | Carboxy | Acyloxyalkyl sulfonamide |
|  | Ester | N-sulfonyl-imidate |

One skilled in the art will readily appreciate that many of these linkages may be produced in a variety of ways and using a variety of conditions. For the preparation of esters, see, e.g., March supra at 1157; for thioesters, see, March, supra at 362-363, 491, 720-722, 829, 941, and 1172; for carbonates, see, March, supra at 346-347; for carbamates, see, March, supra at 1156-57; for amides, see, March supra at 1152; for ureas and thioureas, see, March supra at 1174; for acetals and ketals, see, Greene et al. supra 178-210 and March supra at 1146; for acyloxyalkyl derivatives, see, PRODRUGS: TOPICAL AND OCULAR DRUG DELIVERY, K. B. Sloan, ed., Marcel Dekker, Inc., New York, 1992; for enol esters, see, March supra at 1160; for N-sulfonylimidates, see, Bundgaard et al., *J. Med. Chem.*, 31:2066 (1988); for anhydrides, see, March supra at 355-56, 636-37, 990-91, and 1154; for N-acylamides, see, March supra at 379; for N-Mannich bases, see, March supra at 800-$O_2$, and 828; for hydroxymethyl ketone esters, see, Petracek et al. *Annals NY Acad. Sci.*, 507:353-54 (1987); for disulfides, see, March supra at 1160; and for phosphonate esters and phosphonamidates.

The reactive functional groups can be chosen such that they do not participate in, or interfere with, the reactions necessary to assemble the reactive ligand analogue. Alternatively, a reactive functional group can be protected from participating in the reaction by the presence of a protecting group. Those of skill in the art will understand how to protect a particular functional group from interfering with a chosen set of reaction conditions. For examples of useful protecting groups, see Greene et al., PROTECTIVE GROUPS IN ORGANIC SYNTHESIS, John Wiley & Sons, New York, 1991.

Generally, prior to forming the linkage between the ligand and the targeting (or other) agent, and optionally, the linker group, at least one of the chemical functionalities is activated. One skilled in the art will appreciate that a variety of chemical functionalities, including hydroxy, amino, and carboxy groups, can be activated using a variety of standard methods and conditions. For example, a hydroxyl group of the ligand (or targeting agent) can be activated through treatment with phosgene to form the corresponding chloroformate, or p-nitrophenylchloroformate to form the corresponding carbonate.

In an exemplary embodiment, the invention makes use of a targeting agent that includes a carboxyl functionality. Carboxyl groups may be activated by, for example, conversion to the corresponding acyl halide or active ester. This reaction may be performed under a variety of conditions as illustrated in March, supra pp. 388-89. In an exemplary embodiment, the acyl halide is prepared through the reaction of the carboxyl-containing group with oxalyl chloride. The activated agent is combined with a ligand or ligand-linker arm combination to form a conjugate of the invention. Those of skill in the art will appreciate that the use of carboxyl-containing targeting agents is merely illustrative, and that agents having many other functional groups can be conjugated to the ligands of the invention.

Targeting Groups

The compounds of the invention may also be conjugated to an agent that targets the compound to a specific tissue or region of disease. The compound of the invention can be targeted for specific delivery to the cells to be treated by conjugation of the compounds to a targeting agent. The term "targeting agent" refers to a species that serves to deliver the compound of the invention to a specific site. Targeting agents include, for example, molecules that specifically bind molecules present on a cell surface. Such targeting agents useful in the invention include anti-cell surface antigen antibodies; cytokines, including interleukins, factors such as epidermal growth factor (EGF), and the like, are also specific targeting agents known to bind cells expressing high levels of their receptors. Targeting agents include species that are taken up by cells using either active or passive mechanisms.

Particularly useful targeting agents for targeting the compounds of the invention to cells for therapeutic activity include those ligands that bind antigens or receptors present on virus-infected cells to be treated. For example, antigens present on T-cells, such as CD48, can be targeted with antibodies. Antibody fragments, including single chain fragments, can also be used. Other such ligand-receptor binding pairs are known in the scientific literature for targeting antiviral treatments to target cells. Methods for producing conjugates of the compounds of the invention and the targeting moieties are known.

Membrane translocation polypeptides are another exemplary targeting agent. Membrane translocation polypeptides" have amphiphilic or hydrophobic amino acid subsequences that have the ability to act as membrane-translocating carriers. In one embodiment, homeodomain proteins have the ability to translocate across cell membranes. The shortest internalizable peptide of a homeodomain protein, Antennapedia, was found to be the third helix of the protein, from amino acid position 43 to 58 (see, e.g., Prochiantz, Current Opinion in Neurobiology 6:629-634 (1996)). Another subsequence, the h (hydrophobic) domain of signal peptides, was found to have similar cell membrane translocation characteristics (see, e.g., Lin et al., J. Biol. Chem. 270:14255-14258 (1995)).

Examples of peptide sequences include, but are not limited to: an 11 amino acid peptide of the tat protein of HIV; a 20 residue peptide sequence which corresponds to amino acids 84-103 of the p16 protein (see Fahraeus et al., Current Biology 6:84 (1996)); the third helix of the 60-amino acid long homeodomain of Antennapedia (Derossi et al., J. Biol. Chem. 269:10444 (1994)); the h region of a signal peptide such as the Kaposi fibroblast growth factor (K-FGF) h region (Lin et al., supra); or the VP22 translocation domain from HSV (Elliot & O'Hare, Cell 88:223-233 (1997)). Other suitable chemical moieties that provide enhanced cellular uptake may also be chemically linked to the compounds of the invention.

Such subsequences can be used to translocate compounds of the invention across a cell membrane. Compounds of the invention can be conveniently fused to or derivatized with such sequences. Typically, the translocation sequence is provided as part of a fusion protein. Optionally, a linker as described herein can be used to link the compound of the invention and the translocation sequence. Any suitable linker can be used, e.g., a peptide linker or other chemical linkers.

Toxin molecules also have the ability to transport compounds across cell membranes. Often, such molecules are composed of at least two parts (called "binary toxins"): a translocation or binding domain or polypeptide and a separate toxin domain or polypeptide. Typically, the translocation domain or polypeptide binds to a cellular receptor, and then the toxin is transported into the cell. Several bacterial toxins, including Clostridium perfringens iota toxin, diphtheria toxin (DT), Pseudomonas exotoxin A (PE), pertussis toxin (PT), Bacillus anthracis toxin, and pertussis adenylate cyclase (CYA), have been used in attempts to deliver peptides to the cell cytosol as internal or amino-terminal fusions (Arora et al., J. Biol. Chem., 268: 3334-3341 (1993); Perelle et al., Infect. Immun., 61: 5147-5156 (1993); Stenmark et al., J. Cell Biol. 113: 1025-1032 (1991); Donnelly et al., PNAS U.S.A. 90: 3530-3534 (1993); Carbonetti et al., Abstr. Annu. Meet. Am. Soc. Microbiol. 95: 295 (1995); Sebo et al., Infect. Immun. 63:3851-3857 (1995); Klimpel et al., PNAS U.S.A. 89:10277-10281 (1992); and Novak et al., J. Biol. Chem. 267:17186-17193 1992)).

Non-covalent protein binding groups are also of use to target the compounds of the invention to specific regions of the body and to increase the half-life of the agent through protein binding.

Macromolecular Conjugates

In an exemplary embodiment, the invention provides a macromolecular, i.e., MW > 1000 D, conjugate between the pyrrolidone core and a macromolecular species. In one embodiment, a macromolecular conjugate of the invention is formed by covalently conjugating a pyrrolidone to a macromolecule via a reactive functional group. In another embodiment, the macromolecular conjugate is formed by a non-covalent interaction between a pyrrolidone derivative and a macromolecule, e.g., a serum protein.

In the following discussion, the invention is described by reference to specific macromolecules of use for forming conjugates with the novel pyrrolidone cores of the invention. Those of skill in the art will appreciate that the focus of the discussion is for clarity of illustration and does not limit the scope of the invention. The invention provides macromolecular conjugates that include components derived from biomolecules and synthetic molecules. Exemplary biomolecules include polypeptides (e.g., antibodies, enzymes, receptors, antigens); polysaccharides (e.g., starches, inulin, dextran); lectins, non-peptide antigens and the like. Exemplary synthetic polymers include poly(acrylic acid), poly(lysine), poly (glutamic acid), poly(ethylene imine), etc.

Covalent Conjugation

Selection of an appropriate reactive functional group on a pyrrolidone core of the invention to form a desired macromolecular species is well within the abilities of one of skill in the art. Exemplary reactive functional groups of use in forming the covalent conjugates of the invention are discussed above. It is well within the abilities of one of skill to select and prepare a pyrrolidone core of the invention having an appropriate reactive functional group of complementary reactivity to a reactive group on its conjugation partner.

In one embodiment, the bond formed between reactive functional groups of the macromolecule and that of the pyrrolidone attaches the pyrrolidone to the macromolecule essentially irreversibly via a "stable bond" between the components. A "stable bond", as used herein, is a bond, which maintains its chemical integrity over a wide range of conditions (e.g., amide, carbamate, carbon-carbon, ether, etc.). In another embodiment, a "cleaveable bond" links the macromolecule and the pyrrolidone. A "cleaveable bond", as used herein, is a bond that undergoes scission under selected conditions. Cleaveable bonds include, but are not limited to, disulfide, imine, carbonate and ester bonds. As discussed in the preceding sections, the reactive functional group can be located at one or more positions of the pyrrolidone.

Polysaccharides

In an exemplary embodiment, the present invention provides conjugates between a pyrrolidone core and saccharides, e.g., polysaccharides. In an exemplary embodiment, the invention provides a conjugate between a pyrrolidone and inulin. Inulin is a naturally occurring polysaccharide, which has been previously investigated as a carrier for diagnostic moieties (Rongved, P. K., *J. Carbohydr. Res.* 1991, 214, 315; Corsi, D. M. V. E. et al., *Chem. Eur. J.* 2001, 7, 64). The structure of inulin can be described as a mixture of linear 13-(2→1)-linked α-D-fructofuranosyl chains with a α-D-glucopyranosyl unit at the terminal end. Inulin is commercially available in a variety of molecular weights and the degree of polymerization varies from 10 to 30, resulting in a molecular weight distribution of 1500 to 5000 Da. The high hydrophilicity, pH stability, low solution viscosity and biocompatability of inulin ensure that its conjugates have favorable pharmacological properties.

Dendrimer-Based Agents

In another aspect, the present invention provides a pyrrolidone as set forth above, which is attached to a dendrimer via a reactive functional group. Similar to the polymeric group discussed above, the dendrimer has at least two reactive functional groups. In one embodiment, one or more formed pyrrolidone is attached to the dendrimer. Alternatively, the pyrrolidone is formed directly on the dendrimer.

In an exemplary embodiment, a water-soluble and bioadapted polyester (polypropionate) class of dendrimers has been designed to provide favorable pharmacokinetic properties. See, for example, Ihre, H. et al., *Macromolecules* 1998, 31, 4061; Ihre, H. et al., *.1 Am. Chem. Soc.* 1996, 118, 6388; Anders, H., Ibre, H., Patent WO/9900440 (Sweden)). In an exemplary embodiment, the termini of the dendrimers are conjugated to a pyrrolidone core of the invention.

Poly(ethylene glycol)-based Agents

In another exemplary embodiment, the invention provides a conjugate between a pyrrolidone core of the invention and poly(ethylene glycol). Poly(ethylene glycol) (PEG) is used in biotechnology and biomedical applications. The use of this agent has been reviewed (POLY(ETHYLENE GLYCOL) CHEMISTRY: BIOTECHNICAL AND BIOMEDICAL APPLICATIONS, J. M. Harris, Ed., Plenum Press, New York, 1992). Modification of enzymes (Chiu et al., *J. Bioconjugate Chem.*, 4: 290-295 (1993)), RGD peptides (Braatz et al., *Bioconjugate Chem.*, 4: 262-267 (1993)), liposomes (Zalipsky, S. *Bioconjugate Chem.*, 4: 296- 299 (1993)), and CD4-IgG glycoprotein (Chamow et al., *Bioconjugate Chem.*, 4:133-140 (1993)) are some of the recent advances in the use of polyethylene glycol. Surfaces treated with PEG have been shown to resist protein deposition and have improved resistance to thrombogenicity when coated on blood contacting biomaterials (Merrill, "Poly(ethylene oxide) and Blood Contact: A Chronicle of One Laboratory," in POLY(ETHYLENE GLYCOL) CHEMISTRY: BIOTECHNICAL AND BIOMEDICAL APPLICATIONS, Harris, Ed., Plenum Press, New York, (1992), pp. 199-220).

Many routes are available for attaching a pyrrolidone core of the invention onto a polymeric or oligomeric species. See, for example, Dunn, R.L., et al., Eds. POLYMERIC DRUGS AND DRUG DELIVERY SYSTEMS, ACS Symposium Series Vol. 469, American Chemical Society, Washington, D.C. 1991; Herren et al., *J. Colloid and Interfacial Science* 115: 46-55 (1987); Nashabeh et al., *J. Chromatography* 559: 367-383 (1991); Balachandar et al., *Langmuir* 6:1621-1627 (1990); and Burns et al., *Biomaterials* 19: 423-440 (1998).

Many activated derivatives of poly(ethyleneglycol) are available commercially and in the literature. It is well within the abilities of one of skill to choose, and synthesize if necessary, an appropriate activated PEG derivative with which to prepare a conjugate useful in the present invention. See, Abuchowski et al. *Cancer Biochem. Biophys.*, 7: 175-186 (1984); Abuchowski et al., *J. Biol. Chem.*, 252: 3582-3586 (1977); Jackson et al., *Anal. Biochem.*, 165: 114-127 (1987); Koide et al., *Biochem Biophys. Res. Commun.*, 111: 659-667 (1983)), tresylate (Nilsson et al., *Methods Enzymol.*, 104: 56-69 (1984); Delgado et al., *Biotechnol. Appl. Biochem.*, 12: 119-128 (1990)); N-hydroxysuccinimide derived active esters (Buckmann et al., *Makromol. Chem.*, 182: 1379-1384 (1981); Joppich et al., *Makromol. Chem.*, 180: 1381-1384 (1979); Abuchowski et al., *Cancer Biochem. Biophys.*, 7: 175-186 (1984); Katre et al. *Proc. Natl. Acad. Sci. U.S.A.*, 84: 1487-1491 (1987); Kitamura et al., *Cancer Res.*, 51: 4310-4315 (1991); Boccu et al., *Z. Naturforsch.*, 38C: 94-99 (1983), carbonates (Zalipsky et al., POLY(ETHYLENE GLYCOL) CHEMISTRY: BIOTECHNICAL AND BIOMEDICAL APPLICATIONS, Harris, Ed., Plenum Press, New York, 1992, pp. 347-370; Zalipsky et al., *Biotechnol. Appl. Biochem.*, 15: 100-114 (1992); Veronese et al., *Appl. Biochem. Biotech.*, 11: 141-152 (1985)), imidazolyl formates (Beauchamp et al., *Anal. Biochem.*, 131: 25-33 (1983); Berger et al., *Blood*, 71: 1641-1647 (1988)), 4-dithiopyridines (Woghiren et al., *Bioconjugate Chem.*, 4: 314-318 (1993)), isocyanates (Byun et al., *ASAIO Journal*, M649-M-653 (1992)) and epoxides (U.S. Pat. No. 4,806,595, issued to Noishiki et al., (1989). Other linking groups include the urethane linkage between amino groups and activated PEG. See, Veronese, et al, *Appl. Biochem. Biotechnol.*, 11: 141-152 (1985).

Synthesis and Purification of Pyrrolidones

The compounds of the invention are synthesized by an appropriate combination of generally well-known synthetic methods. Techniques useful in synthesizing the compounds of the invention are both readily apparent and accessible to those of skill in the relevant art. The discussion below is offered to illustrate certain of the diverse methods available for use in assembling the compounds of the invention, it is not intended to define the scope of reactions or reaction sequences that are useful in preparing the compounds of the present invention. Exemplary reaction schemes leading to the formation of pyrrolidones of the invention are set forth below.

Scheme 1

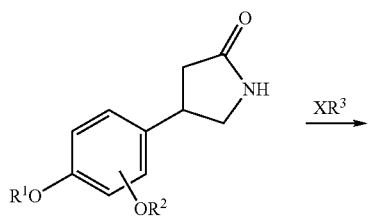
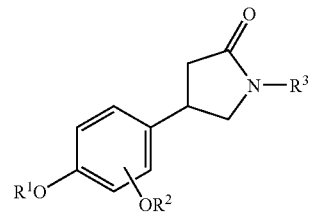

Reagents and condition: $K_3PO_4$, CuI, $R_1ArX$, trans-cyclohexanediamine, DMF, dioxane, 110° C., 20 h One method of synthesizing compounds of invention is shown in Scheme 1, wherein $R^1$, $R^2$ and $R^3$ are as described for formula I of the invention. Coupling of the aryl halide ($XR^3$) with the lactam provides N-arylpyrrolidone. The reaction proceeds in a suitable solvent (e.g. DMF, dioxane and the like) and with a suitable catalyst (e.g. copper iodide/suitable 1,2 diamine (trans-cyclohexanediamine, etc), and the like). The reaction proceeds in the temperature range 60-150° C.

Scheme 2

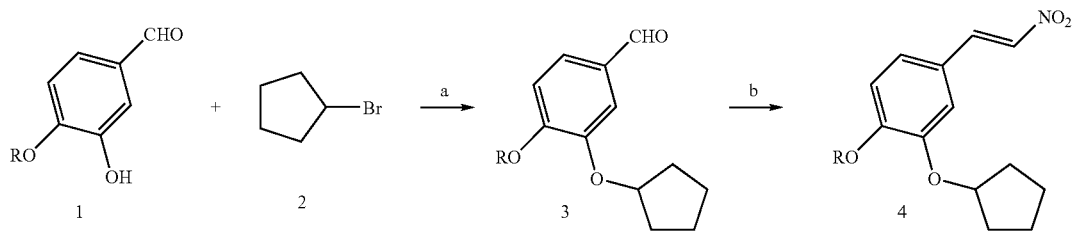

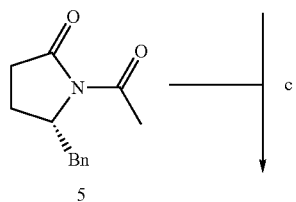

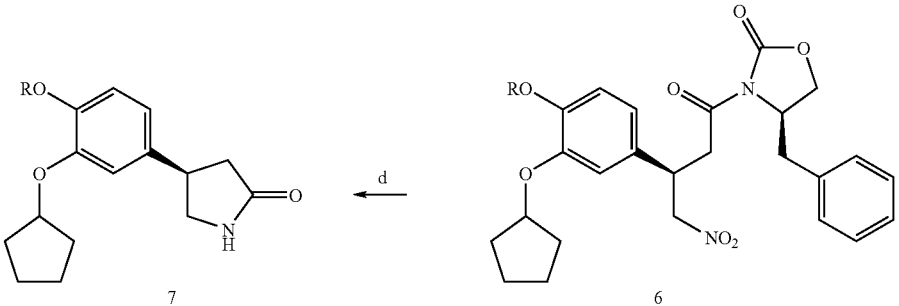

Reagents and conditions. a) $K_2CO_3$, DMF, rt; b) $CH_3NO_2$, $NH_4OAc$—AcOH, reflux, 2 h; c) LDA; 5, THF, −78° C., then 4; d) Raney Ni, EtOH-dioxane, $H_2$;

Another exemplary route to compounds of the invention is set forth in Scheme 2, which illustrates the synthesis of a lactam 7, comprising a 3,4-substituted phenyl group. A 3-hydroxy benzylaldehyde 1 is reacted with cyclopentylbromide 2 under basic condition to form the corresponding 3-cyclopentyloxy-benzaldehyde 3. The aldehyde 3 is then converted to the corresponding nitroethylene 4. Addition of 5 to the benzylnitroethylene 4 is performed in the presence of lithium diisopropylamide to form the imide intermediate 6. The lactam product 7 is obtained by reduction and cyclization.

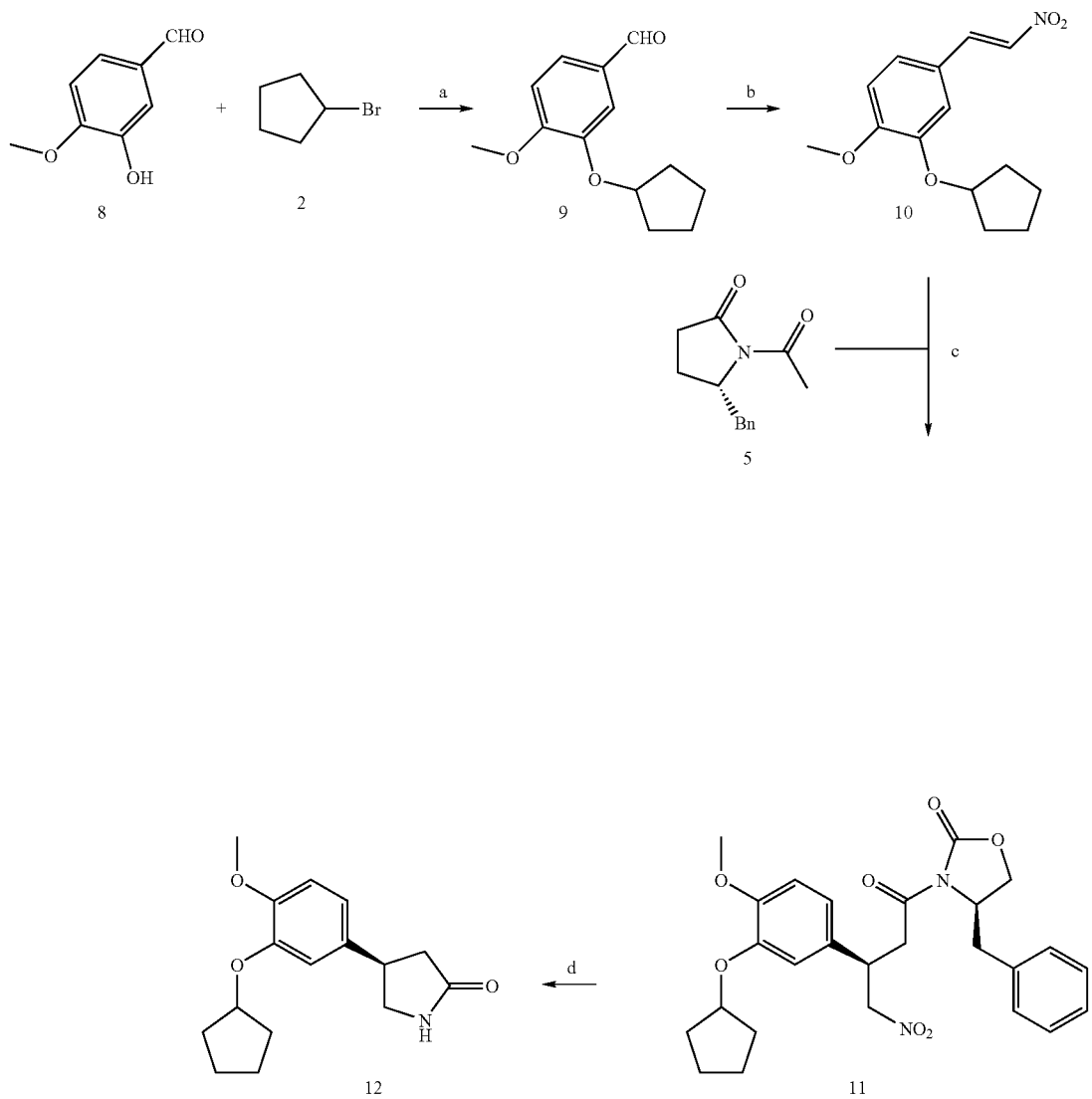

Reagents and conditions: a) K₂CO₃, DMF, rt; b) CH₃NO₂, NH₄OAc—AcOH, reflux, 2 h; c) LDA; 5, THF, −78° C., then 10; d) Raney Ni, EtOH-dioxane, H₂.

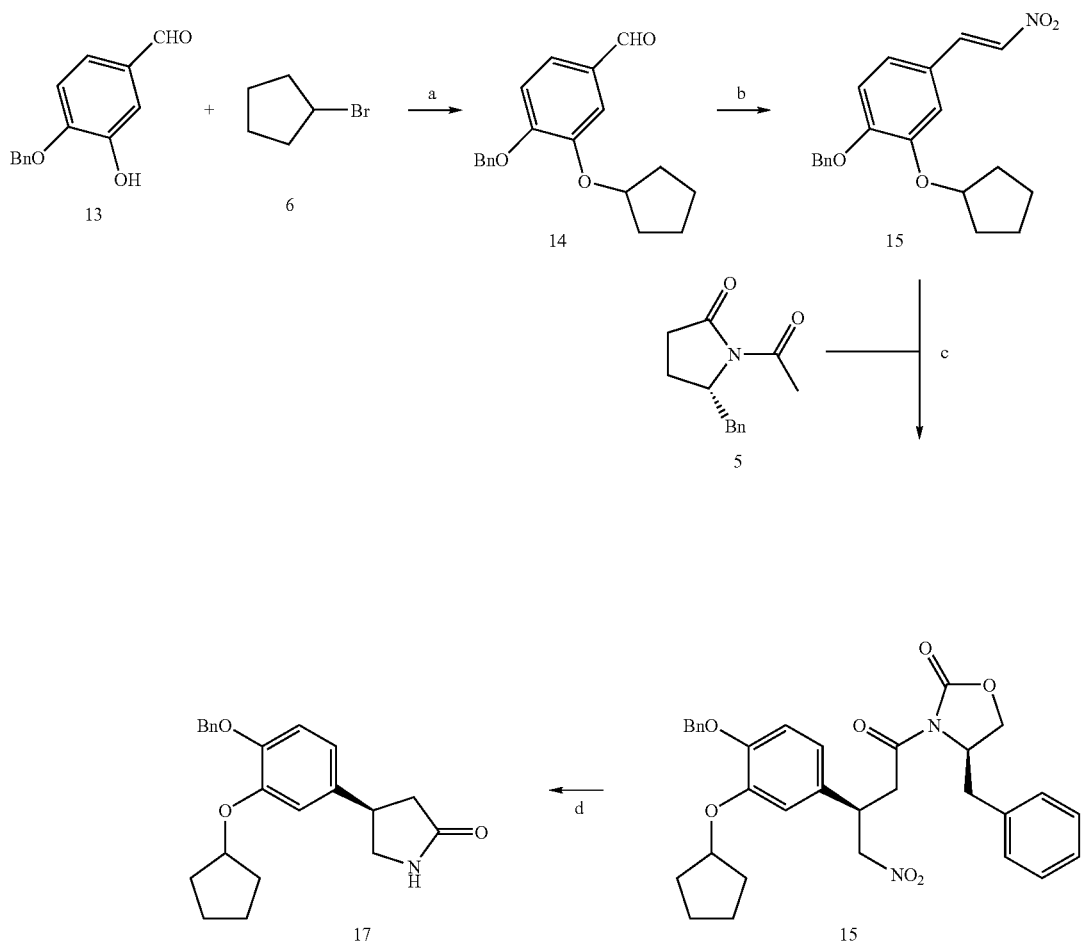

Reagents and conditions: a) K₂CO₃, DMF, rt; b) CH₃NO₂, NH₄OAc—AcOH, reflux, 2 h; c) LDA; 5, THF, −78° C., then 15; d) Raney Ni, EtOH-dioxane, H₂

In further exemplary syntheses, the phenyl ring of the lactam final product in Scheme 1 may be derivatized at the 4 position as shown in Schemes 2, 3 and 4. In Scheme 3, the synthesis begins with a 4-methoxy benzaldehyde 8. The synthesis is carried out to give the lactam 12 comprising the corresponding 4-methoxybenzaldehyde substituent. In Scheme 4, 4-benzyloxybenzaldehyde was employed as starting material. The synthesis is carried through to obtain the 4-benzyloxy lactam 17. One skilled in the art will recognize that a wide variety of lactam derivatives may be obtained using different alkyls, heteroaryls, arylalkyls, heterocycloalkyls and the like at the 4 position of the benzaldehyde reactant.

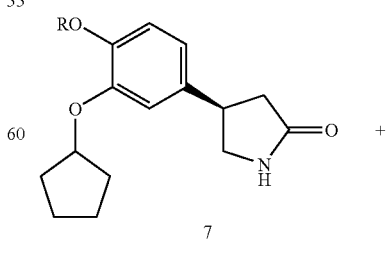

-continued

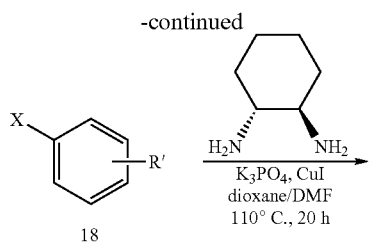

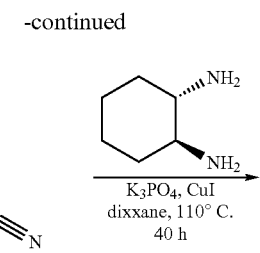

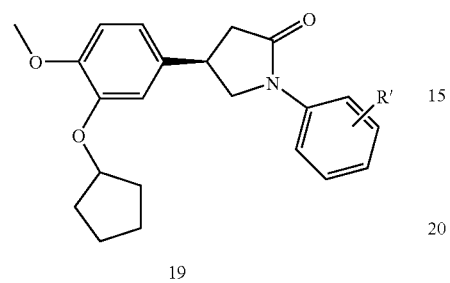

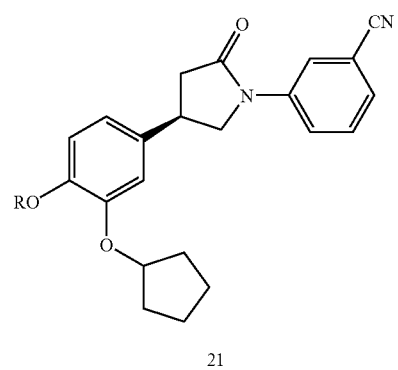

An exemplary N-substitution of the lactam product from Scheme 2 is shown in Scheme 5. An aryl halide 18 is coupled to the lactam 7 under Buchwald coupling conditions to form the N-substituted lactam 19. One skilled in the art will recognize that a wide variety of N-substituted lactam derivatives may be obtained using aryl halides variously substituted with, for example, alkyls, heteroaryls, arylalkyls, and heterocycloalkyls.

Scheme 6

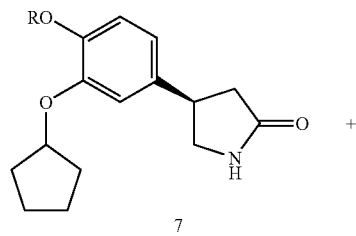

A further exemplary N-substitution of the lactam product from Scheme 1 is shown in Scheme 6. A m-cyanophenyl halide 2 is coupled to the lactam 1 to form the N-substituted lactam 3. One skilled in the art will recognize that 2 is easily substituted with an o-cyanophenyl halide or p-cyanophenyl halide to form the corresponding lactams.

Scheme 7

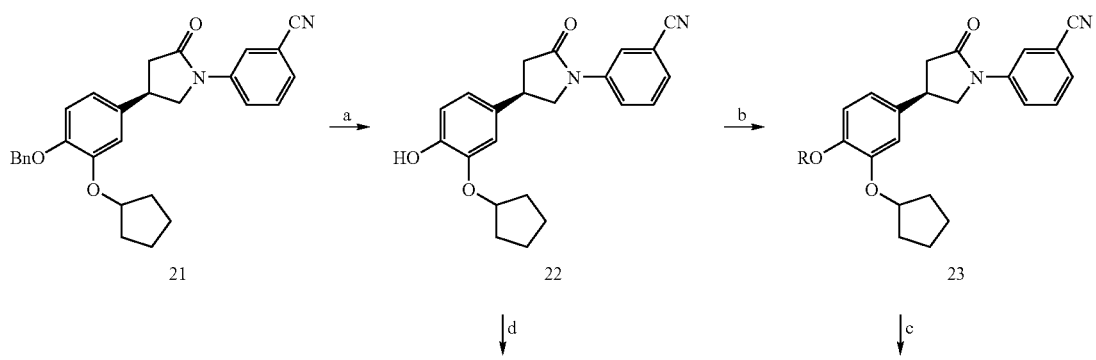

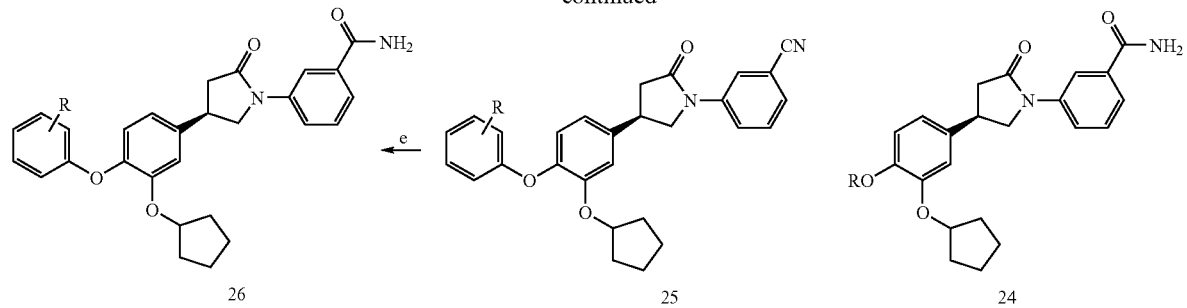

Reagents and conditions: Pd/C, EtOH/EtOAc, $H_2$; b) RX, $K_2CO_3$, DMF; c) NaOH, $H_2O_2$; d) Cu(OAc)$_2$, Et$_3$N, R—ArB(OH)$_2$, $CH_2Cl_2$, 4 Å MS, e) NaOH, $H_2O_2$.

Scheme 7 illustrates the formation of a N-substituted lactam comprising a 4-hydroxy substituent 22 through hydrogenolysis of the N-substituted lactam comprising a 4-hydroxy substituent 21. The N-substituted lactam comprising a phenyl 4-hydroxy 22 is first converted to the corresponding ether 23. Oxidation of the m-cyano substituent of 23 yields the corresponding m-amide 24. Derivatization of amides is well known in the art. Thus, one skilled in the art will immediately recognize that the amide substituent of 24 is an excellent starting point for further derivatization. Furthermore, as discussed above, the m-cyano substituent in 21 may be easily substituted with o-cyano or p-cyano, resulting in the corresponding o-amide or p-amide.

Phenol 22 can also be converted to ether 25 by a Cu-mediated coupling reaction. Oxidative hydrolysis of 25 provided 26. Thus, one skilled in the art will immediately recognize that the amide substituent of 26 is an excellent starting point for further derivatization. As discussed above, the m-cyano substituent in 21 may be easily substituted with o-cyano or p-cyano resulting in the corresponding o-amide or p-amide. Furthermore, coupling of phenol 22 with different arylboric acid would give different substituted 26.

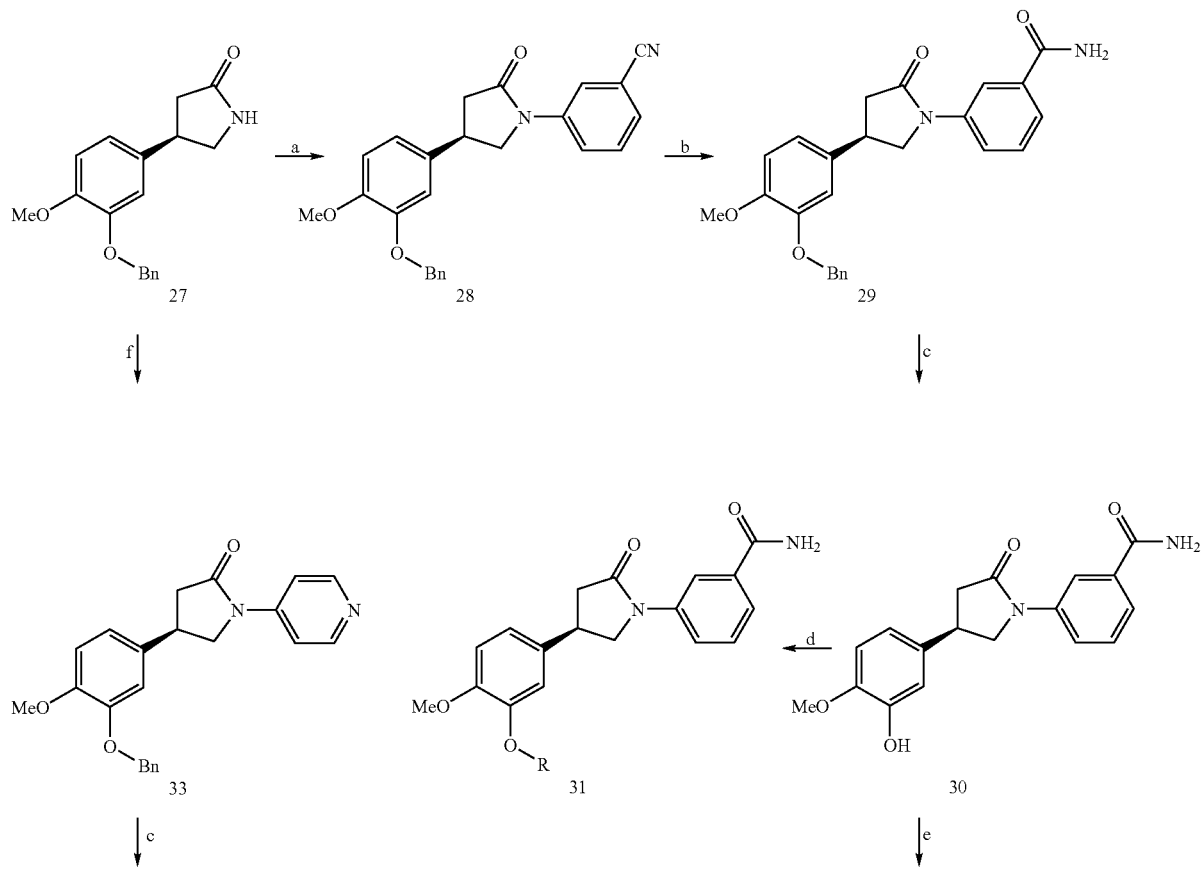

-continued

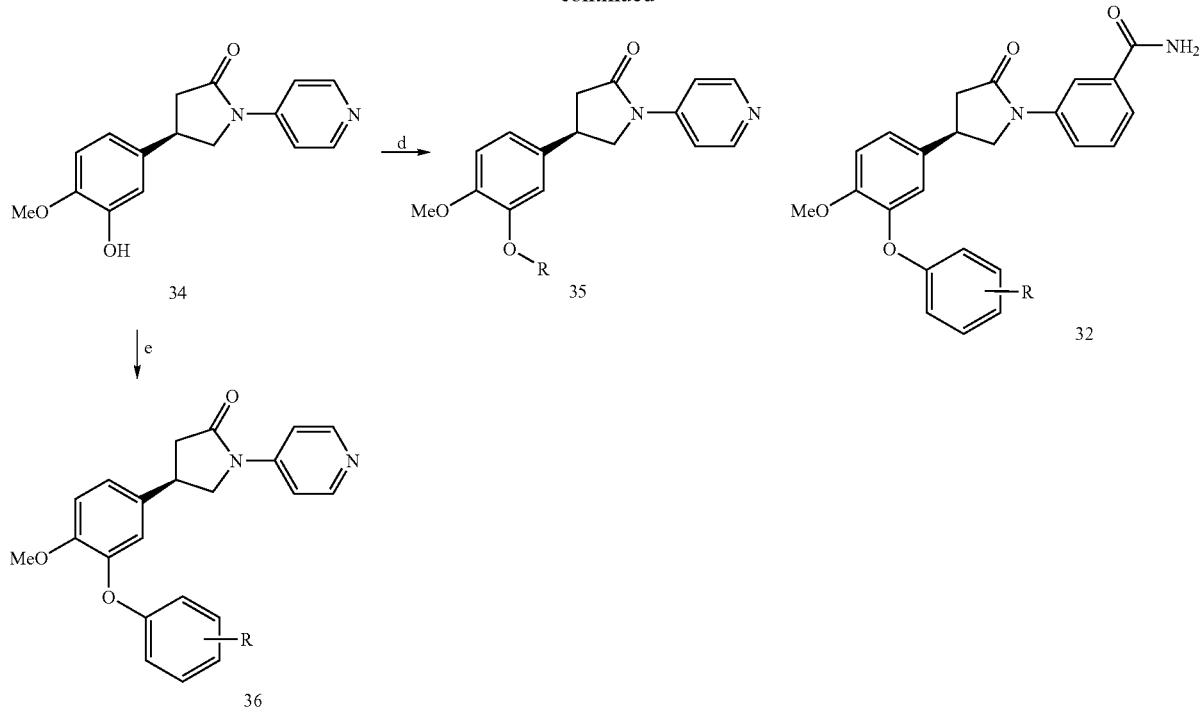

Reagents and conditions: a) K$_3$PO$_4$, CuI, trans-cyclohexanediamine, 3-iodobenzenenitrile, DMF, dioxane, 110° C., 20 h; b) NaOH, H$_2$O$_2$; c) Pd/C, EtOH, H$_2$; d) K$_2$CO$_3$, RX, DMF, e) Cu(OAc)$_2$, CH$_2$Cl$_2$, Et$_3$N, R—ArB(OH)$_2$ Scheme 8 illustrates the synthesis of lactam derivatives with varieties of substituents other than cyclopentyl group at 3-position of the phenyl ring. Bn-protected lactam 27 was employed as staring material. After coupling reaction as described above, the nitrile groups is converted to an amide group. Deprotection of the benzyl group provides the free the phenol for further modification. Etherification of phenol 30 with different halides gave 31. As described above, Cu-mediated coupling of phenol 30 with variety of boric acid gave ether 32. Furthermore, coupling of lactam 27 with bromopyridine provides lactam 33 which is deprotected and coupled with different halides or boric acid to give ether 35 and 36 respectively.

Scheme 9

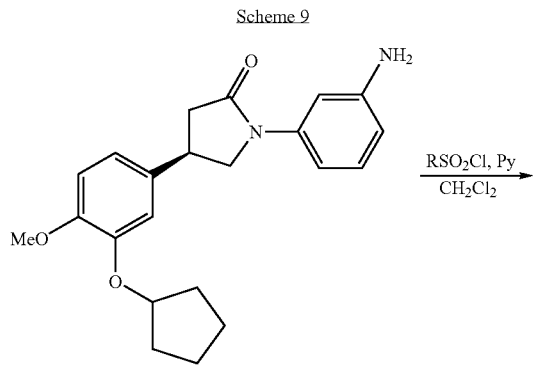

A further exemplary N-substitution of the lactam is shown in Scheme 9. Starting from 37, a variety of sulfonamides are readily synthesized by reacting the lactam with different sulfonyl chlorides. One skilled in the art will recognize that a wide variety of sulfonamides may be obtained using different alkyls, heteroaryls, aryls and sulfonyl chlorides.

-continued

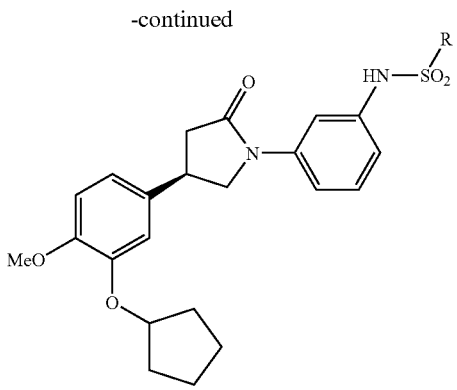

Scheme 10

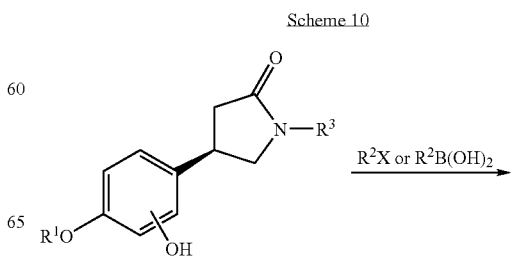

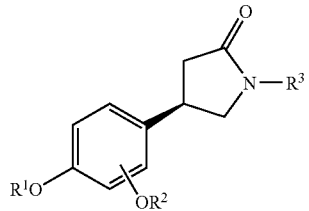

One method of synthesizing compounds of invention is shown in Scheme 10, wherein $R^1$, $R^2$ and $R^3$ are as described for Formula I of the invention. An aryl halide (XR2) is coupled with the hydroxy of a phenol group. The reaction can proceed in a suitable solvent (e.g. DMF, dioxane and the like) and a suitable base (e.g. $K_2CO_3$, and the like). The reaction proceeds in the temperature range 20-80° C. and can take up to 24 hours for completion.

Another method is to couple $R_2B(OH)_2$ with a phenol group. The reaction can proceed in a suitable solvent (e.g. methylene chloride, chloroform, and the like), a suitable catalyst (copper acetate, and the like), a suitable molecular sieve (e.g., 4 Å or the like) and a suitable base (e.g. pyridine, triethylamine, and the like). The reaction proceeds in the temperature range 20-50° C. and can take up to 48 hours for completion.

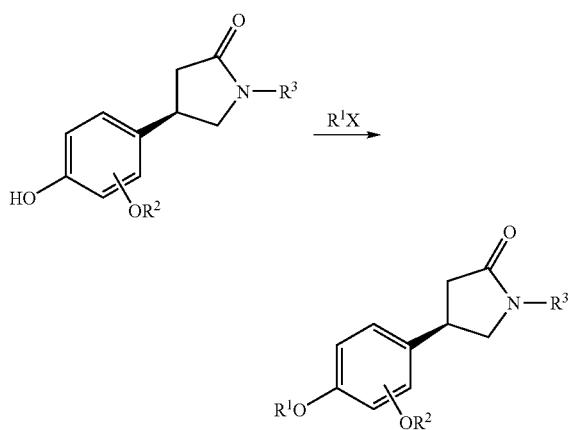

Scheme 11

One method of synthesizing compounds of invention is shown in Scheme 11, wherein $R^1$, $R^2$ and $R^3$ are as described for Formula I of the invention. An aryl halide (XR1) is coupled with the hydroxyl of a phenol group. The reaction can proceed in a suitable solvent (e.g. DMF, dioxane and the like) and a suitable base (e.g. $K_2CO_3$, and the like). The reaction proceeds in the temperature range 20-80° C. and can take up to 24 hours for completion.

Exemplary compounds produced by the methods set forth above are presented in FIG. 1.

The compounds of the invention are synthesized by either solution phase or solid phase synthesis. The solid support used is not a critical feature of the present invention provided that it is capable of binding to the carboxyl group while remaining substantially inert to the reagents utilized in the peptide synthesis procedure. For example, a starting material can be prepared by attaching an amino-protected precursor via a benzyl ester linkage to a chloromethylated resin or a hydroxymethyl resin or via an amide bond to a benzhydrylamine (BHA) resin or p-methylbenzhydrylamine (MBHA) resin. Materials suitable for us as solid supports are well known to those of skill in the art and include, but are not limited to, the following: halomethyl resins, such as chloromethyl resin or bromomethyl resin; hydroxymethyl resins; phenol resins, such as 4-(α-[2,4-dimethoxyphenyl]-Fmoc-aminomethyl) phenoxy resin; tert-alkyloxycarbonylhydrazidated resins, and the like. Such resins are commercially available and their methods of preparation are known to those of ordinary skill in the art.

The compounds of the present invention can be isolated and purified from the reaction mixture by means of purification strategies well known to those of skill in the art. For example, the compounds may be purified using known chromatographic procedures such as reverse phase HPLC, gel permeation, ion exchange, size exclusion, affinity, partition, or countercurrent distribution.

Pharmaceutical Formulations

The compounds of the present invention can be prepared and administered in a wide variety of oral, parenteral and topical dosage forms. Thus, the compounds of the present invention can be administered by injection, that is, intravenously, intramuscularly, intracutaneously, subcutaneously, intraduodenally, or intraperitoneally. Also, the compounds described herein can be administered by inhalation, for example, intranasally. Additionally, the compounds of the present invention can be administered transdermally. Accordingly, the present invention also provides pharmaceutical compositions comprising a pharmaceutically acceptable carrier or excipient and one or more compounds of the invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material.

In powders, the carrier is a finely divided solid, which is in a mixture with the finely divided active component. In tablets, the active component is mixed with the carrier having the necessary binding properties in suitable proportions and compacted in the shape and size desired.

The powders and tablets preferably contain from 5% or 10% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers and thickening agents as desired. Aqueous suspensions suitable for oral use can be made by dispersing the finely divided active component in water with viscous material, such as natural or synthetic gums, resins, methylcellulose, sodium carboxymethylcellulose and other well-known suspending agents.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The dose administered to a patient, in the context of the present invention should be sufficient to provide a beneficial therapeutic response in the patient over time. The dose is determined by the efficacy of the particular compound employed and the condition of the patient, as well as the body weight or surface area of the patient to be treated. The size of the dose also is determined by the existence, nature, and extent of any adverse side effects that accompany the administration of a particular compound in a particular patient.

The compound can also be introduced into an animal cell, preferably a mammalian cell, via a microparticles and liposomes and liposome derivatives such as immunoliposomes. The term "liposome" refers to vesicles comprised of one or more concentrically ordered lipid bilayers, which encapsulate an aqueous phase. The aqueous phase typically contains the compound to be delivered to the cell.

The liposome fuses with the plasma membrane, thereby releasing the drug into the cytosol. Alternatively, the liposome is phagocytosed or taken up by the cell in a transport vesicle. Once in the endosome or phagosome, the liposome either degrades or fuses with the membrane of the transport vesicle and releases its contents.

In current methods of drug delivery via liposomes, the liposome ultimately becomes permeable and releases the encapsulated compound at the target tissue or cell. For systemic or tissue specific delivery, this can be accomplished, for example, in a passive manner wherein the liposome bilayer degrades over time through the action of various agents in the body. Alternatively, active drug release involves using an agent to induce a permeability change in the liposome vesicle. Liposome membranes can be constructed so that they become destabilized when the environment becomes acidic near the liposome membrane (see, e.g., *PNAS* 84:7851 (1987); *Biochemistry* 28:908 (1989)). When liposomes are endocytosed by a target cell, for example, they become destabilized and release their contents. This destabilization is termed fusogenesis. Dioleoylphosphatidyl-ethanolamine (DOPE) is the basis of many "fusogenic" systems.

Such liposomes typically comprise a compound of choice and a lipid component, e.g., a neutral and/or cationic lipid, optionally including a receptor-recognition molecule such as an antibody that binds to a predetermined cell surface receptor or ligand (e.g., an antigen). A variety of methods are available for preparing liposomes as described in, e.g., Szoka et al., *Ann. Rev. Biophys. Bioeng.* 9:467 (1980), U.S. Pat. Nos. 4,186,183, 4,217,344, 4,235,871, 4,261,975, 4,485,054, 4,501,728, 4,774,085, 4,837,028, 4,235,871, 4,261,975, 4,485,054, 4,501,728, 4,774,085, 4,837,028, 4,946,787, PCT Publication No. WO 91\17424, Deamer & Bangham, *Biochim. Biophys. Acta* 443:629-634 (1976); Fraley, et al., *PNAS* 76:3348-3352 (1979); Hope et al., *Biochim. Biophys. Acta* 812:55-65 (1985); Mayer et al., *Biochim. Biophys. Acta* 858: 161-168 (1986); Williams et al., *PNAS* 85:242-246 (1988); Liposomes (Ostro (ed.), 1983, Chapter 1); Hope et al., *Chem. Phys. Lip.* 40:89 (1986); Gregoriadis, *Liposome Technology* (1984) and Lasic, *Liposomes: from Physics to Applications* (1993)). Suitable methods include, for example, sonication, extrusion, high pressure/homogenization, microfluidization, detergent dialysis, calcium-induced fusion of small liposome vesicles and ether-fusion methods, all of which are well known in the art.

In certain embodiments of the present invention, it is desirable to target the liposomes of the invention using targeting moieties that are specific to a particular cell type, tissue, and the like. Targeting of liposomes using a variety of targeting moieties (e.g., ligands, receptors, and monoclonal antibodies) has been previously described (see, e.g., U.S. Pat. Nos. 4,957, 773 and 4,603,044).

Standard methods for coupling targeting agents to liposomes can be used. These methods generally involve incorporation into liposomes lipid components, e.g., phosphatidylethanolamine, which can be activated for attachment of targeting agents, or derivatized lipophilic compounds, such as lipid-derivatized bleomycin. Antibody targeted liposomes can be constructed using, for instance, liposomes which incorporate protein A (see Renneisen et al., *J. Biol. Chem.,* 265:16337-16342 (1990) and Leonetti et al., *PNAS* 87:2448-2451 (1990).

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The quantity of active component in a unit dose preparation may be varied or adjusted from 0.1 mg to 10 g, more typically 1.0 mg to 1 g, most typically 10 mg to 500 mg, according to the particular application and the potency of the active component. The composition can, if desired, also contain other compatible therapeutic or diagnostic agents. Administration can be accomplished via single or divided doses.

The Methods

The present invention also provides methods for treating or ameliorating HIV disease and related diseases. The method includes administering a therapeutically effective dosage of at least one compound of the invention to a subject suffering from HIV disease or HIV-related diseases. The invention also provides a method of combination therapy in which one or more compound of the invention is administered in combination with one or more other compound having activity against HIV disease or HIV-related disease.

Dosage levels of approximately 0.02 to approximately 10.0 grams of a compound of the invention per day are useful in the treatment or prevention of retroviral infection, such as HIV infection, AIDS or AIDS-related complex (ARC), with oral doses 2 to 5 times higher. For example, HIV infection can be treated by administration of from about 0.1 to about 100 milligrams of compound per kilogram of body weight from one to four times per day. In one embodiment, dosages of about 100 to about 400 milligrams of compound are administered orally every six hours to a subject. The specific dosage level and frequency for any particular subject is varied and will depend upon a variety of factors, including the activity of the specific compound the metabolic stability and length of action of that compound, the age, body weight, general health, sex, and diet of the subject, mode of administration, rate of excretion, drug combination, and severity of the particular condition.

The invention provides methods for inhibiting the replication of drug resistant HIV mutants. The high replication rate of HIV leads to genetic variants (mutants), especially when selective pressure is introduced in the form of drug treatment. The mutants frequently display resistance to anti-viral agents previously administered to the patient. Switching agents or using combination therapies may decrease or delay resistance, but because viral replication is not completely suppressed in single drug treatment or even with a two-drug combination, drug-resistant viral strains ultimately emerge. Triple drug combinations employing one (or two) nucleoside analogs and two (or one) non-nucleoside inhibitor (NNI) targeting RT provide a very promising therapy to overcome the drug resistance problem. RT mutant strains resistant to such a triple action drug combination would most likely not be able to function.

Dozens of mutant strains have been characterized as resistant to NNI compounds, including L1001, K103N, V106A, E138K, Y181C and Y188H. In particular, the Y181C and K103N mutants may be the most difficult to treat, because they are resistant to most of the NNI compounds that have been examined.

In an exemplary embodiment, the compound of the invention utilized in the methods set forth herein has the formula:

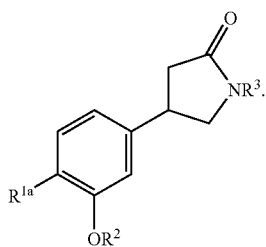

The symbol $R^{1a}$ is a members independently selected from H, and $OR^{1b}$. $R^{1b}$ is a member selected from substituted or unsubstituted alkyl, substituted or unsubstituted cycloalkyl, substituted or unsubstituted heteroalkyl, and substituted or unsubstituted aryl. $R^2$ represents H, substituted or unsubstituted alkyl, substituted or unsubstituted cycloalkyl, substituted or unsubstituted heteroalkyl, or substituted or unsubstituted aryl. $R^3$ is a member selected from substituted or unsubstituted aryl and substituted or unsubstituted heteroaryl.

Combination Therapies

In numerous embodiments, the compounds of the present invention are administered in combination with one or more additional compounds or therapies. For example, multiple reverse transcriptase inhibitors can be co-administered, or one or more compound of the invention can be administered in conjunction with another therapeutic compound. In one embodiment, the other therapeutic agent is one that is used to prevent or treat HIV infection. In another embodiment, the other therapeutic agent is an agent used to treat an opportunistic infection associated with HIV infection and/or to treat or prevent HIV infection.

Suitable therapeutic agents for use in combination with the compounds of the present invention include, but are not limited to, protease inhibitors, non-nucleoside reverse transcriptase inhibitors, nucleoside reverse transcriptase inhibitors, antiretroviral nucleosides, entry inhibitors as well as other anti-viral agents effective to inhibit or treat HIV infection. Further examples of suitable therapeutic agents include, but are not limited to, zidovudine, didanosine, stavudine, interferon, lamivudine, adefovir, nevirapine, delaviridine, loviride, saquinavir, indinavir, and AZT. Other suitable therapeutic agents include, but are not limited to, antibiotics or other anti-viral agents, e.g., acyclovir.

Other combination therapies known to those of skill in the art can be used in conjunction with the compositions and methods of the present invention.

As explained above, it has now been discovered that pyrrolidones of the invention have anti-viral activity. As such, the compounds of the invention can be used to inhibit a wide variety of viruses and, thus, to treat a wide variety of viral infections in a human. Viruses that can be inhibited using the compounds of the invention include, but are not limited, to DNA viruses, RNA viruses as well as retroviruses. Examples of viruses that can be inhibited using the compounds include, but are not limited to, Herpes viruses, Hepatitis (A, B and C) viruses, influenza viruses, POX viruses, Rhino viruses and HTLV (Human T-cell Leukemia) viruses (e.g., HTLV 1 and 2). Based on their anti-viral activity, those of skill in the art are aware of other viruses that can be treated using compounds of the invention.

Assays for Modulators of Reverse Transcriptase

Modulation of a reverse transcriptase, and corresponding modulation of HIV and viral infection, preferably inhibition, can be assessed using a variety of in vitro and in vivo assays, including cell-based models. Such assays can be used to test for inhibitors and activators of reverse transcriptase, and, consequently, inhibitors and activators of HIV infection and HIV-associated diseases. Such modulators of reverse transcriptase are useful for treating disorders related to HIV infection, as described herein. Modulators of reverse transcriptase are tested using either recombinant, chemically synthesized or naturally occurring reverse transcriptase.

Preferred modulators of the invention are those that act to decrease reverse transcriptase activity at the protein level. Preferred modulators also include those that decrease expression of reverse transcriptase at the nucleic acid level, e.g., inhibitors of the reverse transcriptase promoter, compounds that increase chromosome accessibility of the reverse transcriptase gene, compounds that decrease reverse transcriptase RNA stability and processing, and compounds that decrease reverse transcriptase RNA levels in the cytoplasm or nucleus.

Measurement of HIV infection modulation with a reverse transcriptase inhibitor, can be performed using a variety of assays, in vitro, in vivo, and ex vivo, as described herein. A suitable physical, chemical or phenotypic change that affects activity, e.g., enzymatic activity, cell proliferation (e.g., CD4+ lymphocyte proliferation), HIV replication, expression of HIV proteins, or ligand or substrate binding can be used to assess the influence of a test compound on the polypeptide of this invention. When the functional effects are determined using intact cells or animals, one can also measure a variety of effects, such as, viral RNA levels or viral titers in serum, ligand binding, transcriptional changes to both known and uncharacterized genetic markers (e.g., northern blots), changes in cell metabolism, changes related to cellular proliferation, viral marker expression, DNA synthesis, marker and dye dilution assays (e.g., GFP and cell tracker assays), etc.

In Vitro Assays

Assays to identify compounds with reverse transcriptase modulating activity can be performed in vitro. As described below, the assay can be either solid state or soluble.

The protein may be bound to a solid support, either covalently or non-covalently. Often, the in vitro assays of the invention are substrate or ligand binding or affinity assays, either non-competitive or competitive. Other in vitro assays include measuring changes in spectroscopic (e.g., fluorescence, absorbance, refractive index), hydrodynamic (e.g., shape), chromatographic, or solubility properties for the protein.

In one embodiment, a high throughput-binding assay is performed in which the reverse transcriptase or a fragment thereof is contacted with a potential modulator and incubated for a suitable amount of time. In one embodiment, the potential modulator is bound to a solid support, and the reverse transcriptase is added. In another embodiment, the reverse transcriptase is bound to a solid support. A wide variety of assays can be used to identify reverse transcriptase-modulator binding, including labeled protein-protein binding assays, electrophoretic mobility shifts, immunoassays, enzymatic assays such as kinase assays, and the like. In some cases, the binding of the candidate modulator is determined through the use of competitive binding assays, where interference with binding of a known ligand or substrate is measured in the presence of a potential modulator. The modulator or the known ligand or substrate is bound first, and then the competitor is added. After the reverse transcriptase is washed, interference with binding, either of the potential modulator or of the known ligand or substrate, is determined. Often, either the potential modulator or the known ligand or substrate is labeled.

Cell-Based In Vivo assays

In another embodiment, reverse transcriptase is expressed in a cell, and functional, e.g., physical and chemical or phenotypic, changes are assayed to identify modulators of reverse transcriptase and modulators of HIV replication and HIV infected cells. Cells expressing reverse transcriptase can also be used in binding assays and enzymatic assays. Any suitable functional effect can be measured, as described herein. For example, cellular morphology (e.g., cell volume, nuclear volume, cell perimeter, and nuclear perimeter), ligand binding, lymphocyte proliferation, apoptosis, viral marker expression, GFP positivity and dye dilution assays (e.g., cell tracker assays with dyes that bind to cell membranes), DNA synthesis assays (e.g., $^3$H-thymidine and fluorescent DNA-binding dyes such as BrdU or Hoechst dye with FACS analysis), are all suitable assays to identify potential modulators using a cell based system. Suitable cells for such cell based assays include both primary cells such as PBMCs, lymphocytes (e.g., CD4+), neutrophils, polymorphonuclear leukocytes, and other phagocytic cells and cell lines, e.g., Jurkat cells, BJAB cells, etc. The reverse transcriptase can be naturally occurring or recombinant.

Cellular reverse transcriptase RNA and polypeptide levels can be determined by measuring the level of protein or mRNA. The level of reverse transcriptase or proteins related to reverse transcriptase are measured using immunoassays such as western blotting, ELISA and the like with an antibody that selectively binds to the reverse transcriptase polypeptide or a fragment thereof. For measurement of mRNA, amplification, e.g., using PCR, LCR, or hybridization assays, e.g., northern hybridization, RNAse protection, dot blotting, are preferred. The level of protein or mRNA is detected using directly or indirectly labeled detection agents, e.g., fluorescently or radioactively labeled nucleic acids, radioactively or enzymatically labeled antibodies, and the like, as described herein.

Alternatively, reverse transcriptase expression can be measured using a reporter gene system, e.g., utilizing a fusion protein or a gene linked to a reverse transcriptase promoter. Such a system can be devised using an reverse transcriptase protein promoter operably linked to a reporter gene such as chloramphenicol acetyltransferase, firefly luciferase, bacterial luciferase, β-galactosidase and alkaline phosphatase. Furthermore, the protein of interest can be used as an indirect reporter via attachment to a second reporter such as red or green fluorescent protein (see, e.g., Mistili & Spector, *Nature Biotechnology* 15:961-964 (1997)). The reporter construct is typically transfected into a cell. After treatment with a potential modulator, the amount of reporter gene transcription, translation, or activity is measured according to standard techniques known to those of skill in the art.

Animal Models

Animal models of HIV infection also find use in screening for modulators of reverse transcriptase. Similarly, transgenic animal technology including gene knockout technology, for example as a result of homologous recombination with an appropriate gene targeting vector, or gene overexpression, will result in the absence or increased expression of the reverse transcriptase. The same technology can also be applied to make knock-out cells. When desired, tissue-specific expression or knockout of the reverse transcriptase protein may be necessary.

Knock-out cells and transgenic mice can be made by insertion of a marker gene or other heterologous gene into an endogenous reverse transcriptase gene site in the mouse genome via homologous recombination. Such mice can also be made by substituting an endogenous reverse transcriptase with a mutated version of the reverse transcriptase gene by mutating an endogenous reverse transcriptase, e.g., by exposure to carcinogens.

A DNA construct is introduced into the nuclei of embryonic stem cells. Cells containing the newly engineered genetic lesion are injected into a host mouse embryo, which is re-implanted into a recipient female. Some of these embryos develop into chimeric mice that possess germ cells partially derived from the mutant cell line. Therefore, by breeding the chimeric mice it is possible to obtain a new line of mice containing the introduced genetic lesion (see, e.g., Capecchi et al., *Science* 244:1288 (1989)). Chimeric targeted mice can be derived according to Hogan et al., *Manipulating the Mouse Embryo: A Laboratory Manual*, Cold Spring Harbor Laboratory (1988) and *Teratocarcinomas and Embryonic Stem Cells: A Practical Approach*, Robertson, ed., IRL Press, Washington, D.C., (1987).

Solid State and Soluble High Throughput Assays

In one preferred embodiment, high throughput screening methods involve providing a combinatorial small organic molecule or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487-493 (1991) and Houghton et al., *Nature* 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology,* 14(3):309-314 (1996) and PCT/US96/10287), carbohydrate libraries (see, e.g., Liang et al., *Science,* 274:1520-1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

In one embodiment the invention provides soluble assays using a reverse transcriptase protein, or a cell or tissue expressing an reverse transcriptase, either naturally occurring or recombinant. In another embodiment, the invention provides solid phase based in vitro assays in a high throughput format, where the reverse transcriptase is attached to a solid phase. Any one of the assays described herein can be adapted for high throughput screening.

In the high throughput assays of the invention, either soluble or solid state, it is possible to screen up to several thousand different modulators or ligands in a single day. This methodology can be used for reverse transcriptase in vitro, or for cell-based or membrane-based assays comprising an reverse transcriptase protein. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (e.g., 96) modulators. If 1536 well plates are used, then a single plate can easily assay from about 100-about 1500 different compounds. It is possible to assay many plates per day; assay screens for up to about 6,000, 20,000, 50,000, or more than 100,000 different compounds are possible using the integrated systems of the invention.

For a solid state reaction, the protein of interest or a fragment thereof, e.g., an extracellular domain, or a cell or membrane comprising the protein of interest or a fragment thereof as part of a fusion protein can be bound to the solid state component, directly or indirectly, via covalent or non covalent linkage. A tag for covalent or non-covalent binding can be any of a variety of components. In general, a molecule which binds the tag (a tag binder) is fixed to a solid support, and the tagged molecule of interest is attached to the solid support by interaction of the tag and the tag binder.

A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, etc.) Antibodies to molecules with natural binders such as biotin are also widely available and appropriate tag binders; see, SIGMA Immunochemicals 1998 catalogue SIGMA, St. Louis Mo.).

Similarly, any haptenic or antigenic compound can be used in combination with an appropriate antibody to form a tag/tag binder pair. Thousands of specific antibodies are commercially available and many additional antibodies are described in the literature. For example, in one common configuration, the tag is a first antibody and the tag binder is a second antibody that recognizes the first antibody. In addition to antibody-antigen interactions, receptor-ligand interactions are also appropriate as tag and tag-binder pairs. For example, agonists and antagonists of cell membrane receptors (e.g., cell receptor-ligand interactions such as transferrin, c-kit, viral receptor ligands, cytokine receptors, chemokine receptors, interleukin receptors, immunoglobulin receptors and antibodies, the cadherein family, the integrin family, the selectin family, and the like; see, e.g., Pigott & Power, *The Adhesion Molecule Facts Book I* (1993). Similarly, toxins and venoms, viral epitopes, hormones (e.g., opiates, steroids, etc.), intracellular receptors (e.g. which mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors.

Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly gly sequences of between about 5 and 200 amino acids. Such flexible linkers are known to persons of skill in the art. For example, poly(ethelyne glycol) linkers are available from Shearwater Polymers, Inc. Huntsville, Ala. These linkers optionally have amide linkages, sulfhydryl linkages, or heterofunctional linkages.

Tag binders are fixed to solid substrates using any of a variety of methods currently available. Solid substrates are commonly derivatized or functionalized by exposing all or a portion of the substrate to a chemical reagent that fixes a chemical group to the surface, which is reactive with a portion of the tag binder. For example, groups that are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature. See, e.g., Merrifield, *J. Am. Chem. Soc.* 85:2149-2154 (1963) (describing solid phase synthesis of, e.g., peptides); Geysen et al., *J. Immun. Meth.* 102:259-274 (1987) (describing synthesis of solid phase components on pins); Frank & Doring, *Tetrahedron* 44:60316040 (1988) (describing synthesis of various peptide sequences on cellulose disks); Fodor et al., *Science,* 251:767-777 (1991); Sheldon et al., *Clinical Chemistry* 39(4):718-719 (1993); and Kozal et al., *Nature Medicine* 2(7):753759 (1996) (all describing arrays of biopolymers fixed to solid substrates). Non-chemical approaches for fixing tag binders to substrates include other common methods, such as heat, cross-linking by UV radiation, and the like.

General Procedures for the Examples Section

General Procedure I: Alkylation of Phenol

A mixture of phenol (1 mmol), potassium carbonate (2.5 mmol), alkyl halide (2 mmol) and DMF were added to a round bottom flask and then stirred for 20 h. The mixture was diluted with EtOAc (or $CH_3Cl$) and filtered. The filtrate was washed with water brine, dried over $MgSO_4$, and concentrated under reduced pressure. The residue was purified by column chromatography on silica gel to give pure product.

General Procedure II. Coupling of Lactam with Aryl Halide

A mixture of lactam (0.5 mmol), potassium phosphate (0.9 mmol), aryl halide (0.75 mmol), 1,2-trans-cyclohexanediamine (60 μL) and CuI (80 mg) in DMF (5 mL) and dioxane (5 mL) under $N_2$ was stirred and heated at 110° C. for 20 h. After cooling to r.t., the mixture was diluted with EtOAc and filtered. The filtrate was washed with saturated $NH_4Cl$, dried over $MgSO_4$, and concentrated under reduced pressure. The residue was purified by column chromatography on silica gel to give pure product.

General Procedure III. Coupling of Phenol with Arylboronic Acid

To a solution of phenol (0.1 mmol), copper acetate (0.15 mmol), arylboronic acid (0.12 mmol), and 4 Å Molecular Sieves ("MS") (100 mg) in $CH_2Cl_2$ (1 mL) was added $(CH_3)_3N$ (0.22 mmol). The flask was sealed and the mixture was stirred for 24 h. The reaction mixture was then diluted with 10 mL of $CH_2Cl_2$ and filtered. The filtrate was washed with saturated $NH_4Cl$, dried over $MgSO_4$, and concentrated under reduced pressure. The residue was purified by column chromatography on silica gel or preparative liquid chromatography-mass spectrometry LC-MS to give pure product.

General Procedure IV. Conversion of Benzonitrile to Benzamide

Benzonitrile (1 mmol) in 10 mL EtOH was added to a round bottom flask and heated. To this solution was added 50 μL of 25% NaOH solution followed by 0.5 mL 30% hydrogen peroxide. The mixture was stirred at 45 to 50° C. for 4 h, cooled to r.t., and concentrated under reduced pressure. The residue was dissolved in EtOAc (or $CH_3Cl$), washed with saturated $NH_4Cl$, dried over $MgSO_4$, and concentrated under reduced pressure. The residue was purified by column chromatography on silica gel to give pure product.

General Procedure V. Amidation of 3-[4-(3-cyclopentyloxy-4-methoxyphenyl)-2-oxo-pyrrolidin-1-yl]benzoic acid A mixture of 3-[4-(3-cyclopentyloxy-4-methoxyphenyl)-2-oxo-pyrrolidin-1-yl]benzoic acid (0.1 mmol), amine (0.12 mmol), $(CH_3)_3N$ (0.15 mmol) and HATU (0.15 mmol) was stirred at r.t. for 5 h. The mixture was washed with saturated $NH_4Cl$, dried over $MgSO_4$, and concentrated under reduced pressure. The residue was purified by column chromatography on silica gel or preparative liquid chromatography-mass spectrometry (LC-MS) to give pure product.

General Procedure VII: Preparation of Halopyridine Carboxylic Acid Bis-(4-methoxy-benzamide Pyridine carboxylic acid (1 mmol) was heated with $SOCl_2$ (2 mL) at 80° C. for 12 h. After cooling down to r.t., excess $SOCl_2$ was removed under vacuum and flushed twice with toluene. The resulting mixture was diluted with anhydrous $CH_2Cl_2$ (3 mL) and cooled to 0° C. Bis-(4-methoxybenzyl) amine (1.1 mmol) was then added, followed by $(CH_3)_3N$ (1.5 mmol). The mixture was then warmed up to r.t. and stirred for 1 h. $CH_2Cl_2$ (10 mL) was added to dilute the mixture which was washed twice with water (5 mL). The resulting organic layer was washed with brine and dried over $MgSO_4$. After filtration and concentration under reduced pressure, the residue was purified by column chromatography on silica gel to give pure product.

General Procedure VII.: Preparation of Sulfonamide from Aniline and Sulfonyl Chloride A mixture of aniline (0.05 mmol) and sulfonyl chloride (0.05 mmol) in $CH_2Cl_2$ (1 mL) and pyridine (0.2 mL) was created in a dry reaction tube. The mixture was stirred overnight and diluted with 10 mL $CH_2Cl_2$, washed with 1 N HCl, then water, and finally brine. The product was dried over $MgSO_4$, filtered, and concentrated under reduced pressure. Purification of the residue by column chromatography on silica gel or preparative LC-MS gave pure product.

General Procedure VIII. Preparation of Urea or Thiourea from Aniline and Isocyanate or Isothiocyanate A mixture of aniline (0.05 mmol) and urea or thiourea (0.05 mmol) in benzene or toluene (1 mL) was created in a dry reaction tube. The mixture was stirred at r.t. or heated to 80° C. After completion of the reaction, the solvent was removed. The residue was purified by column chromatography on silica gel or by preparative LC-MS to give pure product.

General Procedure IX: Deprotection of OBn by Hydrogenation with Pd/C

To a round bottom flask was added Bn protected phenol (2 mmol) and EtOH (50 mL). 10% Pd/C was added dropwise and the mixture was stirred under $H_2$ atmosphere with a $H_2$ balloon for 4 to 10 h. The mixture was filtered through celite and concentrated under reduced pressure. The residue was purified by column chromatography on silica gel to give pure product.

General Procedure X: Amination of Aniline by Reductive Amination

A mixture of aniline (0.02 mmol), aldehyde (0.024 mmol), $NaB(OAc)_3H$ (0.2 mmol), AcOH (0.06 mmol), and DMF (0.5 mL) was created in a dry reaction flask. The mixture was stirred for 20 h and then concentrated. The residue was dissolved in EtOAc, washed with brine, dried over $MgSO_4$, and concentrated under reduced pressure. The residue was purified by column chromatography on silica gel or by preparative LC-MS to give pure product.

EXAMPLE 1

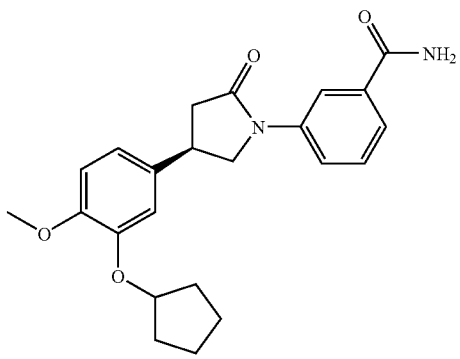

1.1 Preparation of 3-[4-(3-cyclopentyloxy-4-methoxyphenyl)-2-oxo-pyrrolidin-1-yl]-benzonitrile, according to General Procedure II A mixture of 4-(3-cyclopentyloxy-4-methoxyphenyl)-pyrrolidin-2-one (1.5 g, 5 mmol), 3-bromobenzonitrile (1.36 g, 7.5 mmol), potassium phosphate (1.9 g, 9.8 mmol), and 1,2-trans-cyclohexanediamine (60 μL) was created in a dry round bottom flask under nitrogen containing DMF (9 mL) and dioxane (9 mL). The mixture was stirred and CuI (100 mg) was added. The resulting reaction mixture was heated to 110° C. with stirring under $N_2$ for 20 h, and then cooled to r.t. The mixture was diluted with EtOAc and then filtered. The filtrate was washed with saturated aqueous solutions of $NH_4Cl$ and brine, dried over $MgSO_4$, and concentrated under reduced pressure. Chromatography on silica gel (EtOAc:hexane=1:3 to 1:1) gave 1.81 g of 3-[4-(3-cyclopentyloxy-4-methoxyphenyl)-2-oxo-pyrrolidin-1-yl]benzonitrile. Yield: 90%.

1.1a 3-[4-(3-cyclopentyloxy-4-methoxyphenyl)-2-oxo-pyrrolidin-1-yl]-benzonitrile $^1$H NMR (CDCl$_3$): δ 7.97 (1H, s), 7.93 (1H, d, J=8.1 Hz), 7.46 (1H, d, J=8.1 Hz), 7.44 (1H, d, J=8 Hz), 6.81 (3H, m), 4.76 (1H, brs), 4.16 (1H, t, J=11.8 Hz), 3.84 (3H, s), 3.84 (1H, t, J=11.8 Hz) 3.66 (1H, m) 3.03 (1H, q, J=8.4 Hz), 2.81 (1H, q, J=8.4 Hz), 1.60-1.89 (8H, m).

1.2 Preparation of 3-[4-(3-cyclopentyloxy-4-methoxyphenyl)-2-oxo-pyrrolidin-1-yl]benzamide according to General Procedure IV To a solution of 3-[4-(3-cyclopentyloxy-4-methoxyphenyl)-2-oxo-pyrrolidin-1-yl]benzonitrile (12.5 mg, 0.033 mmol) in ethanol (0.5 mL) was added 2 μL of a 25% NaOH solution, followed by 29 μL of 35% $H_2O_2$. The temperature of the reaction mixture was kept at 50° C. for 3 h. Upon completion, 5% $H_2SO_4$ was added until the mixture was neutral (pH 7). The reaction mixture was extracted with EtOAc and dried with $MgSO_4$. Purification on silica gel afforded the product as a white solid. Yield: 94%.

1.2.a 3-[4-(3-cyclopentyloxy-4-methoxyphenyl)-2-oxo-pyrrolidin-1-yl]-benzamide $^1$H NMR (CDCl$_3$): δ 8.01 (brs, 1H), 7.90 (dd, 1H, J=1.5, 8.1 Hz), 7.58 (d, 1H, J=7.7 Hz), 7.46 (t, 1H, J=8.0 Hz), 6.86-6.80 (m, 3H), 6.24 (brs, 1H), 5.68 (brs, 1H), 4.79-4.75 (m, 1H), 4.21 (dd, 1H, J=8.3, 9.4 Hz), 3.84 (s, 3H), 3.90 (dd, 1H, J=7.6, 9.4 Hz), 3.69-3.61 (m, 1H), 3.01 (dd, 1H, J=8.7, 17.0 Hz), 2.79 (dd, 1H, J=8.9, 17.0 Hz), 1.96-1.82 (m, 6H), 1.65-1.59 (m, 2H).

EXAMPLE 2

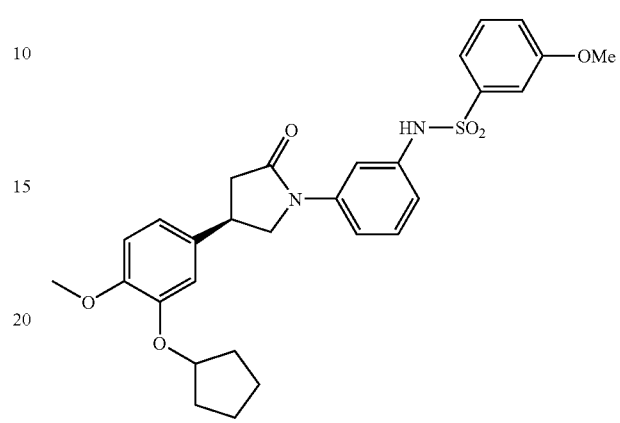

2.1 Preparation of N-{3-[4-(3-cyclopentyloxy-4-methoxyphenyl)-2-oxo-pyrrolidin-1-yl]-phenyl}-3-methoxybenzenesulfonamide according to General Procedure VII A mixture of 1-(3-aminophenyl)-4-(3-cyclopentyloxy-4-methoxyphenyl)-pyrrolidin-2-one (15 mg, 0.04 mmol) and 3-methoxybenzenesulfonyl chloride (10 mg, 0.042 mol) in pyridine (30 μL) and CH$_2$Cl$_2$ (0.5 mL) was created in a dry round bottom flask. The mixture was stirred at r.t. for 15 h. After removal of solvent, the residue was purified by preparative LC-MS to give 14 mg of N-{3-[4-(3-cyclopentyloxy-4-methoxyphenyl)-2-oxo-pyrrolidin-1-yl]phenyl}-3-methoxybenzenesulfonamide. Yield: 65%.

2.1.a N-[3-{4-(3-cyclopentyloxy-4-methoxyphenyl)-2-oxo-pyrrolidin-1-yl]-phenyl}-3-methoxybenzenesulfonamide $^1$H NMR (CDCl$_3$): δ 7.70 (1H, brs), 7.37 (1H, d, J=7.8 Hz), 7.19-7.29 (4H, m), 7.00 (2H, t, J=7.6 Hz); 6.83 (1H, d, J=8 Hz), 6.79 (1H, s), 6.79 (1H, d, J=8 Hz), 4.76 (1H, brs), 4.11 (1H, t, J=8.4 Hz), 3.83 (3H, s), 3.78 (1H, t, J=8.4 Hz), 3.60 (1H, m), 3.02 (1H, q, J=8.1 Hz), 2.85 (1H, q, J=8.1 Hz), 1.61-1.88 (8H, m).

EXAMPLE 3

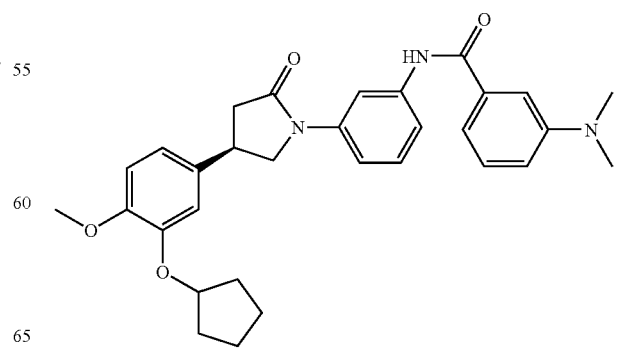

3.1 Preparation of N-{3-[4-(3-cyclopentyloxy-4-methoxyphenyl)-2-oxo-pyrrolidin-1-yl]-phenyl}-3-dimethylaminobenzamide A mixture of carboxylic acid (0.02 mmol), diisopropylethylamine (0.04 mmol) and 1-(3-dimethylaminopropyl)-3-ethylcarbodiimide hydrochloride (EDC) (0.024 mmol, 1.2 eq) in dry THF was stirred for 20 min before the addition of 1-(3-aminophenyl)-4-(3-cyclopentyloxy-4-methoxyphenyl)pyrrolidin-2-one (0.02 mmol). The reaction mixture was then stirred for 30 h. Concentration under reduced pressure and purification by column chromatography on silica gel gave the desired product.

3.1.a N-{3-[4-(3-cyclopentyloxy-4-methoxyphenyl)-2-oxo-pyrrolidin-1-yl]-phenyl}-3-dimethylaminobenzamide
MS m/z 514.2 (M+1).

EXAMPLE 4

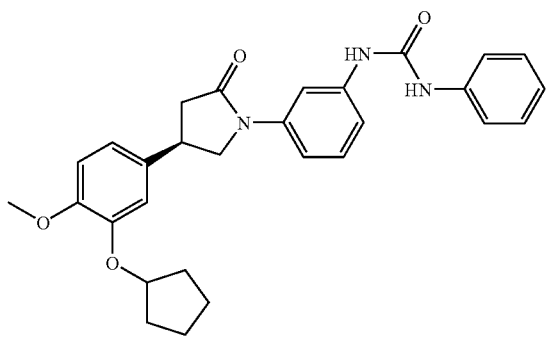

4.1 Preparation of 1-{3-[4-(3-cyclopentyloxy-4-methoxyphenyl)-2-oxo-pyrrolidin-1-yl]-phenyl}-3-phenylurea according to General Procedure VIII A solution of 1-(3-aminophenyl)-4-(3-cyclopentyloxy-4-methoxyphenyl)-pyrrolidin-2-one (8 mg, 0.022 mmol) in $CH_2Cl_2$ (0.5 mL) was created. Phenylisocyanate (0.023 mmol) was added, and the reaction mixture was stirred for 20 h. Concentration under reduced pressure and purification by column chromatography on silica gel (EtOAc:Hexane=1:2) gave the desired product.

4.1.a 1-{3-[4-(3-cyclopentyloxy-4-methoxyphenyl)-2-oxo-pyrrolidin-1-yl]-phenyl}-3-phenylurea
MS m/z: 486.2 (M+1)

EXAMPLE 5

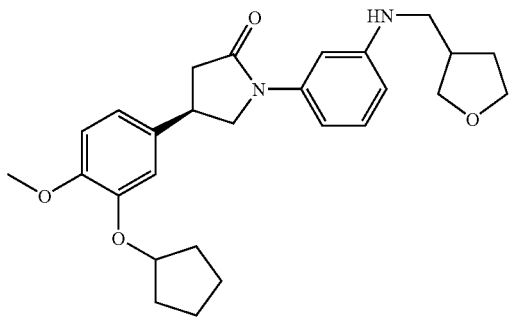

5.1 Preparation of 4-(3-cyclopentyloxy-4-methoxyphenyl)-1-{3-[(tetrahydrofuran-3-ylmethyl)amino]phenyl}-pyrrolidin-2-one according to General Procedure X A mixture of 1-(3-aminophenyl)-4-(3-cyclopentyloxy-4-methoxyphenyl)-pyrrolidin-2-one (8 mg, 0.02 mmol), (tetrahydrofuran-3-yl)-acetaldehyde (0.024 mmol), $NaB(OAc)_3H$ (0.2 mmol), and AcOH (0.06 mmol) in DMF (0.5 mL) was stirred for 20 h. After concentration under reduced pressure, the residue was dissolved in EtOAc (3 mL), washed with brine (2×3 mL), and dried over $Na_2SO_4$. Concentration and chromatography on silica gel (EtOAc: Hexane=1:1) gave 5.2 mg of the desired product. Yield: 57%.

5.1.a 4-(3-cyclopentyloxy-4-methoxyphenyl)-1-{3-[(tetrahydrofuran-3-ylmethyl)amino]phenyl}-pyrrolidin-2-one
MS m/z: 451.2 (M+1).

EXAMPLE 6

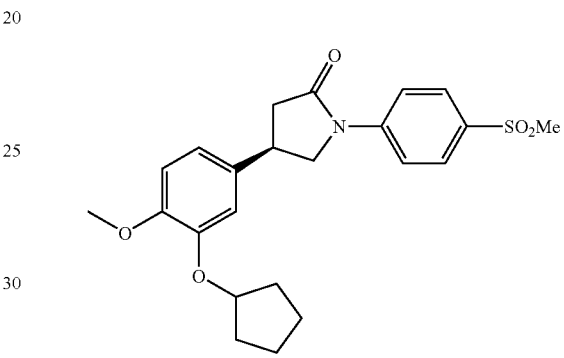

6.1 Preparation of 4-(3-cyclopentyloxy-4-methoxyphenyl)-1-(4-methylsulfanylphenyl)-pyrrolidin-2-one according to General Procedure II A mixture of 4-(3-cyclopentyloxy-4-methoxy-phenyl)-pyrrolidin-2-one (276 mg, 1 mmol), 1-bromo-3-methylsulfanylbenzene (1.4 mmol), $K_3PO_4$ (1.5 mmol), DMF (3 mL), dioxane (3 mL) and 1,2-trans-cyclohexanediamine (25 μL) was stirred under $N_2$ for 5 min before CuI (35 mg) was added. The reaction mixture was heated at 110° C. for 20 h under $N_2$ with stirring, then cooled down to r.t. The mixture was diluted with EtOAc, washed with saturated $NH_4Cl$ (3×10 mL) and dried over $Na_2SO_4$. Concentration and chromatography of the residue on silica gel gave 282 mg of pure product. Yield: 71%.

6.1.a 4-(3-cyclopentyloxy-4-methoxyphenyl)-1-(4-methylsulfanylphenyl)-pyrrolidin-2-one
$^1H$ NMR ($CDCl_3$): δ 7.33-7.30 (m, 2H), 7.21-7.20 (m, 2H), 6.88-6.86 (m, 3H), 4.81-4.78 (m, 1H), 3.87-3.85 (m, 4H), 3.78-3.70 (m, 1H), 3.01-2.90 (m, 2H), 2.75 (dd, 1H, J=9.1, 18.4 Hz), 1.95-1.82 (m, 6H), 1.63-1.60 (m, 2H).

6.2 Preparation of 4-(3-cyclopentyloxy-4-methoxyphenyl)-1-(4-methanesulfonylphenyl)-pyrrolidin-2-one After cooling 4-(3-Cyclopentyloxy-4-methoxyphenyl)-1-(3-methylsulfanylphenyl)-pyrrolidin-2-one (90 mg, 0.23 mmol) in $CH_2Cl_2$ (5 mL) in an ice water bath, m-CPBA (2.2 eq) was added and the reaction mixture was stirred for 3 h at r.t. The reaction was quenched with 10% $Na_2S_2O_3$ and the mixture was extracted with EtOAc. The organic layer was washed with saturated solutions of $NaHCO_3$ and brine and dried over $Na_2SO_4$. Concentration and purification by silica gel afforded 94 mg of a white solid. Yield: 95%.

6.2.a 4-(3-cyclopentyloxy-4-methoxphenyl)-1-(4-methanesulfonylphenyl)-pyrrolidin-2-one $^1$H NMR (CDCl$_3$): δ 18.12 (d, 1H, J=7.8 Hz), 7.73-7.69 (m, 1H), 7.60-7.56 (m, 1H), 7.34 (brs, 1H), 6.99-6.85 (m, 3H), 4.80 (brs, 1H), 4.26 (brs, 1H), 3.84-3.75 (m, 4H), 3.66 (brs, 1H), 3.22 (s, 3H), 2.98-2.92 (m, 1H), 2.77 (dd, 1H, J=9.7, 16.9 Hz), 1.90-1.77 (m, 6H), 1.63-1.60 (m, 2H).

EXAMPLE 7

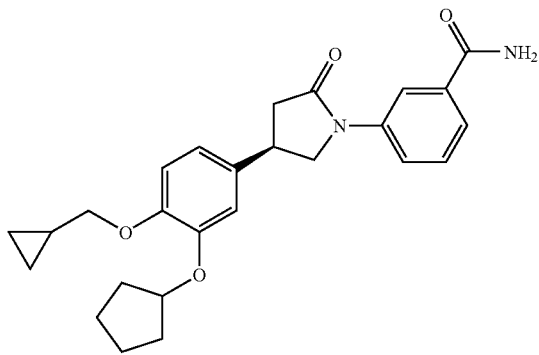

7.1 Preparation of 4-benzyloxy-3-cyclopentyloxybenzaldehyde according to General Procedure I To a solution of 4-benzyloxy-3-hydroxybenzaldehyde (5 g, 21.9 mmol) in DMF (50 mL) was added cyclopentyl bromide (4.7 mL, 43.8 mmol) and K$_2$CO$_3$ (12.1 g, 87.6 mmol). The reaction mixture was stirred at r.t. overnight. K$_2$CO$_3$ was then filtered from the mixture. The mixture was extracted with EtOAc, and the organic layer was washed with water (2×) and then brine, and finally dried over Na$_2$SO$_4$. The product was concentrated under reduced pressure and purified by silica gel to provide a colorless oil which solidified to a white solid upon standing. Yield: 98%.

7.1.a 4-benzyloxy-3-cyclopentyloxy-benzaldehyde $^1$H NMR (CDCl$_3$): 9.83 (s, 1H), 7.44-7.26 (m, 7H), 6.99 (d, 1H, J=8.2 Hz), 5.21 (s, 2H), 4.88-4.86 (m, 1H), 1.99-1.82 (m, 6H), 1.68-1.56 (m, 2H).

7.2 Preparation of 1-benzyloxy-2-cyclopentyloxy-4-(2-nitro-vinyl)-benzene

A mixture of 4-benzyloxy-3-cyclopentyloxybenzaldehyde (6.3 g, 21.3 mmol) in AcOH (13 mL) and CH$_3$NO$_2$ (5.8 mL, 106.5 mmol) was created. NH$_4$OAc (3.3 g, 42.5 mmol) was added and the mixture was heated under reflux for 2 h. After cooling to r.t., the mixture was extracted with CH$_2$Cl$_2$. The organic layer separated and washed with water, sat. NaHCO$_3$, and sat. NaCl, and dried over Na$_2$SO$_4$. Concentration under reduced pressure and purification by column chromatography on silica gel (CH$_2$Cl$_2$/hexane) gave 3.2 g of yellow solids. Yield: 44%.

7.2.a 1-benzyloxy-2-cyclopentyloxy-4-(2-nitro-vinyl)-benzene $^1$H NMR (CDCl$_3$): 7.94 (d, 1H, J=13.5 Hz), 7.49 (d, 1H, J=13.6 Hz), 7.41-7.32 (m, 5H), 7.10-7.04 (m, 2H), 6.93 (d, 1H, J=8.3 Hz), 5.18 (s, 2H), 4.84-4.82 (m, 1H), 1.93-1.83 (m, 6H), 1.76-1.74 (m, 2H).

7.3 Preparation of 4-benzyl-3-[3-(4-benzyloxy-3-cyclopentyloxyphenyl)-4-nitrobutyryl]-oxazolidin-2-one A mixture of 3-acetyl-4-benzyl-oxazolidin-2-one (2.1 g, 9.4 mmol) in THF (40 mL) was stirred under N$_2$ at −78° C. Lithium diisopropyl amine (5.2 mL, 10.3 mmol, 2.0 M in heptane/THF/ethylbenzene) was then added dropwise. The mixture was stired for 20 min. 1-Benzyloxy-2-cyclopentyloxy-4-(2-nitrovinyl)benzene (3.2 g, 9.4 mmol) dissolved in 20 mL THF was cannulated over and the mixture was stirred for 2 h at −78° C. After quenching the reaction sat. NH$_4$Cl, the mixture was warmed to r.t., extracted with CH$_3$Cl, washed with water and brine, dried and concentrated. Filtration of the solids with 1:1 hexane/EtOAc, afforded 4 g of white solids. Yield: 75%.

7.3.a 4-benzyl-3-[3-(4-benzyloxy-3-cyclopentyloxyphenyl)-4-nitrobutyryl]-oxazolidin-2-one $^1$H NMR (CDCl$_3$): 7.42-7.26 (m, 8H), 7.17 (d, 2H, J=7.6 Hz), 6.86 (d, 1H, J=8.2), 6.81 (s, 1H), 6.74 (d, 1H, J=8.2), 5.06 (s, 2H), 4.80 (t, 1H, J=4.06 Hz), 4.72-4.55 (m, 4H), 4.13-4.07 (m, 3H), 3.53 (dd, 1H, J=7.7, 17.2 Hz), 3.30-3.21 (m, 2H), 2.73 (dd, 1H, J=9.7, 13.3 Hz), 1.89-1.78 (m, 6H), 1.64-1.63 (m, 2H).

7.4 Preparation of 4-(4-benzyloxy-3-cyclopentyloxyphenyl)-pyrrolidin-2-one 4 g of 4-benzyl-3-[3-(4-benzyloxy-3-cyclopentyloxyphenyl)-4-nitrobutyryl]-oxazolidin-2-one was partially dissolved in 75 mL EtOAc/75 mL EtOH/75 mL dioxane. To this suspension was added a suspension of Raney Ni. The mixture was then flushed three times with H$_2$. The mixture was then stirred under H$_2$ at 50° C. overnight and filtered through celite. Concentration under reduced pressure and purification by column chromatography on silica gel 2.2 g of the desired product. Yield: 88%.

7.4.a 4-(4-benzyloxy-3-cyclopentyloxyphenyl)-pyrrolidin-2-one $^1$H NMR (CDCl$_3$): 7.44-7.42 (m, 2H), 7.37-7.34 (m, 2H), 7.31 (d, 1H, J=4.9 Hz), 6.87 (d, 1H, J=8.2 Hz), 6.79 (d, 1H, J=2.0 Hz), 6.72 (dd, 1H, J=2.06, 8.2 Hz), 5.86 (brs, 1H), 5.08 (s, 2H), 4.81 (m, 1H), 3.75 (t, 1H, J=8.4 Hz), 3.62 (p, 1H, J=8.5 Hz), 3.38 (dd, 1H, J=7.5, 9.2 Hz), 2.71 (dd, 1H, J=8.8, 16.9 Hz), 2.47 (dd, 1H, J=8.9, 16.9 Hz), 1.90-1.81 (m, 6H), 1.64-1.61 (m, 2H); MS m/z 352.20 [M+H]$^+$.

7.5 Preparation of 3-[4-(4-benzyloxy-3-cyclopentyloxyphenyl)-2-oxo-pyrrolidin-1-yl]-benzonitrile according to General Procedure II A mixture of 4-(4-benzyloxy-3-cyclopentyloxyphenyl) pyrrolidin-2-one, 3-bromobenzonitrile, phenol (0.1 mmol), copper acetate (0.15 mmol), arylboronic acid (0.12 mmol), 4 Å Molecular Sieves ("MS") (~100 mg) and CH$_2$Cl$_2$ (1 mL) was created in a dry round bottom flask. (CH$_3$)$_3$N (0.22 mmol) was added, the flask was sealed, and the mixture was stirred for 24 h. The reaction mixture was then diluted with 10 mL of CH$_2$Cl$_2$ and filtered. The filtrate was washed with saturated NH$_4$Cl, dried over MgSO$_4$, and concentrated under reduced pressure. The residue was purified by column chromatography on silica gel or preparative liquid chromatography-mass spectrometry LC-MS to give pure product. Yield: 74%.

7.5.a 3-[4-(4-benzyloxy-3-cyclopentyloxyphenyl)-2-oxo-pyrrolidin-1-yl]-benzonitrile MS m/z 453.2 [M+H]$^+$.

7.6 Preparation of 3-[4-(3-cyclopentyloxy-4-hydroxyphenyl)-2-oxo-pyrrolidin-1-yl]-benzonitrile according to General Procedure IX 200 mg of Pd—C was added to 3-[4-(4-benzyloxy-3-cyclopentyloxyphenyl)-2-oxo-pyrrolidin-1-yl]-benzonitrile (1.7 g. 3.8 mmol) in EtOH/EtOAc and flushed with H$_2$ three times. The mixture was then stirred under H$_2$ at r.t. for 72 h. The mixture was filtered through celite and then concentrated under reduced pressure. The residue was then dissolved in EtOAc and washed with 2N HCl, sat. NaHCO$_3$, and sat. NaCl. Purification by silica gel gave 350 mg of the desired product. Yield: 26%.

7.6.a 3-[4-(3-cyclopentyloxy-4-hydroxyphenyl)-2-oxo-pyrrolidin-1-yl]benzonitrile $^1$H NMR (CDCl$_3$): 7.97-7.92 (m, 2H), 7.50-7.42 (m, 2H), 6.90 (d, 1H, J=10.9 Hz), 6.77-6.74 (m, 2H), 5.59 (s, 1H), 4.88-4.80 (m, 1H), 4.16 (t, 1H, J=8.6 Hz), 3.83 (t, 1H, J=7.7 Hz), 3.65 (p, 1H, J=8.3 Hz), 3.02 (dd, 1H, J=8.7, 17.1 Hz), 2.79 (dd, 1H, J=8.9, 17.1 Hz), 1.94-1.80 (m, 6H), 1.72-1.66 (m, 2H); MS m/z 363.20 [M+H]$^+$.

7.7 Preparation of 3-[4-(3-cyclopentyloxy-4-cyclopropylmethoxyphenyl)-2-oxo-pyrrolidin-1-yl]benzonitrile according to General Procedure I A mixture of 3-[4-(3-cyclopentyloxy-4-hydroxyphenyl)-2-oxo-pyrrolidin-1-yl]benzonitrile (1 mmol), potassium carbonate (2.5 mmol), cyclopropylmethyl bromide (2 mmol) in DMF was created in a dry round bottom flask. The mixture was stirred for 20 h, diluted with EtOAc (or CH$_3$Cl) and filtered through celite. The filtrate was washed with water and then brine, dried over MgSO$_4$, and concentrated under reduced pressure. The residue was purified by column chromatography on silica gel to give pure product. Yield: 83%.

7.7.a 3-[4-(3-cyclopentyloxy-4-cyclopropylmethoxy-phenyl)-2-oxo-pyrrolidin-1-yl]-benzonitrile $^1$H NMR (CDCl$_3$): 7.97-7.92 (m, 2H), 7.50-7.42 (m, 2H), 6.88 (d, 1H, J=7.9 Hz), 6.79-6.77 (m, 2H), 4.78 (brs, 1H), 4.16 (t, 1H, J=8.4 Hz), 3.85-3.80 (m, 3H), 3.69-3.61 (m, 1H), 3.01 (dd, 1H, J=8.7, 17.1 Hz), 2.80 (dd, 1H, J=9.0, 17.2 Hz), 1.87-1.83 (m, 6H), 1.65-1.56 (m, 2H), 1.29-1.27 (m, 1H), 0.60 (dd, 2H, J=5.8, 13.2 Hz), 0.33 (dd, 2H, J=4.4, 9.2 Hz).

7.8 Preparation of 3-[4-(3-cyclopentyloxy-4-cyclopropylmethoxyphenyl)-2-oxo-pyrrolidin-1-yl]benzamide according to General Procedure IV To a dry round bottom flask was added 3-[4-(3-cyclopentyloxy-4-cyclopropylmethoxy-phenyl)-2-oxo-pyrrolidin-1-yl]benzonitrile (1 mmol) in 10 mL EtOH.

This mixture was then heated, and 50 µL of 25% NaOH solution followed by 0.5 mL 30% H$_2$O$_2$ was added to the solution. The mixture was stirred at 45 to 50° C. for 4 h, cooled to r.t., and concentrated under reduced pressure. The residue was dissolved in EtOAc (or CH$_3$Cl), washed with saturated NH$_4$Cl, dried over MgSO$_4$, and concentrated under reduced pressure. The residue was purified by column chromatography on silica gel to give pure product. Yield: 87%.

7.8.a 3-[4-(3-cyclopentyloxy-4-cyclopropylmethoxyphenyl)-2-oxo-pyrrolidin-1-yl]benzamide $^1$H NMR (CDCl$_3$): 8.08, (s, 1H), 7.88 (d, 1H, J=8.0 Hz), 7.59 (d, 1H, J=7.6 Hz), 7.46 (t, 1H, J=8.0 Hz), 6.88 (d, 1H, J=8.0 Hz), 6.80-6.77 (m, 2H), 6.27 (brs, 1H), 5.62 (brs, 1H), 4.79 (brs, 1H), 4.21 (t, 1H, J=8.7 Hz), 3.90 (t, 1H, J=7.8 Hz), 3.82 (d, 2H, J=6.8 Hz), 3.69-3.60 (m, 1H), 3.01 (dd, 1H, J=8.7, 17.0 Hz), 2.79 (dd, 1H, J=9.0, 17.0 Hz), 1.87-1.84 (m, 6H), 1.29-1.25 (m, 3H), 0.60 (dd, 2H, J=5.9, 12.8 Hz), 0.33 (dd, 2H, J=4.6, 10.3 Hz).

EXAMPLE 8

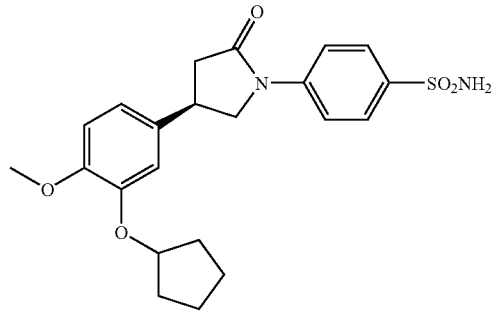

8.1 Preparation of 4-[4-(3-cyclopentyloxy-4-methoxyphenyl)-2-oxo-pyrrolidin-1-yl]-benzenesulfonamide 4-Iodobenzensulfonamide Rink resin was prepared according to the procedure by Spear et al. (*Tetrahedron Letters*, 37:81145-1148 (1998)). A mixture of 4-iodobenzensulfonamide Rink resin (0.125 mmol), K$_3$PO$_4$ (1 mmol), 4-(3-cyclopentyloxy-4-methoxy-phenyl)-pyrrolidin-2-one (0.375 mmol), CuI (0.07 mmol), and trans-1,2-diamine-cyclohexane (0.07 mmol) in DMF (0.5 mL) was stirred at 110° C. overnight. The reaction was then cooled to r.t. and the resin filtered and washed with water, methanol and CH$_2$Cl$_2$ several times. The resin was then treated with a 25% TFA/DCM solution for 30 min. Concentration of the mixture gave a brown residue which was purified by prep LC-MS to obtain 9.3 mg of product. Yield: 17%.

8.1.a 4-[4-(3-cyclopentyloxy-4-methoxyphenyl)-2-oxo-pyrrolidin-1-yl]-benzenesulfonamide $^1$H NMR (CDCl$_3$): 7.93 (d, 2H, J=8.9 Hz), 7.81 (d, 2H, J=8.9 Hz), 6.93-6.78 (m, 3H), 4.78-4.74 (m, 3H), 4.20 (t, 1H, J=9.3 Hz), 3.89-3.83 (m, 4H), 3.70-3.62 (m, 1H), 3.03 (dd, 1H, J=8.6, 17.2 Hz), 2.82 (dd, 1H, J=9.0, 17.1 Hz), 1.92-1.81 (m, 4H), 1.63-1.59 (s, 4H); MS m/z 431.20 [M+H]$^+$.

EXAMPLE 9

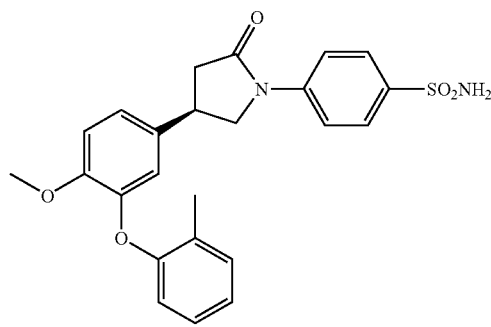

9.1 Preparation of 4-(3-benzyloxy-4-methoxyphenyl)-2-oxo-pyrrolidine-1-carboxylic acid tert-butyl ester Boc protection of 4-(3-Benzyloxy-4-methoxy-phenyl)-pyrrolidin-2-one was performed using the procedure from (Hansen et al., *Tetrahedron Letters* 36:498949-8952 (1995)).

9.2 Preparation of 4-(3-hydroxy-4-methoxyphenyl)-2-oxo-pyrrolidine-1-carboxylic acid tert-butyl ester To a solution of 4-(3-benzyloxy-4-methoxyphenyl)-2-oxo-pyrrolidine-1-carboxylic acid tert-butyl ester (0.8 g, 2.02 mmol) in 20 mL of ethanol was added 10% Pd/C (60 mg). After flushing with $H_2$, the mixture was stirred under $H_2$ for 3 h, filtered, and concentrated to give crude phenol which was used in the next step without purification.

9.3 Preparation of 4-(4-methoxy-3-o-tolyloxyphenyl)-2-oxo-pyrrolidine-1-carboxylic acid tert-butyl ester according to General Procedure III A mixture of 4 Å MS, phenol (0.98 mmol), 2-methylphenyl boronic acid (1.5 mmol), $Cu(OAc)_2$ (1.5 mmol), $(CH_3)_3N$ (4.9 mmol) in $CH_2Cl_2$ (5 mL) was stirred at r.t. overnight. The mixture was filtered through celite and then concentrated under reduced pressure. The residue was purified by silica gel to obtain a colorless product. Yield: 33%.

9.3.a 4-(4-methoxy-3-o-tolyloxyphenyl)-2-oxo-pyrrolidine-1-carboxylic acid tert-butyl ester $^1$H NMR (CDCl$_3$): 7.25-7.23 (m, 1H), 7.12-7.10 (m, 1H), 7.05-7.01 (m, 1H), 6.98-6.92 (m, 2H), 6.74 (dd, 1H, J=0.8, 8.0 Hz), 6.63 (d, 1H, J=2.0 Hz), 4.07 (dd, 1H, J=8.0, 10.8 Hz), 3.86 (s, 3H), 3.57 (dd, 1H, J=8.8, 10.8 Hz), 3.41-3.37 (m, 1H), 2.80 (dd, 1H, J=8.4, 17.2 Hz), 2.59 (dd, 1H, J=10.0, 17.2 Hz), 2.29 (s, 3H), 1.56 (s, 9H); MS m/z 298.20 [M-tBoc].

9.4 Preparation of 4-(4-methoxy-3-o-tolyloxyphenyl)-pyrrolidin-2-one

The deprotection of 4-(4-methoxy-3-o-tolyloxyphenyl)-2-oxo-pyrrolidine-1-carboxylic acid tert-butyl ester was performed in a 25% TFA/DCM solution. This solution was stirred for 30 min at r.t. After neutralization and extraction in EtOAc, the mixture was concentrated under reduced pressure to give the desired compound without purification.

9.4.a 4-(4-methoxy-3-o-tolyloxyphenyl)-pyrrolidin-2-one
MS m/z 298.20 [M+H]$^+$.

9.5 Preparation of 4-[4-(4-methoxy-3-o-tolyloxyphenyl)-2-oxo-pyrrolidin-1-yl]-benzenesulfonamide The coupling of 4-(4-methoxy-3-o-tolyloxyphenyl)-pyrrolidin-2-one (0.28 mmol) onto resin (0.09 mmol) and subsequent deprotection was performed according to Example 8 to obtain 20 mg of the desired product. Yield: 49%.

9.5.a 4-[4-(4-methoxy-3-o-tolyloxyphenyl)-2-oxo-pyrrolidin-1-yl]-benzenesulfonamide $^1$H NMR (CDCl$_3$): 7.91 (d, 2H, J=8.8 Hz), 7.76 (d, 2H, J=8.8 Hz), 7.24-7.22 (m, 1H), 7.13-7.09 (m, 1H), 7.04-7.00 (m, 1H), 6.98 (d, 2H, J=1.2 Hz), 6.74 (dd, 1H, J=0.8, 8.0 Hz), 6.68 (s, 1H), 4.78 (s, 2H), 4.15 (dd, 1H, J=8.0, 9.6 Hz), 3.87 (s, 3H), 3.79 (dd, 1H, J=7.6, 9.2 Hz), 3.64-3.56 (m, 1H), 2.97 (dd, 1H, J=8.8, 17.2 Hz), 2.73 (dd, 1H, J=9.2, 17.2 Hz), 2.29 (s, 3H); MS m/z 453.20 [M+H]$^+$.

EXAMPLE 10

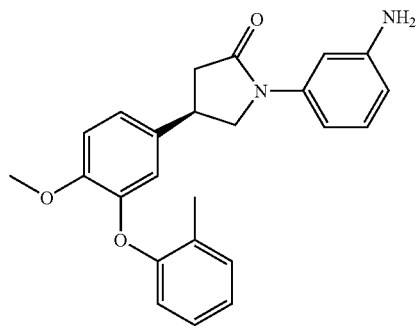

10.1 Preparation of 4-(3-benzyloxy-4-methoxyphenyl)-1-(3-nitrophenyl)-pyrrolidin-2-one according to General Procedure II To a round bottom flask was added 4-(3-benzyloxy-4-methoxyphenyl)-pyrrolidin-2-one (1.76 g, 5.9 mmol), 3-iodonitrobenzene (2.64 g, 10.6 mmol), $K_3PO_4$ (2.79 g, 13 mmol), trans-cyclohexanediamine (50 µL), DMF (8 mL) and dioxane (8 mL). The mixture was stirred under $N_2$ for 5 min before the addition of CuI (150 mg). After heating to 110° C. for 20 h, the mixture was cooled to r.t. After filtration, the reaction mixture was diluted with EtOAc (100 mL), washed with saturated $NH_4Cl$, brine and dried over $Na_2SO_4$. Concentration and purification by column chromatography on silica gel (EtOAc:hexane=1:3) gave 1.4 g of the desired product. Yield: 57%.

10.2 Preparation of 1-(3-aminophenyl)-4-(3-benzyloxy-4-methoxyphenyl)-pyrrolidin-2-one To a solution of 4-(3-benzyloxy-4-methoxyphenyl)-1-(3-nitrophenyl)-pyrrolidin-2-one (100 mg) in EtOAc/EtOH (2 mL, 1:1) was added Raney Ni. The mixture was then put under vacuum and recharged with $H_2$. The mixture was stirred under $H_2$ for 10 h. After filtration, concentration gave crude product.

10.3 Protection of 1-(3-aminophenyl)-4-(3-benzyloxy-4-methoxyphenyl)-pyrrolidin-2-one Crude 1-(3-aminophenyl)-4-(3-benzyloxy-4-methoxyphenyl)-pyrrolidin-2-one (1.08 g) was dissolved in THF (20 mL). A solution of $Boc_2O$ (8 mL, 1 M) was added followed by 4-dimethylaminopyridine (DMAP) (2 eq) and diisopropylethylamine (1 mL) at 0° C. The mixture was stirred overnight at 0° C. After dilution with EtOAc (100 mL), the mixture was washed with brine (2×30 mL), and then dried over $Na_2SO_4$. Concentration and purification by column chromatography on silica gel gave 0.18 g of Boc protected product.

10.3.a 1-(3-aminophenyl)-4-(3-benzyloxy-4-methoxyphenyl)-pyrrolidin-2-one $^1$H NMR (CDCl$_3$): δ 7.54 (1H, brs), 7.48 (1H, d, J=7.6 Hz), 7.33 (1H, d, J=7.5 Hz), 7.31 (1H, m), 6.80-6.92 (3H, m), 5.28 (2H, s), 4.09 (1H, t, J=8.1), 3.90 (3H, s), 3.72 (1H, t, J=8.0 Hz), 3.56 (1H, m), 2.96 (1H, q, J=7.8 Hz), 2.69 (1H, q, J=7.9 Hz), 1.49 (18H, s).

10.4 Preparation of 1-(3-aminophenyl)-4-[3-(2,6-dimethylphenoxy)-4-methoxyphenyl]-pyrrolidin-2-one Fully protected amine (300 mg) was dissolved in EtOH (3 mL). 10% Pd/C (~20 mg) was added and it was put under vacuum and recharged with $H_2$. The solution was stirred under $H_2$ overnight and filtered. Concentration under reduced pressure gave phenol which was used for the next step. Phenol (15 mg, 0.03 mmol) was dissolved in $CH_2Cl_2$ (1 mL). $Cu(OAc)_2$ (0.04 mmol), $(CH_3)_3N$ (0.07 mmol) and 2-methylbenzeneboric acid (8 mg, 0.05 mmol) were added to a followed by 4 Å MS. The mixture was stirred at r.t. for 30 h.

After filtration, the solvent was removed under reduced pressure. The residue was dissolved in 50% THF/$CH_2Cl_2$, stirred for 2 h, concentrated and purified by preparative LC-MS to give 5.2 mg of the desired product. Yield: 43%.

10.4.a 1-(3-aminophenyl)-4-[3-(2,6-dimethylphenoxy)-4-methoxyphenyl]-pyrrolidin-2-one MS m/z 389.1 (M+1).

EXAMPLE 11

11.1 Preparation of 6-{5-[1-(3-amino-phenyl)-5-oxo-pyrrolidin-3-yl]-2-methoxy-phenoxy}-hexanenitrile according to General Procedure I To a solution of phenol (30 mg, 0.1 mmol) in DMF (0.5 mL) was added $K_2CO_3$ (28 mg, 0.2 mmol) followed by 6-bromohexanylnitrile (17 mg, 0.1 mmol). The mixture was stirred at r.t. for 15 h. After filtration, the solution was diluted with EtOAc (5 mL) and washed with water (5 mL), brine (5 mL) and dried over $Na_2SO_4$. The solvent was removed under reduced pressure and the residue was dissolved in 50% TFA/$CH_2Cl_2$, stirred for 2 h, concentrated and purified on preparative LC-MS to give 16 mg of the desired product. Yield: 40%.

11.1.a 6-{5-[1-(3-aminophenyl)-5-oxo-pyrrolidin-3-yl]-2-methoxyphenoxy}-hexanenitrile $^1$H NMR (CDCl$_3$): δ 7.82 (1H, brs), 7.29 (1H, m), 7.14 (1H, d, J=7.2 Hz), 6.91 (1H, d, J=7.2 Hz), 6.85 (1H, d, J=8 Hz), 6.81 (1H, d, J=8 Hz), 6.77 (1H, s), 5.62 (2H, brs), 4.11 (1H, t, J=8.2 Hz), 4.02 (2H, t, J=6.4 Hz), 3.82 (3H, s), 3.81 (1H, t, J=8.2 Hz), 3.61 (1H, m), 2.96 (1H, q, J=8.2 Hz), 2.77 (1H, q, J=8.2 Hz), 2.36 (2H, t, J=6.8 Hz), 1.85 (2H, m), 1.73 (2H, m) 1.65 (2H, m).

EXAMPLE 12

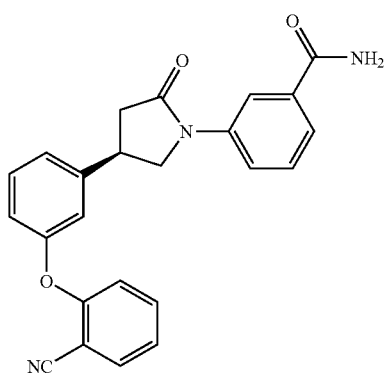

12.1 Preparation of 3-(3-benzyloxyphenyl)-4-nitro-butyric acid ethyl ester

To a dry round bottom flask was added 2.7 mL of diisopropylamine and 20 mL THF. The mixture was cooled to −78° C.
with stirring. A solution of n-BuLi (11.4 mL, 1.6 M) was added dropwise and the resulting solution was stirred for 20 min. EtOAc (1.5 mL) was added slowly to quench and the mixture was stirred for an additional 20 min. 1-Benzyloxy-3-(2-nitrovinyl)benzene (3.4 g, 13 mmol) in 50 mL THF was then added and the solution was stirred for 2 h. The mixture was warmed to r.t., quenched with sat. NH$_4$Cl solution (50 mL), extracted with EtOAc, washed with brine, dried over MgSO$_4$, and concentrated under reduced pressure. The residue was purified by column chromatography on silica gel to give 3.2 g of the desired product.

12.1.a 3-(3-benzyloxyphenyl)-4-nitro-butyric acid ethyl ester

MS m/z 344.2 (M+1).

12.2 Preparation of 4-(3-benzyloxyphenyl)-pyrrolidin-2-one

A mixture of 3-(3-benzyloxyphenyl)-4-nitrobutyric acid ethyl ester (3.2 g) in 10 mL EtOAc and 20 mL EtOH was created in a dry round bottom flask. Raney Ni was added and the resulting mixture was stirred under H$_2$ for 10 h at r.t. and filtered through celite. The solution was heated under reflux for 40 h, cooled to r.t., and concentrated. Chromatography of the residue on silica gel (EtOAc:Hexane=1:1 to 3:1) gave 1.89 g of the desired product.

12.2.a 4-(3-benzyloxyphenyl)-pyrrolidin-2-one

MS m/z 268.1 (M+1).

12.3 Preparation of 3-[4-(3-benzyloxyphenyl)-2-oxo-pyrrolidin-1-yl]benzonitrile

A mixture of 4-(3-benzyloxyphenyl)-pyrrolidin-2-one (1.8 g, 6.7 mmol), 3-bromobenzonitrile (1.83 g, 1.5 eq) and potassium phosphate (2.6 g, 1.8 eq) was created in a dry flask with a stir bar under N$_2$. This mixture was dissolved in 10 mL DMF and 10 mL dioxane. To this solution was added 60 μL of 1,2-trans-cyclohexanediamine and CuI (100 mg). The solution was stirred and heated at 100° C. under N$_2$ for 20 h, and then cooled down to r.t. EtOAc (100 mL) was added and the mixture was filtered, washed with NH$_4$Cl solution, water and brine. The solution was also dried over MgSO$_4$ and concentrated under a reduced pressure. The residue was purified by column chromatography on silica gel (EtOAc:Hexane=1:3) to give 1.36 g of the desired product. Yield: 55%.

12.3.a 3-[4-(3-benzyloxyphenyl)-2-oxo-pyrrolidin-1-yl]benzonitrile

MS m/z 369.1 (M+1).

12.4 Preparation of 3-[4-(3-benzyloxyphenyl)-2-oxo-pyrrolidin-1-yl]benzamide according to General Procedure IV To a solution of 3-[4-(3-benzyloxyphenyl)-2-oxo-pyrrolidin-1-yl]benzonitrile (1.3 g, 3.36 mmol) in 25 mL EtOH was added 25% NaOH (0.15 mL) followed by the slow addition of 1.5 mL H$_2$O$_2$ (30%). The reaction mixture was heated to 45° C. and stirred for 5 h. The mixture was then cooled down and concentrated under reduced pressure. The residue was dissolved in 100 mL EtOAc, washed with water and brine, dried over MgSO$_4$ and concentrated again. The residue was purified by column chromatography on silica gel (EtOAc:Hexane=1:3) to give 1.3 g of the desired product. Yield: 99%.

12.4.a 3-[4-(3-benzyloxyphenyl)-2-oxo-pyrrolidin-1-yl]benzamide

MS m/z 387.1 (M+1).

12.5 Preparation of 3-[4-(3-hydroxyphenyl)-2-oxo-pyrrolidin-1-yl]benzamide according to General Procedure IX To a solution of 3-[4-(3-benzyloxyphenyl)-2-oxo-pyrrolidin-1-yl]benzamide (1.2 g) in 50 mL EtOH was added 10% Pd/C (100 mg). The resulting mixture was stirred under H$_2$ for 4 h, filtered, and concentrated under reduced pressure to give 0.8 g of crude product.

12.6 Preparation of 3-{4-[3-(2-cyanophenoxy)phenyl]-2-oxo-pyrrolidin-1-yl}benzamide according to General Procedure III A mixture of 3-[4-(3-hydroxyphenyl)-2-oxo-pyrrolidin-1-yl]benzamide (30 mg), 2-cyanobenzeneboronic acid (12 mg), and copper acetate (2 eq) was created in a dry tube. The mixture was dissolved in 2 mL $CH_2Cl_2$ followed by the addition of $(CH_3)_3N$ (3 eq). The mixture was stirred at r.t. for 24 h, and then diluted with 10 mL $CH_2Cl_2$. The resulting mixture was filtered and washed with $NH_4Cl$ solution, water and brine. After removal of solvent, the residue was purified by preparative LC-MS to give 14 mg of the desired product. Yield: 35%.

12.6.a 3-{4-[3-(2-cyanophenoxy)phenyl]-2-oxo-pyrrolidin-1-yl}benzamide

MS m/z 398.4 (M+1).

EXAMPLE 13

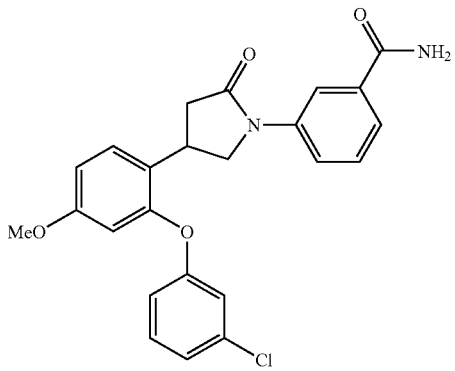

13.1 Preparation of 3-(2-benzyloxy-4-methoxyphenyl)-4-nitrobutyric acid ethyl ester To a dry round bottom flask was added 3.5 mL of diisopropylamine and 20 mL THF under $N_2$. The solution was cooled to −78° C. and stirred. A solution of n-BuLi (15 mL, 1.6 mL) was added and the reaction mixture was stirred for an additional 20 min. EtOAc (2.0 mL in 10 mL THF) was added slowly at −78° C. and the resulting solution was stirred for 20 min. 2-Benzyl-4-methoxy-1-(2-nitrovinyl)benzene (5.46 g, 19.1 mmol) was added (in 30 mL THF) and stirred for 2 h. The mixture was slowly warmed up to r.t. and quenched with sat. $NH_4Cl$ solution. The mixture was extracted with EtOAc (2×100 mL), washed with water and brine, and then dried. After removal of the solvent, the residue was purified on silica gel to give 5.3 g of the desired product. Yield: 74%.

13.1.a 3-(2-benzyloxy-4-methoxyphenyl)-4-nitrobutyric acid ethyl ester

MS m/z 374.1 (M+1).

13.2 Preparation of 4-(2-benzyloxy-4-methoxyphenyl)-pyrrolidin-2-one 3-(2-Benzyloxy-4-methoxyphenyl)-4-nitro-butyric acid ethyl ester (5.2 g) was dissolved in 20 mL EtOAc and 30 mL of EtOH. Raney Ni was added and the mixture was stirred under $H_2$ for 10 h. The mixture was filtered through celite, heated at 90° C. for 20 h and then cooled down to r.t. The mixture was then concentrated and purified on silica gel to give 3 g of the desired product. Yield: 72%.

13.2.a 4-(2-benzyloxy-4-methoxyphenyl)-pyrrolidin-2-one

MS m/z 298.1 (M+1).

13.3 Preparation of 3-[4-(2-benzyloxy-4-methoxyphenyl)-2-oxo-pyrrolidin-1-yl]benzonitrile according to General Procedure I 4-(2-Benzyloxy-4-methoxyphenyl)-pyrrolidin-2-one (2.0 g. 6.8 mmol), potassium phosphate (2.56 g, 1.8 eq), and 3-bromobenzonitrile (1.82 g, 1.5 eq) was added to a flask under $N_2$. The mixture was charged with 10 mL DMF and 10 mL dioxane followed by the addition of 1,2-trans-cyclohexanediamine (100 µL) and CuI (180 mg). The mixture was heated at 110° C. for 20 h and cooled down to r.t. Next the mixture was diluted with 150 mL EtOAc, washed with sat. $NH_4Cl$, water, and brine, and then dried. After concentration, the residue was purified on silica gel (EtOAc: Hexane=3:1) to give 2.2 g of the desired product. Yield: 81%.

13.3.a 3-[4-(2-benzyloxy-4-methoxyphenyl)-2-oxo-pyrrolidin-1-yl]benzonitrile

MS m/z 399.1 (M+1).

13.4 Preparation of 3-[4-(2-benzyloxy-4-methoxyphenyl)-2-oxo-pyrrolidin-1-yl]benzamide according to General Procedure IV 3-[4-(2-Benzyloxy-4-methoxyphenyl)-2-oxo-pyrrolidin-1-yl]benzonitrile (2 g) was dissolved in 30 mL EtOH. A solution of 25% NaOH (0.23 mL) was added followed by 2.3 mL $H_2O_2$ (30%). The mixture was heated to 45° C. for 5 h and cooled to r.t. After concentration the residue was dissolved in $CH_3Cl$ (100 mL), washed with $NH_4Cl$, water, and brine, dried over $MgSO_4$, and concentrated to give 1.83 g of crude product which was used in the next step without purification.

13.5 Preparation of 3-[4-(2-hydroxy-4-methoxyphenyl)-2-oxo-pyrrolidin-1-yl]benzamide according to General Procedure IX 3-[4-(2-Benzyloxy-4-methoxyphenyl)-2-oxo-pyrrolidin-1-yl]benzamide (1.8 g, crude) was dissolved in 50 mL of EtOH and 20 mL of EtOAc. 10% Pd/C (200 mg) was added and the mixture was stirred under $H_2$ for 20 h. After filtration and concentration, the residue was purified on silica gel to give 1.2 g of the desired product.

13.5.a 3-[4-(2-hydroxy-4-methoxyphenyl)-2-oxo-pyrrolidin-1-yl]benzamide

MS m/z 327.1 (M+1).

13.6 Preparation of 3-{4-[2-(3-chlorophenoxy)-4-methoxyphenyl]-2-oxo-pyrrolidin-1-yl}-benzamide 3-[4-(2-Hydroxy-4-methoxyphenyl)-2-oxo-pyrrolidin-1-yl]benzamide (32 mg, 0.1 mmol), 3-chlorobenzeneboronic acid (19 mg, 1.2 eq), and copper acetate (1 eq) were added to a dry tube. The mixture was charged with 2 mL $CH_2Cl_2$, $(CH_3)_3N$ (3 eq) followed by addition of 4 Å MS. The mixture was stirred for 24 h and diluted with 10 mL $CH_2Cl_2$. After filtration, the mixture was washed with $NH_4Cl$, water, and brine, and then dried. After concentration, the residue was purified by preparative LC-MS to give 7.8 mg of the desired product. Yield: 18%.

13.6.a 3-{4-[2-(3-chlorophenoxy)-4-methoxyphenyl]-2-oxo-pyrrolidin-1-yl}-benzamide MS m/z 437.1 (M+1).

EXAMPLE 14

Step A:

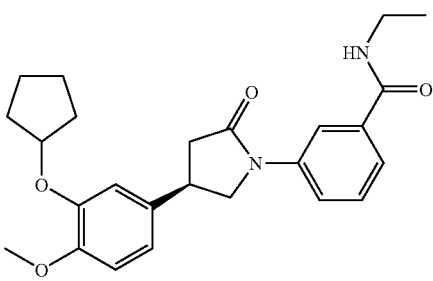

Step A:

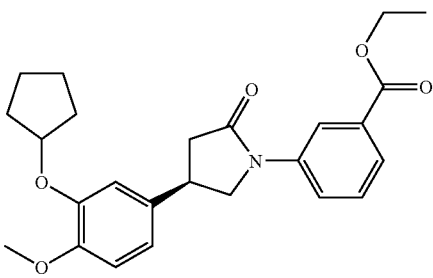

14.1 Preparation of 3-[4-(3-cyclopentyloxy-4-methoxyphenyl) -2-oxo-pyrrolidin-1-yl]benzoic acid ethyl ester A mixture of 4-(3-cyclopentyloxy-4-methoxyphenyl)-pyrrolidin-2-one (300 mg, 1.1 mmol) and 3-bromobenzoic acid ethyl ester (303 mg, 1.32 mmol) was treated according to General Procedure I to provide 310 mg of the desired product as a white solid. Yield: 67%.

Step B:

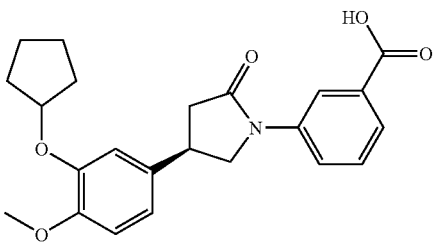

14.2 Preparation of 3-[4-(3-cyclopentyloxy-4-methoxyphenyl) -2-oxo-pyrrolidin-1-yl]-benzoic acid 3-[4-(3-Cyclopentyloxy-4-methoxyphenyl)-2-oxo-pyrrolidin-1-yl]benzoic acid ethyl ester (180 mg, 0.43 mmol) was mixed with EtOH:water (1:1, 20 mL) and NaOH (1N, 1.3 mL). The mixture was heated to 90° C. for 12 h and then cooled down to r.t. After neutralizing to pH=2 with HCl (1N), the mixture was extracted twice with EtOAc. The organic layer was combined, washed with brine and dried over $MgSO_4$. After concentration 150 mg of the desired product was obtained as a light brown solid. Yield: 89%.

Step C:

14.3 Preparation of 3-[4-(3-cyclopentyloxy-4-methoxyphenyl) -2-oxo-pyrrolidin-1-yl]-N-ethylbenzamide 3-[4-(3-Cyclopentyloxy-4-methoxyphenyl)-2-oxo-pyrrolidin-1-yl]benzoic acid and ethyl amine was treated according to General Procedure V to provide the desired product.

14.3.a 3-[4-(3-cyclopentyloxy-4-methoxyphenyl)-2-oxo-pyrrolidin-1-yl]-N-ethylbenzamide MS m/z 423.1 (M+1).

EXAMPLE 15

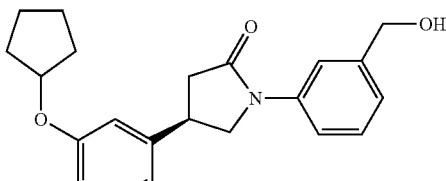

15.1 Preparation of 4-(3-cyclopentyloxy-4-methoxyphenyl)-1-(3-hydroxymethylphenyl)-pyrrolidin-2-one A solution of 3-[4-(3-cyclopentyloxy-4-methoxyphenyl)-2-oxo-pyrrolidin-1-yl]benzoic acid ethyl ester (20 mg, 0.05 mmol) in EtOH (0.5 mL) was added $NaBH_4$ (5 mg, 0.135 mmol)). The mixture was stirred at r.t. for 12 h when water (1 mL) was added to quench the reaction. The mixture was poured into water (4 mL) and extracted twice with EtOAc. The combined organic layer was concentrated and purified by preparative LC-MS.

15.1.a 4-(3-cyclopentyloxy-4-methoxyphenyl)-1-(3-hydroxymethylphenyl)-pyrrolidin-2-one MS m/z 382.1 (M+1).

EXAMPLE 16

Step A:

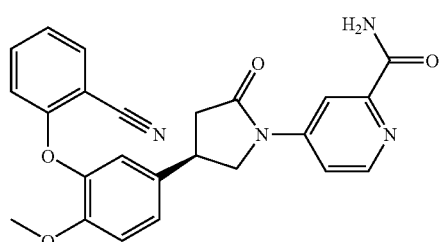

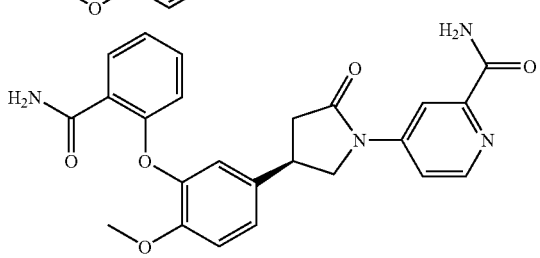

Step A:

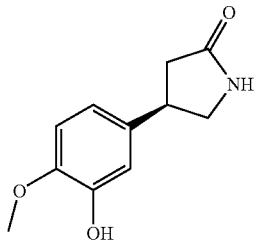

16.1 Preparation of 4-(3-hydroxy-4-methoxyphenyl)-pyrrolidin-2-one

To a solution of (3-benzyloxy-4-methoxyphenyl)-pyrrolidin-2-one (1 mmol) in EtOH (10 mL) was added Pd/C (30 mg). The reaction mixture was then degassed, filled with H$_2$ and stirred at r.t. for 12 h. Pd/C was filtered off through celite, and the filtrate was concentrated to provide 207 mg of the desired product as a white solid. Yield: 100%.

16.1.a 4-(3-hydroxy-4-methoxyhenyl)-pyrrolidin-2-one

MS m/z 208.1 (M+1).

Step B:

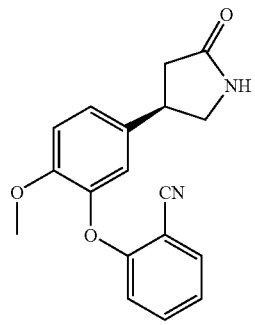

16.2 Preparation of 2-[2-methoxy-5-(5-oxo-pyrrolidin-3-yl)phenoxy]benzonitrile A mixture of the product from Example 16.1 (1 mmol), 2-fluorobenzonitrile (1.1 mmol), potassium carbonate (1.5 mmol) and DMSO was heated to 80° C. for 2 h. After cooling down to r.t., the mixture was treated with sat. NH$_4$Cl and extracted three times with EtOAc. The combined organic layer was washed with brine and dried (MgSO$_4$). After filtration and concentration, the residue was purified by column chromatography (silica gel, EtOAc) to give 277 mg of the desired product as a white solid. Yield: 90%.

16.2.a 2-[2-methoxy-5-(5-oxo-pyrrolidin-3-yl)phenoxy]benzonitrile

MS m/z 309.1 (M+1).

Step C:

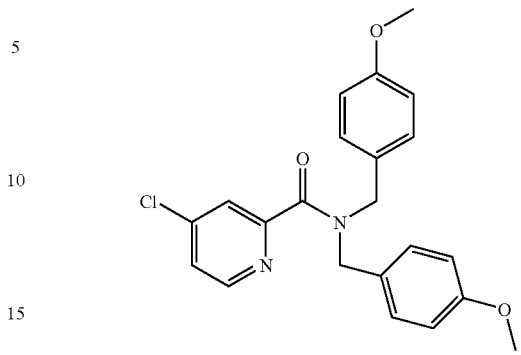

16.3 Preparation of 4-chloro-pyridine-2-carboxylic acid bis-4-methoxybenzamide 4-Chloropyridine-2-carbonyl chloride (1 mmol, prepared according to the procedure by Gudmundsson et al. in *Syn. Comm.* 1997, 861) and bis-4-methoxybenzylamine (1.1 mmol) were treated according to General Procedure VI to provide the desired product as a white solid.

16.3.a 4-chloro-pyridine-2-carboxylic acid bis-4-methoxybenzamide

MS m/z 397.2 (M+1).

Step D:

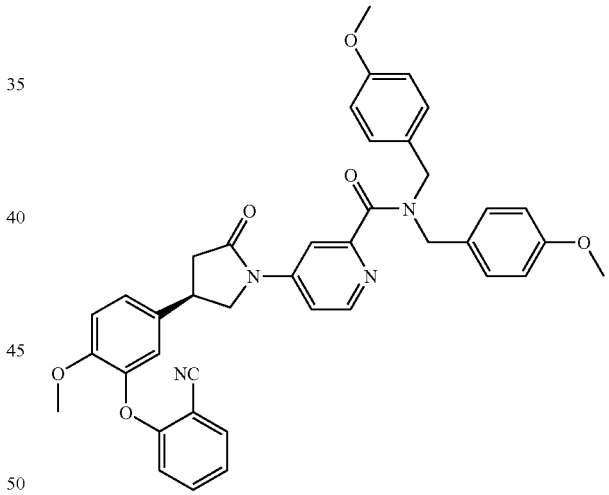

16.4 Preparation of 4-{4-[3-(2-cyanophenoxy)-4-methoxyphenyl]-2-oxo-pyrrolidin-1-yl}-pyridine-2-carboxylic acid bis-(4-methoxybenzamide 2-[2-Methoxy-5-(5-oxo-pyrrolidin-3-yl)phenoxy]benzonitrile (0.05 mmol) and 4-chloropyridine-2-carboxylic acid bis-4-methoxybenzamide (0.06 mmol) were treated according to General Procedure II to provide crude product which was used directly for the next step without purification.

Step E:

16.5 Preparation of 4-{4-[3-(2-cyanophenoxy)-4-methoxyphenyl]-2-oxo-pyrrolidin-1-yl}pyridine-2-carboxylic acid amide and 4-{4-[3-(2-carbamoylphenoxy)-4-methoxyphenyl]-2-oxo-pyrrolidin-1-yl}pyridine-2-carboxylic acid amide Crude product of 4-{4-[3-(2-cyanophenoxy)-4-methoxyphenyl]-2-oxo-pyrrolidin-1-yl}pyridine-2-carboxylic acid bis-(4-methoxy-benzyl)-amide was added to a TFA (0.5 mL) solution and heated to 100° C. for 8 h. After cooling down to r.t., the mixture was concentrated and purified by preparative LC-MS to provide two products.

16.5.a 4-{4-[3-(2-cyanophenoxy)-4-methoxyphenyl]-2-oxo-pyrrolidin-1-yl}pyridine-2-carboxylic acid amide MS m/z 429.1 (M+1).

16.5.b 4-{4-[3-(2-carbamoylphenoxy)-4-methoxyphenyl]-2-oxo-pyrrolidin-1-yl}pyridine-2-carboxylic acid amide (byproduct)

MS m/z 447.1 (M+1).

EXAMPLE 17

Step A:

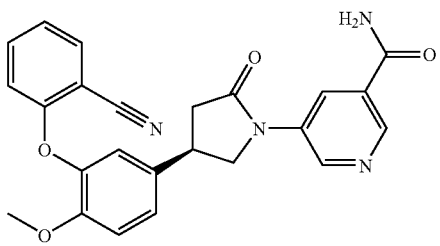

Step A:

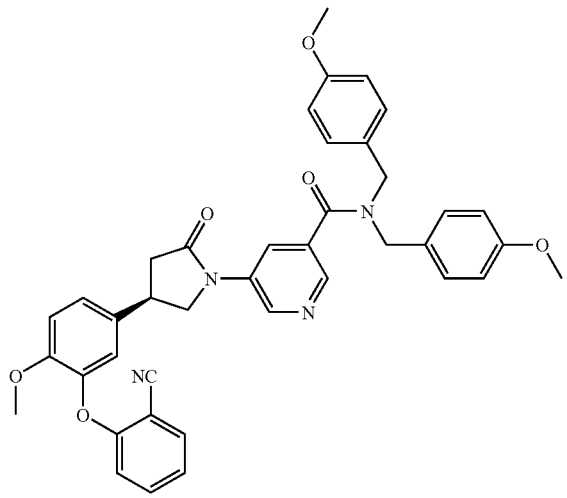

17.1 Preparation of 5-{4-[3-(2-cyanophenoxy)-4-methoxyphenyl]-2-oxo-pyrrolidin-1-yl}-N,N-bis-(4-methoxybenzyl)-nicotinamide Lactam from Example 16 step B (0.05 mmol) and 3-bromopyridine-3-carboxylic acid bis-4-methoxybenzamide (prepared from General Procedure VI) were treated according to General Procedure II to provide crude product which was used directly for the next step without purification.

Step B:

17.2 Preparation of 5-{4-[3-(2-cyanophenoxy)-4-methoxyphenyl]-2-oxo-pyrrolidin-1-yl}-nicotinamide and 5-{4-[3-(2-carbamoylphenoxy)-4-methoxyphenyl]-2-oxo-pyrrolidin-1-yl}-nicotinamide Crude product of 5-{4-[3-(2-cyanophenoxy)-4-methoxyphenyl]-2-oxo-pyrrolidin-1-yl}-N,N-bis-(4-methoxybenzyl)-nicotinamide was added to a TFA (0.5 mL) solution and heated to 100° C. for 8 h. After cooling down to r.t., mixture was concentrated and purified by preparative LC-MS to provide two products.

17.2.a 5-{4-[3-(2-cyanophenoxy)-4-methoxyphenyl]-2-oxo-pyrrolidin-1-yl}-nicotinamide MS m/z 429.1 (M+1).

17.2.b 5-{4-[3-(2-carbamoylphenoxy)-4-methoxyphenyl]-2-oxo-pyrrolidin-1-yl}-nicotinamide MS m/z 447.1 (M+1).

EXAMPLE 18

Step A:

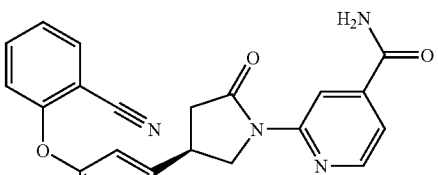

Step A:

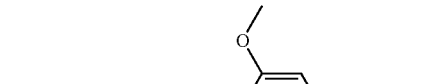
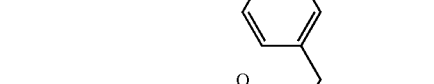
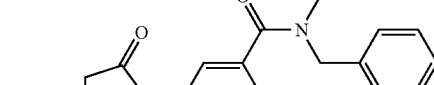
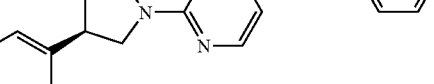

18.1 Preparation of 2-{4-[3-(2-cyanophenoxy)-4-methoxyphenyl]-2-oxo-pyrrolidin-1-yl}-N,N-bis-(4-methoxybenzyl)-isonicotinamide Lactam from Example 16 step B (0.05 mmol) and 2-chloro-pyridine-4-carboxylic acid bis-(4-methoxybenzyl) amide (prepared from General Procedure VI) were treated according to General Procedure I to provide crude product which was used directly for the next step without purification.

Step B:

18.2 Preparation of 2-{4-[3-(2-cyanophenoxy)-4-methoxyphenyl]-2-oxo-pyrrolidin-1-yl}-isonicotinamide and 2-{4-[3-(2-carbamoylphenoxy)-4-methoxyphenyl]-2-oxo-pyrrolidin-1-yl}-isonicotinamide Crude product of 2-{4-[3-(2-cyanophenoxy)-4-methoxyphenyl]-2-oxo-pyrrolidin-1-yl}-N,N-bis-(4-methoxybenzyl)-isonicotinamide was added to a TFA (0.5 mL) solution and heated to 100° C. for 8 h. After cooling down to r.t., the mixture was concentrated and purified by preparative LC-MS to provide two products.

18.2.a 2-{4-[3-(2-cyanophenoxy)-4-methoxyphenyl]-2-oxo-pyrrolidin-1-yl}-isonicotinamide
MS m/z 429.1 (M+1).

18.2.b 2-{4-[3-(2-carbamoylphenoxy)-4-methoxyphenyl]-2-oxo-pyrrolidin-1-yl}-isonicotinamide
MS m/z 447.1 (M+1).

EXAMPLE 19

Step A:

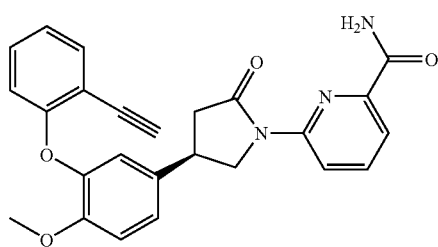

Step A:

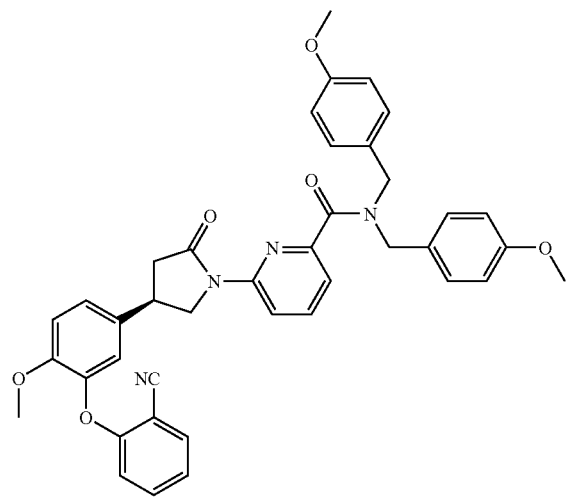

19.1 Preparation of 6-{4-[3-(2-cyanophenoxy)-4-methoxyphenyl]-2-oxo-pyrrolidin-1-yl}-pyridine-2-carboxylic acid bis-(4-methoxybenzyl)amide Lactam from Example 16 step B (0.05 mmol) and 2-bromo-pyridine-6-carboxylic acid bis-(4-methoxybenzyl)amide (prepared from General Procedure VI) were treated according to General Procedure I to provide crude product which was used directly for the next step without purification.

Step B:

19.2 Preparation of 6-{4-[3-(2-cyanophenoxy)-4-methoxyphenyl]-2-oxo-pyrrolidin-1-yl}-pyridine-2-carboxylic acid amide Crude product of 6-{4-[3-(2-cyanophenoxy)-4-methoxyphenyl]-2-oxo-pyrrolidin-1-yl}pyridine-2-carboxylic acid bis-(4-methoxy-benzyl)-amide was added to a TFA (0.5 mL) solution and heated to 100° C. for 8 h. After cooling down to r.t., the mixture was concentrated and purified by preparative LC-MS to provide the desired product.

19.2.a 6-{4-[3-(2-cyanophenoxy)-4-methoxyphenyl]-2-oxo-pyrrolidin-1-yl}-pyridine-2-carboxylic acid amide
MS m/z 429.1 (M+1).

EXAMPLE 20

Step A:

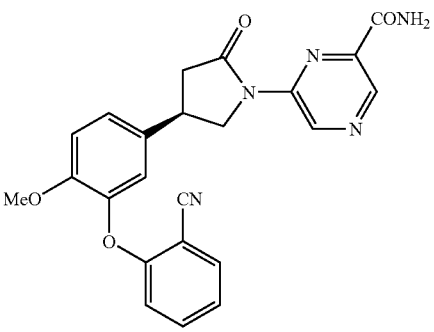

Step A:

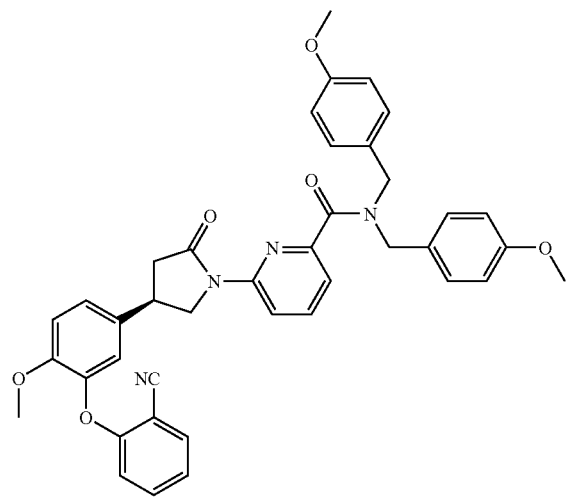

20.1 Preparation of 6-chloropyrazine-2-carboxylic acid amide

To a solution of 2,6-dichloropyrazine (50 mg, 0.34 mmol) in DMF (1 mL) was added a solution of potassium cyanide (24 mg, 0.37 mmol) in H$_2$O (1 mL). After stirring for 3 h at 100° C., the reaction mixture was cooled to r.t., poured into H$_2$O (10 mL) and extracted with EtOAc three times. The combined organic layer was dried over MgSO$_4$, filtered and concentrated. The crude product wa purified by column chromatography (silica gel, EtOAc:Hexane, 3:7) to give 15 mg of the desired product. Yield: 32%.

20.1.a 6-chloropyrazine-2-carboxylic acid amide
MS m/z 158.1 (M+1).

Step B:

20.2 Preparation of 6-{4-[3-(2-cyanophenoxy)-4-methoxyphenyl]-2-oxo-pyrrolidin-1-yl}-pyrazine-2-carboxylic acid amide Lactam from Example 16 step B (0.05 mmol) and 2-chloropyrazine-2-carboxylic acid amide (0.06 mmol) were treated according to General Procedure II to provide the desired product by preparative LC-MS.

20.2.a 6-{4-[3-(2-cyanophenoxy)-4-methoxyphenyl]-2-oxo-pyrrolidin-1-yl}-pyrazine-2-carboxylic acid amide
MS m/z 430.1 (M+1).

EXAMPLE 21

Step A:

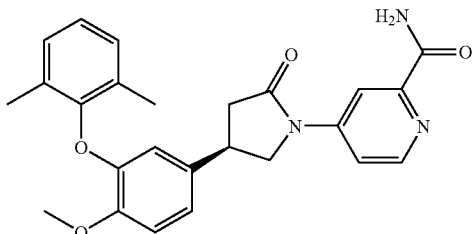

Step A:

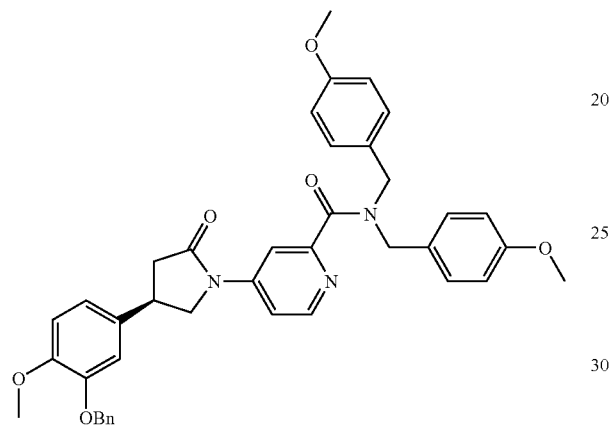

1 OBn 21.1 Preparation of 4-[4-(3-benzyloxy-4-methoxyphenyl)-2-oxo-pyrrolidin-1-yl]-pyridine-2-carboxylic acid bis-(4-methoxybenzyl)-amide (3-Benzyloxy-4-methoxyphenyl)-pyrrolidin-2-one (1 mmol) and 2-chloropyridine-4-carboxylic acid bis-(4-methoxybenzyl)-amide (1.1 mmol) were treated according to General Procedure II to provide the desired product. Yield: 63%.

21.1.a 4-[4-(3-benzyloxy-4-methoxyphenyl)-2-oxo-pyrrolidin-1-yl]-pyridine-2-carboxylic acid bis-(4-methoxybenzyl)-amide MS m/z 658.4 (M+1).

Step B:

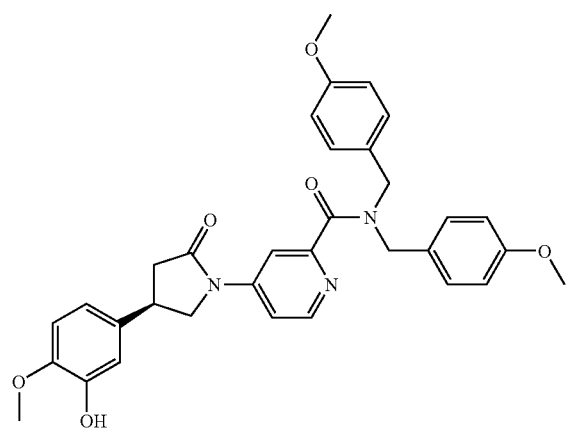

21.2 Preparation of 4-[4-(3-hydroxy-4-methoxy-phenyl)-2-oxo-pyrrolidin-1-yl]-pyridine-2-carboxylic acid bis-(4-methoxy-benzyl)-amide 2-[4-(3-Benzyloxy-4-methoxyphenyl)-2-oxo-pyrrolidin-1-yl]-N,N-bis-(4-methoxybenzyl)-isonicotinamide from above was debenzylated following the General Procedure IX to provide the desired product. Yield: 90%.

21.2.a 4-[4-(3-hydroxy-4-methoxy-phenyl)-2-oxo-pyrrolidin-1-yl]-pyridine-2-carboxylic acid bis-(4-methoxy-benzyl)-amide MS m/z 568.4 (M+1).

Step C:

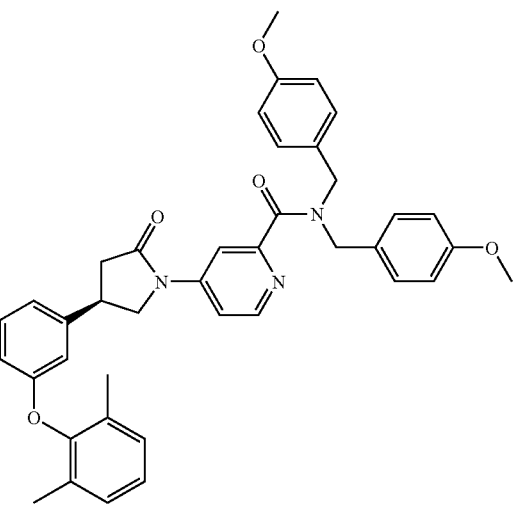

21.3 Preparation of 4-{4-[3-(2,6-dimethylphenoxy)-4-methoxyphenyl]-2-oxo-pyrrolidin-1-yl}-pyridine-2-carboxylic acid bis-(4-methoxybenzyl)amide A mixture of phenol from step B (15 mg, 0.026 mmol), 2,6-dimethylphenylboronic acid (20 mg, 0.132 mmol), Cu(OAc)$_2$ (7.2 mg, 0.039 mmol), pyridine (21 mg, 0.26 mmol) and 4 Å MS in anhydrous CH$_2$Cl$_2$ (1 mL) were stirred at r.t. for 3 days. After filtering through celite, the solvent was removed and the residue was purified by column chromatography (silica gel, EtOAc/hexane, 0% to 50%) to provide 13 mg of the desired product. Yield: 73%.

21.3.a 4-{4-[3-(2,6-dimethylphenoxy)-4-methoxyphenyl]-2-oxo-pyrrolidin-1-yl}-pyridine-2-carboxylic acid bis-(4-methoxybenzyl)amide MS m/z 672.4 (M+1).

Step D:

Following a same procedure as in Example 16 step E, 2-{4-[3-(2,6-dimethylphenoxy)-4-methoxyphenyl]-2-oxo-pyrrolidin-1-yl}-N,N-bis-(4-methoxybenzyl)-isonicotinamide was deprotected and was purified by preparative LC-MS. MS m/z 432.1 (M+1).

EXAMPLE 22

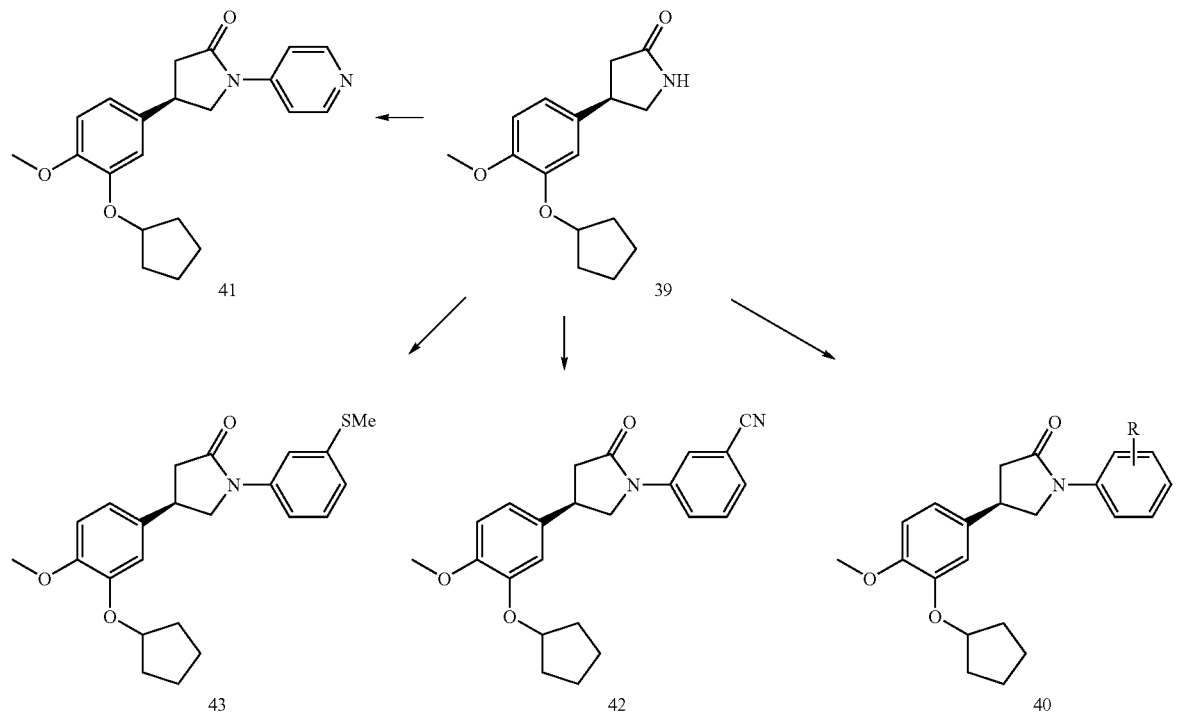

22.1 Amidation of lactam 39: General procedure for 40

To a round bottom flask was added 39 (1 mmol), aryl halide (1.4 mmol), K₃PO₄ (1.5 mmol), DMF (3 mL), dioxane (3 mL) and trans-cyclohexanediamine (25 µL).

The mixture was stirred under N₂ for 5 min before CuI (35 mg) was added. The reaction mixture was heated at 110° C. for 20 h under N₂ with stirring, then cooled down to r.t. The mixture was diluted with EtOAc, washed with saturated NH₄Cl (3×10 mL) and dried over Na₂SO₄. Concentration and chromatography of the residue on silica gel gave pure product 40.

22.1.a 4-(3-Clopentyloxy-4-methoxy-phenyl)-1-pyridin-4-yl-pyrrolidin-2-one (41)

¹H NMR (CDCl₃): δ 8.68 (2H, brs), 7.67 (2H, brs), 6.84 (1H, d, J=8.1 Hz), 6.80 (1H, d, J=8.0 Hz), 6.78 (1H, s), 4.76 (1H, m), 4.17 (1H, t, J=8.4 Hz), 3.83 (3H, s), 3.80 (1H, t, J=8.3 Hz), 3.64 (1H, m), 3.02 (1H, q, J=8.6 Hz), 2.80 (1H, q, J=8.5 Hz), 1.82-1.91 (6H, m), 1.60-1.62 (2H, brs).

22.1.b 3-[4-(3-cyclopentyloxy-4-methoxy-phenyl)-2-oxo-pyrrolidin-1-yl]-benzonitrile (42)

¹H NMR (CDCl₃): δ 7.97 (1H, s), 7.93 (1H, d, J=8.1 Hz), 7.46 (1H, d, J=8.1 Hz), 7.44 (1H, d, J=8 Hz), 6.81 (3H, m), 4.76 (1H, brs), 4.16 (1H, t, J=11.8 Hz), 3.84 (3H, s), 3.84 (1H, t, J=11.8 Hz) 3.66 (1H, m) 3.03 (1H, q, J=8.4 Hz), 2.81 (1H, q, J=8.4 Hz), 1.60-1.89 (8H, m).

22.1.c 4-(3-cyclopentyloxy-4-methoxyphenyl)-1-(3-methylsulfonylphenyl)-pyrrolidin-2-one (6)

¹H NMR (CDCl₃): δ 7.33-7.30 (m, 2H), 7.21-7.20 (m, 2H), 6.88-6.86 (m, 3H), 4.81-4.78 (m, 1H), 3.87-3.85 (m, 4H), 3.78-3.70 (m, 1H), 3.01-2.90 (m, 2H), 2.75 (dd, 1H, J=9.1, 18.4 Hz), 1.95-1.82 (m, 6H), 1.63-1.60 (m, 2H). Yield: 71%.

EXAMPLE 23

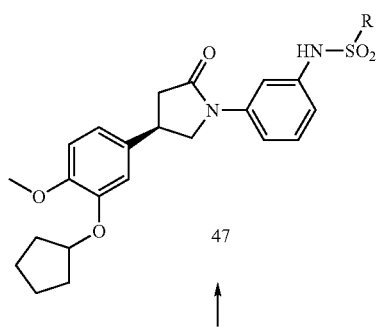

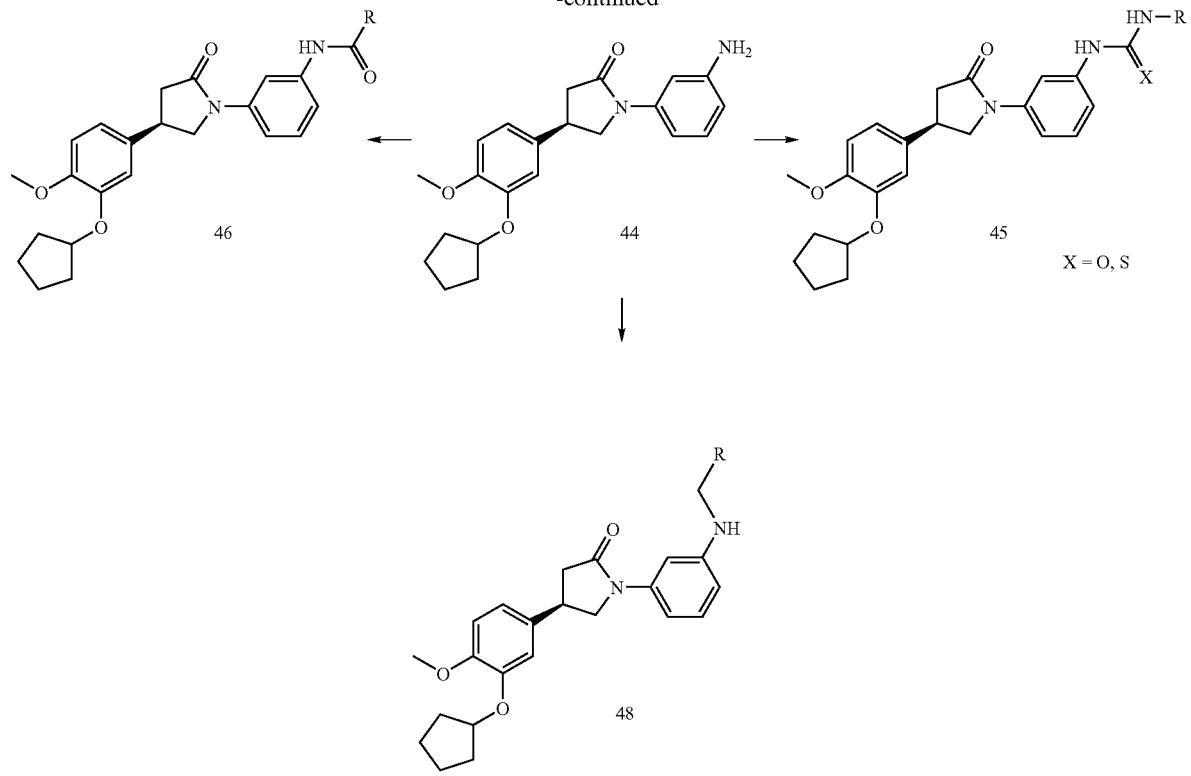

23.1 Reaction of Amine with Isocyanate and Isothiocyanate: General Procedure

Aniline 44 (0.022 mmol) was dissolved in CH$_2$Cl$_2$ (1 mL). To this solution was added isocyanate (0.023 mmol) or isothiocyanate (0.024 mmol). The reaction mixture was stirred for 20 h (or refluxed over night). Concentration and purification of the residue by column chromatography on silica gel gave the desired product.

23.1.a 1-{3-[4-(3-cyclopentyloxy-4-methoxy-phenyl)-2-oxo-pyrrolidin-1-yl]-phenyl}-3-(2-nitro-phenyl)-urea (45)

$^1$H NMR (CDCl$_3$): δ 8.39 (1H, brs), 8.10 (1H, brs), 7.80 (1H, s), 7.79 (1H, d, J=7.2 Hz), 7.72 (1H, d, J=7.2 Hz), 7.63 (1H, s), 7.34 (1H, t, J=6.8 Hz), 7.11 (1H, t, J=6.9 Hz), 6.91-6.96 (2H, m), 6.83-6.85 (3H, m), 4.80 (1H, brs), 4.13 (1H, t, J=8.1 Hz), 3.88 (1H, t, J=8.1 Hz), 3.85 (3H, s), 3.70 (1H, m), 3.04 (1H, q, J=8.2 Hz), 2.88 (1H, q, J=8.2 Hz), 1.96 (8H, m).

23.2 Amidation of Aniline 44: General Procedure

To a dry flask was added carboxylic acid (0.02 mmol), diisopropenylethyl amine (0.04 mmol) and EDC (0.024 mmol, 1.2 eq) in dry THF. The mixture was stirred for 20 min before aniline 44 (0.02 mmol) was added. The reaction mixture was stirred for 30 h. Concentration and purification of the residue by column chromatography on silica gel gave the desired product.

23.2.a N-{3-[4-(3-cyclopentyloxy-4-methoxyphenyl)-2-oxo-pyrrolidin-1-yl]phenyl}-3-nitrobenzamide (46)

$^1$H NMR (CDCl$_3$): δ 8.05 (1H, brs), 7.91 (1H, brs), 7.41 (1H, m), 7.10-7.28 (5H, m), 7.13 (1H, m), 6.79-6.83 (3H, m), 4.77 (1H, m), 4.21 (1H, t, J=8.1 Hz), 3.83 (1H, t, J=8.1 Hz), 3.61 (1H, m), 2.98 (3H, s), 2.96 (1H, q, J=8.2 Hz), 2.75 (1H, q, J=8.1 Hz), 1.91-1.99 (8H, m).

23.3 Reaction of Aniline with Sulfonyl Chloride: General Procedure

Aniline 44 (0.02 mmol), sulfonyl chloride (0.022 mmol), pyridine (0.03 mmol) and CH$_2$Cl$_2$ (1 mL) were combined. The reaction mixture was stirred for 15 h. After removal of the solvent, the residue was purified by preparative LC-MS to give the desired product.

23.3.a N-{3-[4-R-(3-cyclopentyloxy-4-methoxyphenyl)-2-oxo-pyrrolidin-1-yl]-phenyl}-3-methoxybenzenesulfonamide (47)

$^1$H NMR (CDCl$_3$): δ 7.70 (1H, brs), 7.37 (1H, d, J=7.8 Hz), 7.19-7.29 (4H, m), 7.00 (2H, t, J=7.6 Hz); 6.83 (1H, d, J=8 Hz), 6.79 (1H, s), 6.79 (1H, d, J=8 Hz), 4.76 (1H, brs), 4.11 (1H, t, J=8.4 Hz), 3.83 (3H, s), 3.78 (1H, t, J=8.4 Hz), 3.60 (1H, m), 3.02 (1H, q, J=8.1 Hz), 2.85 (1H, q, J=8.1 Hz), 1.61-1.88 (8H, m).

23.4 Amination of Aniline 3: General Procedure

To a reaction flask was added aniline 44 (0.02 mmol), aldehyde (0.024 mmol), NaB(OAc)$_3$H (0.2 mmol), AcOH (0.06 mmol) and DMF (0.5 mL). The mixture was stirred for 20 h, then concentrated. The residue was dissolved in EtOAc (3 mL) and washed with brine (2×3 mL) before being dried over Na$_2$SO$_4$. Concentration and purification of the residue by column chromatography on silica gel gave the desired product.

EXAMPLE 24

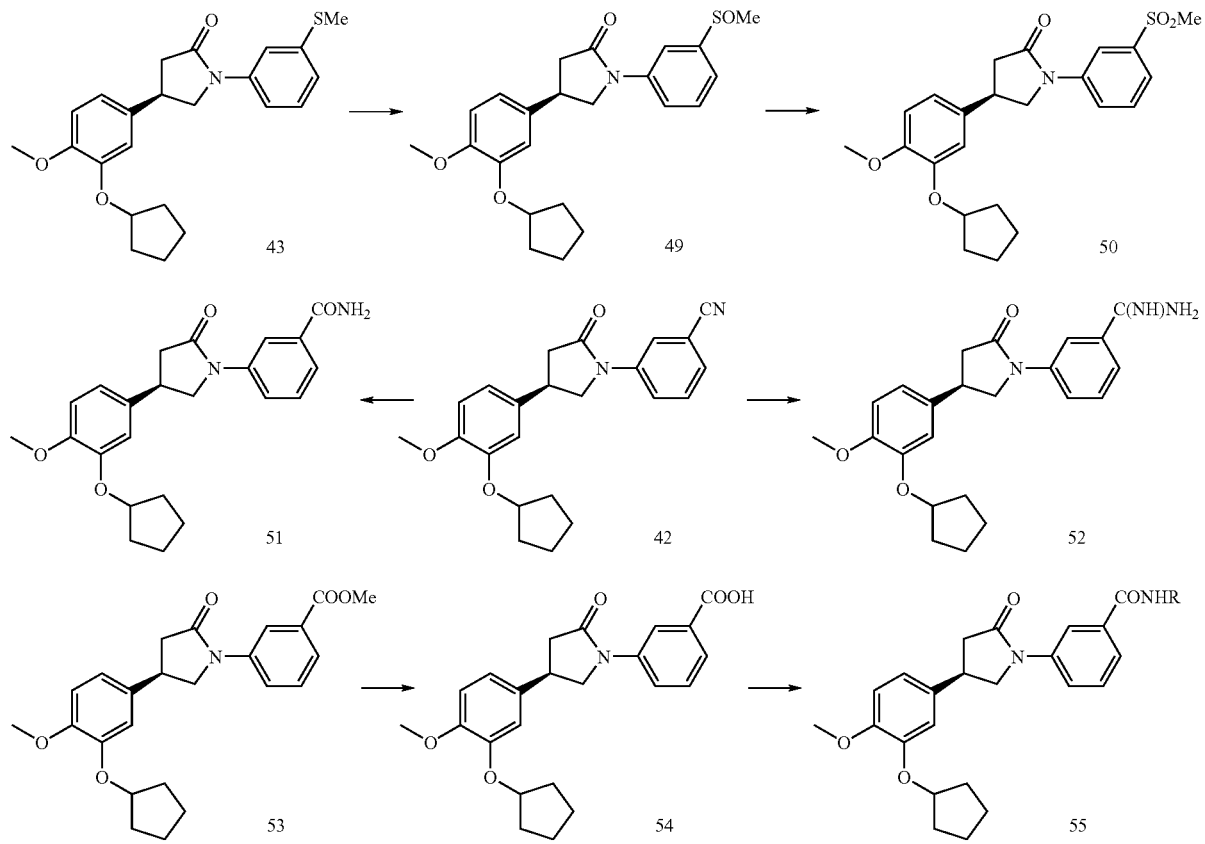

24.1 Preparation of 4-(3-cyclopentyloxy-4-methoxyphenyl)-1-(3-methanesulfinylphenyl)-pyrrolidin-2-one (49)

Pyrrolidinone 43 (20 mg, 0.05 mmol) in $CH_2Cl_2$ was cooled by an ice water bath. m-CPBA (1 eq) was added and the reaction mixture was stirred for 3 h at r.t. The reaction was quenched with 10% $Na_2S_2O_3$ and the mixture was extracted with EtOAc. The organic layer was washed with sat. $NaHCO_3$, water, and brine. Concentration and purification of the residue by column chromatography on silica gel gave the desired product. Yield: 57%.

24.1.a 4-(3-cyclopentyloxy-4-methoxyphenyl)-1-(3-methanesulfinylphenyl)-pyrrolidin-2-one (49)

$^1$H NMR ($CDCl_3$): δ 8.12-8.08 (m, 1H), 7.61-7.52 (m, 2H), 7.26-7.19 (m, 1H), 6.88-6.81 (m, 3H), 4.82-4.77 (m, 1H), 4.21 (t, 1H, J=8.4 Hz), 4.08 (t, 1H, J=8.9 Hz), 3.88-3.82 (m, 4H), 3.79-3.70 (m, 1H), 2.96-2.91 (m, 4H), 2.74 (dd, 1H, J=8.8, 16.9 Hz), 1.94-1.82 (m, 6H), 1.64-1.59 (m, 2H).

24.2 Preparation of 4-(3-cyclopentyloxy-4-methoxyphenyl)-1-(3-methanesulfonylphenyl)-pyrrolidin-2-one (50)

Pyrrolidinone 43 (90 mg, 0.23 mmol) in $CH_2Cl_2$ (5 mL) was cooled in an ice water bath, m-CPBA (2.2 eq) was added and the reaction mixture was stirred for 3 h at r.t. The reaction was quenched with 10% $Na_2S_2O_3$ and the mixture was extracted with EtOAc. The organics was washed with sat. $NaHCO_3$, brine and dried with $Na_2SO_4$. Concentration and purification by silica gel afforded 50 as a white solid/oil. Yield: 95%.

24.2.a 4-(3-cyclopentyloxy-4-methoxyphenyl)-1-(3-methanesulfonylphenyl)-pyrrolidin-2-one (50)

$^1$H NMR ($CDCl_3$): δ 18.12 (d, 1H, J=7.8 Hz), 7.73-7.69 (m, 1H), 7.60-7.56 (m, 1H), 7.34 (brs, 1H), 6.99-6.85 (m, 3H), 4.80 (brs, 1H), 4.26 (brs, 1H), 3.84-3.75 (m, 4H), 3.66 (brs, 1H), 3.22 (s, 3H), 2.98-2.92 (m, 1H), 2.77 (dd, 1H, J=9.7, 16.9 Hz), 1.90-1.77 (m, 6H), 0.63-1.60 (m, 2H).

24.3 Preparation of 3-[4-(3-cyclopentyloxy-4-methoxyphenyl)-2-oxo-pyrrolidin-1-yl]benzamide (51)

To 12.5 mg of benzonitrile 42 (0.033 mmol) in 0.5 mL of ethanol was added 2 μL of a 25% NaOH solution followed by 29 μL of 35% $H_2O_2$. The temperature of the reaction mixture was kept at 50° C. for 3 h. Upon completion, 5% $H_2SO_4$ was added until the mixture was neutral (pH 7). The reaction mixture was extracted with EtOAc and dried with $MgSO_4$. Concentration and purification of the residue by column chromatography on silica gel gave the desired product as a white solid. Yield: 94%.

24.3.a 3-[4-(3-cyclopentyloxy-4-methoxyphenyl)-2-oxo-pyrrolidin-1-yl]benzamide (51)

$^1$H NMR ($CDCl_3$): δ 8.01 (brs, 1H), 7.90 (dd, 1H, J=1.5, 8.1 Hz), 7.58 (d, 1H, J=7.7 Hz), 7.46 (t, 1H, J=8.0 Hz), 6.86-6.80 (m, 3H), 6.24 (brs, 1H), 5.68 (brs, 1H), 4.79-4.75 (m, 1H), 4.21 (dd, 1H, J=8.3, 9.4 Hz), 3.84 (s, 3H), 3.90 (dd, 1H, J=7.6, 9.4 Hz), 3.69-3.61 (m, 1H), 3.01 (dd, 1H, J=8.7, 17.0 Hz), 2.79 (dd, 1H, J=8.9, 17.0 Hz), 1.96-1.82 (m, 6H), 1.65-1.59 (m, 2H).

24.4 Preparation of 3-[4-(3-cyclopentyloxy-4-methoxyphenyl)-2-oxo-pyrrolidin-1-yl]benzamidine (52)

A methanol solution (2 mL) containing 71 mg of benzonitrile 42 (0.19 mmol) was cooled to 0° C. and bubbled with dry HCl gas for 15 min. The reaction flask was sealed and stirred at r.t. overnight. The solvent was removed under reduced pressure and treated with 7N $NH_3$ in methanol (4 mL). The mixture was stirred at r.t. overnight. Concentration and purification of the residue by preparative LC-MS gave the desired product as a white powder.

24.4.a 3-[4-(3-cyclopentyloxy-4-methoxyphenyl)-2-oxo-pyrrolidin-1-yl]benzamidine (52)

$^1$H NMR (DMSO-$d_6$): δ 8.30 (s, 1H), 8.99 (s, 1H), 8.15 (d, 1H, J=8.3 Hz), 7.96 (s, 1H), 7.61 (t, 1H; J=8.0), 7.53 (d, 1H, J=7.7 Hz), 7.08 (s, 1H), 6.99-6.86 (m, 2H), 4.79 (brs, 1H), 4.21 (t, 1H, J=8.8 Hz), 3.87 (t, 1H, J=9.2 Hz), 3.71 (s, 3H), 3.68-3.63 (m, 1H), 2.89 (dd, 1H, J=8.5, 16.7 Hz), 2.77 (dd, 1H, J=9.6, 16.7 Hz), 1.86 (brs, 2H), 1.69 (brs, 2H), 1.54 (brs, 2H).

EXAMPLE 25

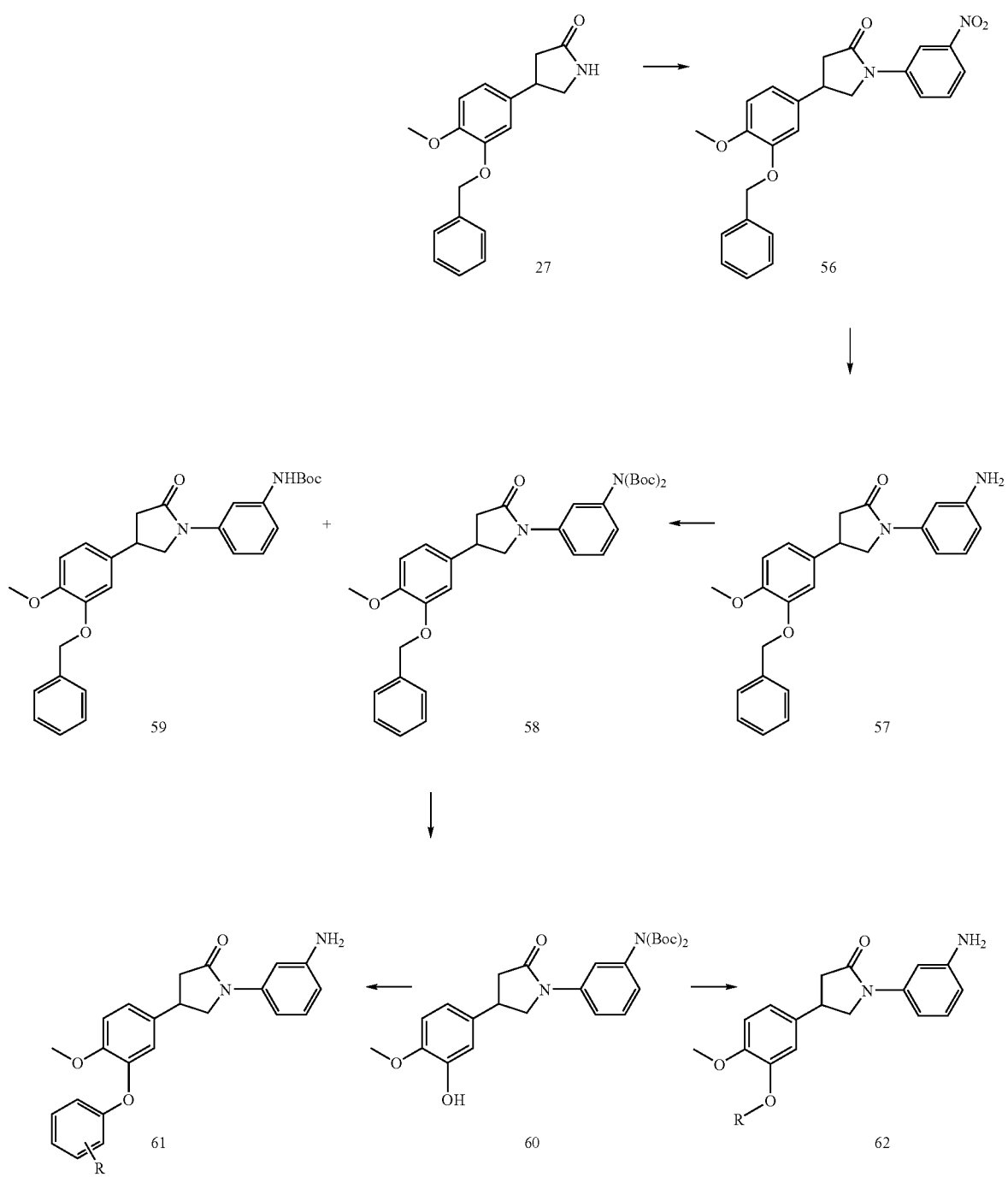

25.1 Synthesis of 58

To a round bottom flask was added 27 (1.76 g, 5.9 mmol), 3-iodonitrobenzene (2.64 g, 10.6 mmol), $K_3PO_4$ (2.79 g, 13 mmol), trans-cyclohexanediamine (50 µL), DMF (8 mL) and dioxane (8 mL). The mixture was stirred under $N_2$ for 5 min before the addition of CuI (150 mg). The mixture was heated at 110° C. for 20 h and cooled to r.t. After filtration, the reaction mixture was diluted with EtOAc (100 mL), washed with saturated $NH_4Cl$ and brine, and then dried over $Na_2SO_4$. Concentration and purification of the residue by column chromatography on silica gel (EtOAc: hexane=1:3) gave 1.4 g of the desired product.

Compound 56 (100 mg) was dissolved in 2 mL of EtOAc: EtOH (1:1). To this solution was added Raney Ni. The solution was then placed under vacuum, recharged with $H_2$, and stirred for 10 h under $H_2$. Filtration and concentration of the solution gave crude 57.

Crude 57 (1.08 g) was dissolved in THF (20 mL). A solution of $Boc_2O$ (8 mL, 1 M) was added followed by addition of DMAP (2 eq) and diisopropylethylamine (1 mL) at 0° C. The mixture was stirred at 0° C. for 4 h and stirred overnight. The mixture was then diluted with EtOAc (100 mL), washed with brine (2×30 mL), and dried over $Na_2SO_4$. Concentration and chromatography gave 58 (0.18 g).

25.1.a 58

$^1$H NMR (CDCl$_3$): δ 7.54 (1H, brs), 7.48 (1H, d, J=7.6 Hz), 7.33 (1H, d, J=7.5 Hz), 7.31 (1H, m), 6.80-6.92 (3H, m), 5.28 (2H, s), 4.09 (1H, t, J=8.1), 3.90 (3H, s), 3.72 (1H, t, J=8.0 Hz), 3.56 (1H, m), 2.96 (1H, q, J=7.8 Hz), 2.69 (1H, q, J=7.9 Hz), 1.49 (18H, s).

EXAMPLE 26

26.1 General Procedure for Preparing Compound 61

Compound 58 (300 mg) was dissolved in EtOH (3 mL). 10% Pd/C (~20 mg) was added and the mixture was put under vacuum, recharged with $H_2$, and stirred under $H_2$ overnight. Filtration and concentration of the solution gave crude compound 60.

Compound 60 (30 mg, 0.1 mmol) was dissolved in DMF (0.5 mL). $K_2CO_3$ (28 mg, 0.2 mmol) was added followed by addition of 6-bromohexanylnitrile (17 mg, 0.1 mmol). The mixture was stirred at r.t. for 15 h. After filtration, the solution was diluted with EtOAc (5 mL) and washed with water (5 mL), brine (5 mL) and dried over $Na_2SO_4$. Removal of solvent gave residue which was dissolved in 1 mL of a $CH_2Cl_2$: TFA (1:1) solution. The resulting mixture was stirred at r.t. for 2 h. The solvent was removed under reduced pressure and the residue was purified on preparative LC-MS to give 61.

26.1.a 6-{5-[1-(3-aminophenyl)-5-oxo-pyrrolidin-3-yl]-2-methoxyphenoxy}-hexanenitrile $^1$H NMR (CDCl$_3$): δ 7.82 (1H, brs), 7.29 (1H, m), 7.14 (1H, d, J=7.2 Hz), 6.91 (1H, d, J=7.2 Hz), 6.85 (1H, d, J=8 Hz), 6.81 (1H, d, J=8 Hz), 6.77 (1H, s), 5.62 (2H, brs), 4.11 (1H, t, J=8.2 Hz), 4.02 (2H, t, J=6.4 Hz), 3.82 (3H, s), 3.81 (1H, t, J=8.2 Hz), 3.61 (1H, m), 2.96 (1H, q, J=8.2 Hz), 2.77 (1H, q, J=8.2 Hz), 2.36 (2H, t, J=6.8 Hz), 1.85 (2H, m), 1.73 (2H, m) 1.65 (2H, m).

26.2 General Procedure for Compound 62

Compound 60 (15 mg, 0.03 mmol) was dissolved in $CH_2Cl_2$ (1 mL).

Cu(OAc)$_2$ (0.04 mmol), (CH$_3$)$_3$N (0.07 mmol) and 3-cyanobenzeneboric acid (8 mg, 0.05 mmol) were then added, followed by 4 Å molecular sieves. The mixture was stirred at r.t. for 30 h. After filtration, the solvent was removed under reduced pressure. The residue was purified by preparative LC-MS to give the desired product.

EXAMPLE 27

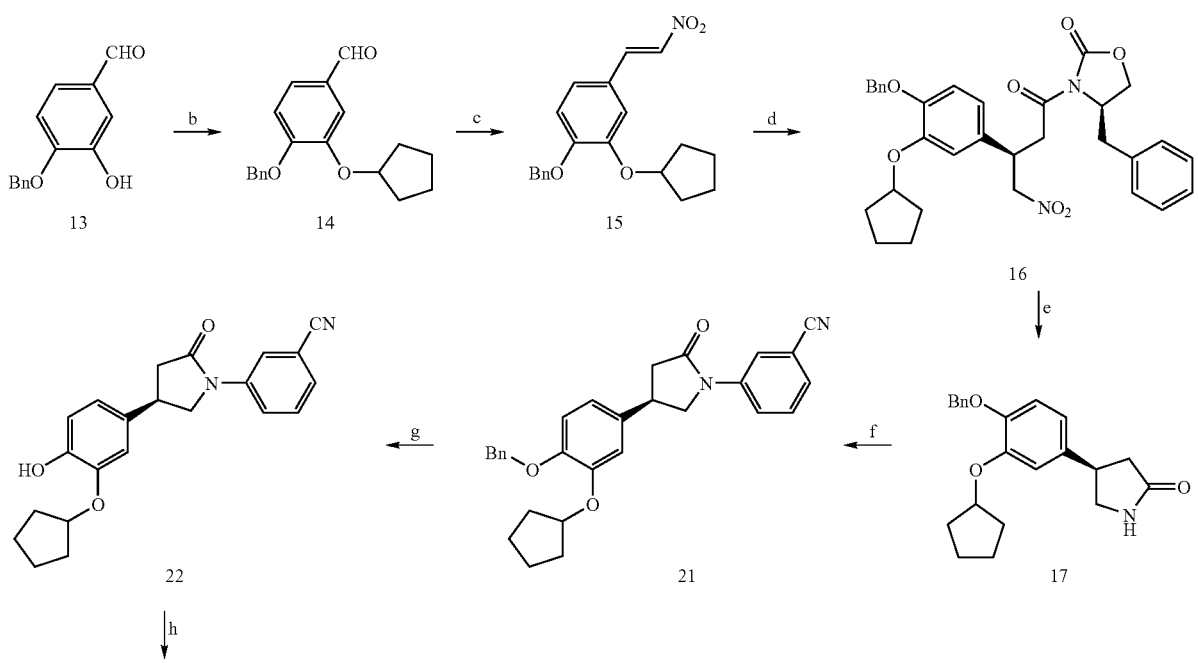

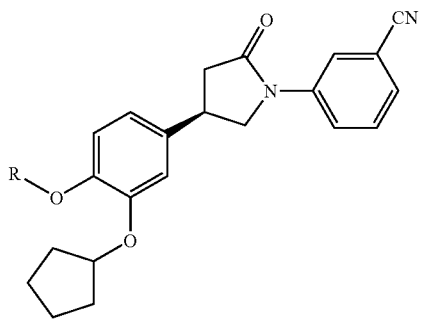 23

→ i

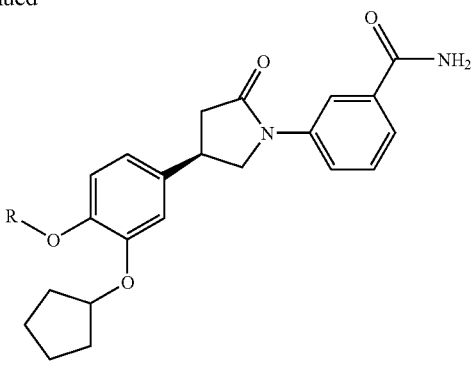 24

-continued 27.1 Preparation of 4-benzyloxy-3-cyclopentyloxybenzaldehyde (14)

To a solution of 4-benzyloxy-3-hydroxybenzaldehyde 13 (5 g, 21.9 mmol) in DMF (50 mL) was added cyclopentyl bromide (4.7 mL, 43.8 mmol) and $K_2CO_3$ (12.1 g, 87.6 mmol). The reaction mixture was stirred at r.t. overnight. $K_2CO_3$ was filtered from the mixture, and the filtrate was extracted with EtOAc. The organic layer was washed with water (2×) and saturated NaCl, dried with $Na_2SO_4$ and concentrated under reduced pressure. Purification by silica gel gave the desired product as a colorless oil (98%). Under high vacuum the oil solidified to a white solid.

27.1.a 4-benzyloxy-3-cyclopentyloxy-benzaldehyde (14)

$^1$H NMR (CDCl$_3$): δ 9.83 (s, 1H), 7.44-7.26 (m, 7H), 6.99 (d, 1H, J=8.2 Hz), 5.21 (s, 2H), 4.88-4.86 (m, 1H), 1.99-1.82 (m, 6H), 1.68-1.56 (m, 2H).

27.2 Preparation of Compound 15

Aldehyde 14 (6.3 g, 21.3 mmol) was dissolved in a mixture of 13 mL of AcOH and 5.8 mL of $CH_3NO_2$ (106.5 mmol). NH$_4$OAc (3.3 g, 42.5 mmol) was added and the mixture was heated under reflux for 2 h. The mixture was then cooled to r.t. and extracted with $CH_2Cl_2$. The organic layer was washed with water, sat. NaHCO$_3$, sat. NaCl and dried with Na$_2$SO$_4$. Concentration under reduced pressure and purification on silica gel with $CH_2Cl_2$/hexane gave 3.2 g of yellow solid. Yield: 44%.

27.2.a 15

$^1$H NMR (CDCl$_3$): δ 7.94 (d, 1H, J=13.5 Hz), 7.49 (d, 1H, J=13.6 Hz), 7.41-7.32 (m, 5H), 7.10-7.04 (m, 2H), 6.93 (d, 1H, J=8.3 Hz), 5.18 (s, 2H), 4.84-4.82 (m, 1H), 1.93-1.83 (m, 6H), 1.76-1.74 (m, 2H).

27.3 Preparation of 4-benzyl-3-[3-(4-benzyloxy-3-cyclopentyloxyphenyl)-4-nitrobutyryl]-oxazolidin-2-one (16)

Lithium diisopropyl amine (5.2 mL, 10.3 mmol, 2.0 M in heptane/THF/ethylbenzene) was added dropwise to a solution of N-acetylbenzyloxazolidinone (2.1 g, 9.4 mmol) in THF (40 mL) under N$_2$ at −78° C. The mixture was stirred for 20 min. The olefin 70 (3.2 g, 9.4 mmol) dissolved in 20 mL THF was cannulated over and the mixture was stirred for 2 h at −78° C., then quenched with sat. NH$_4$Cl.

The mixture was warmed to r.t., extracted with $CH_3Cl$, washed with water and brine, dried over MgSO$_4$, and concentrated. Filtration of the solids from hexane:EtOAc (1:1), afforded 4 g of white solid. Yield: 75%.

27.3.a 4-benzyl-3-[3-(4-benzyloxy-3-cyclopentyloxyphenyl)-4-nitrobutyryl]-oxazolidin-2-one (16)

$^1$H NMR (CDCl$_3$): δ 7.42-7.26 (m, 8H), 7.17 (d, 2H, J=7.6 Hz), 6.86 (d, 1H, J=8.2), 6.81 (s, 1H), 6.74 (d, 1H, J=8.2), 5.06 (s, 2H), 4.80 (t, 1H, J=4.06 Hz), 4.72-4.55 (m, 4H), 4.13-4.07 (m, 3H), 3.53 (dd, 1H, J=7.7, 17.2 Hz), 3.30-3.21 (m, 2H), 2.73 (dd, 1H, J=9.7, 13.3 Hz), 1.89-1.78 (m, 6H), 1.64-1.63 (m, 2H).

27.4 Preparation of 4-(4-benzyloxy-3-cyclopentyloxyphenyl)-pyrrolidin-2-one (17)

Nitro-compound 16 (4 g) was partially dissolved in 75 mL EtOAc/75 mL EtOH/75 mL dioxane, and a suspension of Raney Ni was added. The mixture was flushed with H$_2$ three times. The mixture was stirred under H$_2$ at 50° C. overnight, then filtered through celite. Concentration and chromatography of the residue on silica gel gave 2.2 g of the desired product. Yield: 88%.

27.4.a 4-(4-benzyloxy-3-cyclopentyloxyphenyl)-pyrrolidin-2-one (17)

$^1$H NMR (CDCl$_3$): δ 7.44-7.42 (m, 2H), 7.37-7.34 (m, 2H), 7.31 (d, 1H, J=4.9 Hz), 6.87 (d, 1H, J=8.2 Hz), 6.79 (d, 1H, J=2.0 Hz), 6.72 (dd, 1H, J=2.06, 8.2 Hz), 5.86 (brs, 1H), 5.08 (s, 2H), 4.81 (m, 1H), 3.75 (t, 1H, J=8.4 Hz), 3.62 (p, 1H, J=8.5 Hz), 3.38 (dd, 1H, J=7.5, 9.2 Hz), 2.71 (dd, 1H, J=8.8, 16.9 Hz), 2.47 (dd, 1H, J=8.9, 16.9 Hz), 1.90-1.81 (m, 6H), 1.64-1.61 (m, 2H).

27.5 Preparation of 3-[4-(4-benzyloxy-3-cyclopentyloxyphenyl)-2-oxo-pyrrolidin-1-yl]benzonitrile (21)

The preparation of compound 21 was similar to the amidation of lactam, see Example 22 for compound 40. Yield: 74%.

27.6 Preparation of 3-[4-(3-cyclopentyloxy-4-hydroxyphenyl)-2-oxo-pyrrolidin-1-yl]benzonitrile (22)

To benzonitrile 21 (1.7 g 3.8 mmol) in EtOH/EtOAc was added 200 mg of Pd—C and flushed with H$_2$ three times. The mixture was stirred under H$_2$ at r.t. for 72 h. The mixture was filtered through celite and the filtrate was concentrated. Extraction of the filtrate with EtOAc and washing with 2N HCl, sat. NaHCO$_3$, sat. NaCl, followed by purification with silica gel gave 350 mg of the desired product. Yield: 26%.

27.6.a 3-[4-(3-cyclopentyloxy-4-hydroxyphenyl)-2-oxo-pyrrolidin-1-yl]benzonitrile (22)

$^1$H NMR (CDCl$_3$): δ 7.97-7.92 (m, 2H), 7.50-7.42 (m, 2H), 6.90 (d, 1H, J=10.9 Hz), 6.77-6.74 (m, 2H), 5.59 (s, 1H), 4.88-4.80 (m, 1H), 4.16 (t, 1H, J=8.6 Hz), 3.83 (t, 1H, J=7.7

Hz), 3.65 (p, 1H, J=8.3 Hz), 3.02 (dd, 1H, J=8.7, 17.1 Hz), 2.79 (dd, 1H, J=8.9, 17.1 Hz), 1.94-1.80 (m, 6H), 1.72-1.66 (m, 2H).

27.7 General Procedure

To a reaction flask was added phenol 22 (0.1 mmol), alkyl halide (0.1 mmol), K$_2$CO$_3$ (0.2 mmol) and DMF (0.5 mL). The reaction mixture was stirred at r.t. for 10 h. After filtration, the solution was diluted with EtOAc (5 mL) and washed with water and brine, and then dried over Na$_2$SO$_4$. Concentration and purification of the residue by preparative LC-MS gave pure product.

27.7.a 3-[4-(4-cycloheptyloxy-3-cyclopentyloxyphenyl)-2-oxo-pyrrolidin-1-yl]-benzonitrile (23a)

$^1$H NMR (CDCl$_3$): δ 7.97-7.92 (m, 2H), 7.52-7.43 (m, 2H), 6.86 (d, 1H, J=7.9 Hz), 6.78-6.76 (m, 2H), 4.77 (brs, 1H), 4.33-4.27 (m, 1H), 4.16 (t, 1H, J=8.9 Hz), 3.84 (t, 1H, J=7.8 Hz), 3.69-3.61 (m, 1H), 3.01 (dd, 1H, J=8.7, 17.1 Hz), 2.80 (dd, 1H, J=9.1, 17.2 Hz), 2.00-1.96 (m, 2H), 1.89-1.55 (m, 16H), 1.45-1.36 (m, 2H). Yield: 67%.

27.7.b 3-[4-(3-cyclopentyloxy-4-cyclopropylmethoxyphenyl)-2-oxo-pyrrolidin-1-yl]-benzonitrile (23b)

$^1$H NMR (CDCl$_3$): δ 7.97-7.92 (m, 2H), 7.50-7.42 (m, 2H), 6.88 (d, 1H, J=7.9 Hz), 6.79-6.77 (m, 2H), 4.78 (brs, 1H), 4.16 (t, 1H, J=8.4 Hz), 3.85-3.80 (m, 3H), 3.69-3.61 (m, 1H), 3.01 (dd, 1H, J=8.7, 17.1 Hz), 2.80 (dd, 1H, J=9.0, 17.2 Hz), 1.87-1.83 (m, 6H), 1.65-1.56 (m, 2H), 1.29-1.27 (m, 1H), 0.60 (dd, 2H, J=5.8, 13.2 Hz), 0.33 (dd, 2H, J=4.4, 9.2 Hz). Yield: 83%.

27.7.c 3-[4-(4-cycloheptyloxy-3-cyclopentyloxyphenyl)-2-oxo-pyrrolidin-1-yl]benzamide (24a)

$^1$H NMR (CDCl$_3$): δ 8.08 (s, 1H), 7.93 (d, 1H, J=14.5 Hz), 7.58 (d, 1H, J=7.6 Hz), 7.46 (t, 1H, J=7.9 Hz), 6.86 (d, 1H, J=8.0 Hz), 6.79-6.76 (m, 2H), 6.24 (brs, 1H), 5.68 (brs, 1H), 4.77 (brs, 1H), 4.32-4.26 (m, 1H), 4.21 (t, 1H, J=8.9 Hz), 3.90 (t, 1H, J=7.8 Hz), 3.68-3.60 (m, 1H), 3.01 (dd, 1H, J=8.7, 17.0 Hz), 2.79 (dd, 1H, J=9.0, 17.0 Hz), 2.03-1.96 (m, 2H), 1.87-1.58 (m, 16H), 1.58-1.39 (m, 2H). Yield: 92%.

27.7.d 3-[4-(3-cyclopentyloxy-4-cyclopropylmethoxyphenyl)-2-oxo-pyrrolidin-1-yl]-benzamide (24b)

$^1$H NMR (CDCl$_3$): δ 8.08, (s, 1H), 7.88 (d, 1H, J=8.0 Hz), 7.59 (d, 1H, J=7.6 Hz), 7.46 (t, 1H, J=8.0 Hz), 6.88 (d, 1H, J=8.0 Hz), 6.80-6.77 (m, 2H), 6.27 (brs, 1H), 5.62 (brs, 1H), 4.79 (brs, 1H), 4.21 (t, 1H, J=8.7 Hz), 3.90 (t, 1H, J=7.8), 3.82 (d, 2H, J=6.8), 3.69-3.60 (m, 1H), 3.01 (dd, 1H, J=8.7, 17.0 Hz), 2.79 (dd, 1H, J=9.0, 17.0 Hz), 1.87-1.84 (m, 6H), 1.55-1.68 (m, 2H), 1.29-1.25 (m, 3H), 0.60 (dd, 2H, J=5.9, 12.8 Hz), 0.33 (dd, 2H, J=4.6, 10.3 Hz). Yield: 87%.

EXAMPLE 28

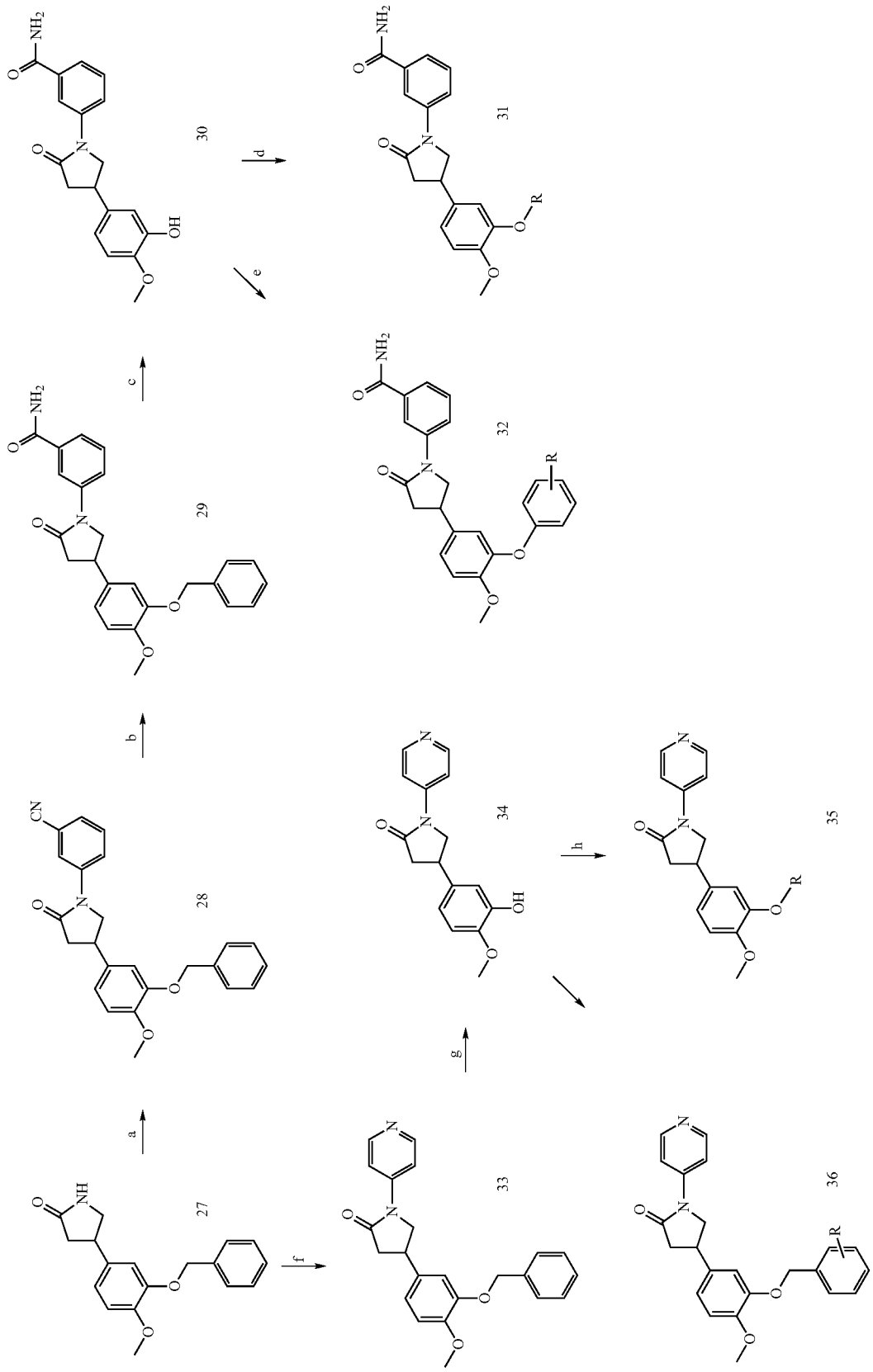

28.1 Preparation of Compound 28

Compound 28 was prepared using the procedure set forth in Example 1 as for compound 40.

28.1.a Compound 28

$^1$H NMR (CDCl$_3$): δ 7.91 (2H, m), 7.23-7.47 (2H, m), 6.89 (1H, d, J=8 Hz), 6.82 (1H, d, J=8 Hz), 6.76 (1H, s), 5.15 (2H, s), 4.09 (1H, t, J=7.7 Hz), 3.89 (3H, s), 3.72 (1H, t, J=7.7 Hz), 3.62 (1H, m), 2.97 (1H, q, J=8.5 Hz), 2.72 (1H, q, J=8.5 Hz).

28.2 Preparation of 3-[4-(3-benzyloxy-4-methoxyphenyl)-2-oxo-pyrrolidin-1-yl]benzamide (29)

To a round bottom flask was added 28 (1.10 g, 2.75 mmol) and 25 mL EtOH.

A solution of 25% NaOH was added followed by slow addition of 1.2 mL H$_2$O$_2$ (30%) to prevent the temperature from rising above 45° C. The reaction was stirred for 3 h, an additional 2 mL of 30% H$_2$O$_2$ was added and the resulting mixture was stirred overnight at 45° C. After concentration, the residue was purified on silica gel to give the product, 0.91 g.

28.3 Preparation of 3-[4-(3-hydroxy-4-methoxyphenyl)-2-oxo-pyrrolidin-1-yl]benzamide (30)

To a solution of 29 (0.9 g, 2.26 mmol) in EtOH (15 mL) was added 10% Pd/C. The solution was then placed under vacuum and recharged with H$_2$. The reaction mixture was stirred under H$_2$ overnight. After filtration and removal of solvent, the residue was placed under vacuum for 10 h to give 30. Etherification of 30 was performed as set forth in Example 27.

28.4 Preparation of Compound 31

Compound 30 (20 mg, 0.06 mmol) was dissolved in DMF (0.3 mL). K$_2$CO$_3$ (28 mg, 0.2 mmol) was added followed by the addition of 4-bromohexanylnitrile (17 mg, 0.1 mmol). The mixture was stirred at r.t. for 15 h. After filtration, the solution was diluted with EtOAc (3 mL) and washed with water (3 mL), brine (3 mL) and dried over Na$_2$SO$_4$. Removal of solvent gave a residue which was purified on preparative LC-MS to give 31.

28.5 Preparation of Compound 32

Compound 60 (20 mg, 0.06 mmol) was dissolved in CH$_2$Cl$_2$ (1 mL). Cu(OAc)$_2$ (11 mg, 0.06 mmol), (CH$_3$)$_3$N (0.12 mmol) and 3-cyanobenzeneboric acid (10 mg, 0.06 mmol) were then added, followed by 4 Å molecular sieves. The mixture was stirred at r.t. for 30 h. After filtration, the solvent was removed under reduced pressure. The residue was purified by preparative LC-MS to give the desired product.

28.6 Preparation of Compound 33

To a round bottom flask was added 27 (2 g, 6.7 mmol), 4-bromopyridine (1.9 g, 10 mmol), K$_3$PO$_4$ (2.8 g, 13 mmol), K$_2$CO$_3$ (0.92 g, 6.7 mmol), DMF (10 mL), dioxane (10 mL) and trans-cyclohexanediamine (60 µL). The mixture was stirred under N$_2$ for 5 min before the addition of CuI (100 mg). The mixture was heated at 110° C. for 20 h and cooled to r.t. The mixture was then diluted with EtOAc (100 mL) and washed with saturated NH$_4$Cl (50 mL) and brine, and dried over Na$_2$SO$_4$. Concentration and chromatography of the residue gave 33 (1.4 g).

28.7 Preparation of Compound 34

Compound 34 was prepared using the procedure of Example 27 for compound 22.

28.8 Preparation of Compound 35

Compound 34 (20 mg, 0.056) was dissolved in DMF (0.3 mL). K$_2$CO$_3$ (28 mg, 0.2 mmol) was added followed by addition of 4-bromohexanylnitrile (17 mg, 0.1 mmol). The mixture was stirred at r.t. for 15 h. After filtration, the solution was diluted with EtOAc (3 mL) and washed with water (3 mL) and brine (3 mL), and dried over Na$_2$SO$_4$. Removal of solvent gave a residue which was purified on preparative LC-MS to give 35.

28.9 Preparation of Compound 36

Compound 34 (20 mg, 0.056 mmol) was dissolved in CH$_2$Cl$_2$ (1 mL).

Cu(OAc)$_2$ (11 mg, 0.06 mmol), (CH$_3$)$_3$N (0.12 mmol) and 3-cyanobenzeneboric acid (10 mg, 0.06 mmol) were added, followed by 4 Å molecular sieves. The mixture was stirred at r.t. for 30 h. After filtration, the solvent was removed under reduced pressure. The residue was purified by preparative LC-MS to give the desired product.

EXAMPLE 29

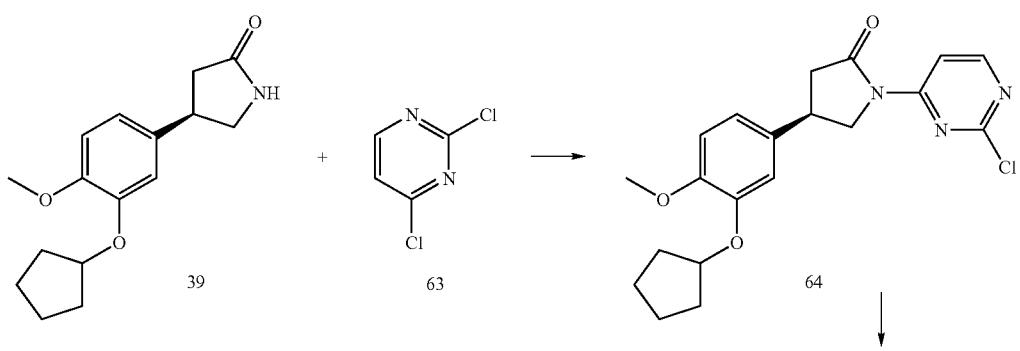

-continued

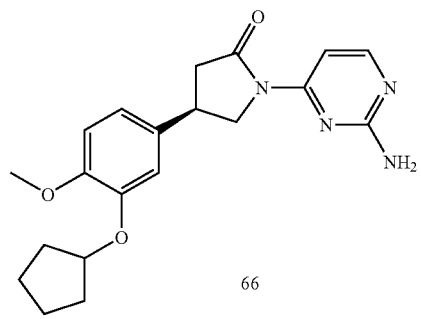

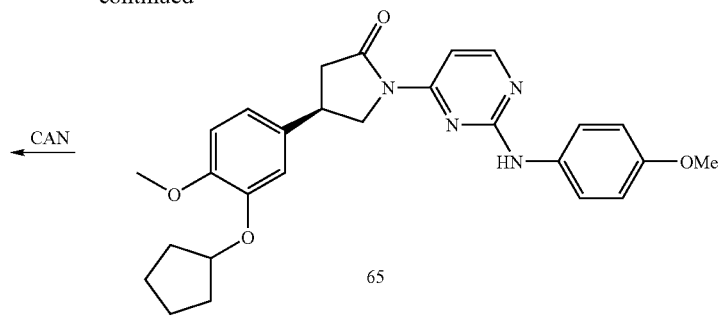

29.1 Preparation of Compound 64

To a dry round bottom flask was added 39 (120 mg, 0.43 mmol), 63 (300 mg, 2 mmol) and DMF (3 mL). This solution was cooled to 0° C. NaH (40 mg, 2.5 mmol) was then added and the reaction mixture was stirred for 2 h, quenched with NH$_4$Cl, extracted with EtOAc, washed with brine and dried over Na$_2$SO$_4$. Concentration and purification by column chromatography on silica gel gave 42 mg of the desired product.

29.2 Preparation of Compound 65

To a round bottom flask was added 64 (20 mg, 0.05 mmol) and 4-methoxylaniline (100 mg) in HOAc (2 mL). The mixture was heated to reflux for 3 h, cooled, and concentrated. Purification of the residue on silica gel gave 65.

29.3 Preparation of Compound 66

To a round bottom flask was added 65 (12 mg), acetonitrile (1 mL) and water (0.5 mL). To this solution was added CAN (28 mg) and the mixture was stirred at 0° C. overnight. The mixture was extracted with EtOAc, washed with brine, and dried over Na$_2$SO$_4$. Concentration and purification of the residue by preparative LC-MS gave 66.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A compound having the formula:

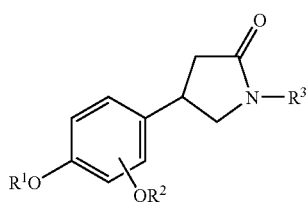

wherein

R$^1$ is a member selected from hydrogen, substituted C$_1$-C$_4$ alkyl and substituted or unsubstituted C$_{3-6}$ cycloalkyl;

R$^2$ is a member selected from substituted or unsubstituted phenyl, substituted or unsubstituted benzyl and substituted or unsubstituted C$_3$-C$_6$ cycloalkyl;

R$^3$ is a member selected from substituted or unsubstituted pyridyl, substituted or unsubstituted pyrimidyl, substituted or unsubstituted pyrazinyl, and phenyl substituted with a member elected from cyano S(O)$_n$NR$^{3a}$R$^{3b}$, NR$^{3a}$S(O)$_n$R$^{3b}$, S(O)$_n$R$^{3a}$, NR$^{3a}$R$^{3b}$, OC(O)OR$^{3b}$, C(O)R$^{3b}$, and C(O)NR$^{3a}$R$^{3b}$;

wherein R$^{3a}$ and R$^{3b}$ are members independently selected from H, substituted or unsubstituted C$_1$-C$_6$ alkyl and substituted or unsubstituted aryl; and n is a member selected from 0, 1 and 2.

2. The compound according to claim 1 wherein R$^3$ has a formula which is a member selected from:

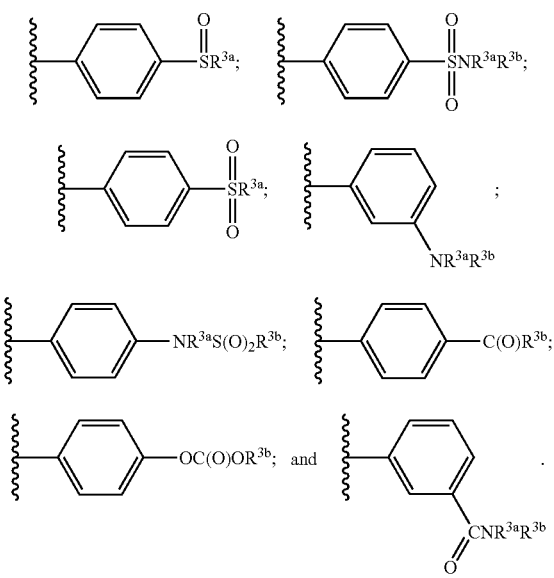

3. The compound according to claim 1, wherein R$^1$ is C$_1$-C$_3$ haloalkyl.

4. The compound according to claim 1, wherein R$^2$ is cyclopentyl.

5. A compond having the formula:

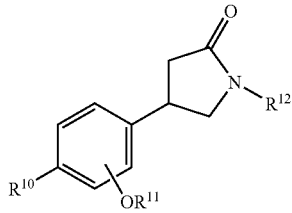

wherein
- $R^{10}$ is a member selected from hydrogen, hydroxy, $C_{1-4}$ alkyl, $C_{1-4}$ alkyloxy, $C_{3-6}$ cycloalkyl-oxy, halo and cyano;
- $R^{11}$ is a member selected from substituted or unsubstituted pyridyl, substituted or unsubstituted pyrimidyl, substituted or unsubstituted $C_{3-6}$ cycloalkyl, substituted or unsubstituted phenyl, substituted or unsubstituted benzyl, and a group selected from (a) or (b):

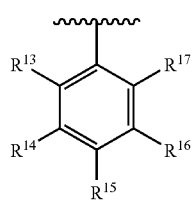

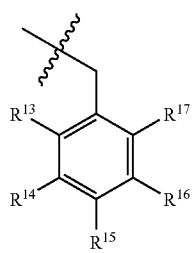

wherein $R^{13}$, $R^{14}$, $R^{15}$, $R^{16}$, and $R^{17}$ are members independently selected from hydrogen, halo, hydroxy, methyl, ethenyl, methoxy, ethoxy, nitro, trifluoromethyl, ditluoromerhyl, difluoromethoxy, trifluoroethoxy, trifluoromethoxy, $OC_2H_5$, $CH_2OH$, $C(O)CH_3$, $S(O)_nCH_3$, $S(O)_nC_2H_5$ and cyano;

wherein n is 0, 1 or 2;

$R^{12}$ is a member selected from substituted aryl, substituted or unsubstituted arylalkyl, substituted or unsubstituted pyridyl, and substituted or unsubstituted heteroaryl other than pyridyl;

wherein said substituted aryl is substituted with halo, methyl, ethenyl, amino, cyano, trifluoromethyl, $CH_2OH$, $S(O)_nNR^{3a}R^{3b}$, $NR^{3a}S(O)_nR^{3a}$, $S(O)_nR^{3a}$, $NHR^{3b}$, $OC(O)OR^{3b}$, $C(O)NR^{3a}R^{3b}$, $NH-C(=O)-NR^{3a}R^{3b}$, $C(=NH)-NH_2$, $NH-C(=S)-NHPh$, $C(O)NH-OH$, tetrazolyl,

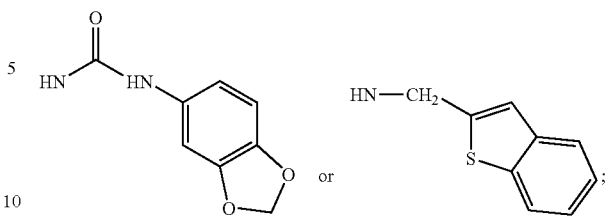

said substituted pyridyl is substituted with methyl, ethenyl, amino, nitro, cyano, trifluoroinethyl, ethoxy-carbonyl. $C(O)OH$, $C(O)OCH_3$, $S(O)_2NH_2$, $C(O)NH_2$, $C(O)NHC_2H_5$, $NHS(Q)_2CH_3$, $CH_2OH$, $S(O)_2CH_3$, $SCH_3$, and $SC_2H_5$; and $R^{3a}$, $R^{3b}$ and $R^{3b-}$ are members independently selected from substituted or unsubstituted $C_1$-$C_6$ alkyl and substituted or unsubstituted aryl; or $R^{3a}$ and $R^{3b}$ may be H.

6. The compound according to claim 5 in which at least one of $R^{13}$, $R^{14}$, $R^{15}$, $R^{16}$, and $R^{17}$ is CN.

7. The compound according to claim 5 in which $R^{13}$ is halogen and $R^{17}$ is CN.

8. The compound according to claim 5 in which $R^{12}$ is selected from substituted phenyl, and substituted or unsubstituted benzyl, pyridinyl, quinolinyl, pyridazinyl, pyrazinyl, or pyrimidinyl.

9. The compound according to claim 8 in which said substitutions on said benzyl, quinolinyl, pyridazinyl, pyrazinyl or pyrimidinyl include up to 2 members independently selected from halo, methyl, ethenyl, amino, nitro, cyano, trifluoromethyl, ethoxy-carbonyl, $C(O)OH$, $C(O)OCH_3$, $S(O)_2NH_2$, $C(O)NH_2$, $C(O)NHC_2H_5$, $NHS(O)_2CH_3$, $CH_2OH$, $S(O)_2CH_3$, $SCH_3$, and $SC_2H_5$.

10. The compound according to claim 5, wherein said $R^{12}$ is substituted phenyl, and said substituted phenyl is a member selected from

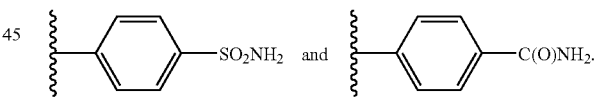

11. The compound according to claim 10 wherein said compound is a member selected from:

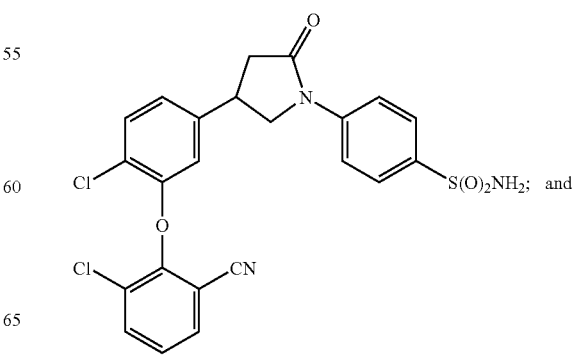

-continued

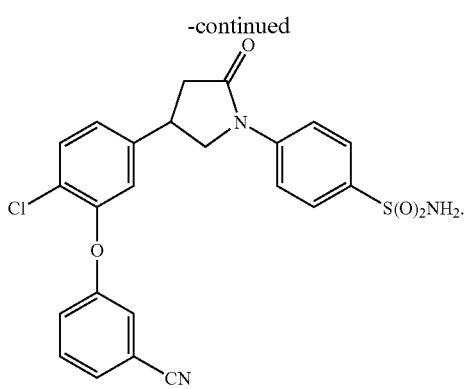

12. A compound having the formula:

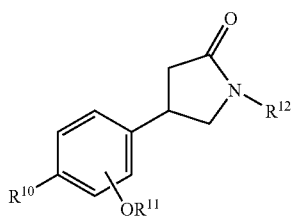

wherein:

R$^{10}$ is haloeen;

R$^{11}$ is a member selected from substituted or unsubstituted pyridinyl, substituted or unsubstituted pyrimidyl, substituted or unsubstituted C$_{3-6}$ cycloalkyl, substituted or unsubstituted phenyl, substituted or unsubstituted benzyl, and a group selected from (a) or (b):

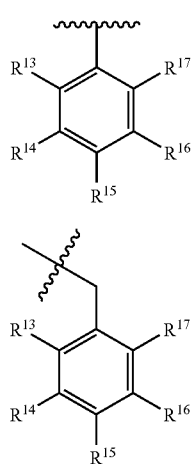

wherein R$^{13}$, R$^{14}$, R$^{15}$, R$^{16}$, and R$^{17}$ are members independently selected from hydrogen, halo, hydroxy, methyl, ethenyl, methoxy, ethoxy, nitro, trifluoromethyl, ditluoromethyl, difluoromethoxy, trifluoroethoxy, trifluoromethoxy, OC$_2$H$_5$, CH$_2$OH, C(O)CH$_3$, S(O)$_n$CH$_3$, S(O)$_n$C$_2$H$_5$ and cyano;

n is 0, 1 or 2; and R$^{12}$ is a substituted or unsubstituted aryl, or a substituted or unsubstituted heteroaryl.

13. The compound according to claim 12 in which

R$^{10}$ is halogen;

R$^{11}$ is a member selected from substituted pyridinyl, substituted pyrimidyl, and a group selected from (a) or (b):

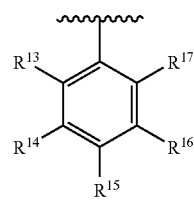

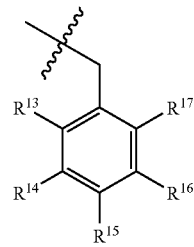

wherein R$^{13}$, R$^{14}$, R$^{15}$, R$^{6}$, and R$^{17}$ are members independently selected from hydrogen, halo, hydroxy. methyl, ethenyl, methoxy, ethoxy, nitro, trifluoromethyl, ditluoromethyl, di tluoromethoxy, trifluoroethoxy, trifluoromethoxy, OC$_2$H$_5$, CH$_2$OH, C(O)CH$_3$, S(O)$_n$CH$_3$, S(O)$_n$C$_2$H$_5$ and cyano;

wherein n is 0, 1 or 2; and

R$^{12}$ is a member selected from substituted pyridinyl and substituted aryl..

14. The compound according to claim 13 in which R$^{11}$ is a member selected from:

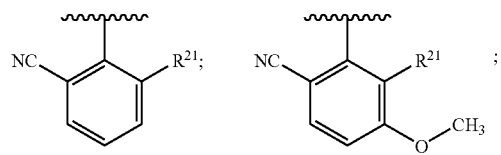

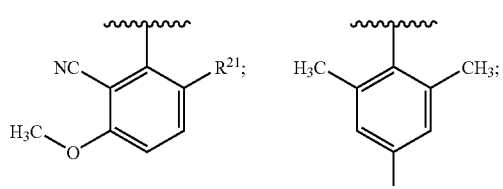

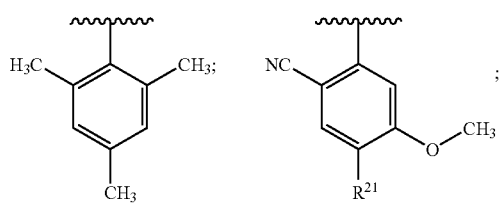

-continued

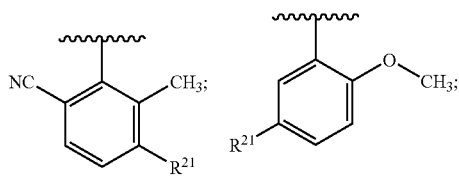

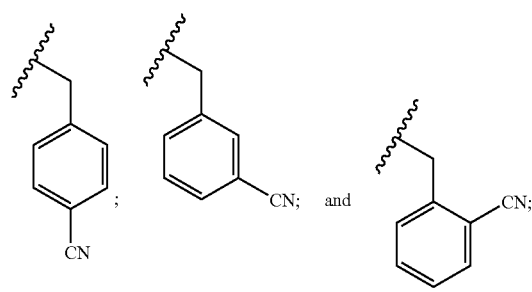

wherein $R^{21}$ is halogen; and
$R^{12}$ is a member selected from:

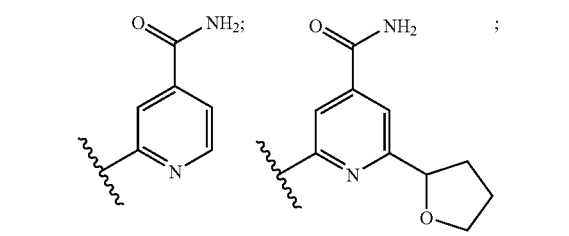

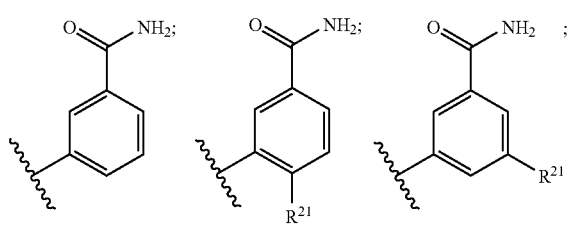

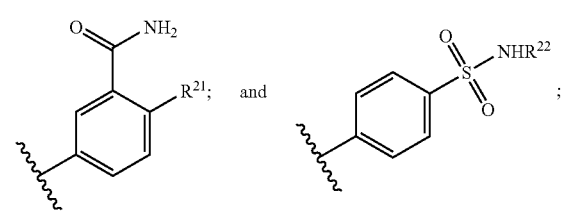

wherein $R^{21}$ is halogen and $R^{22}$ is a member selected from H, $CH_3$,

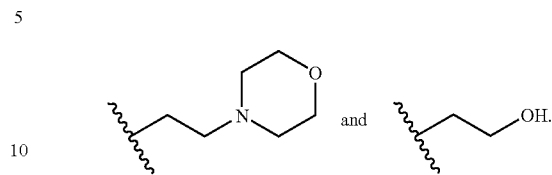

15. The compound of claim 12, having the formula:

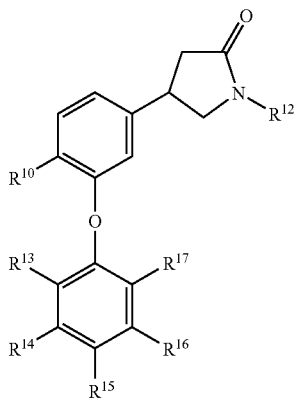

wherein
$R^{12}$ is a member selected from substituted or unsubstituted aryl and substituted or unsubstituted heteroaryl; and
$R^{13}$, $R^{14}$, $R^{15}$, $R^{16}$, and $R^{17}$ are members independently selected from H, halogen, and CN.

16. The compound according to claim 15 in which at least one of $R^3$, $R^{14}$, $R^{15}$, $R^{16}$, and $R^{17}$ is CN.

17. The compound according to claim 15 in which $R^3$ is halogen and $R^{17}$ is CN.

18. The compound according to claim 15 in which $R^{12}$ is substituted or unsubstituted phenyl.

19. The compound according to claim 18 in which said substituted phenyl is substituted with a member selected from $S(O)_2NH_2$ and $C(O)NH_2$.

20. The compound according to claim 19 wherein said substituted phenyl is a member selected from:

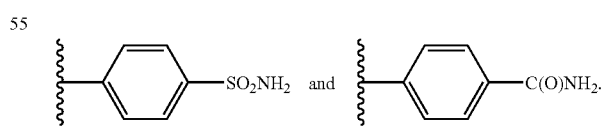

21. A pharmaceutical composition comprising the compound of claim 5 and a pharmaceutically acceptable excipient.

22. A pharmaceutical composition comprising the compound of claim 12 and a pharmaceutically acceptable excipient.

23. The compound of claim 1, wherein said compound is selected from the group consisting of
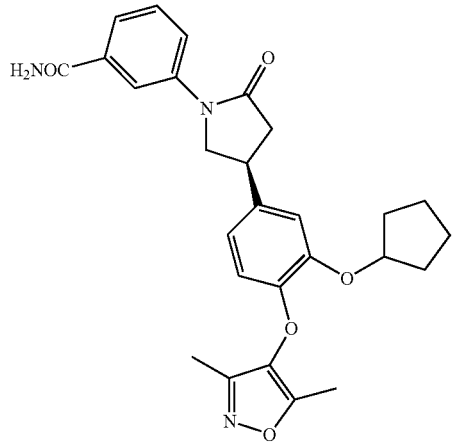
52
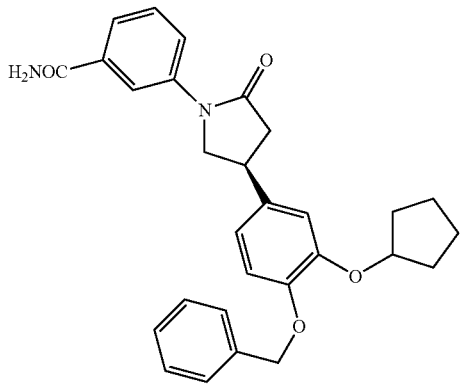
57
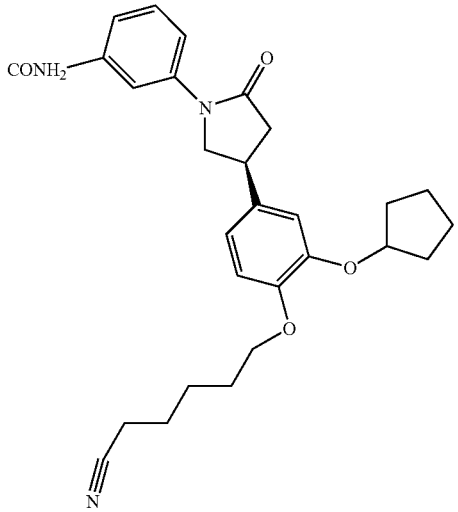
53
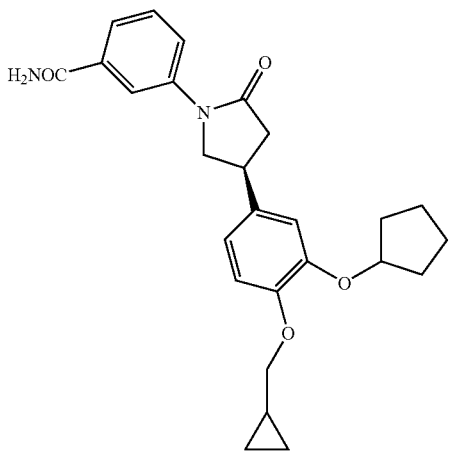
61
; and
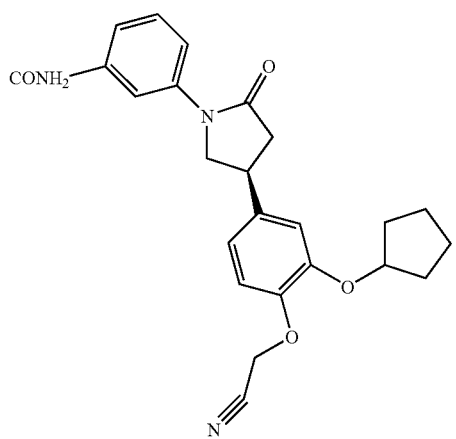
54
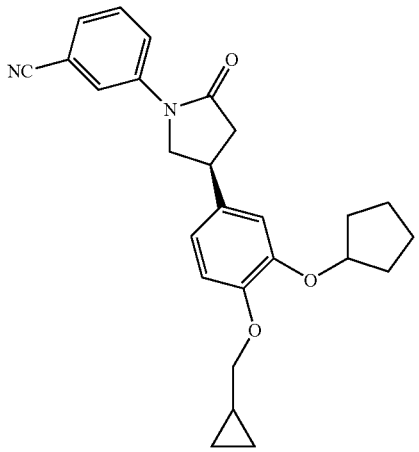
66
24. A pharmaceutical composition comprising the compound of claim 23 and a pharmaceutically acceptable excipient.

25. The compound of claim 5, wherein said compound is selected from the group consisting of
3
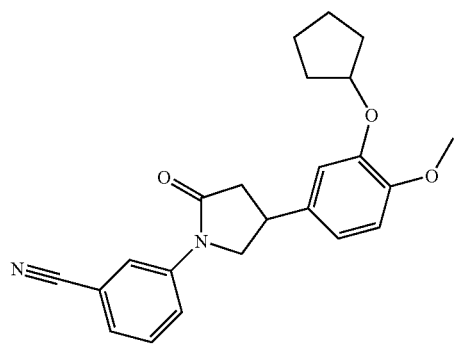
4
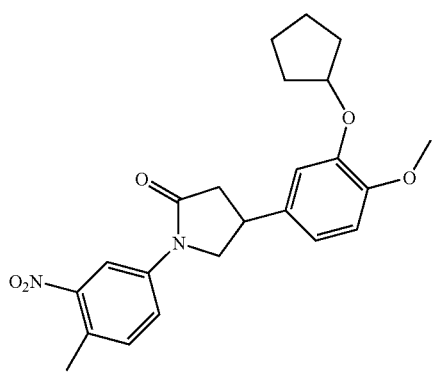
5
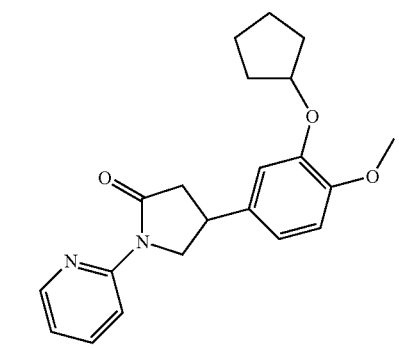
6
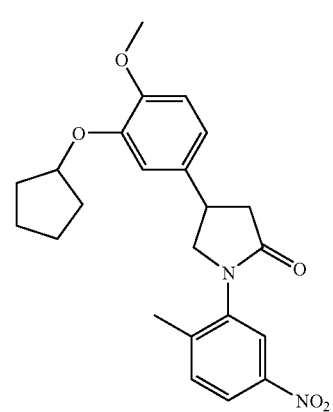
-continued
7
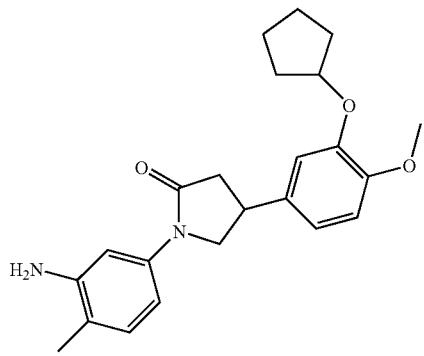
8
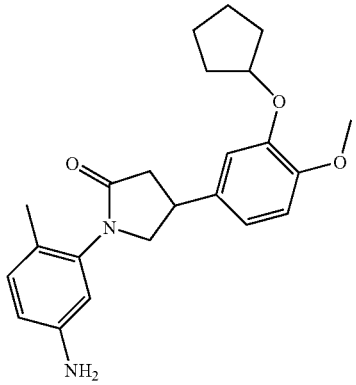
9
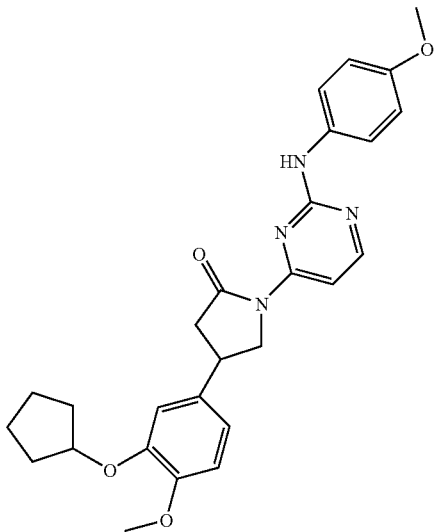
10
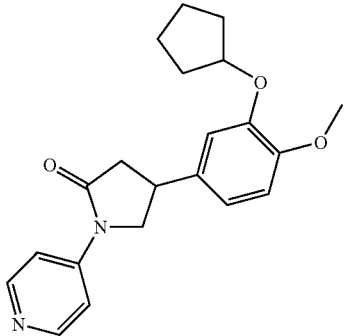

-continued
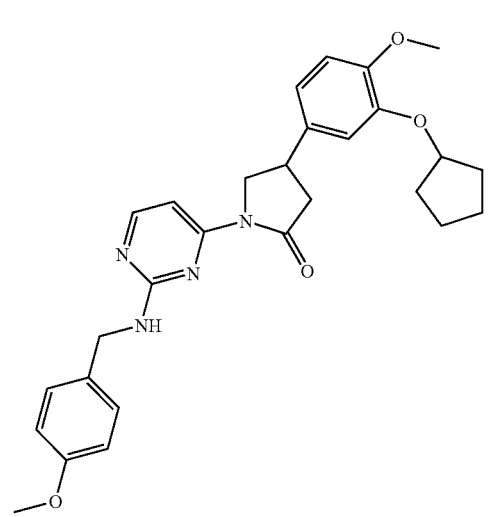
11
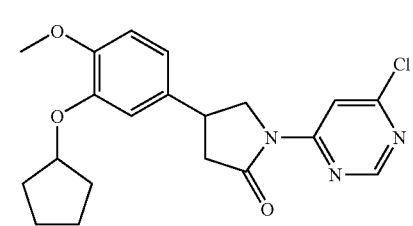
12
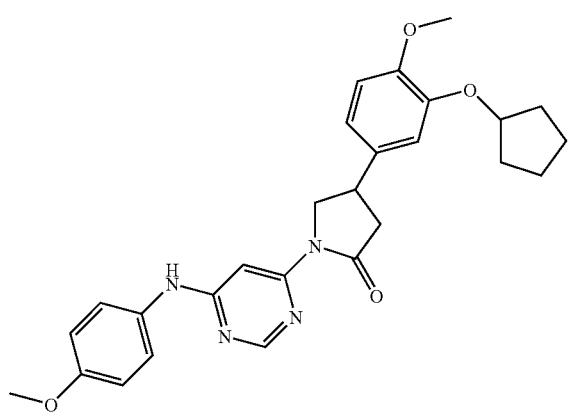
13
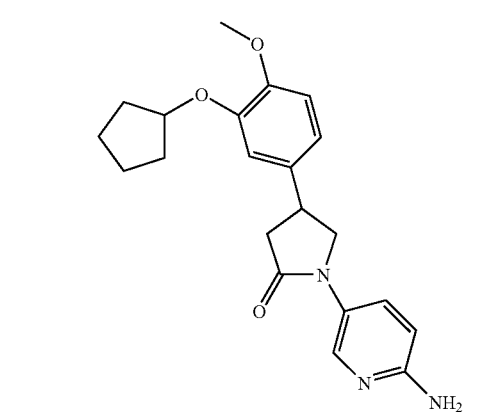
14
-continued
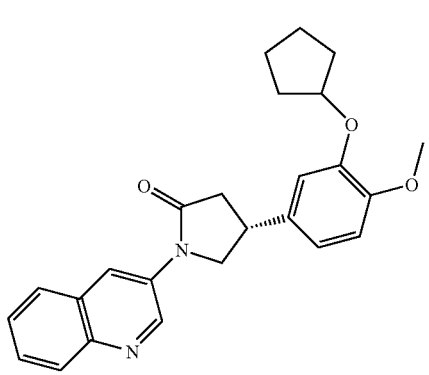
17
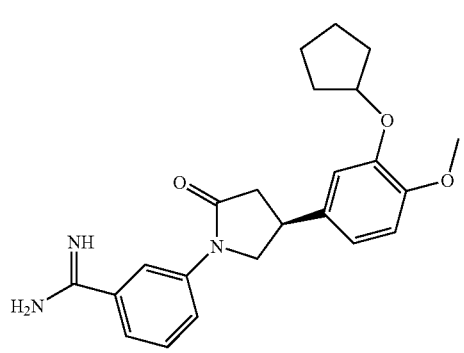
18
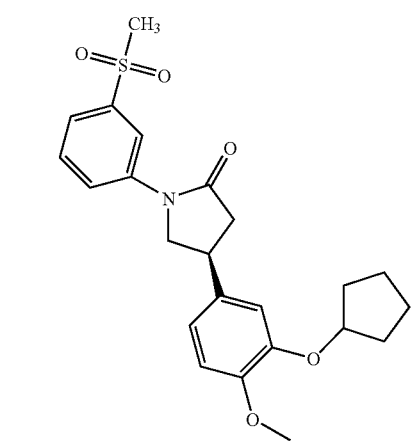
19

-continued
21
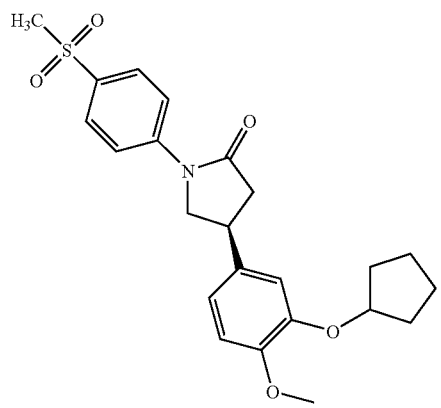
23
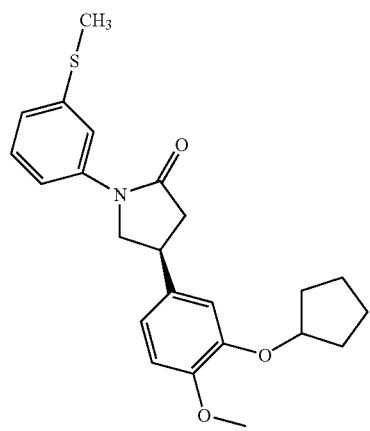
24
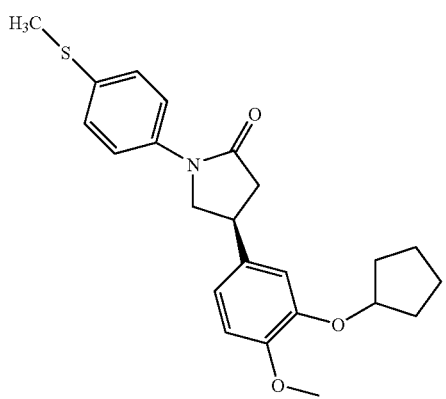
25
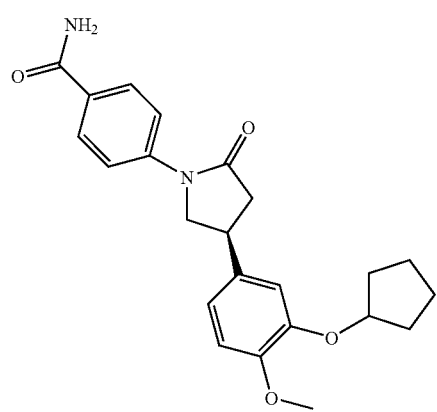
-continued
26
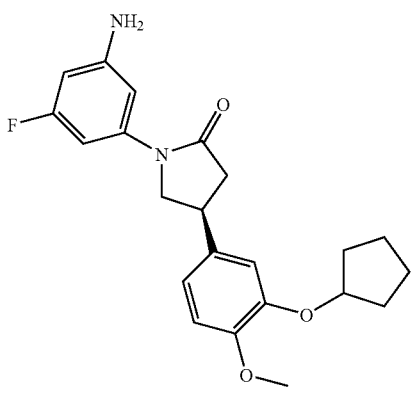
27
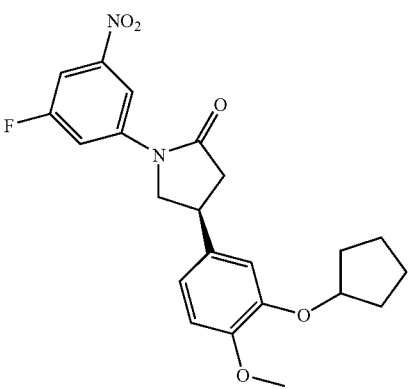
28
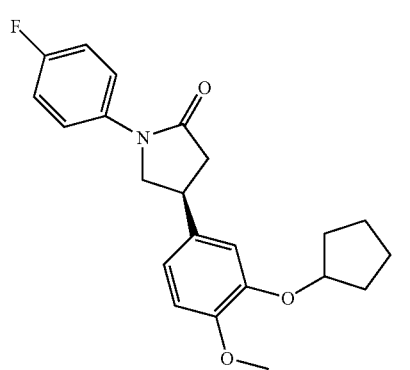
29
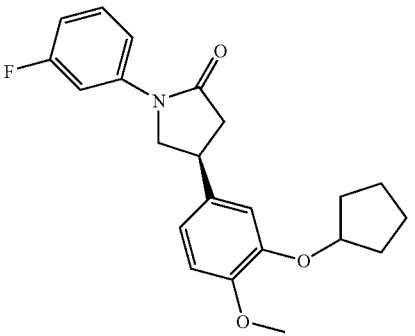

-continued
30
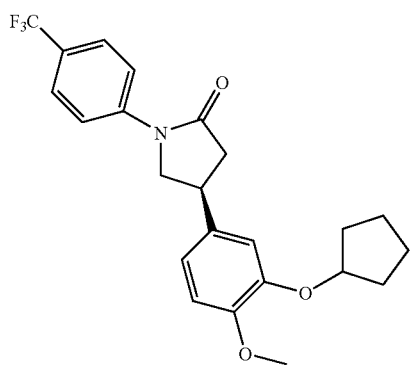
31
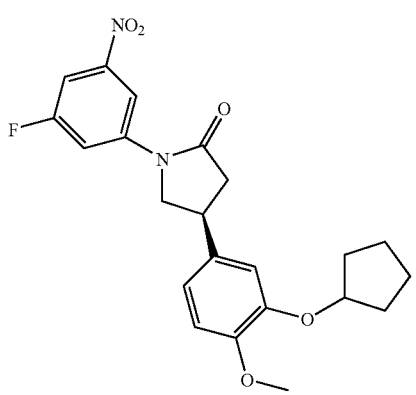
32
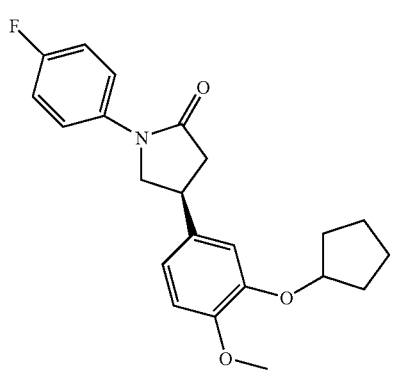
33
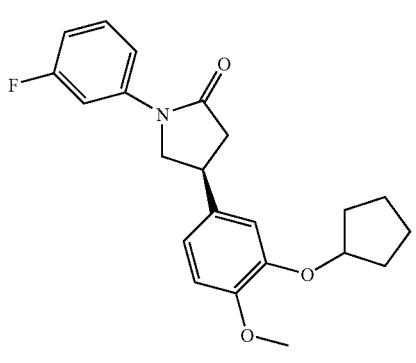
-continued
34
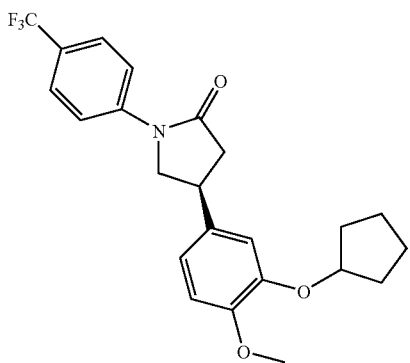
35
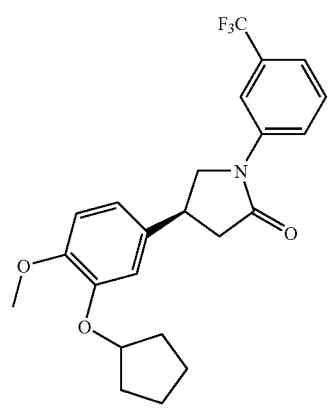
37
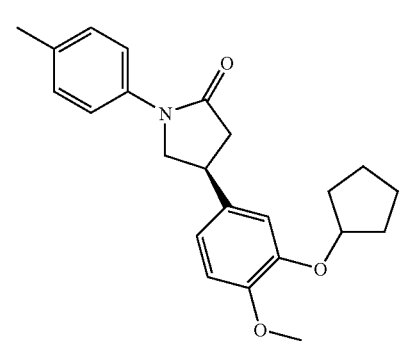
38
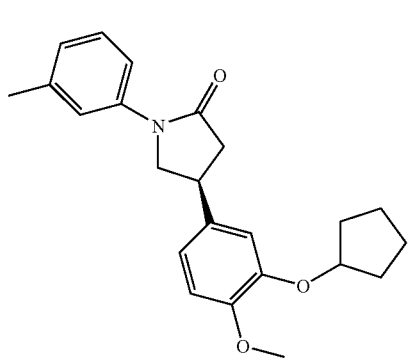

103
-continued
39
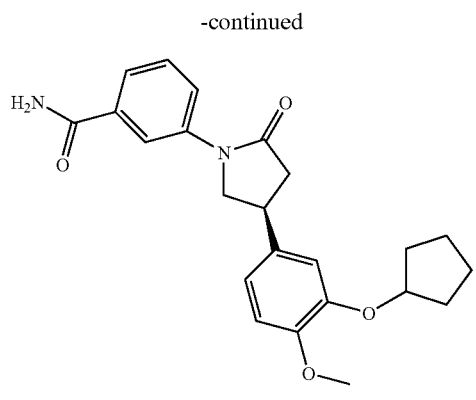
40
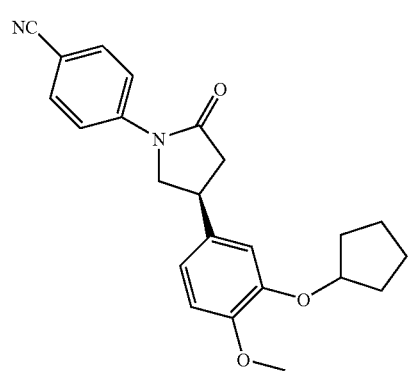
44
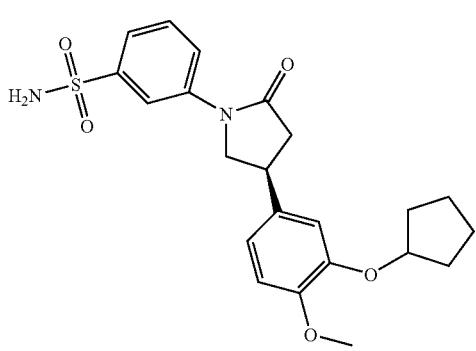
104
-continued
45
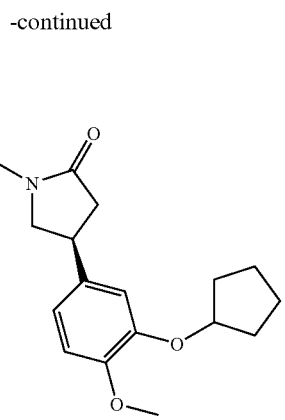
46
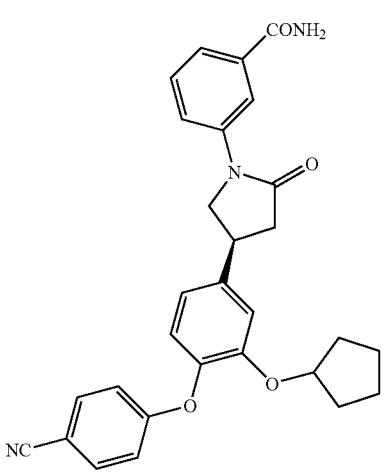
47
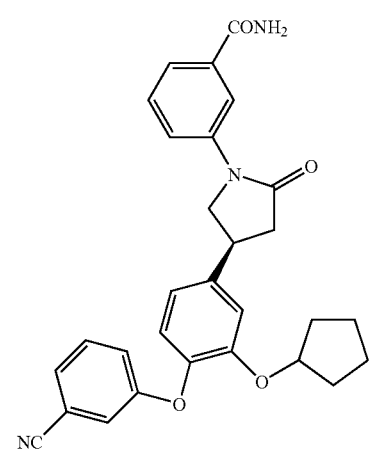
41
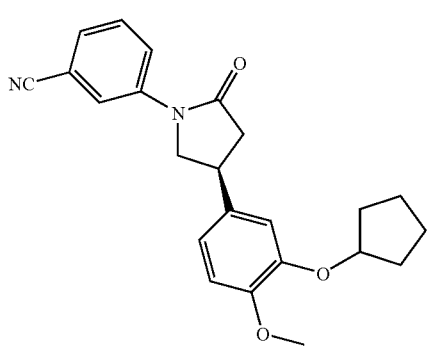

-continued
48
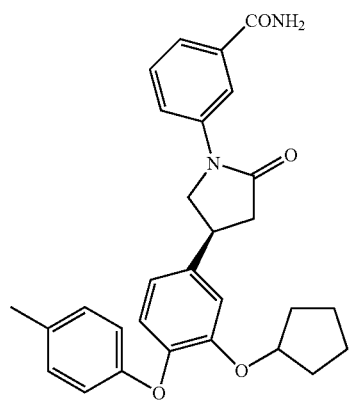
49
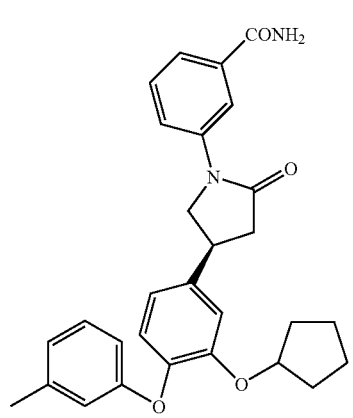
50
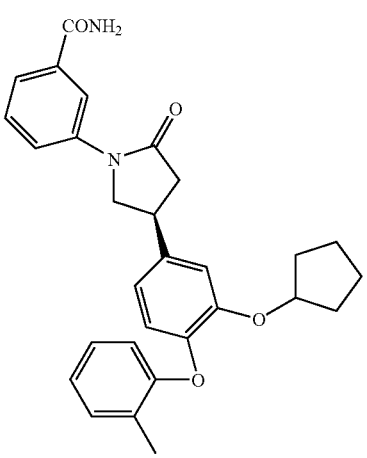
-continued
51
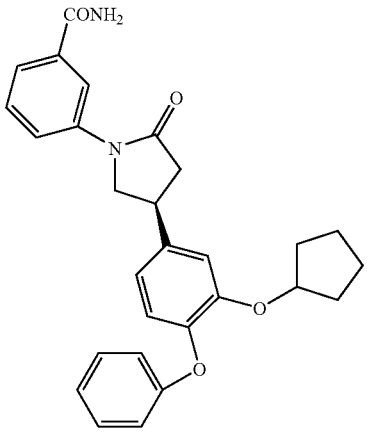
55
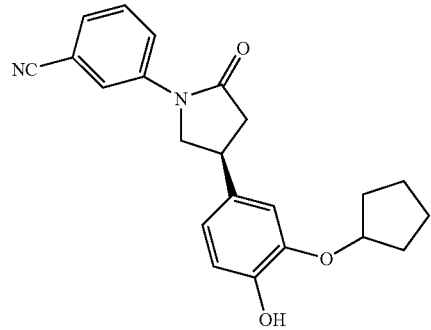
56
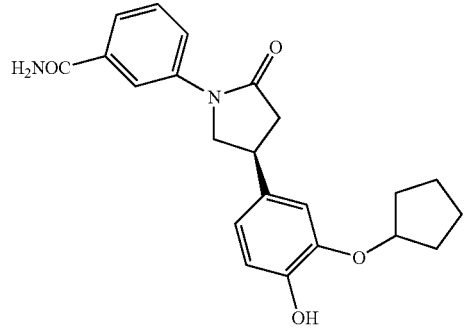
59
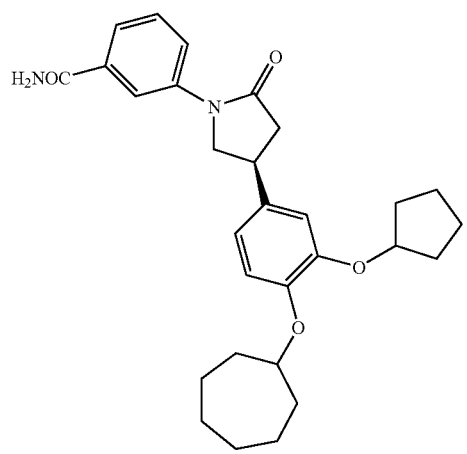

| 107 | 108 |
|---|---|
| -continued | -continued |
60
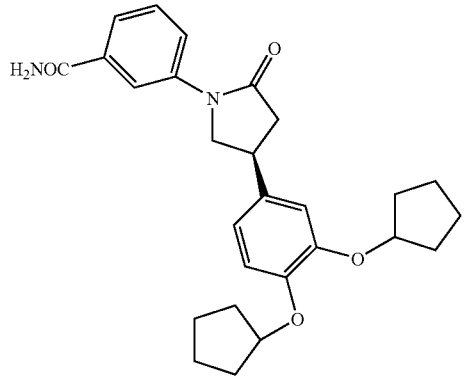
62
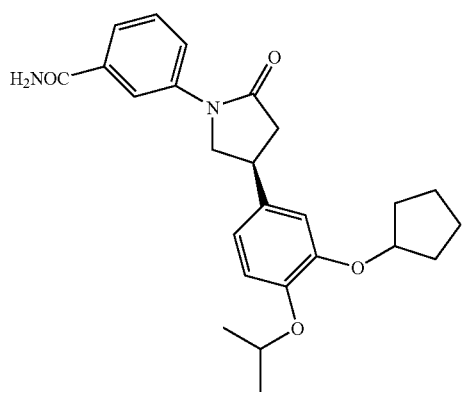
63
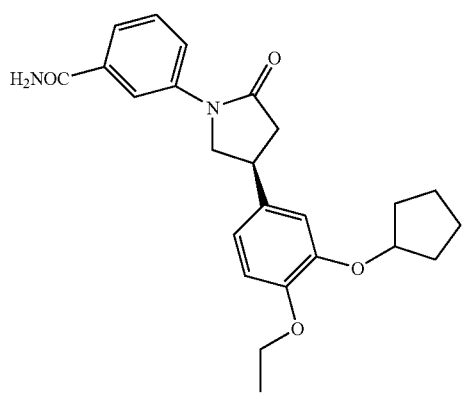
64
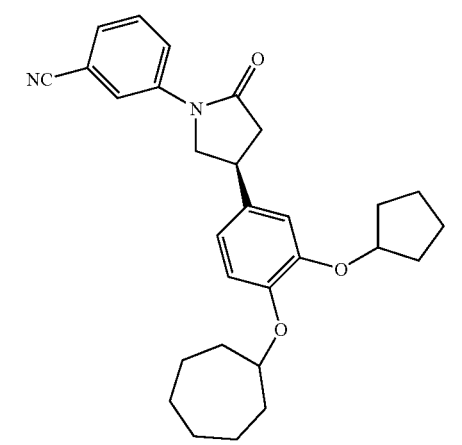
65
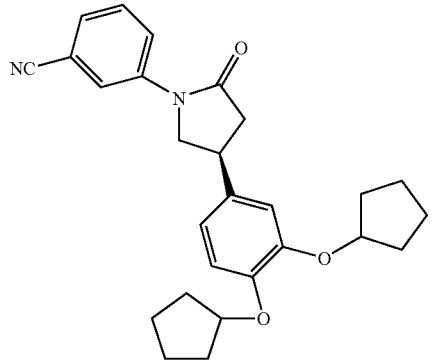
67
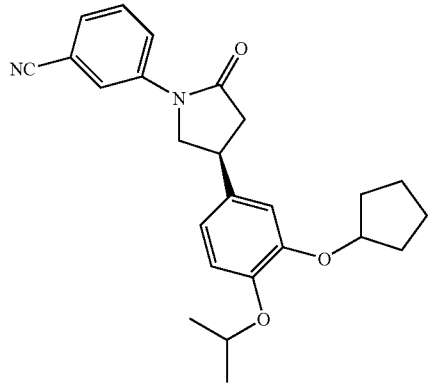
68
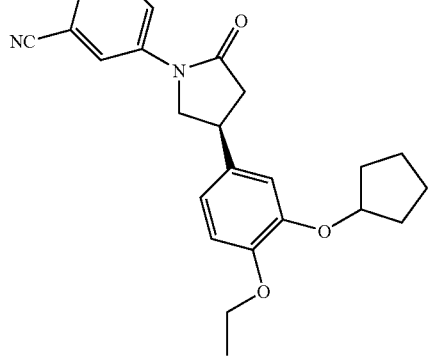
69
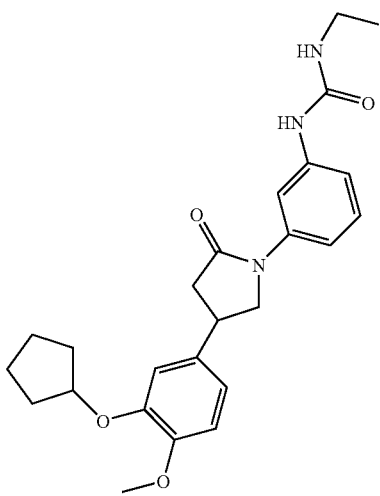

-continued
70
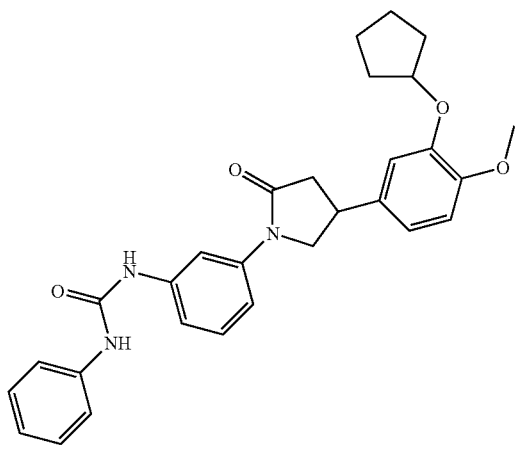
71
73
-continued
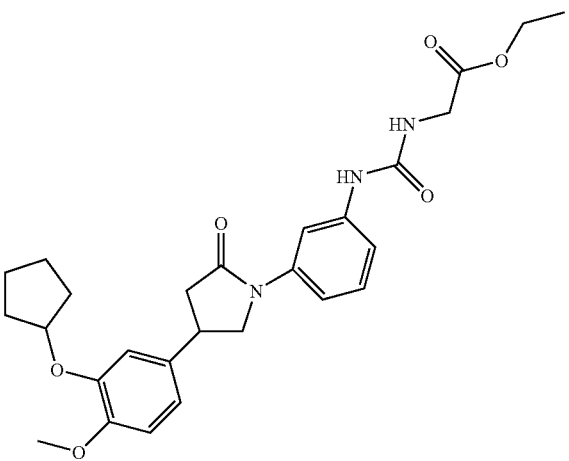
74
72
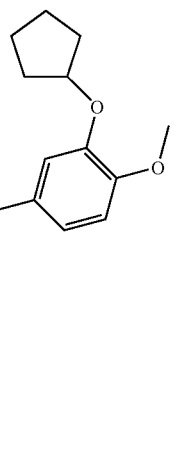
75
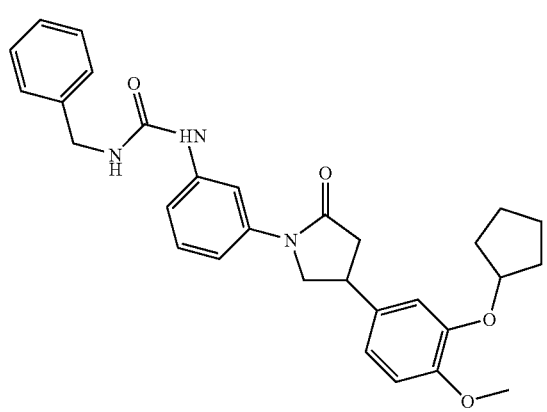

-continued
76
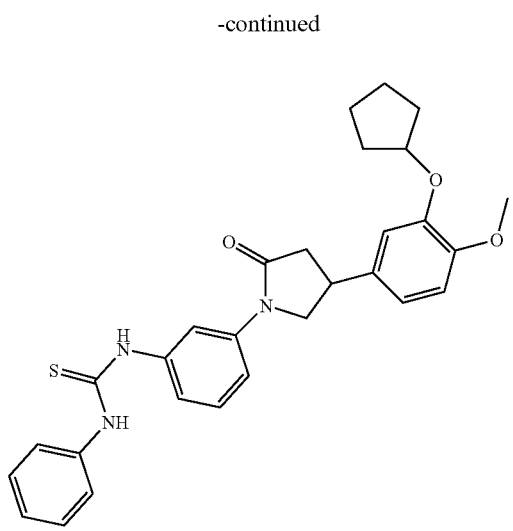
88
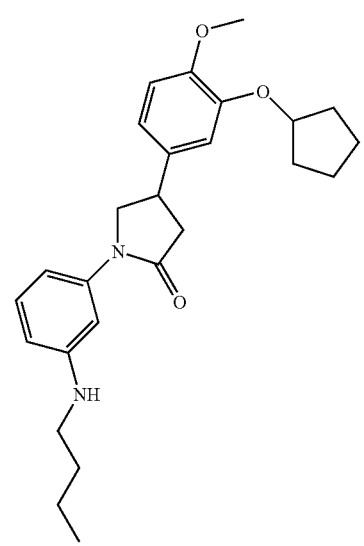
89
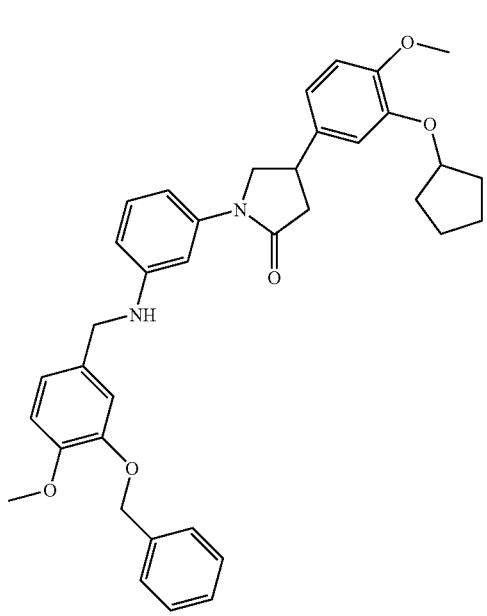
-continued
90
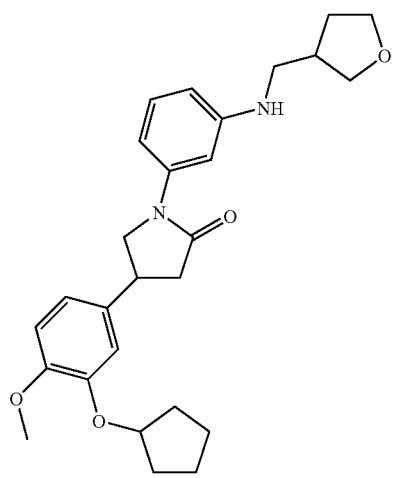
91
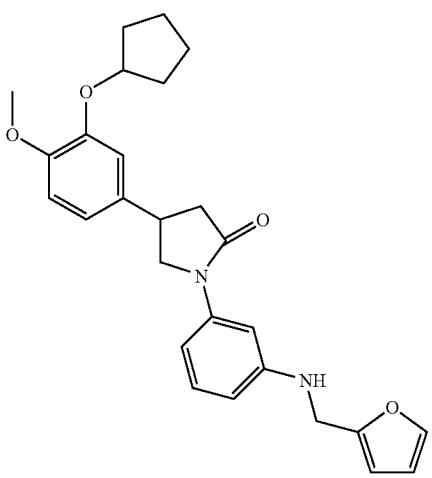
92
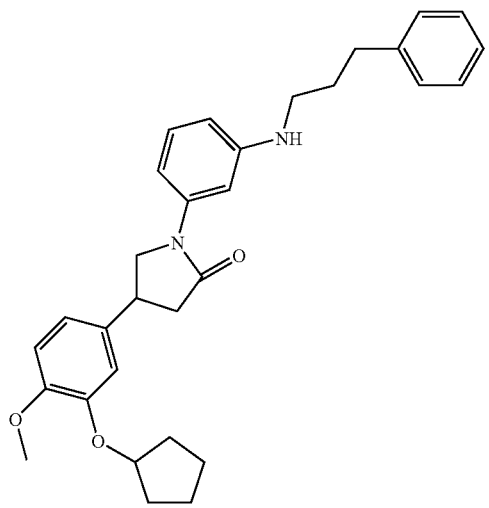

-continued
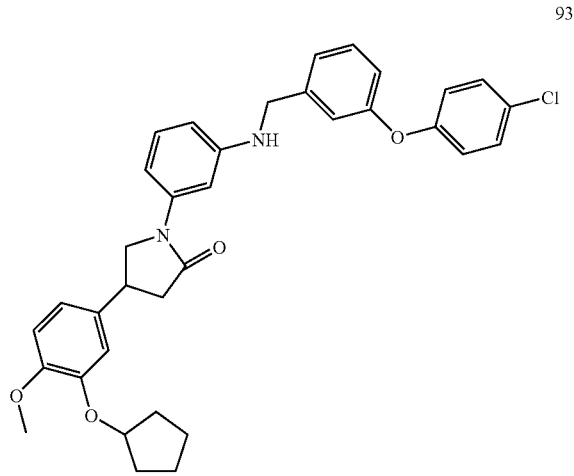
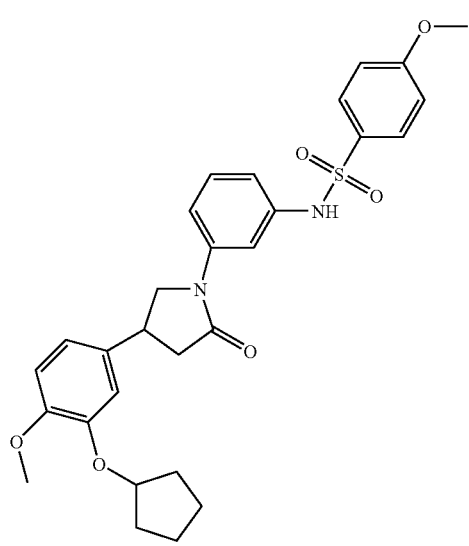
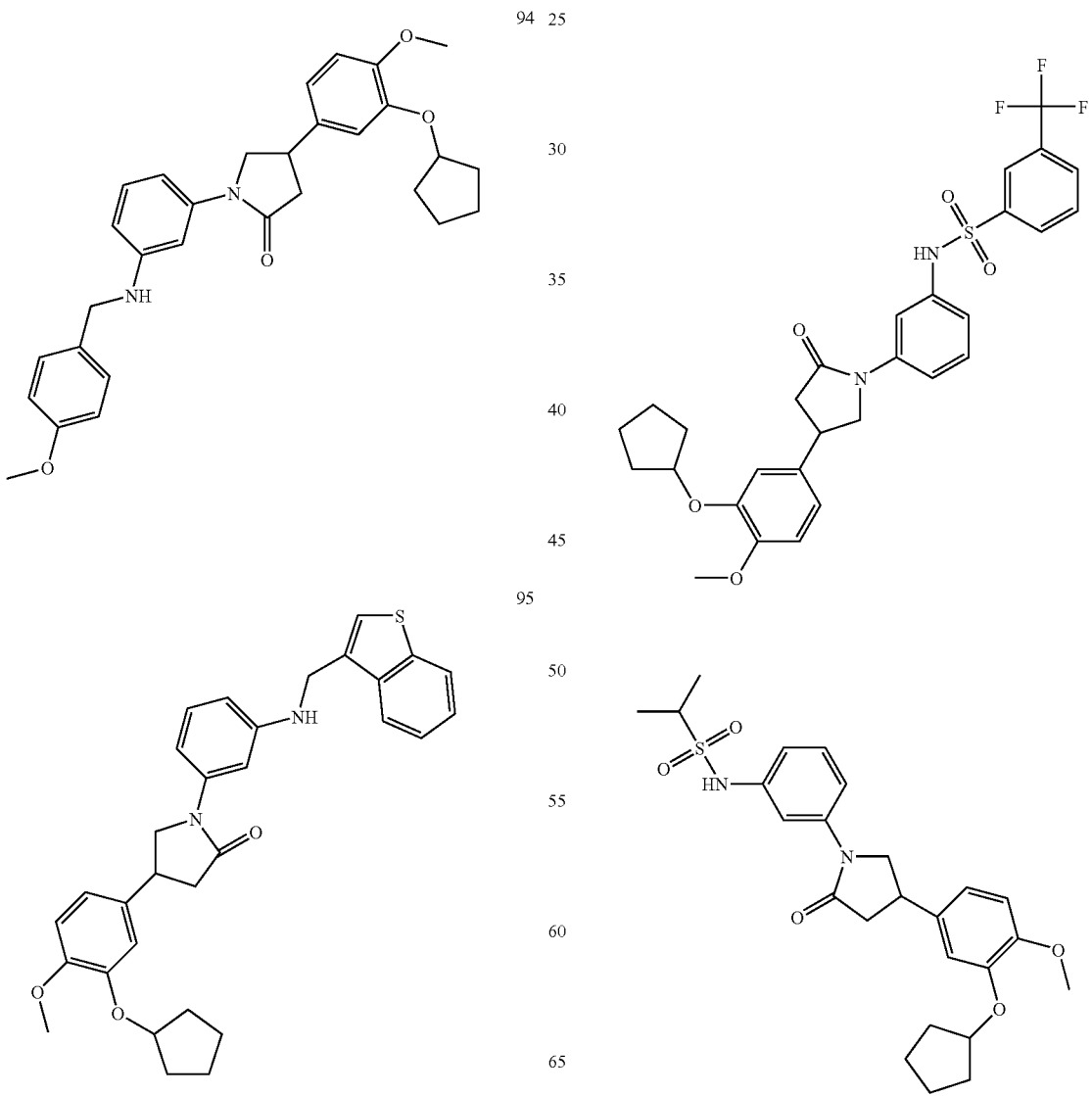

-continued
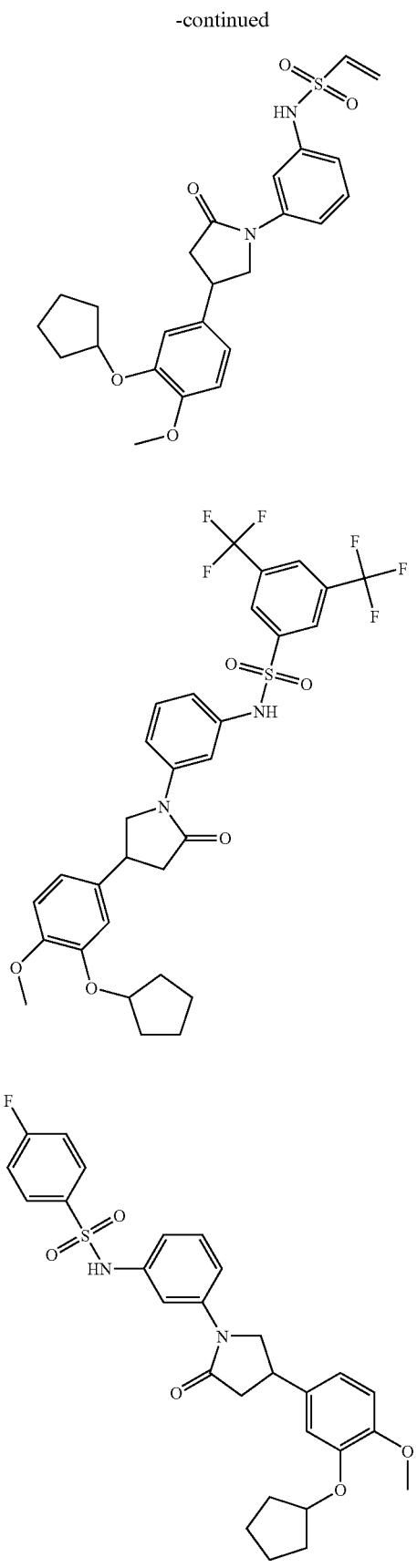
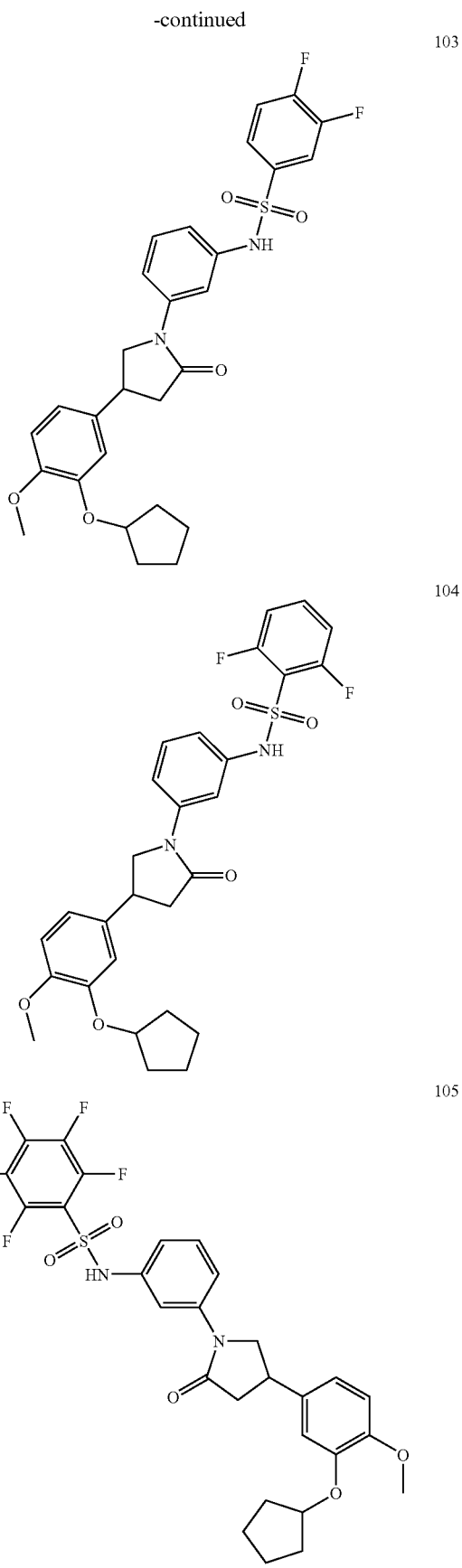

117
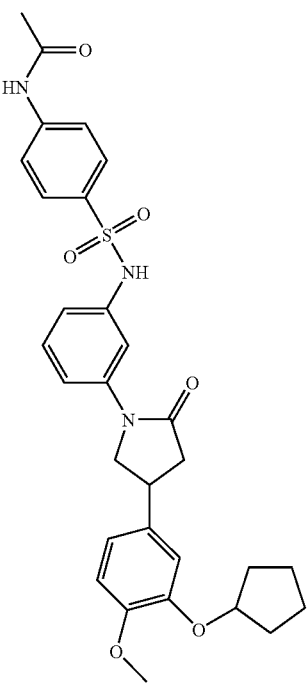
106
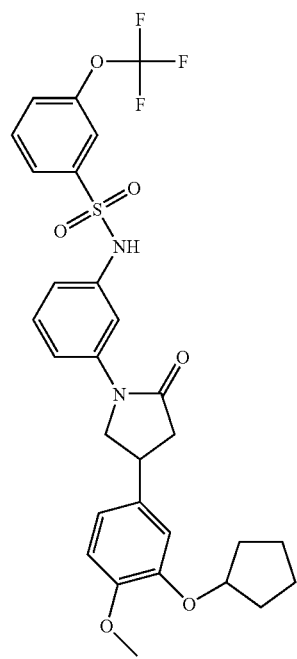
107
118
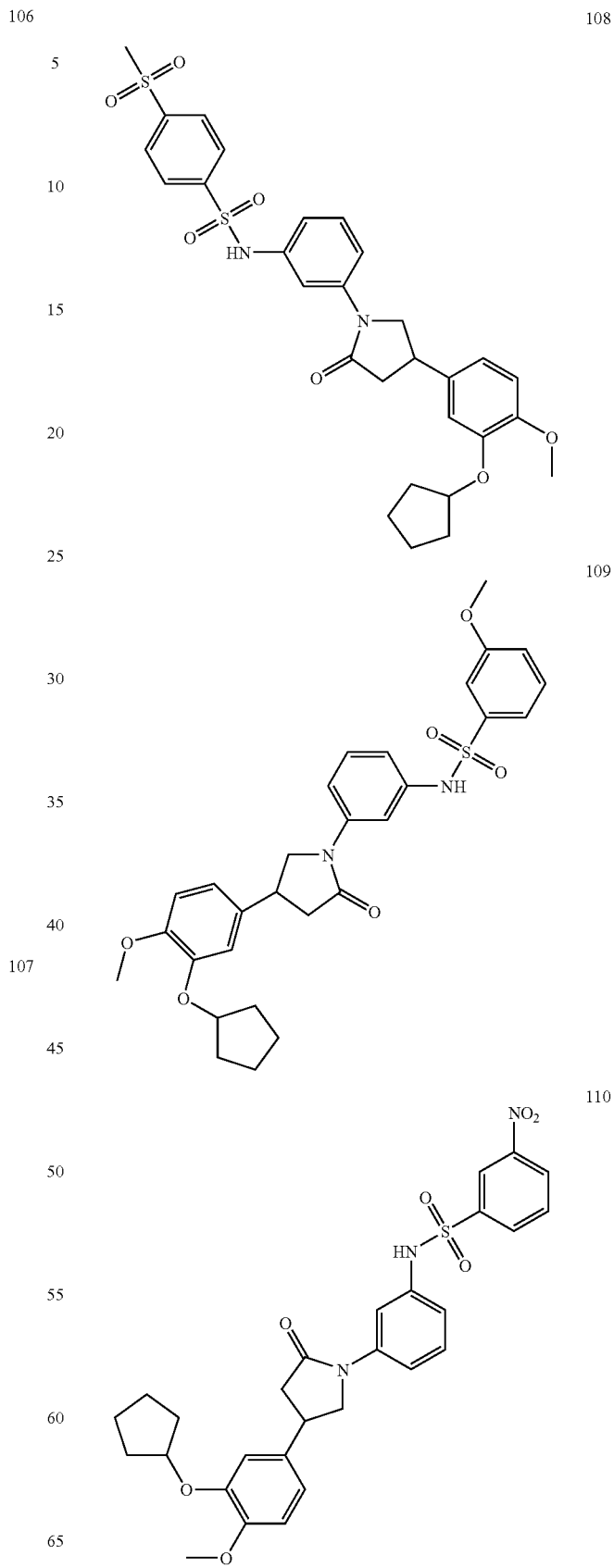

119
-continued
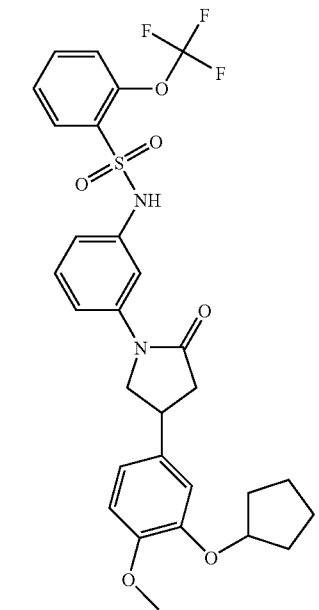
111
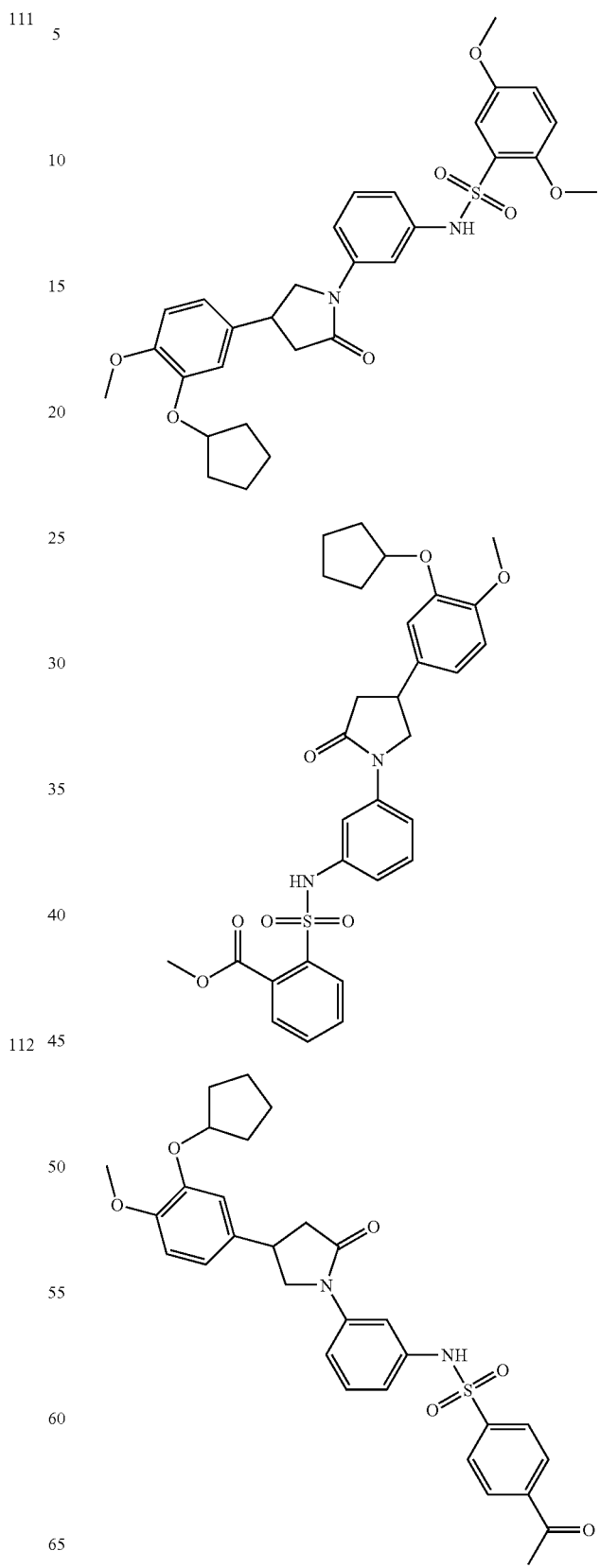

-continued
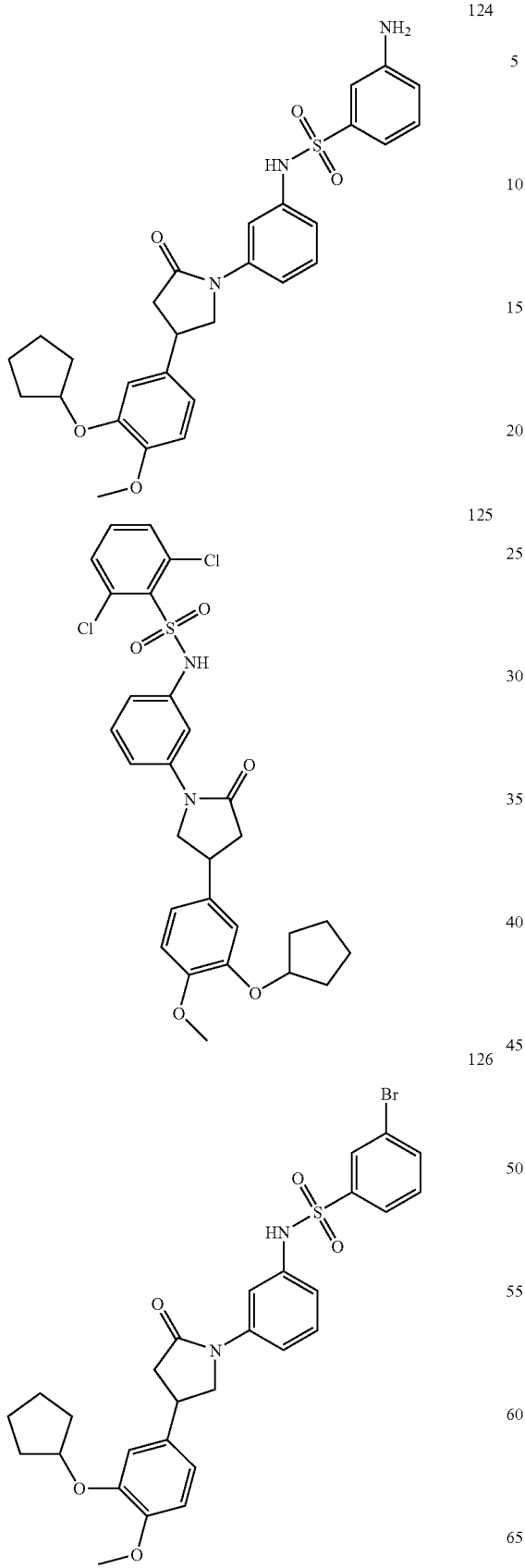
-continued
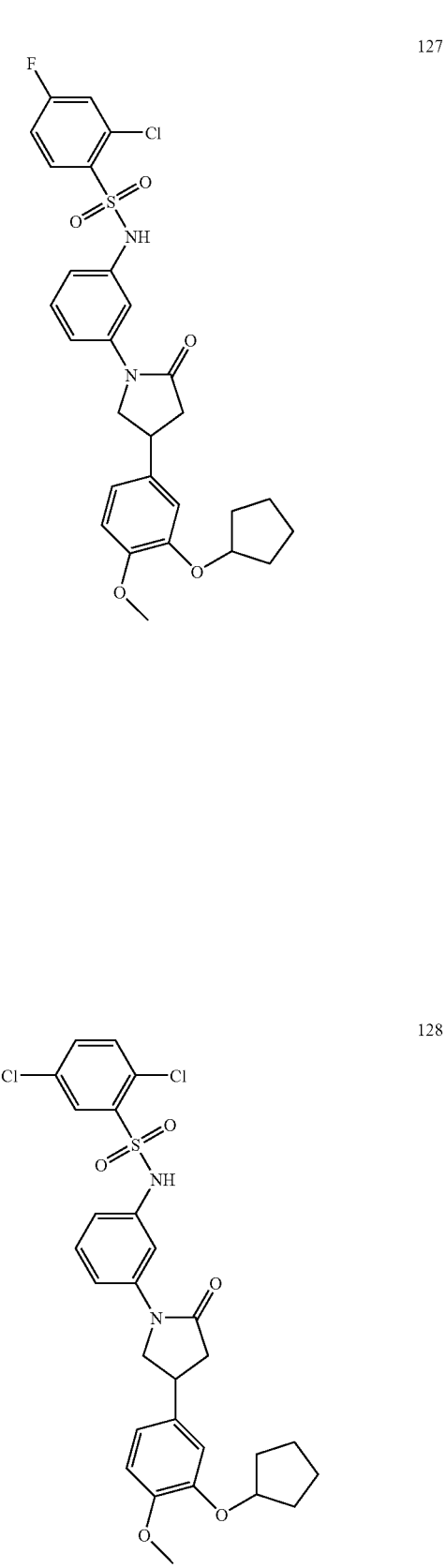

123 | 129 | 124
131
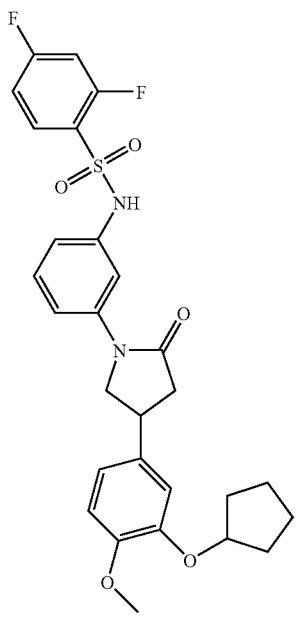
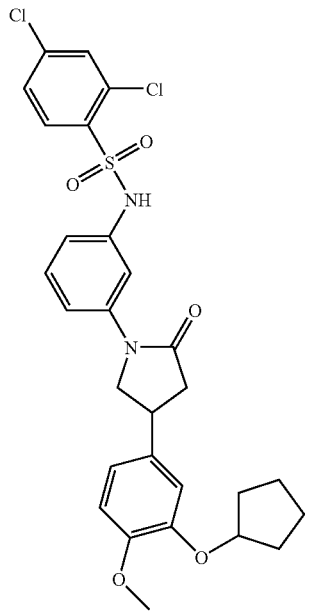
130
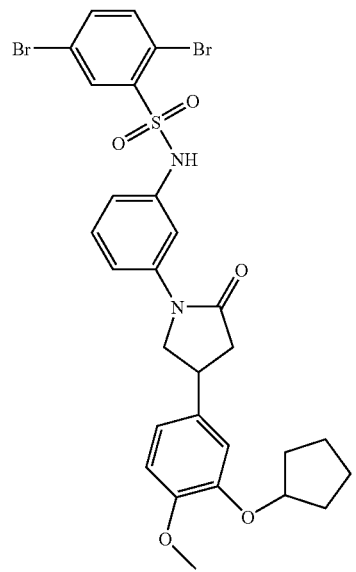
132
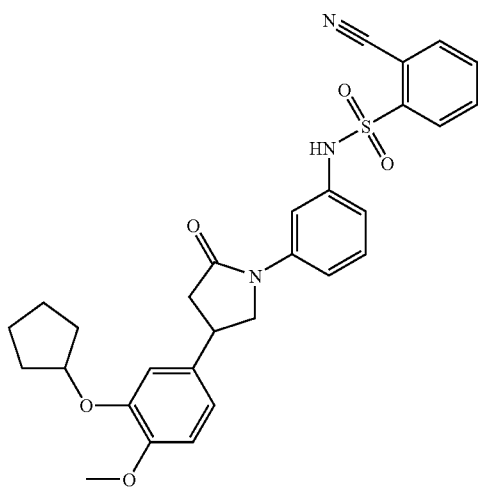
133
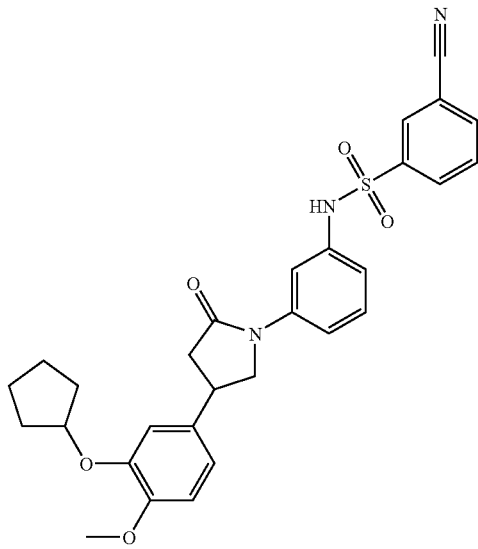

125
-continued
134
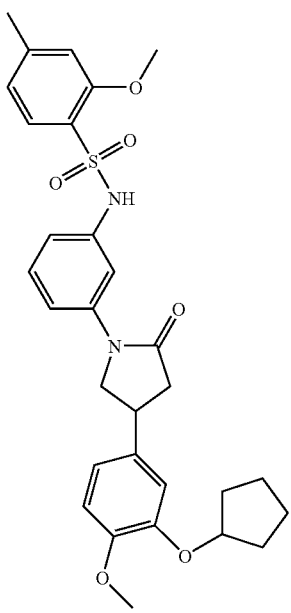
135
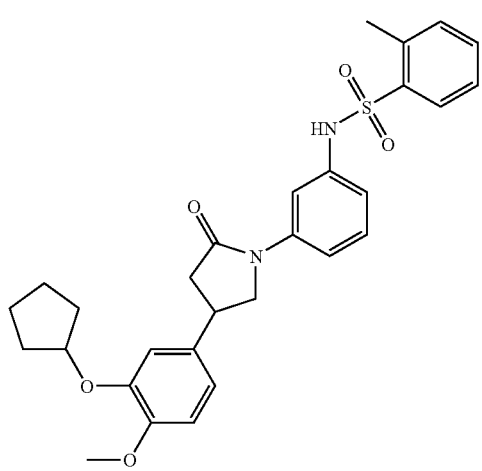
136
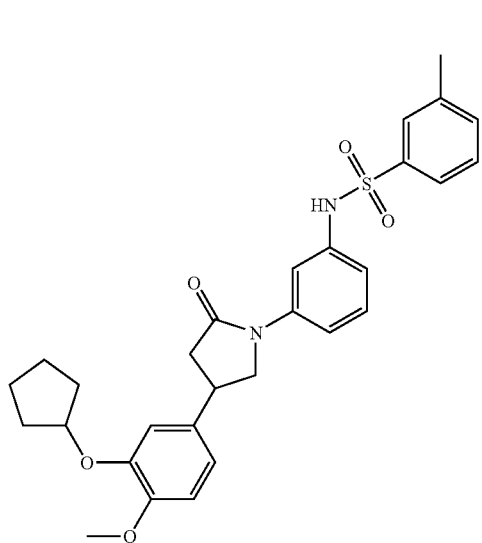
126
-continued
137
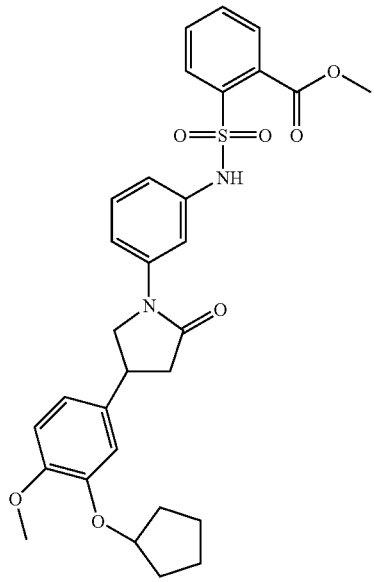
138
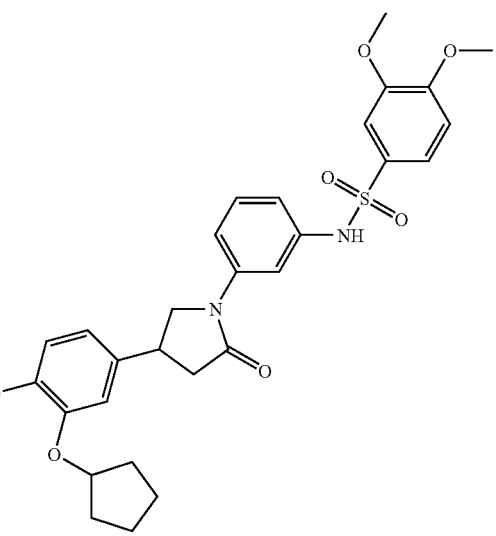

127
-continued
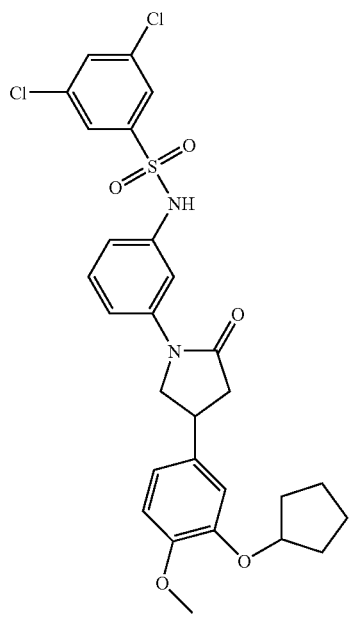
139
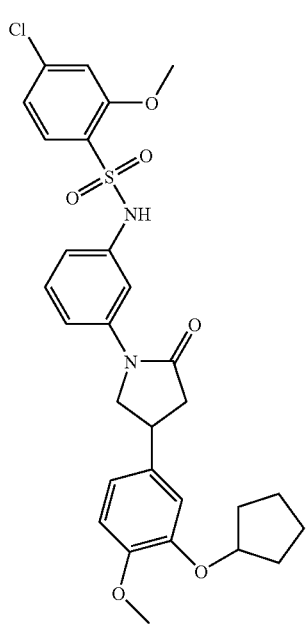
128
-continued
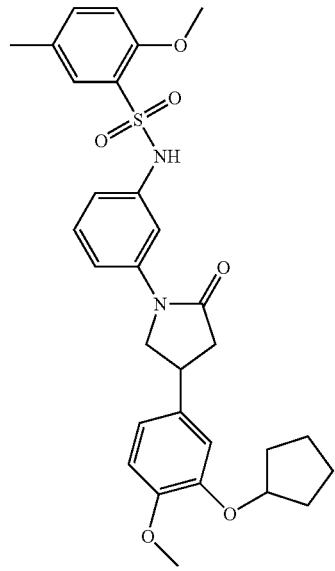
141
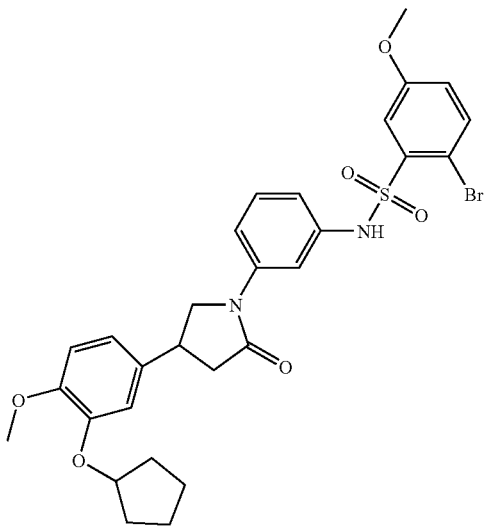
142
143

144
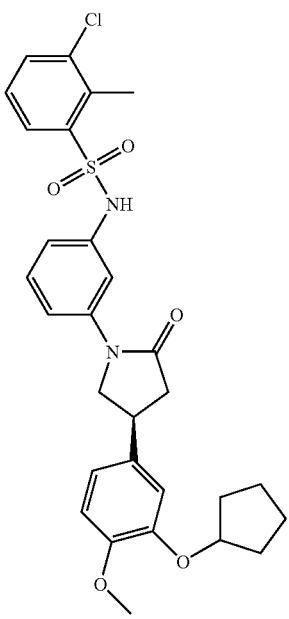
145
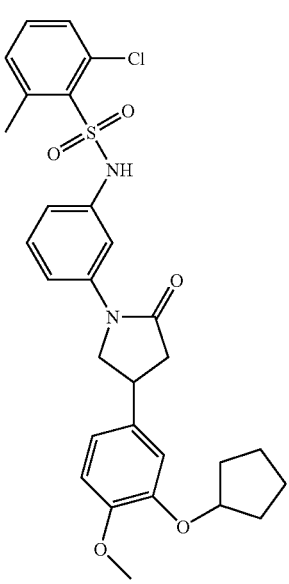
146
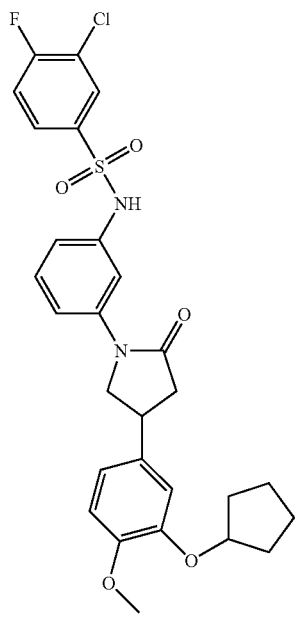
147
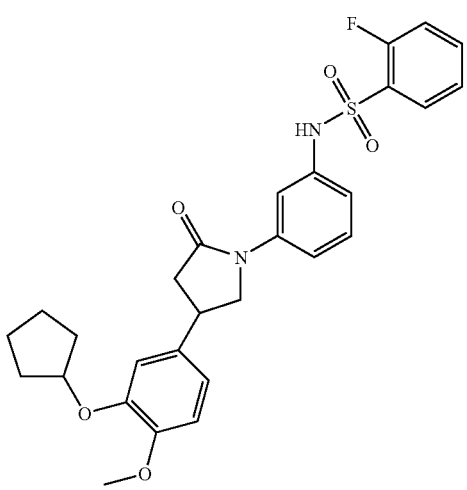
148
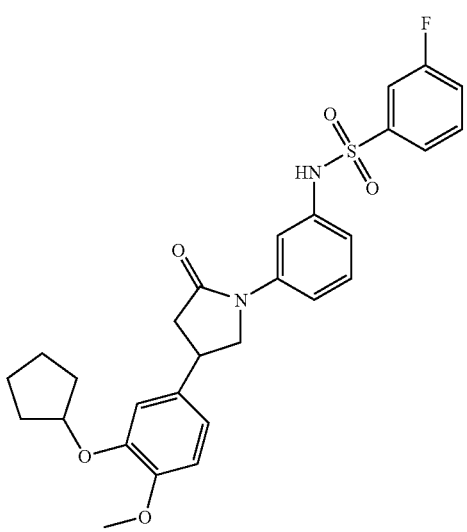

-continued
149
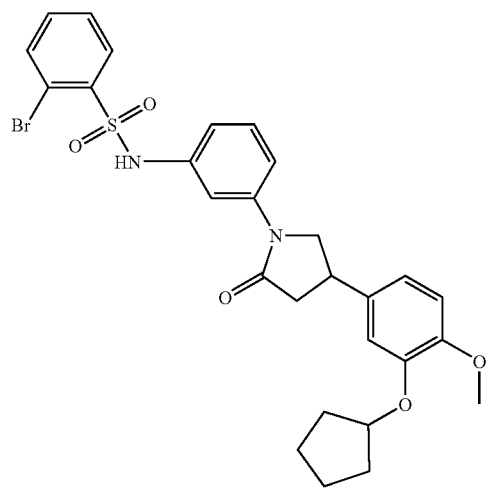
150
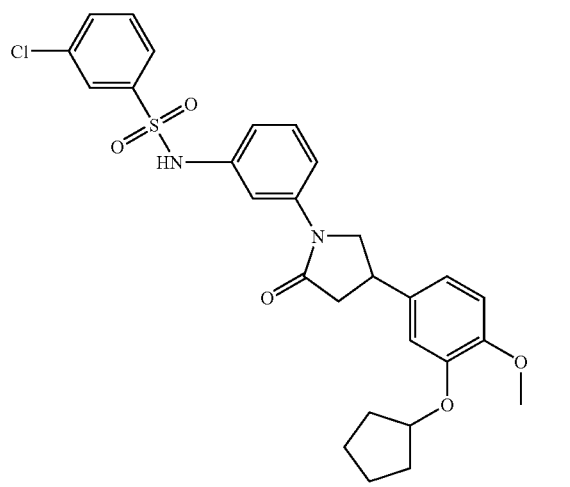
151
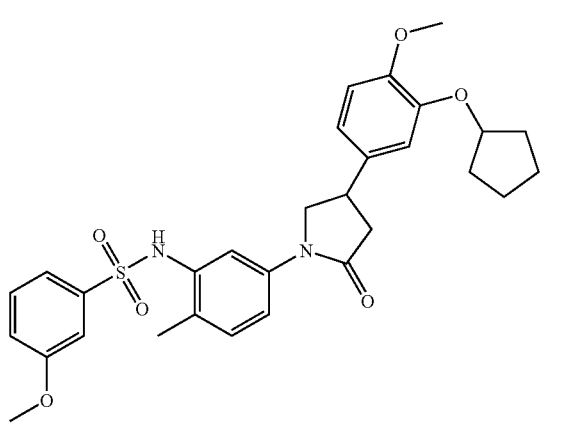
-continued
152
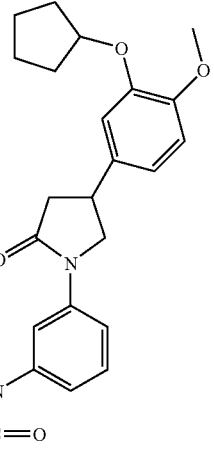
210
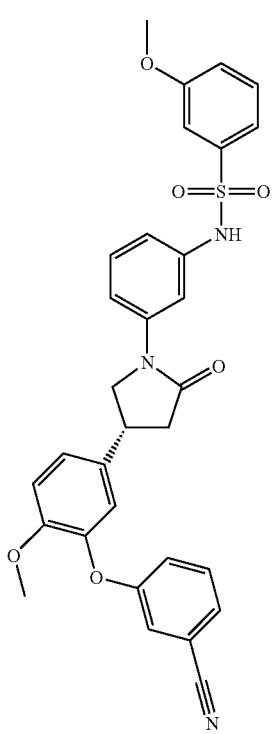

-continued
211
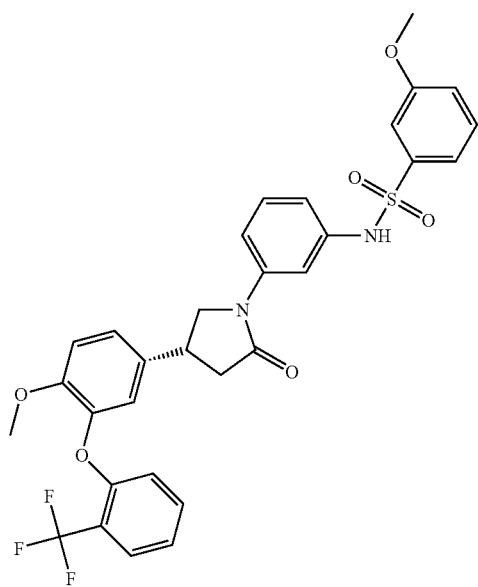
219
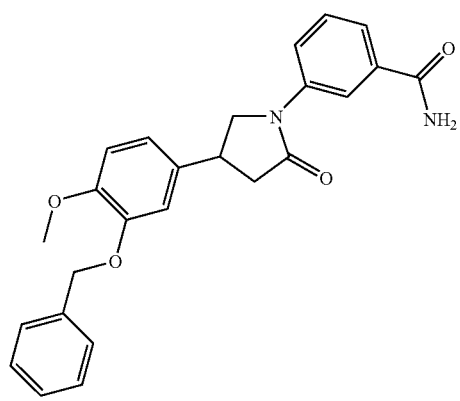
220
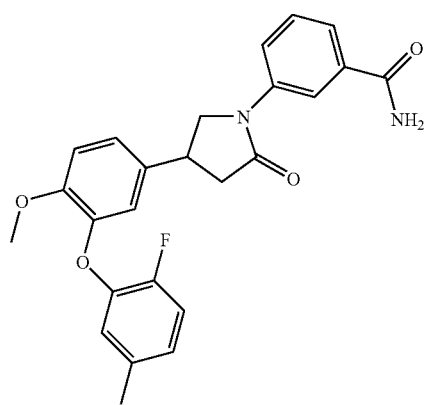
-continued
221
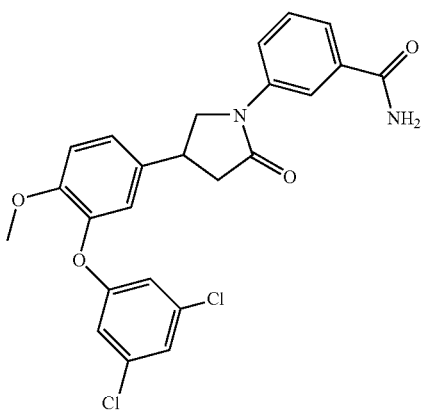
222
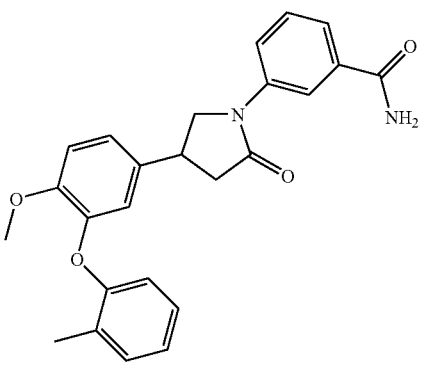
223
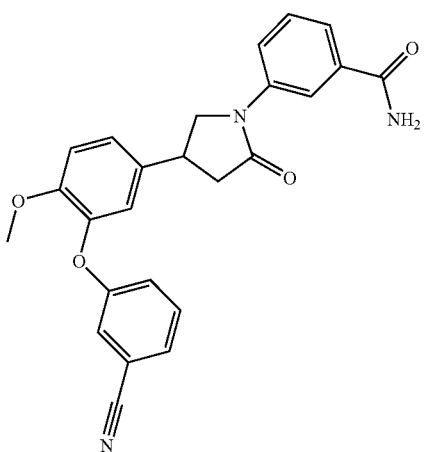

-continued
224
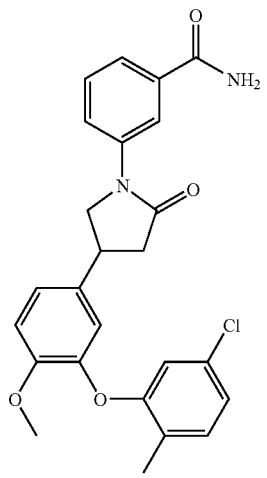
225
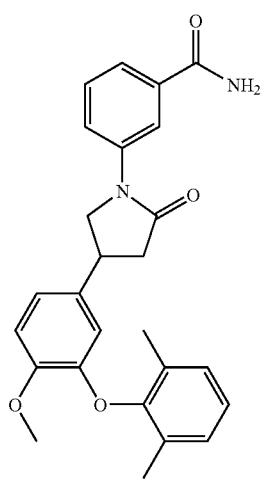
226
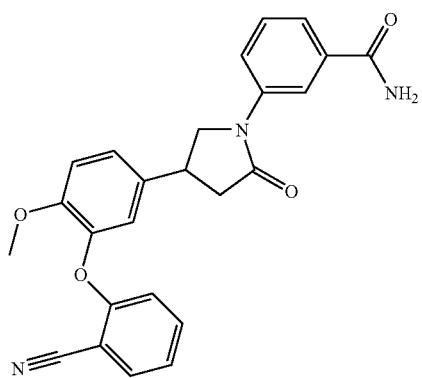
-continued
228
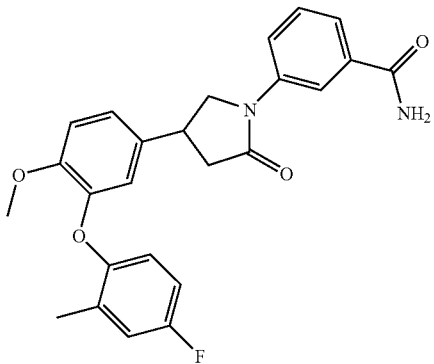
229
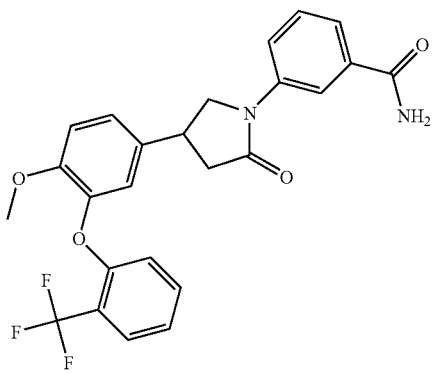
230
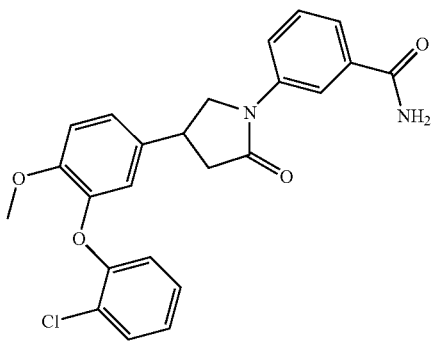
231
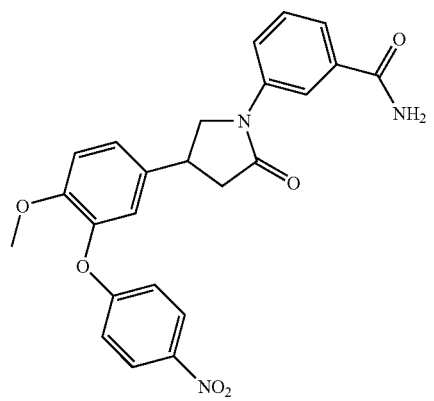

-continued
232
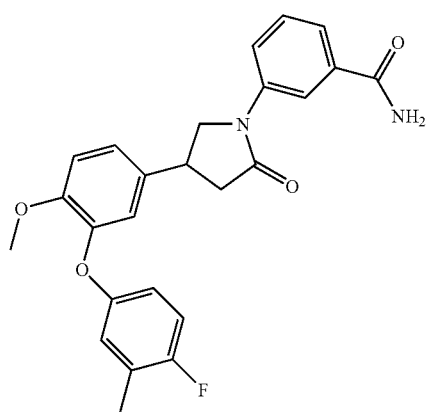
237
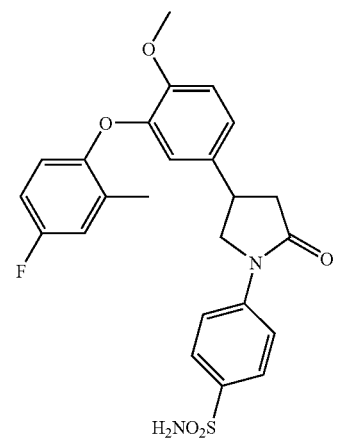
238
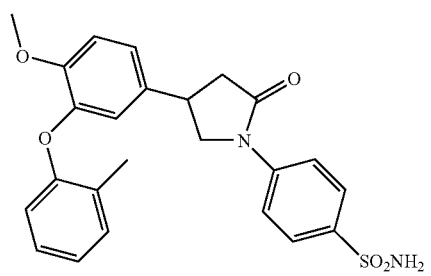
239
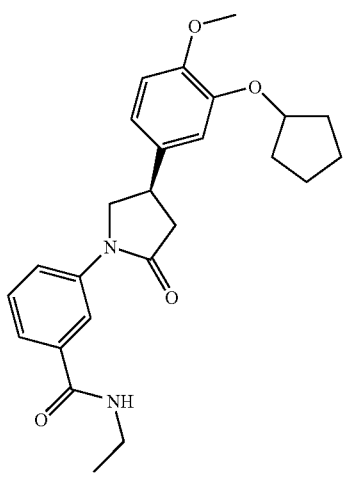
-continued
240
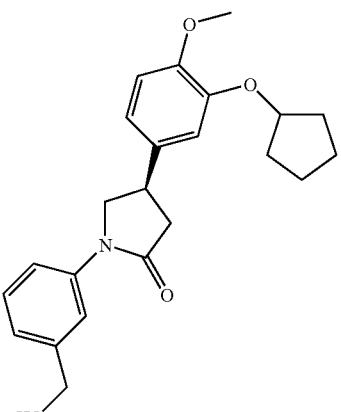
241
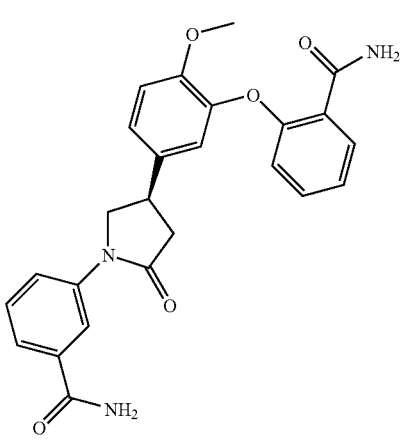
242
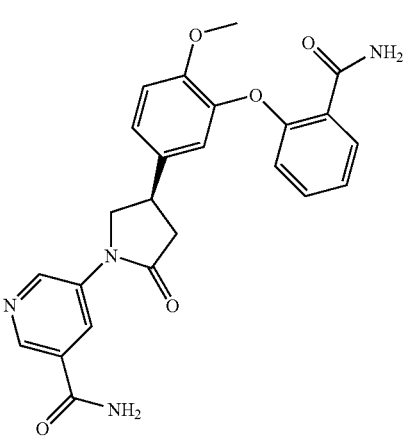
243
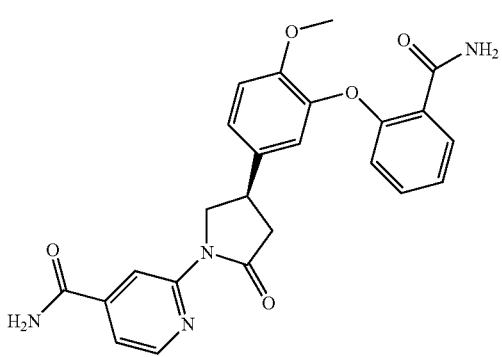

244
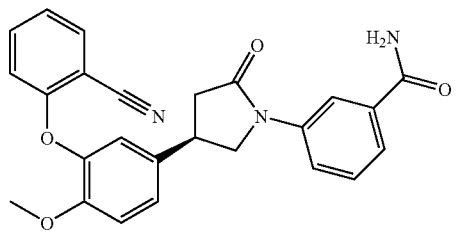
245
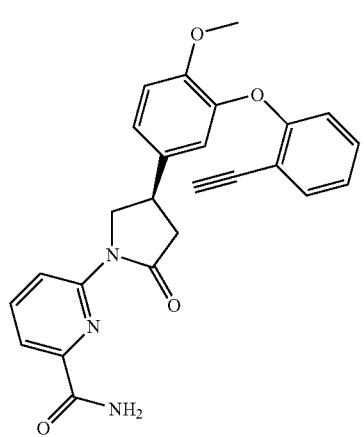
246
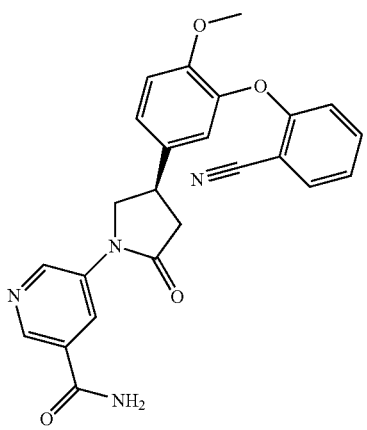
247
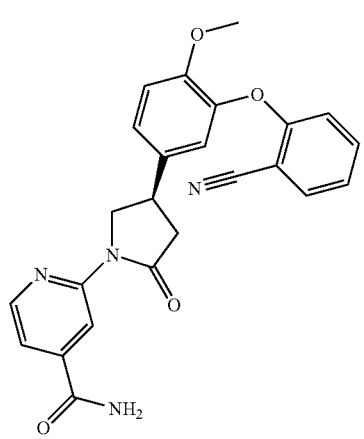
248
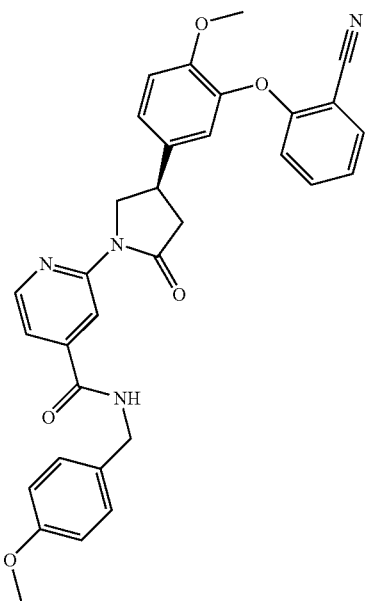
249
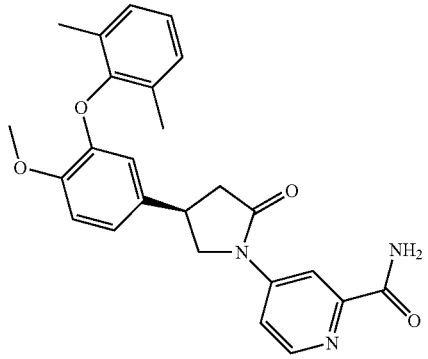
250
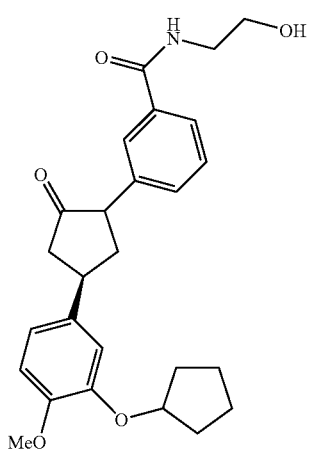

-continued
251 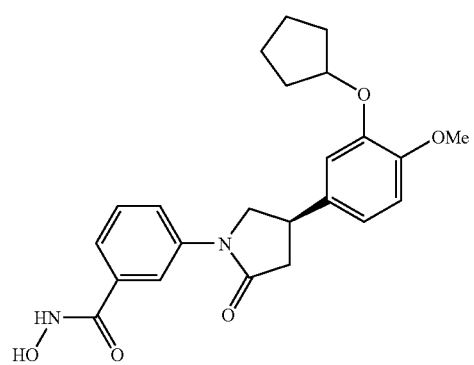
252 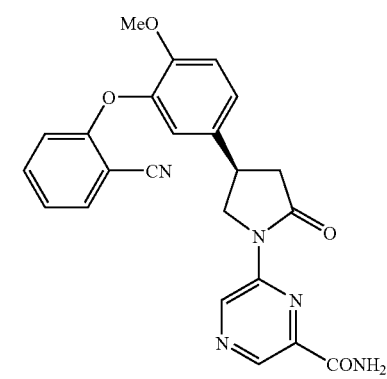
253 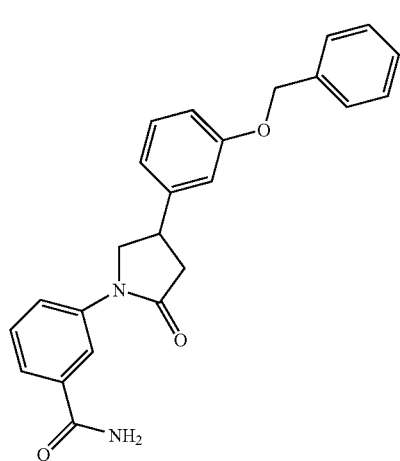
-continued
261 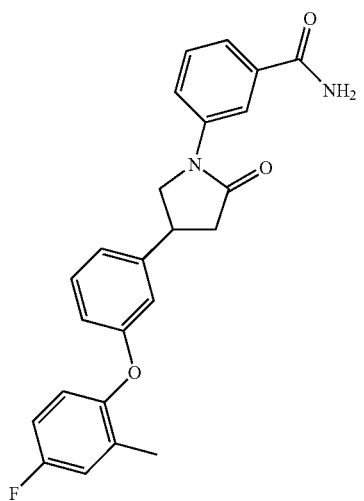
262 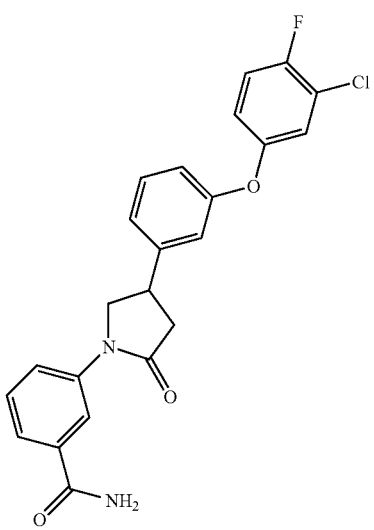
263 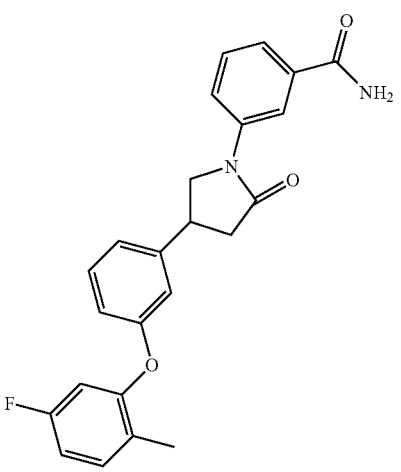

-continued
264
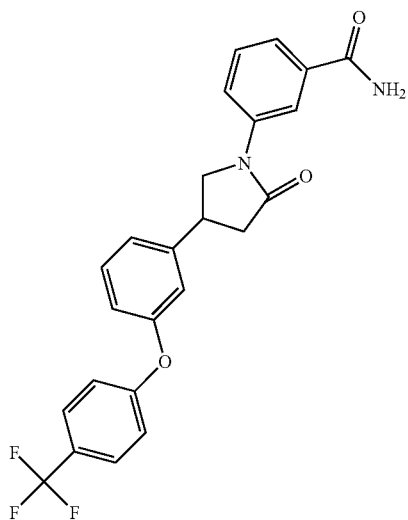
265
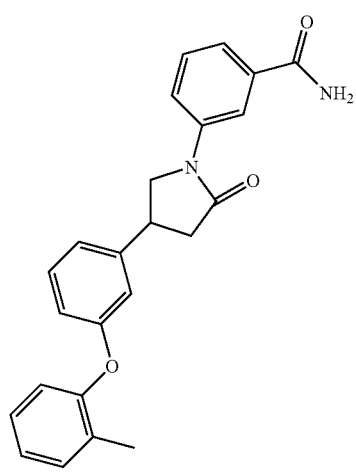
266
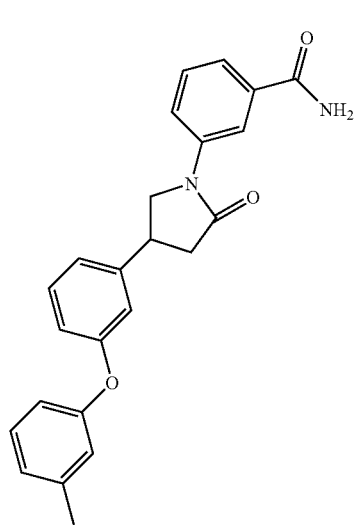
-continued
267
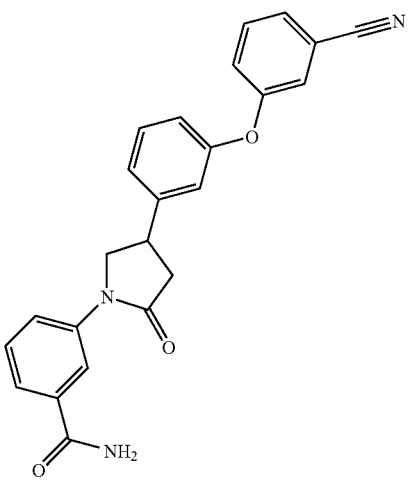
268
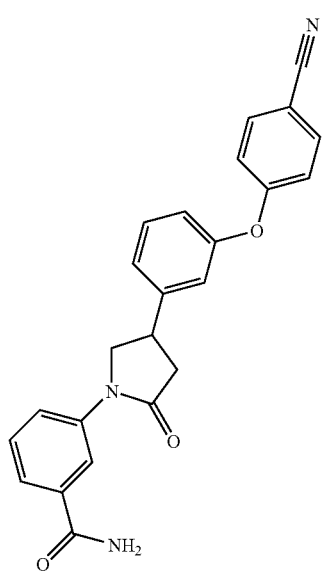
270
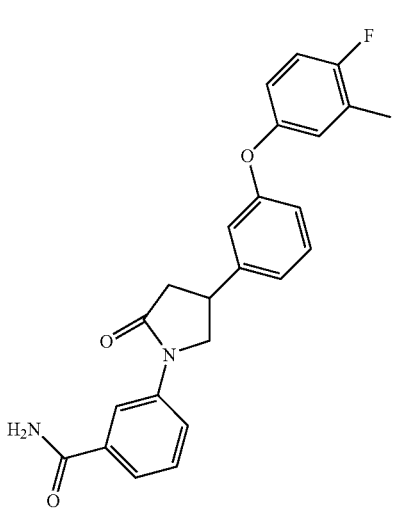

-continued

271

272

281

282

283

284

285
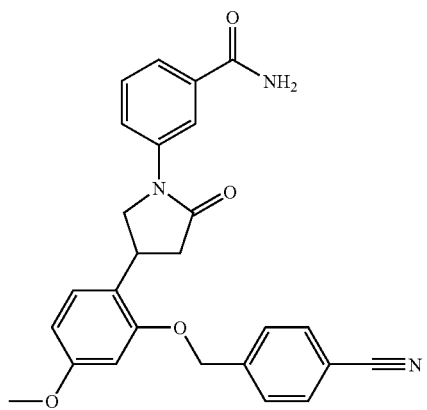
286
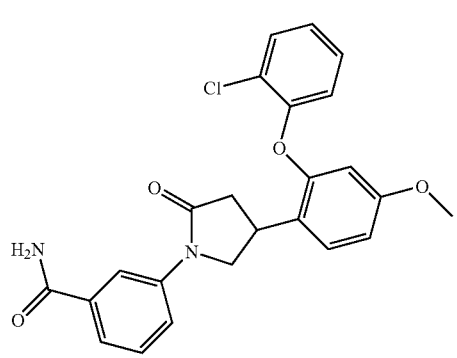
287
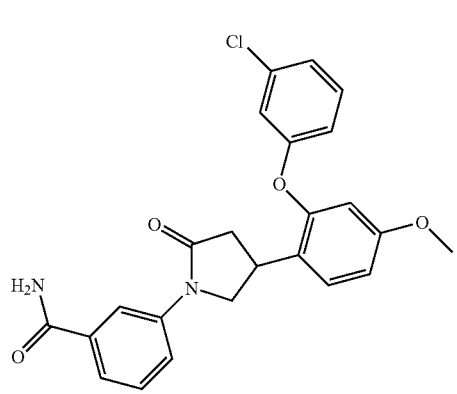
288
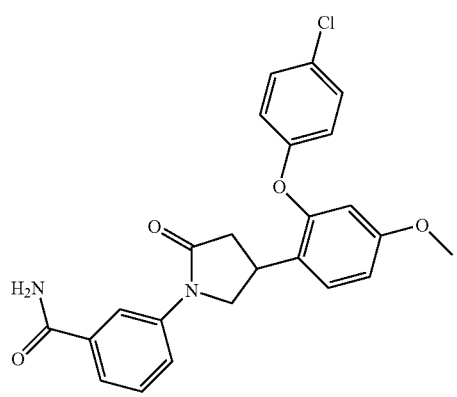
289
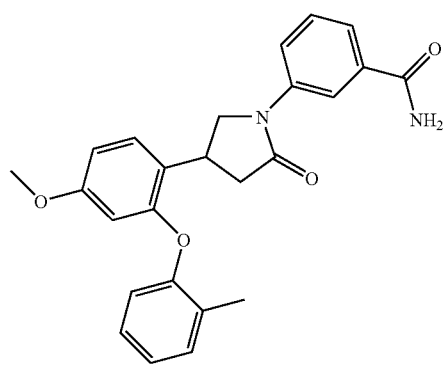
290
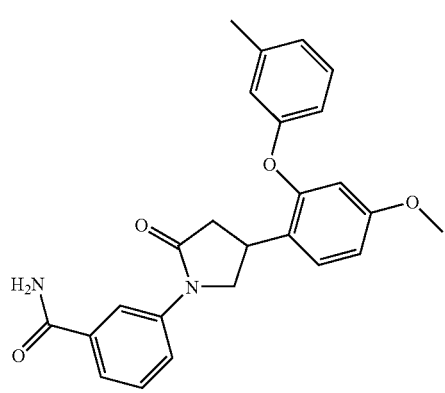
291
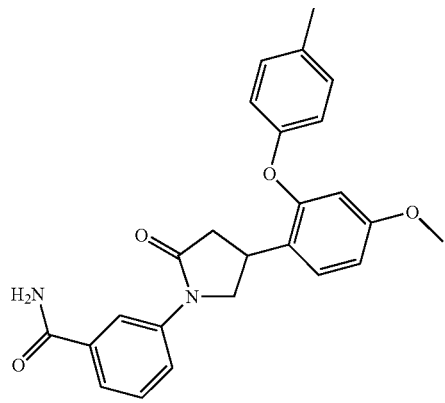
292
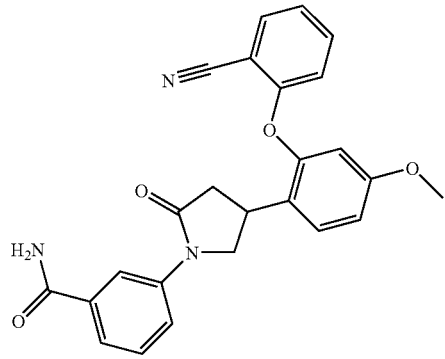

293
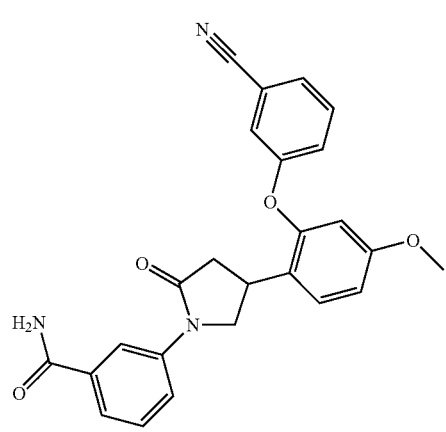
294
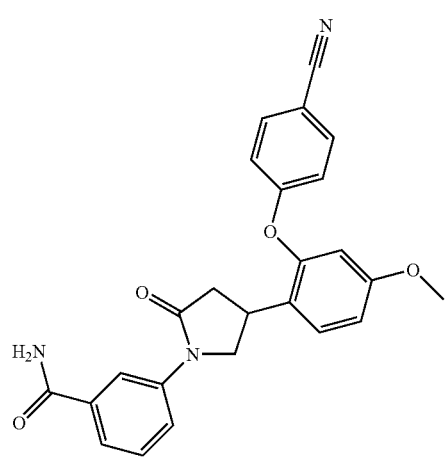
295
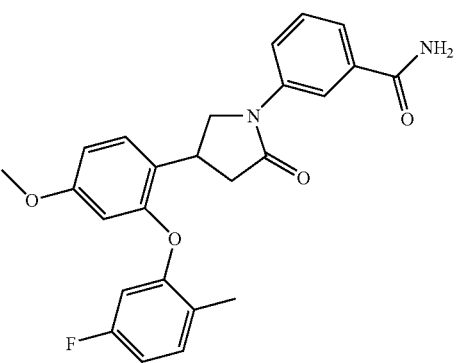
296
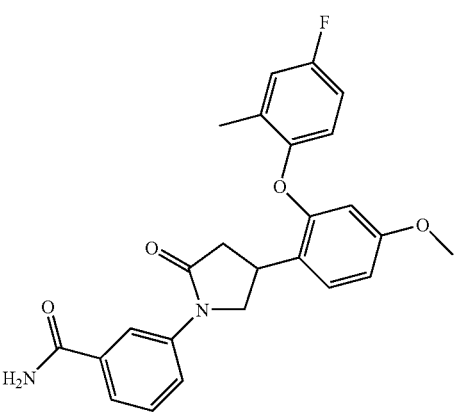
297
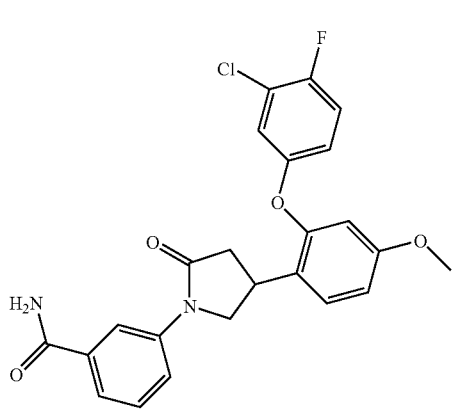
298
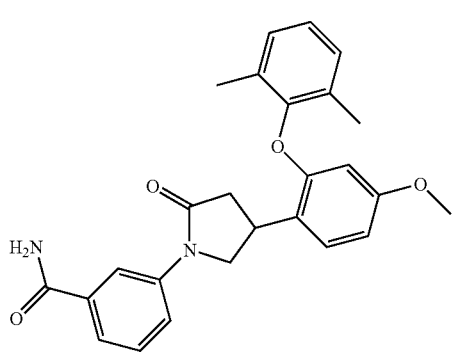
299
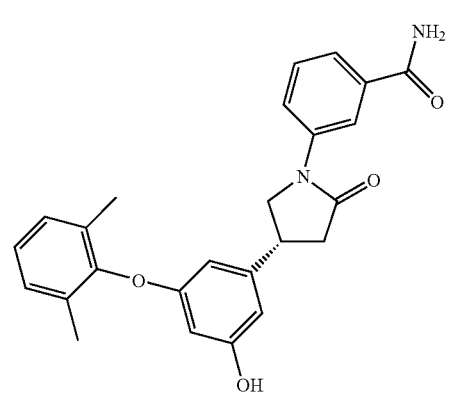
300
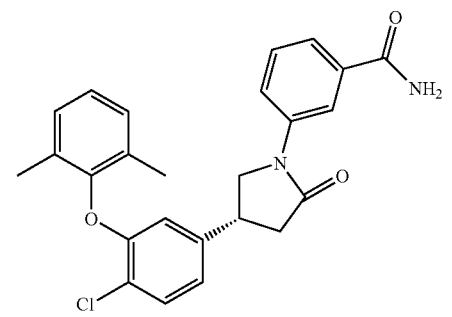

-continued
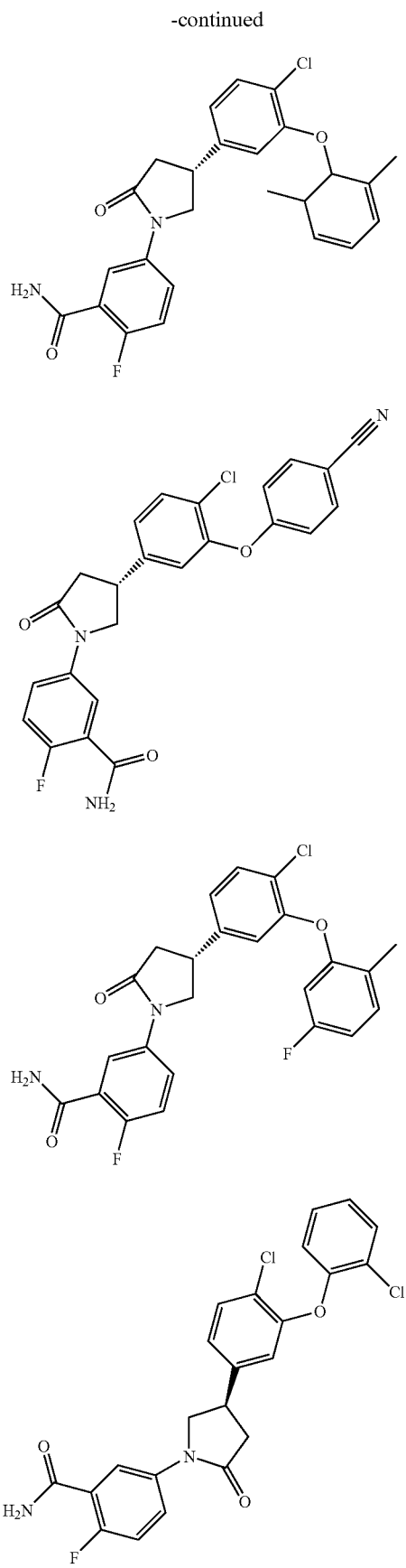
301
302
303
304
-continued
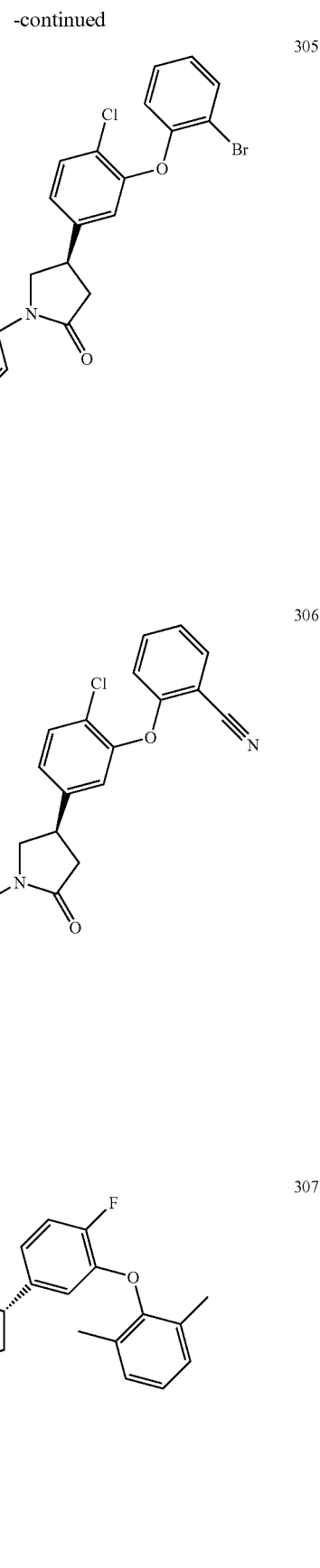
305
306
307

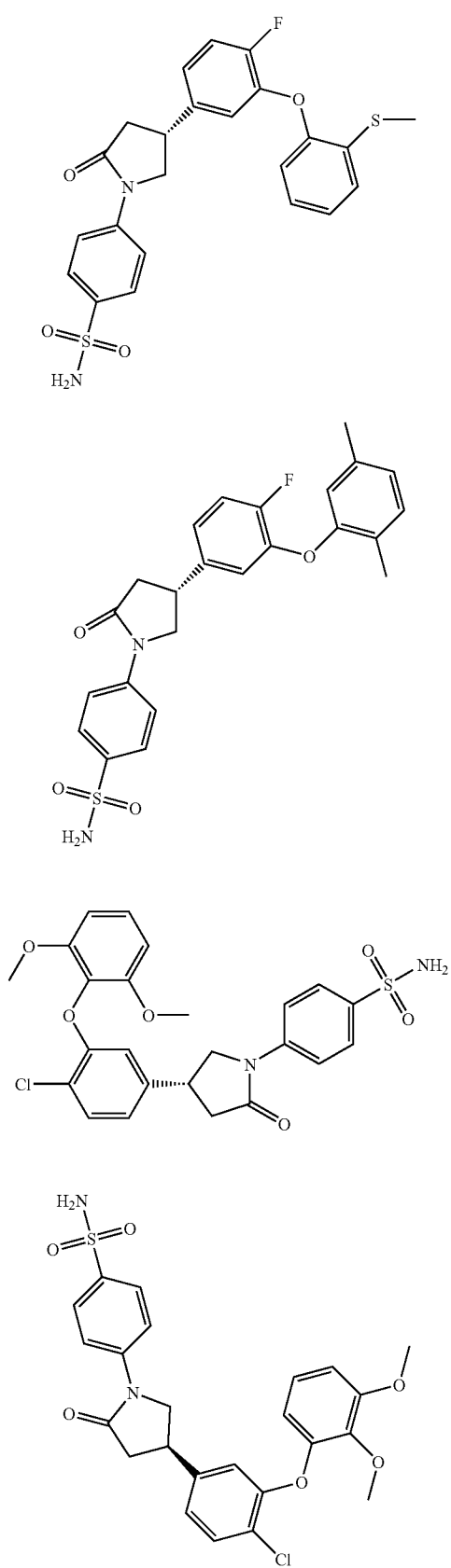
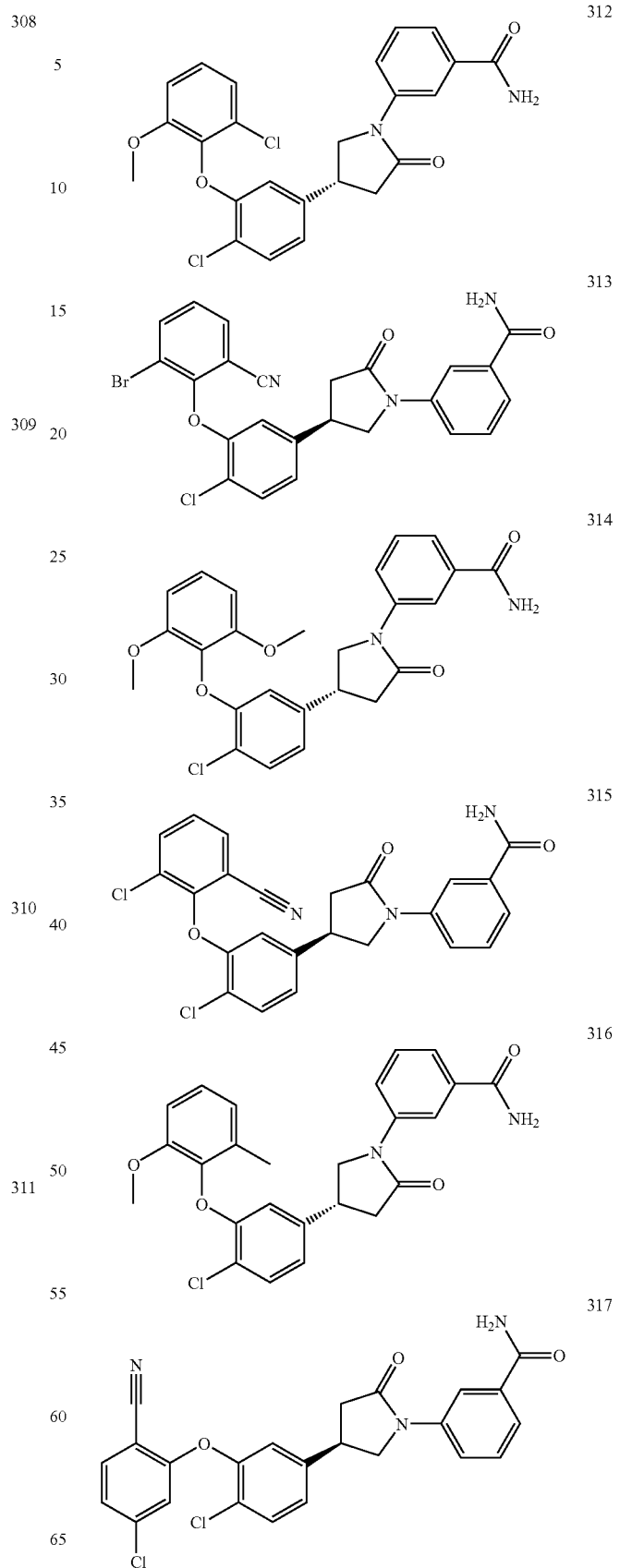

-continued
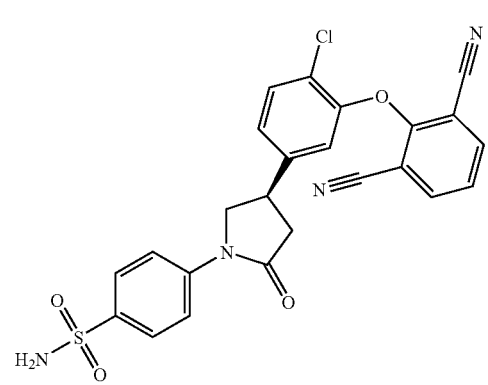
318
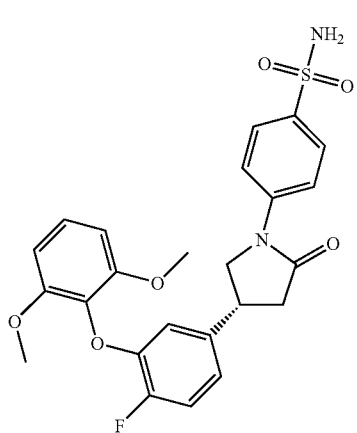
322
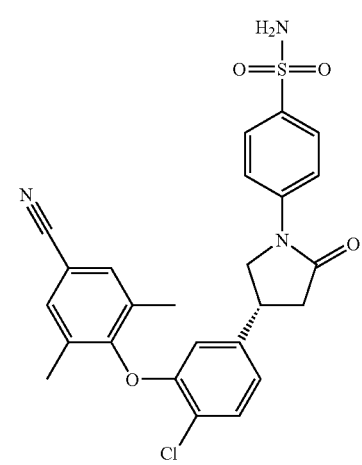
319
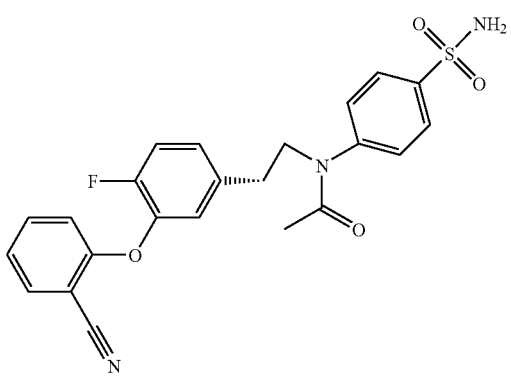
320
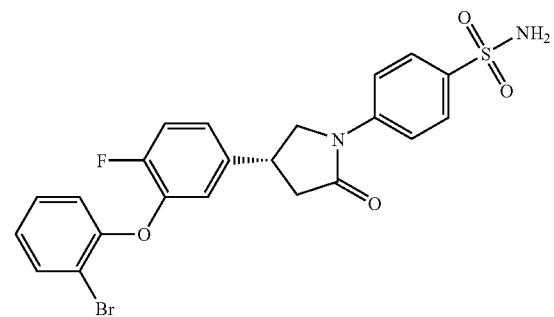
323
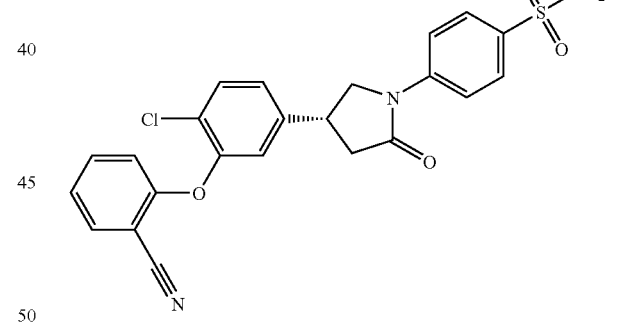
324
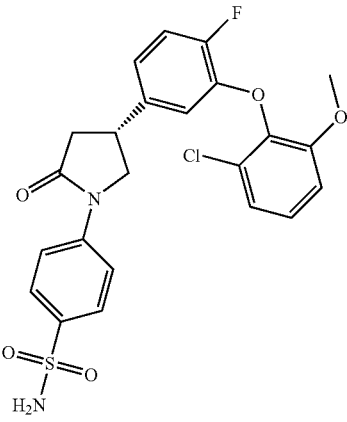
321
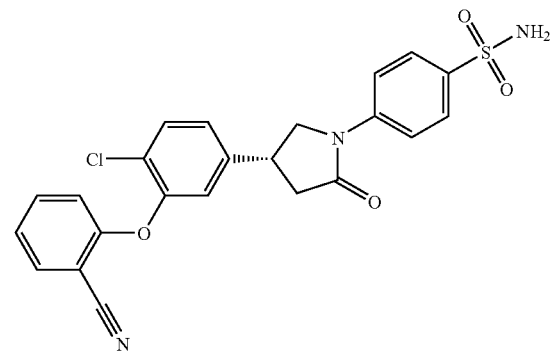
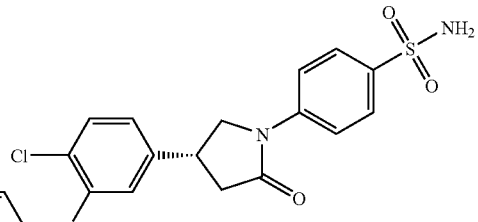
325

-continued
326
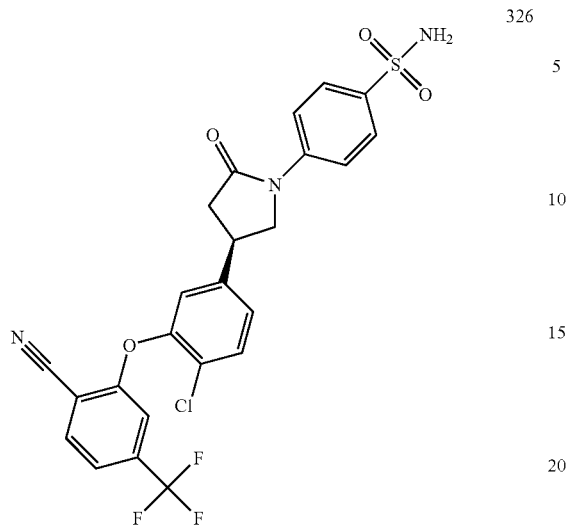
327
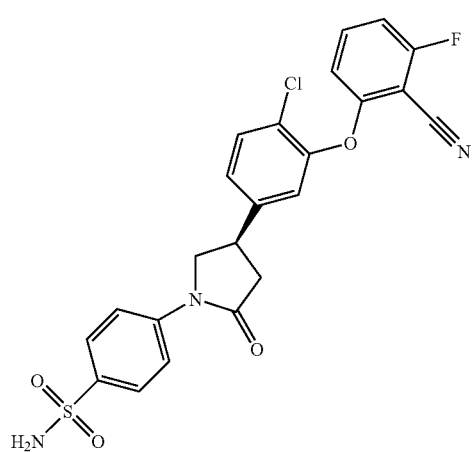
328
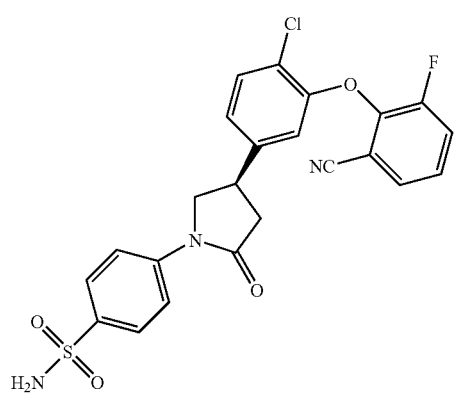
-continued
329
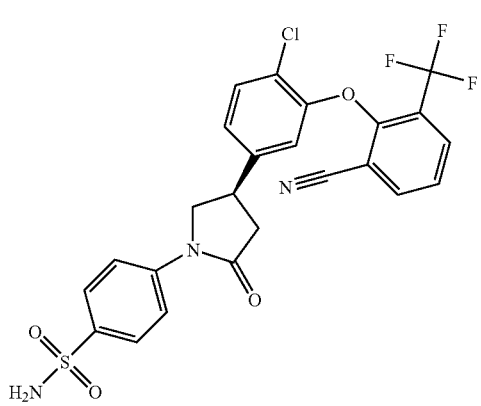
330
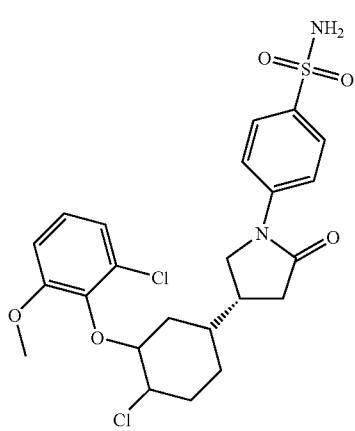
331
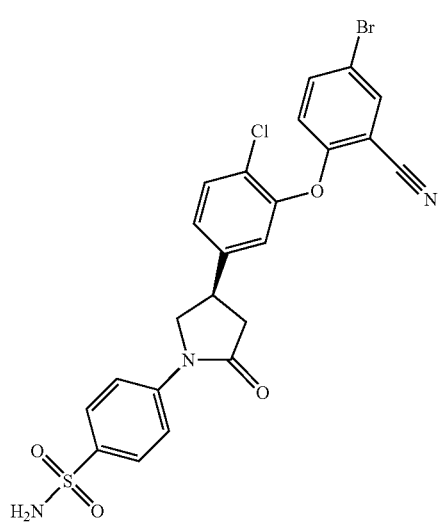

-continued
332
335
336
-continued
339
340
341
342
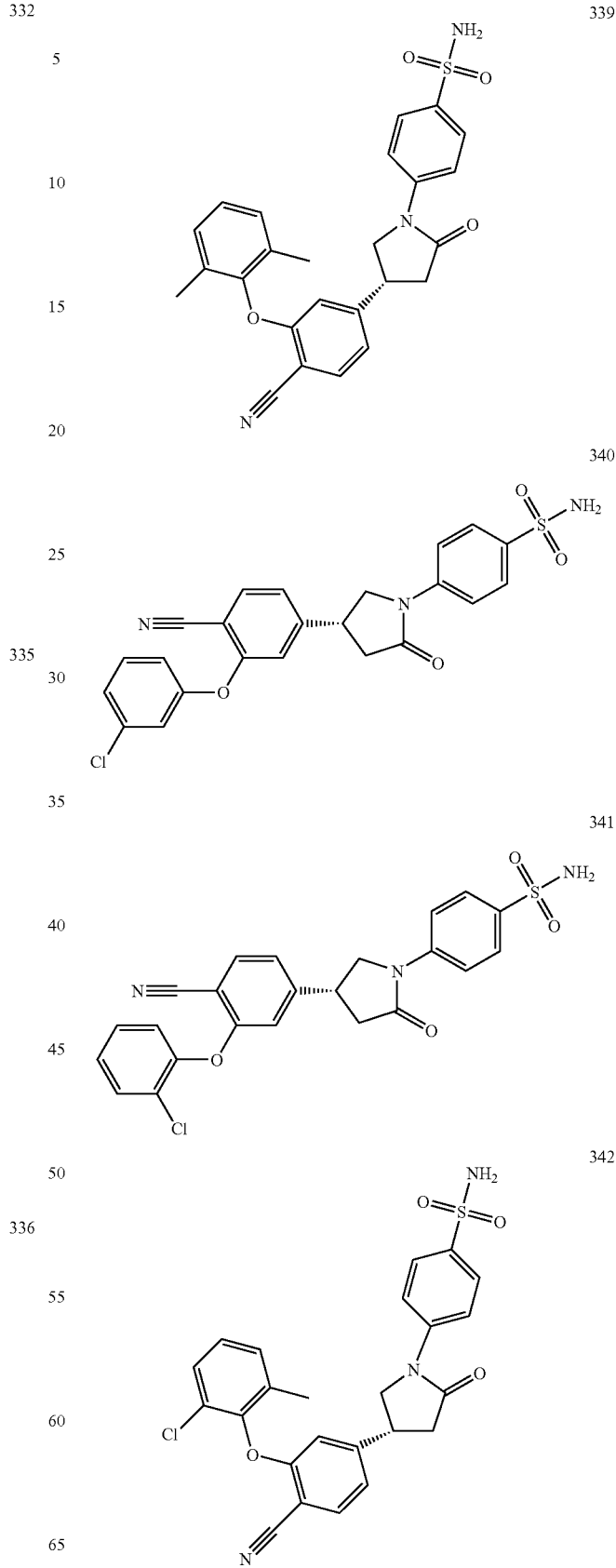

-continued
344
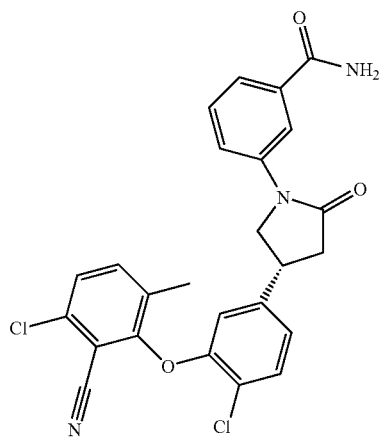
345
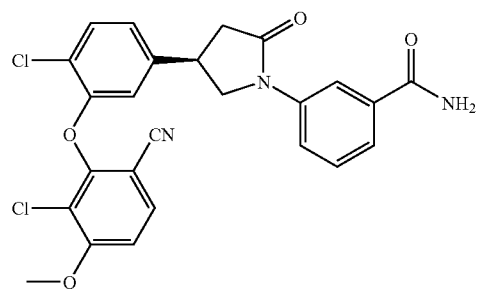
346
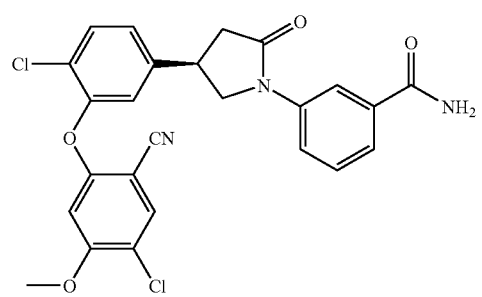
347
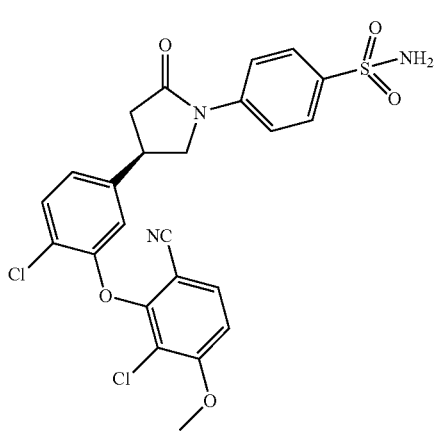
-continued
348
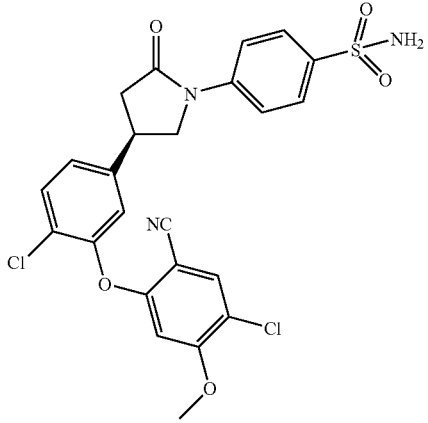
349
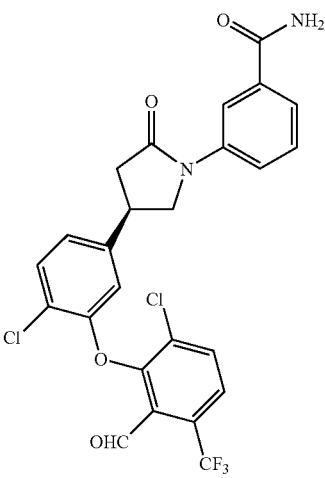
350
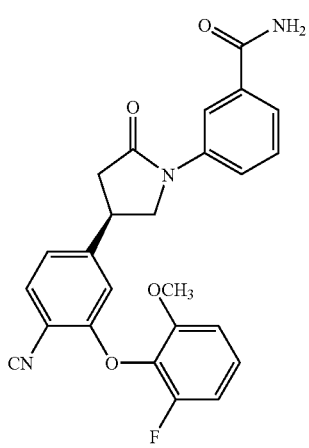

-continued
356 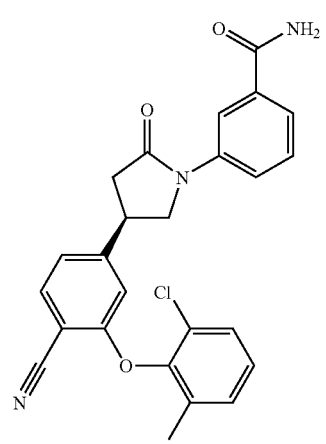
357 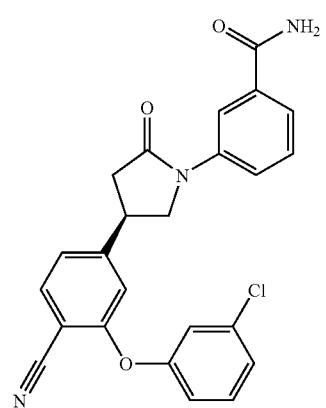
358 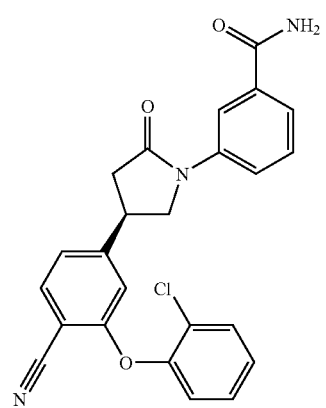
359 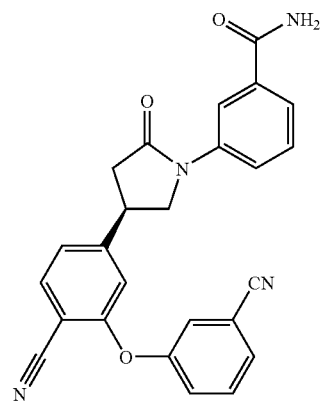
-continued
360 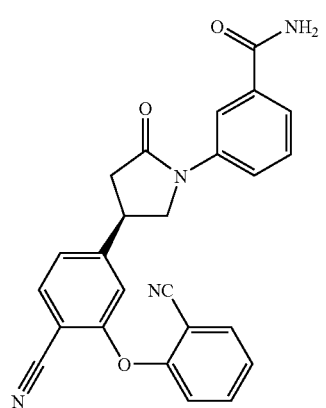
361 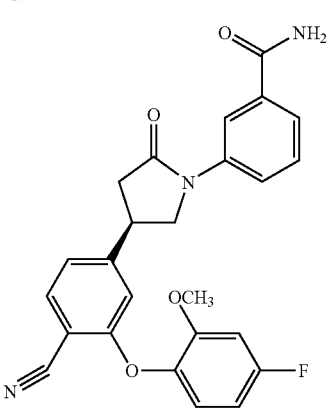
362 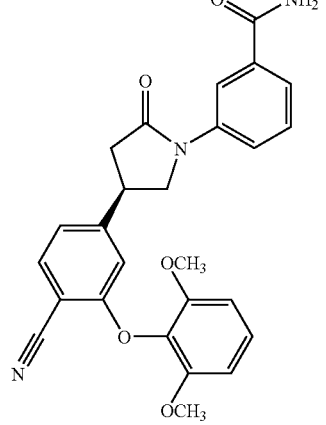
363 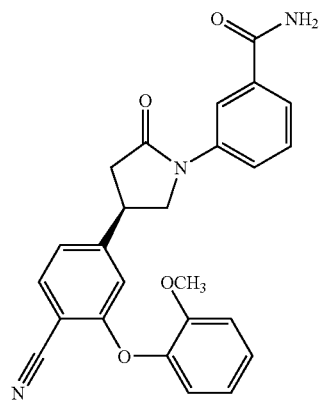

-continued
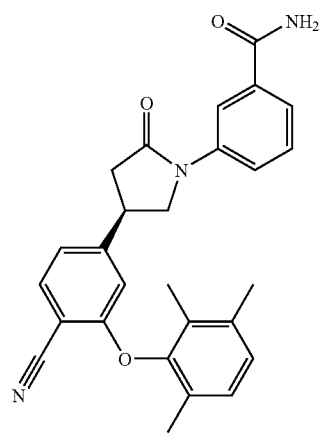
364
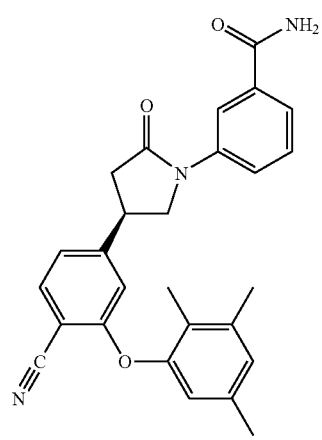
365
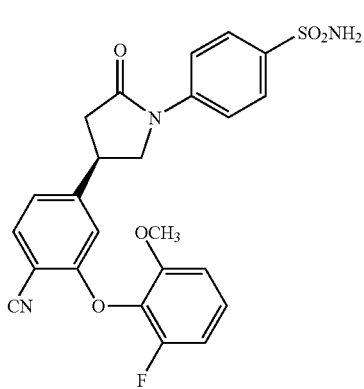
371
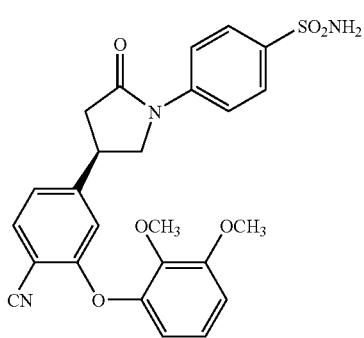
372
-continued
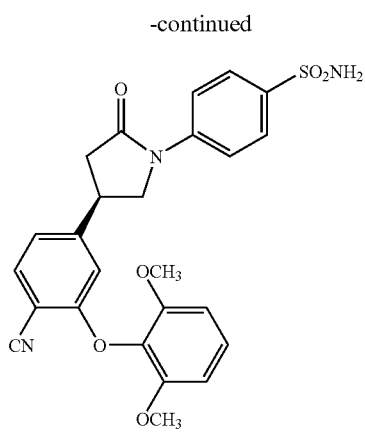
373
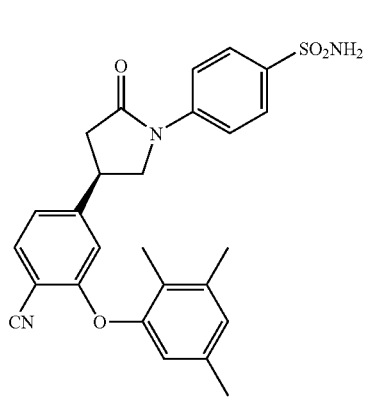
374
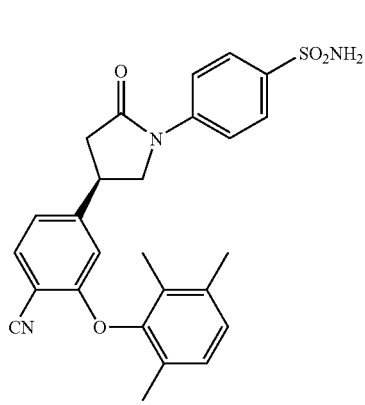
375
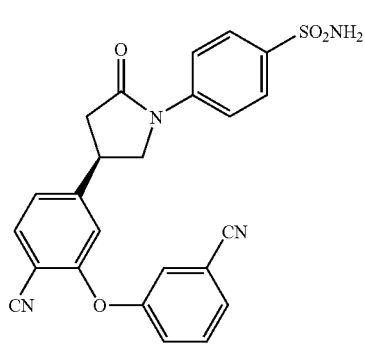
376

167 -continued
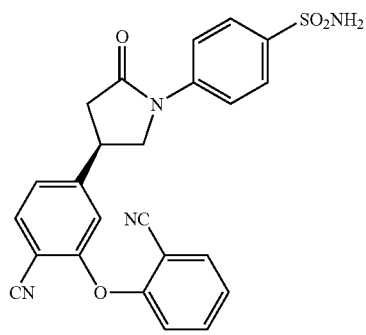
377
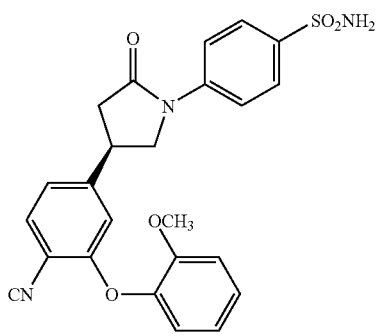
378
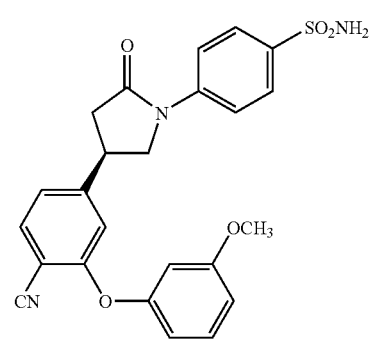
379
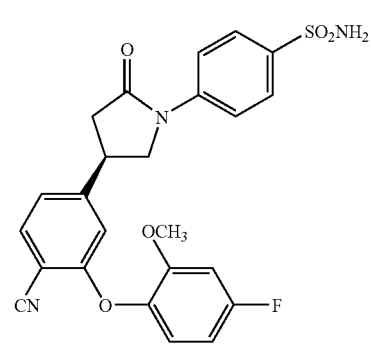
380
168 -continued
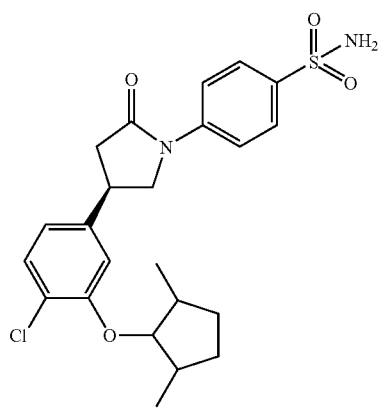
381
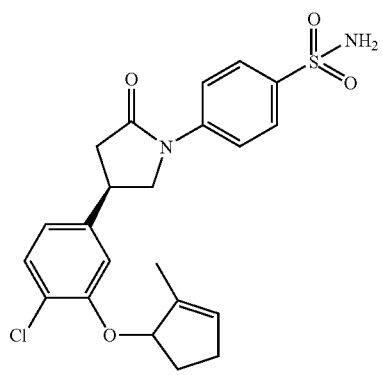
382
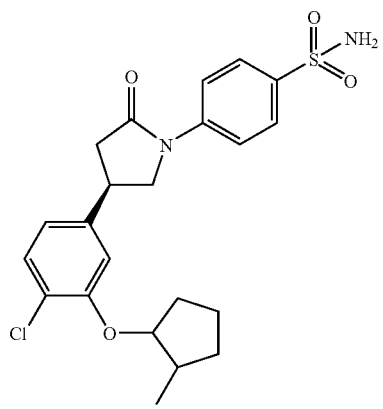
383
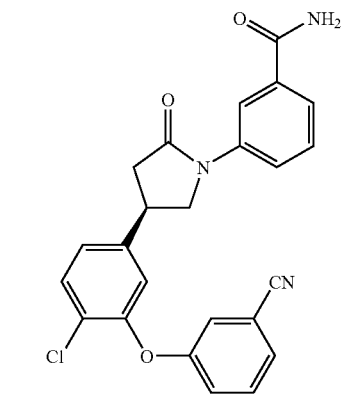
384

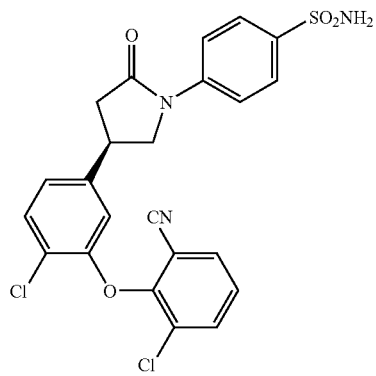
385
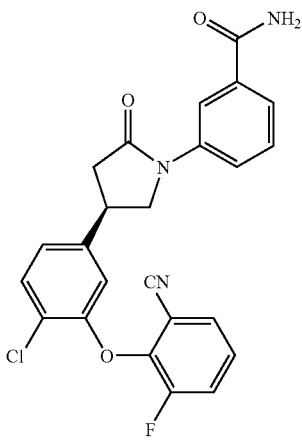
388
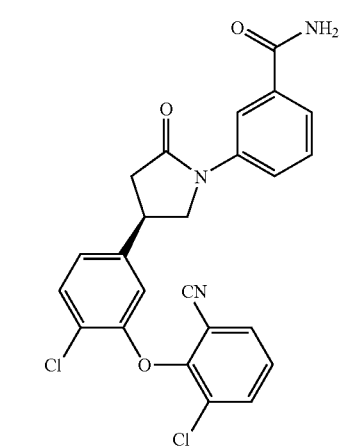
386
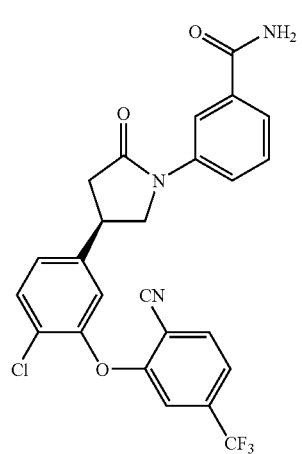
389
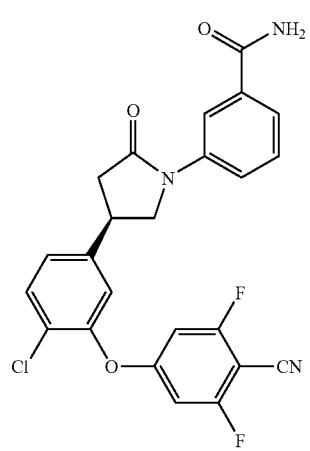
387
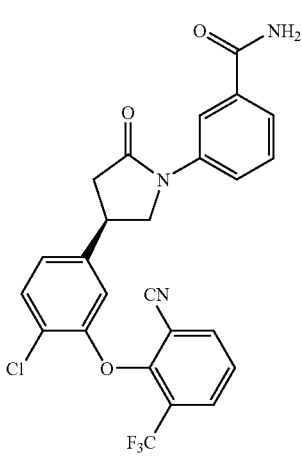
390

171
391
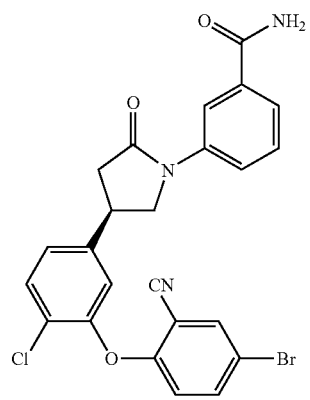
392
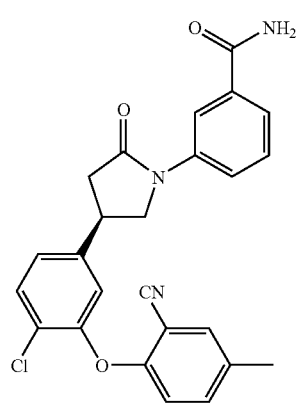
393
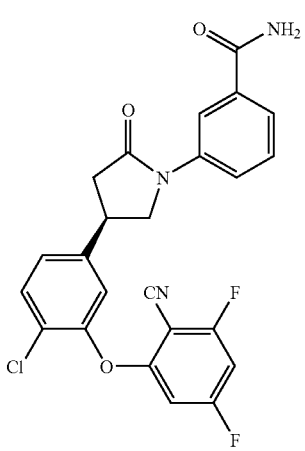
172
394
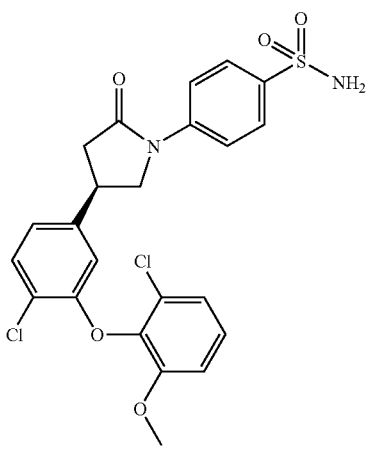
395
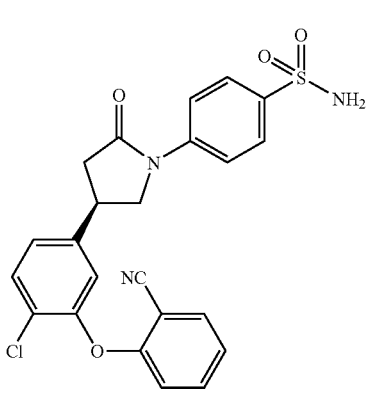
396
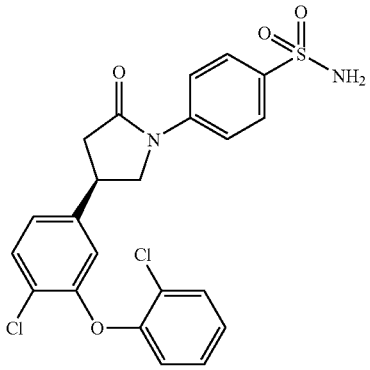
397
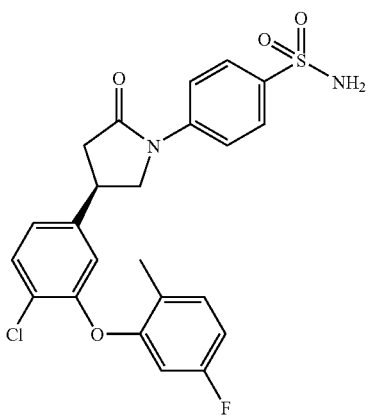

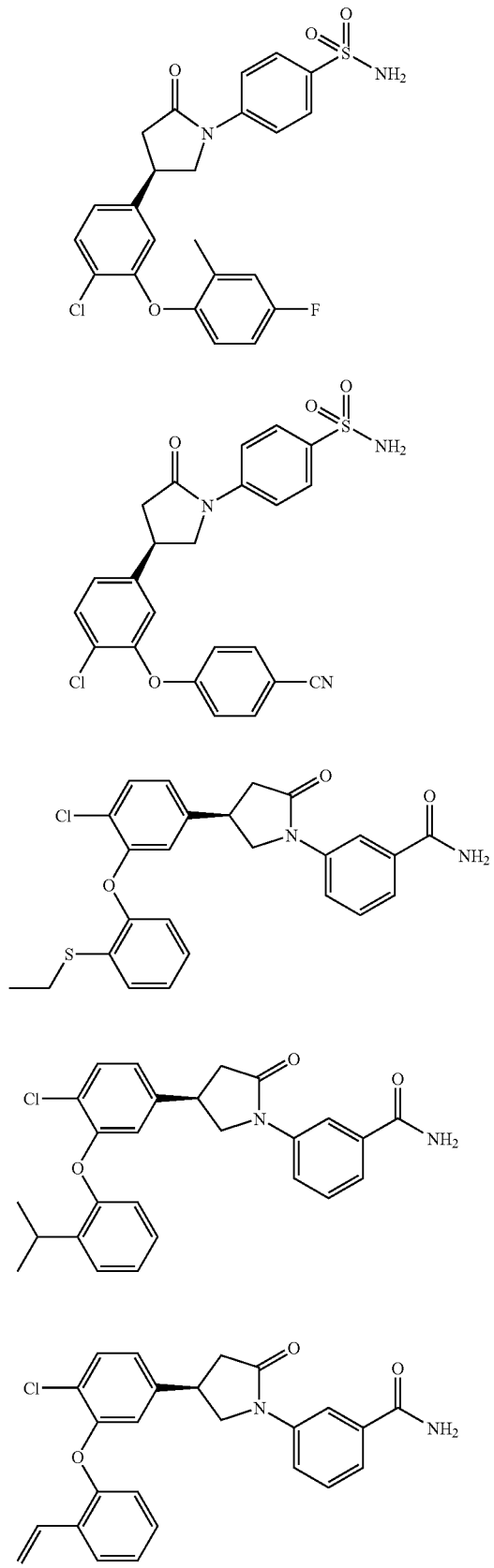
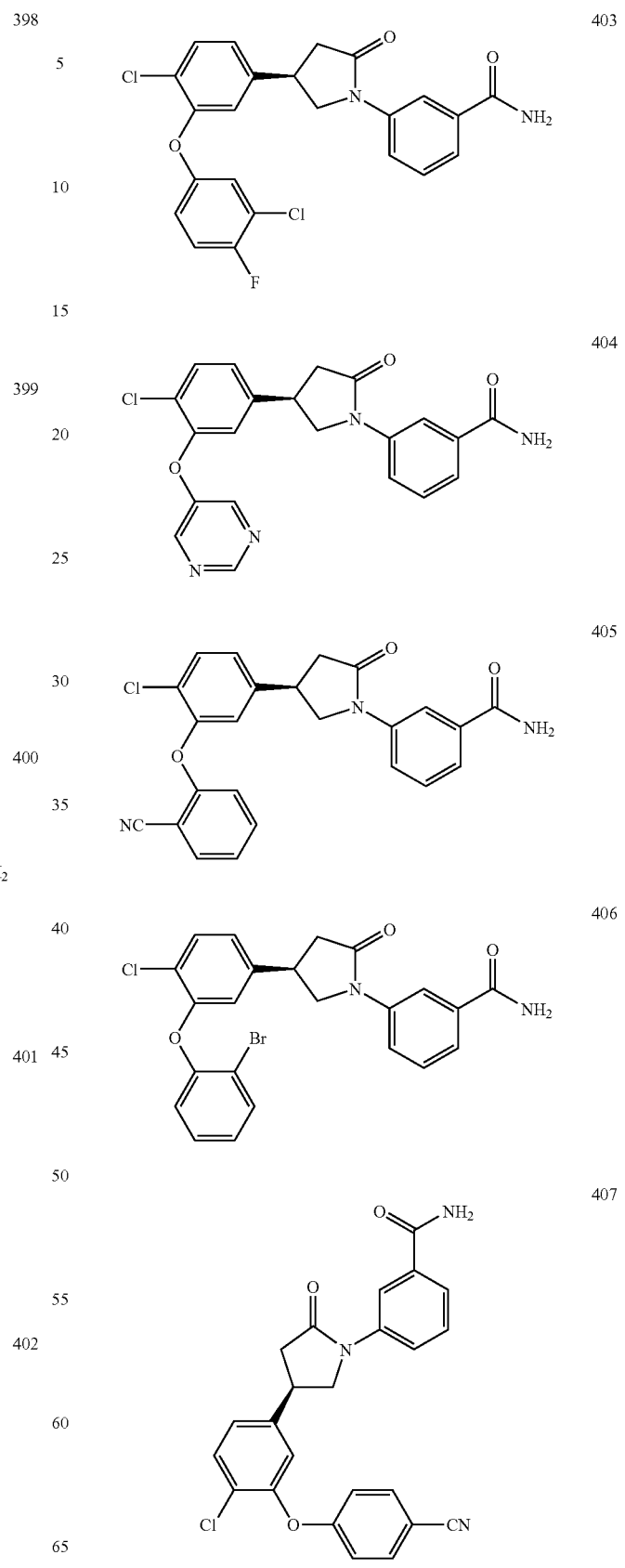

-continued
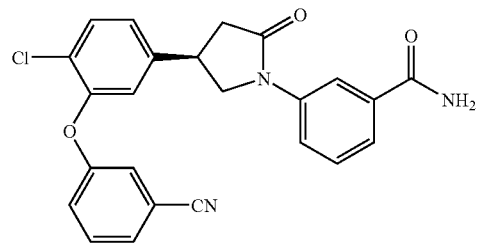
408
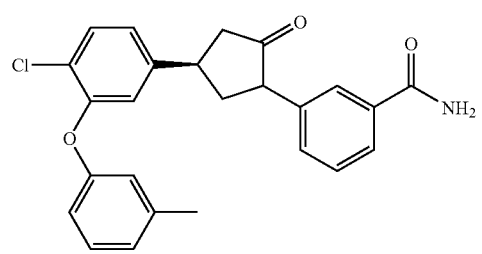
409
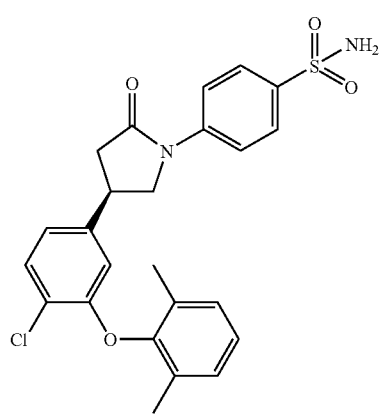
410
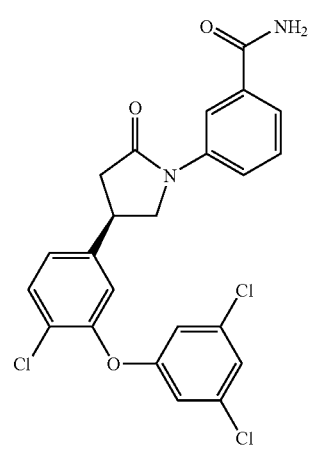
411
-continued
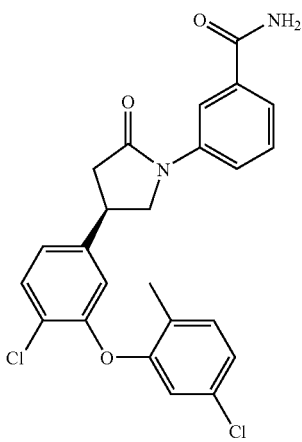
412
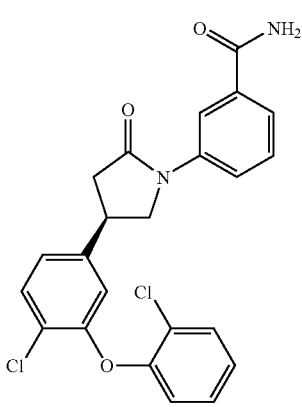
413
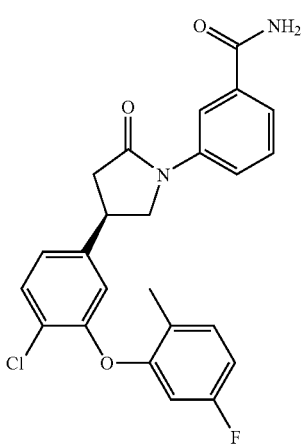
414

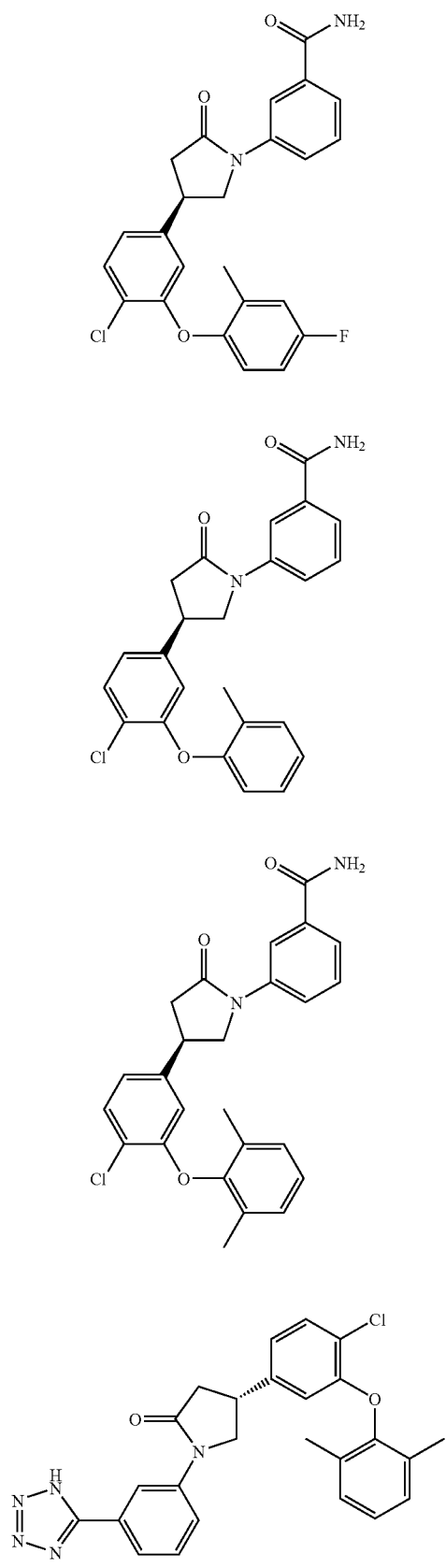

179 | 180
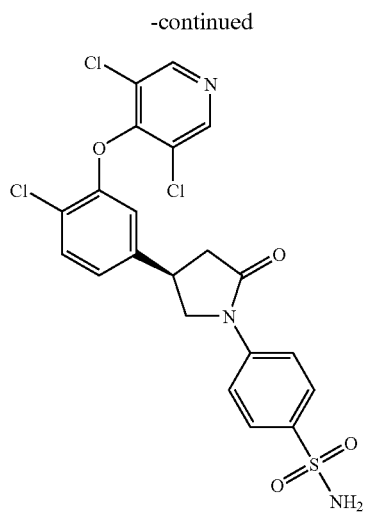
422
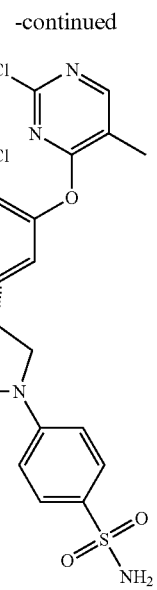
425
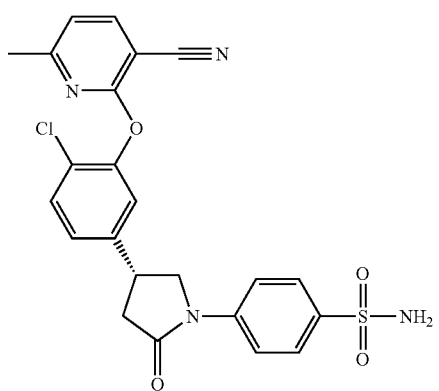
423
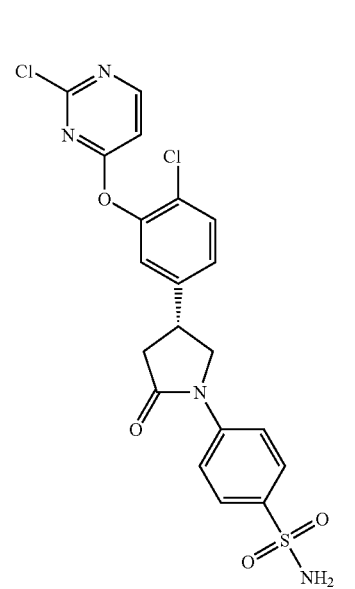
424
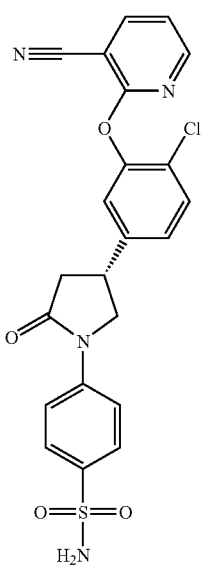
430

| 432 | 435 |
| 433 | 436 |
| 434 | 437 |

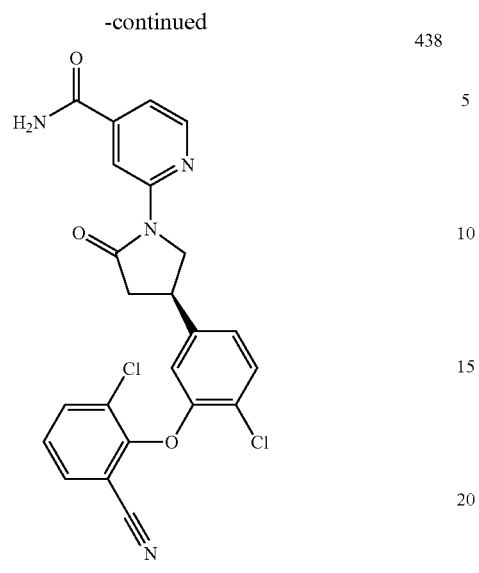
438
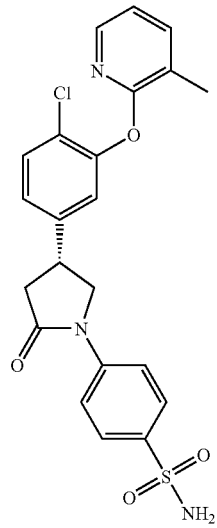
439
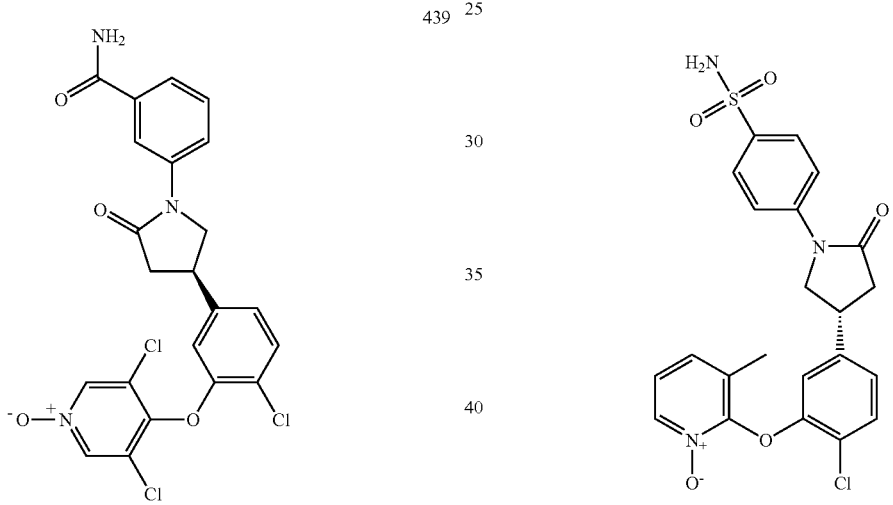
440
441
442
443
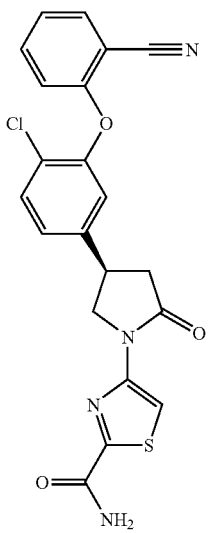

444
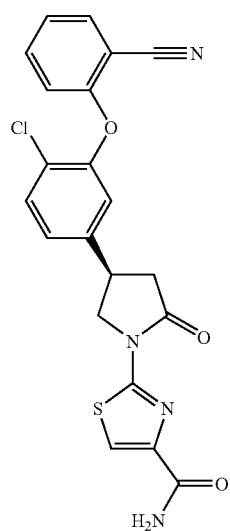
445
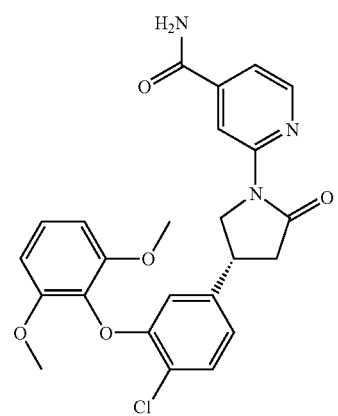
446
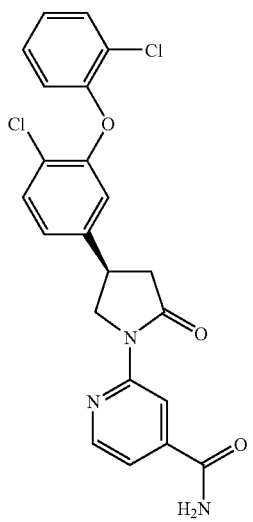
447
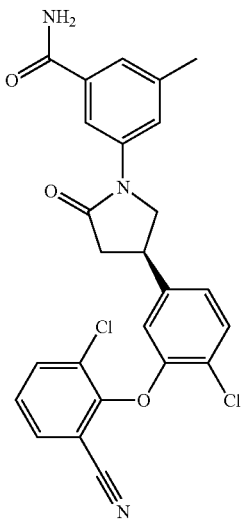
448
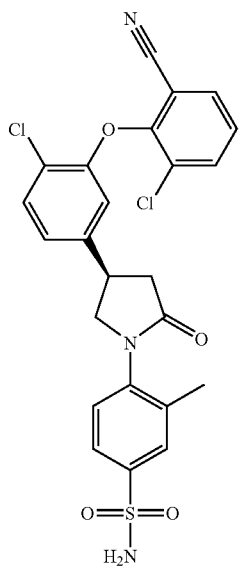
449
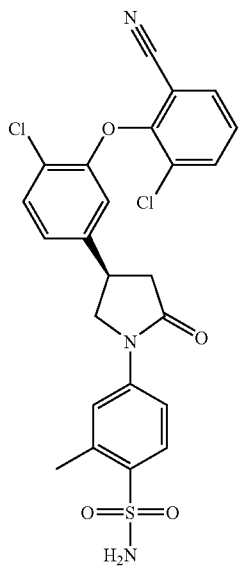

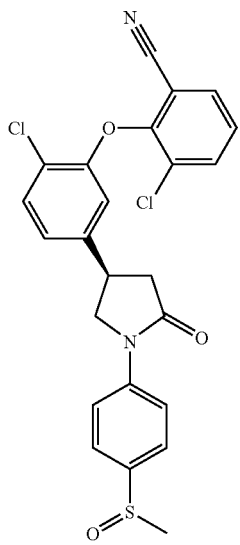
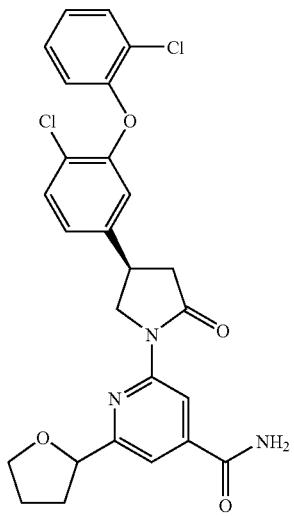

463 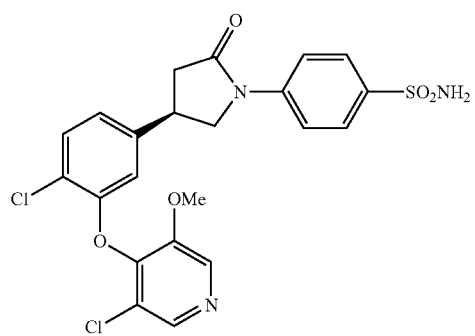
464 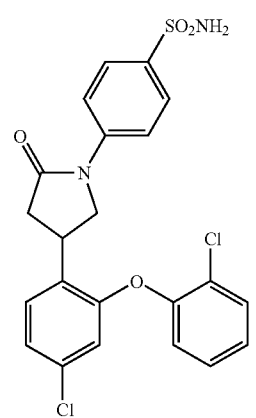
465 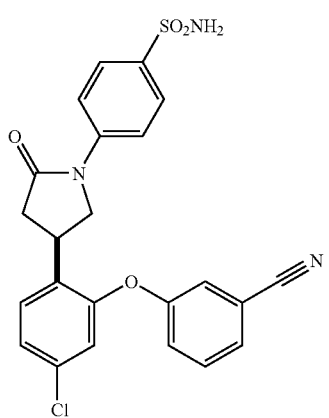
466 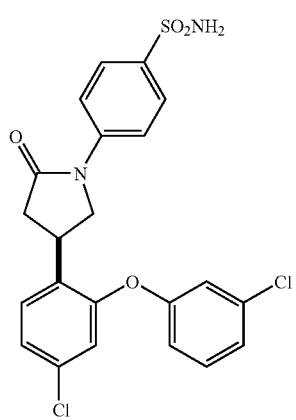
467 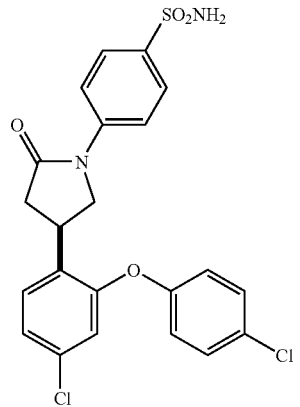
468 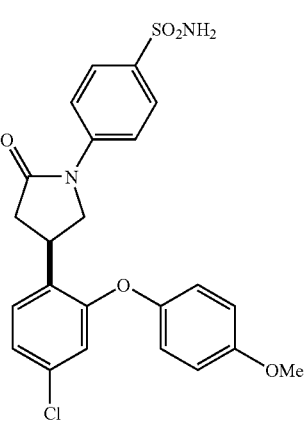
469 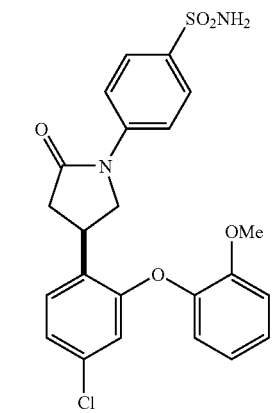
470 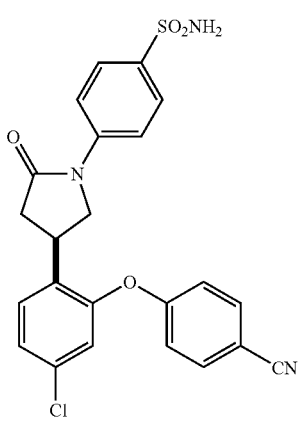

471 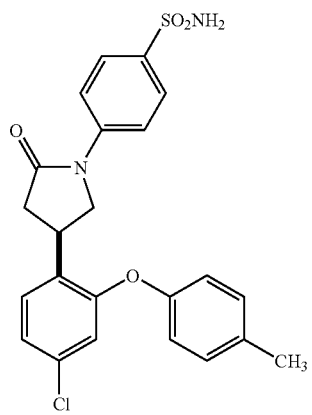
472 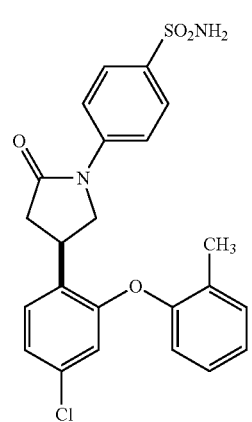
473 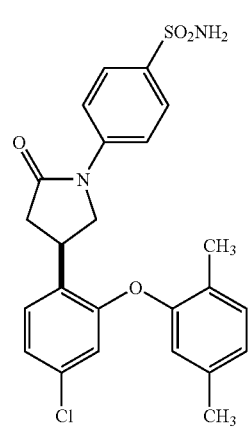
474 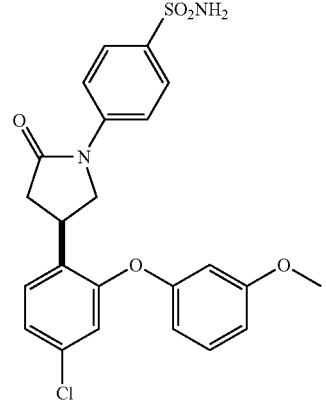
475 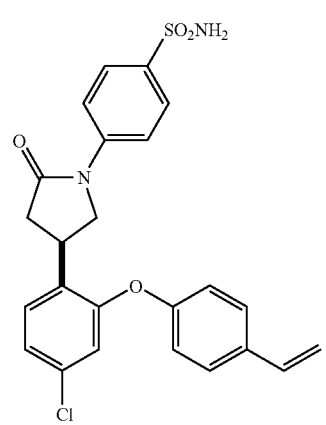
476 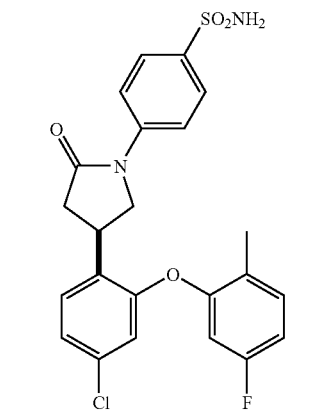
477 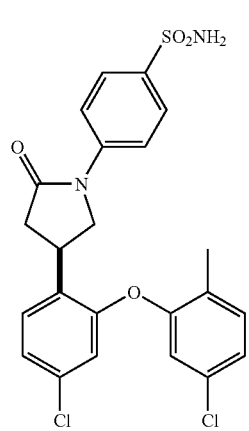

-continued
478
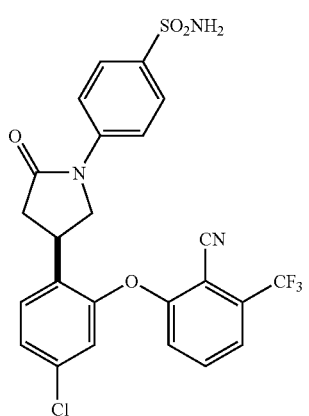
479
480
481
-continued
482
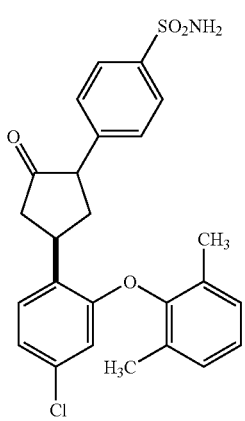
483
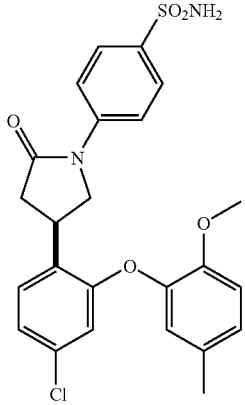
484
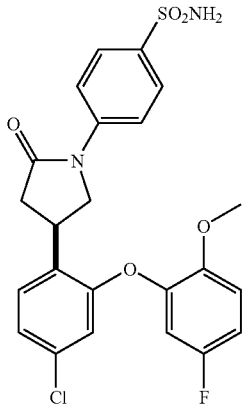
485
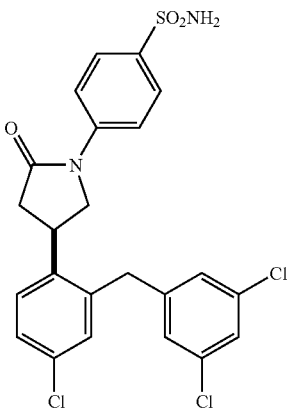

-continued
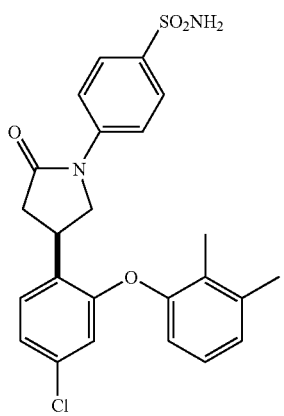
486
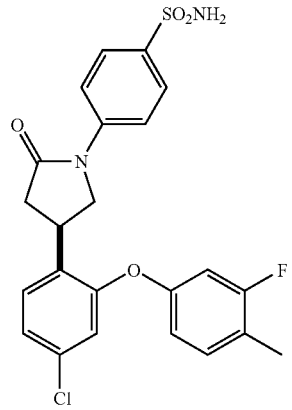
489
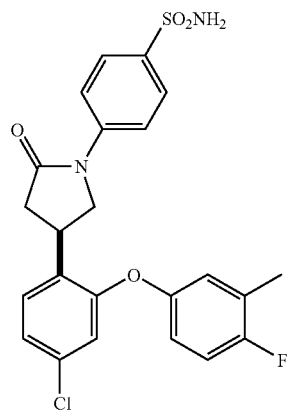
490
487
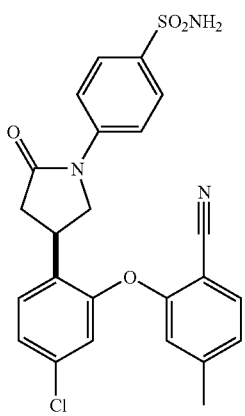
491
488
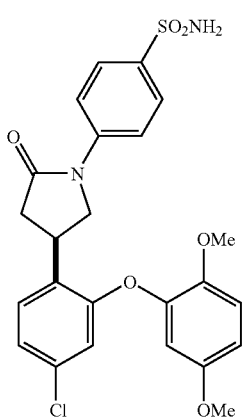
492

493 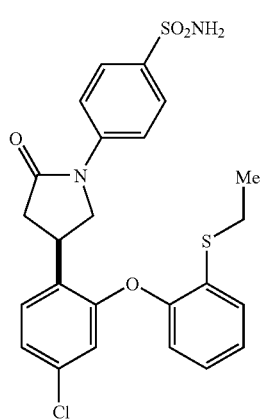
494 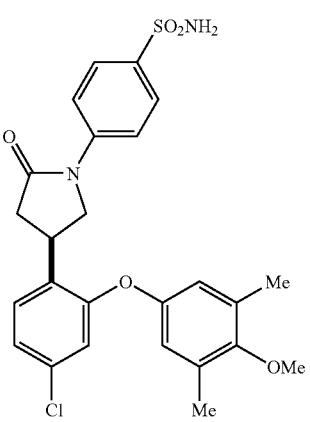
495 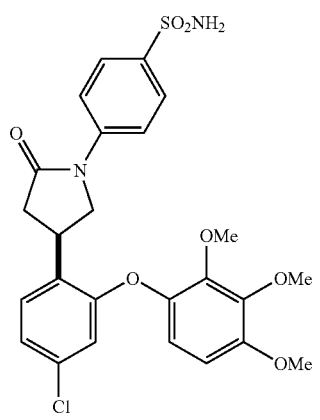
499 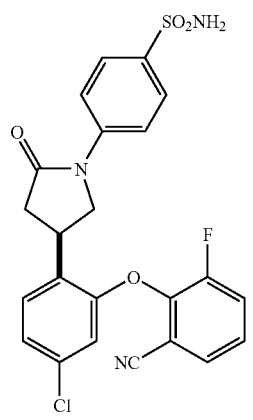
502 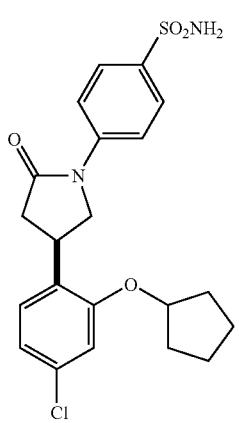
503 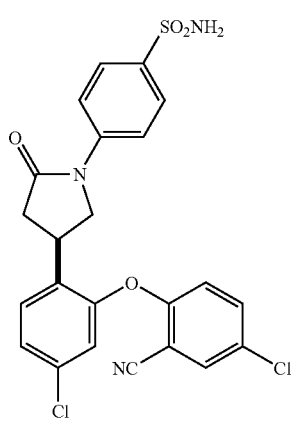
504 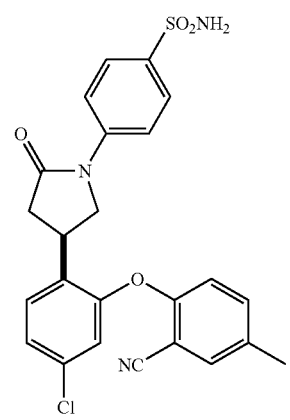
505 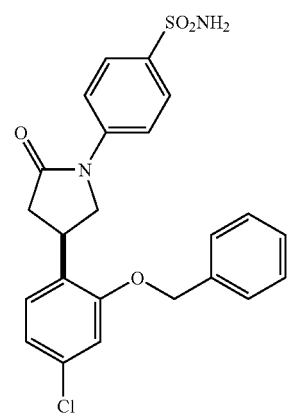

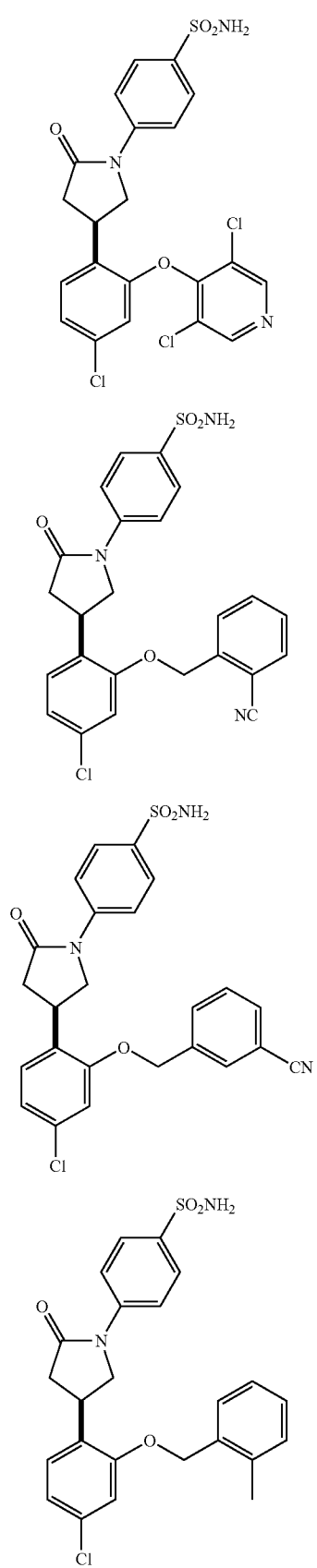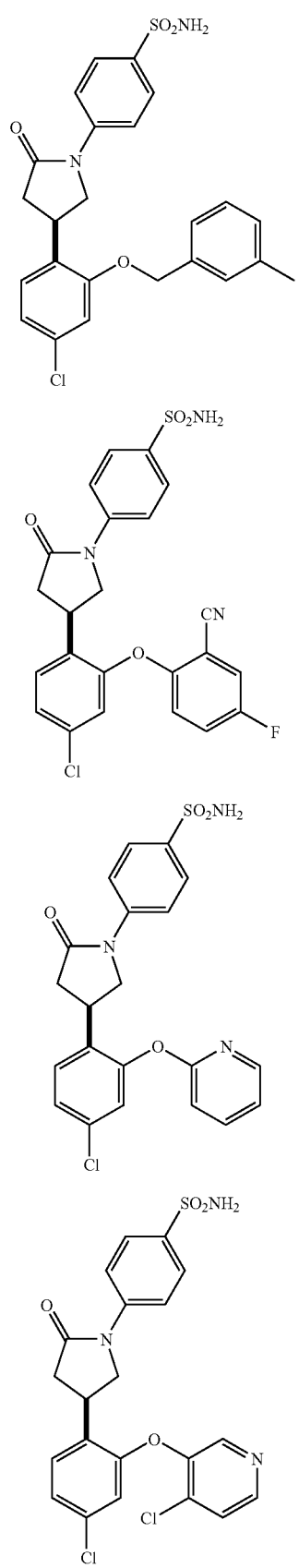

-continued
516
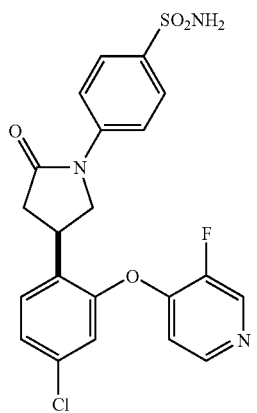
517
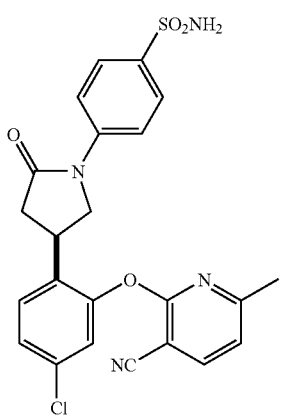
518
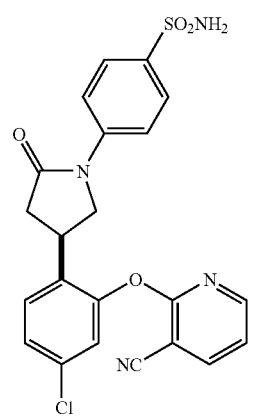
521
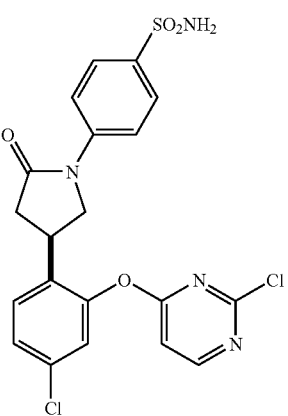
-continued
522
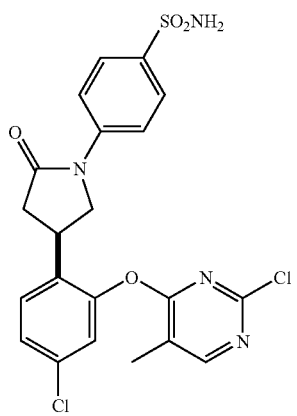
523
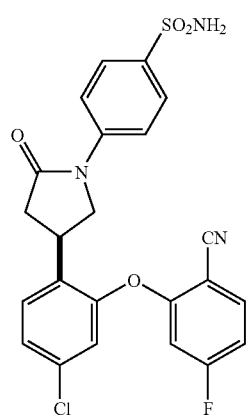
524
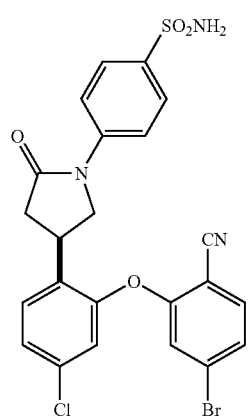
525
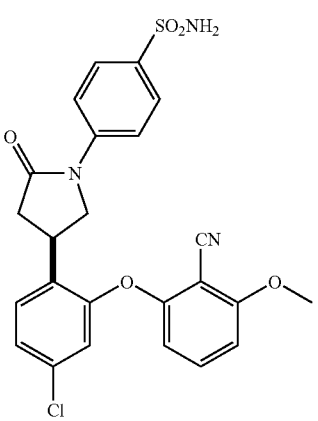

-continued
526
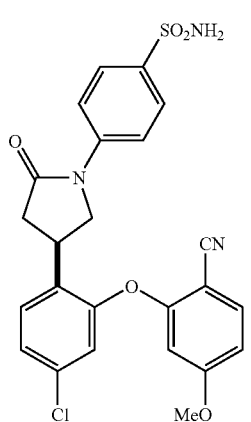
527
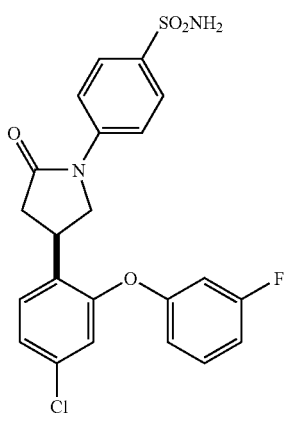
528
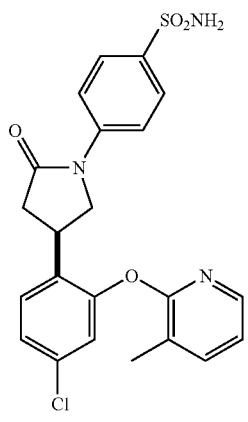
529
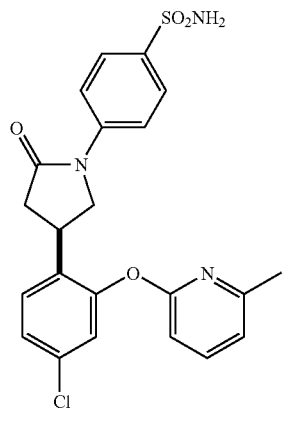
-continued
530
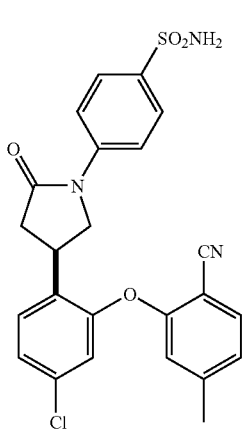
531
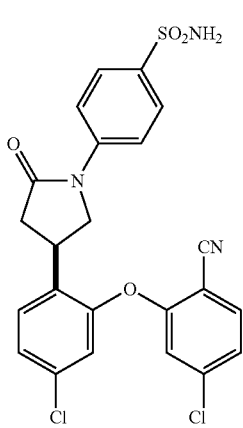
532
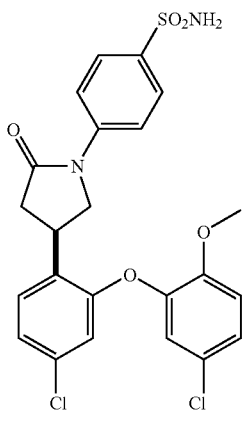

533
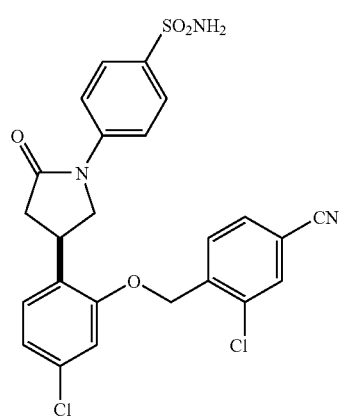
534
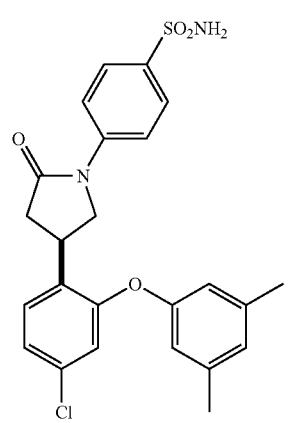
535
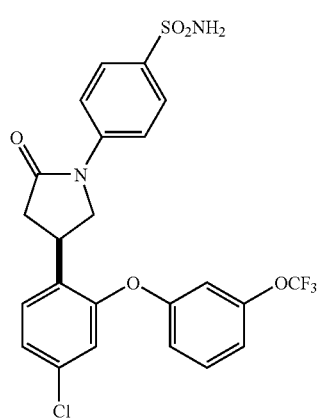
536
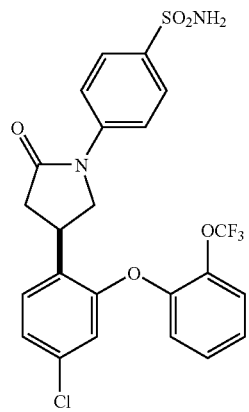
537
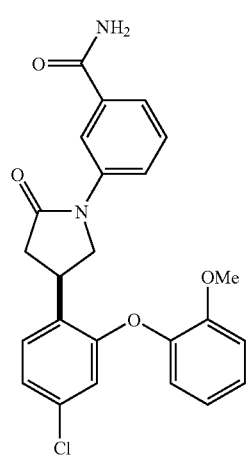
539
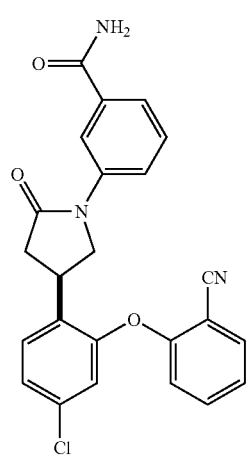

-continued

| 540 | 543 |
| 541 | 544 |
| 542 | 545 |

| 546 | 551 |
|---|---|
| 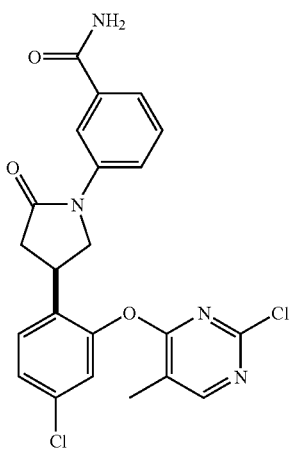 | 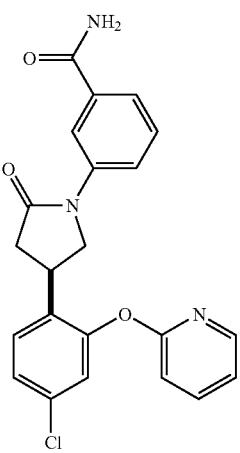 |
| 549 | 552 |
|---|---|
| 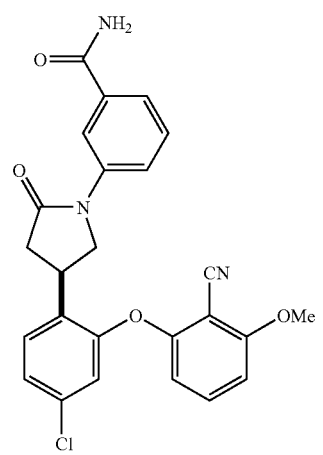 | 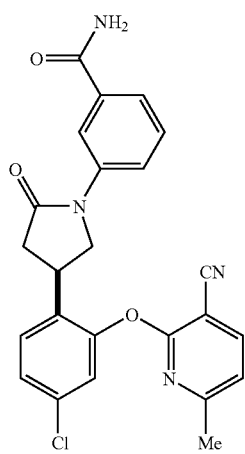 |
| 550 | 553 |
|---|---|
| 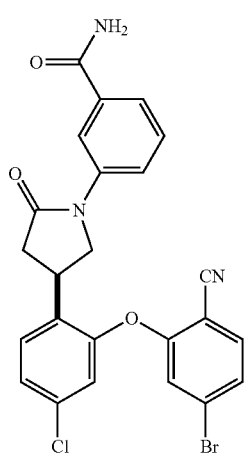 | 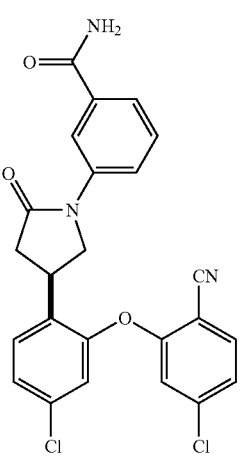 |

-continued
554
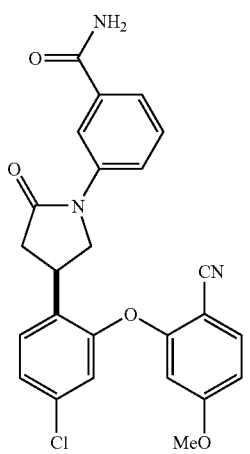
555
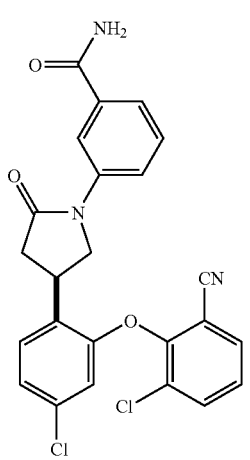
556
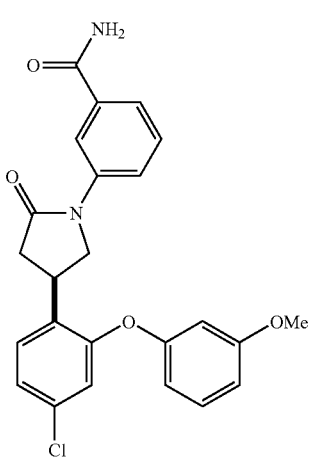
-continued
557
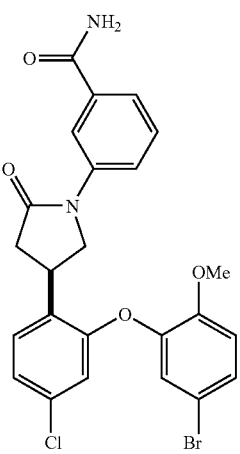
558
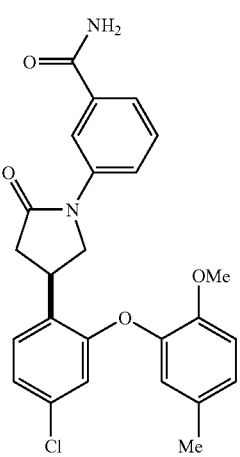
559
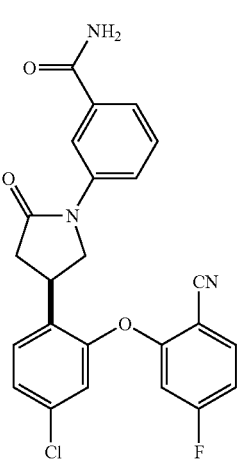

560 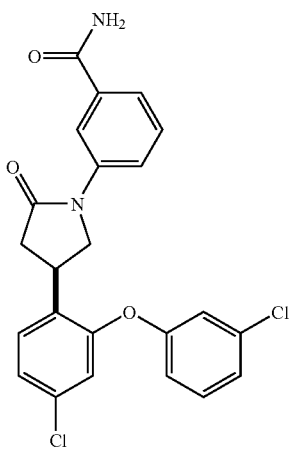
561 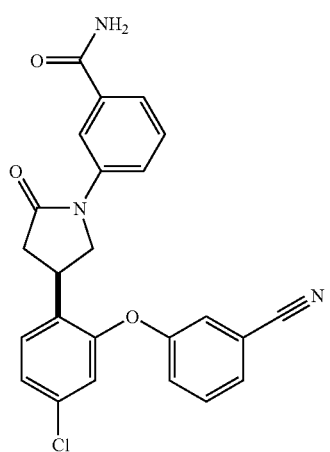
562 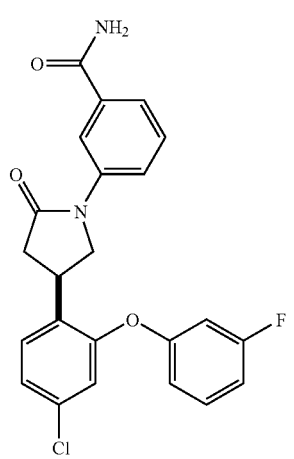
563 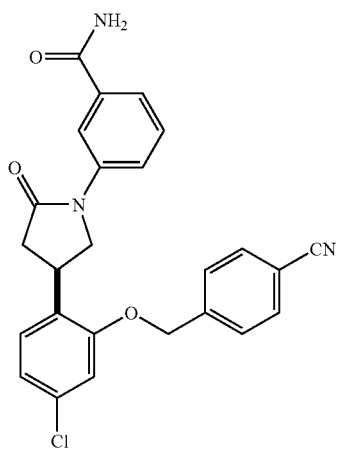
564 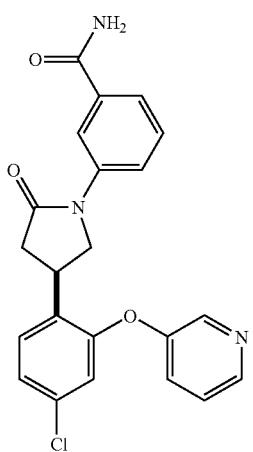
565 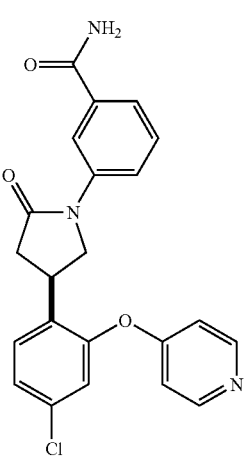

-continued
566
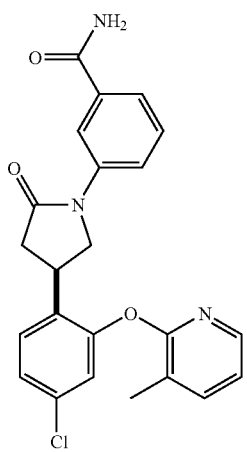
567
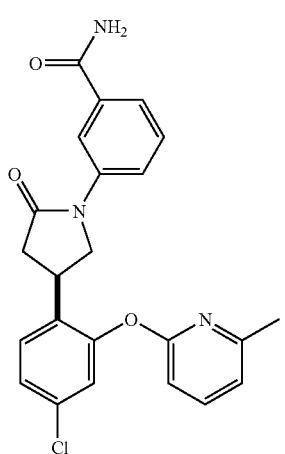
568
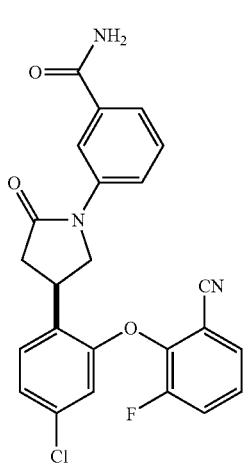
-continued
569
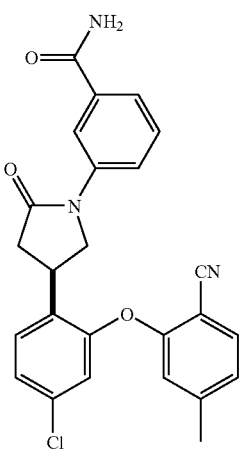
570
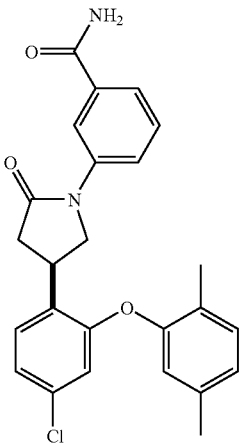
571
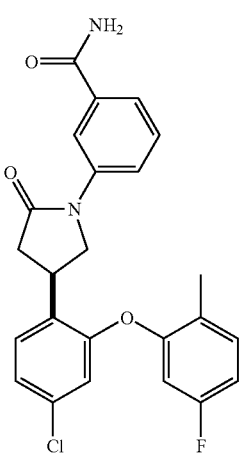

572 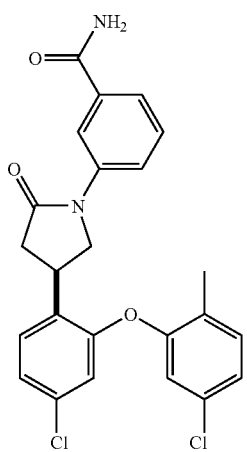
573 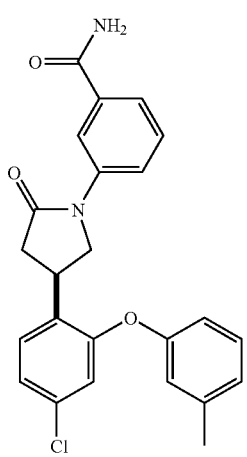
574 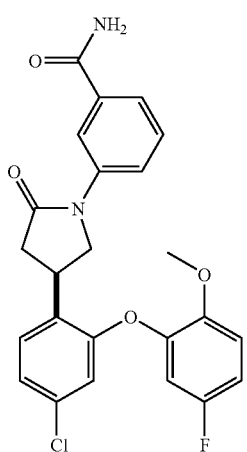
575 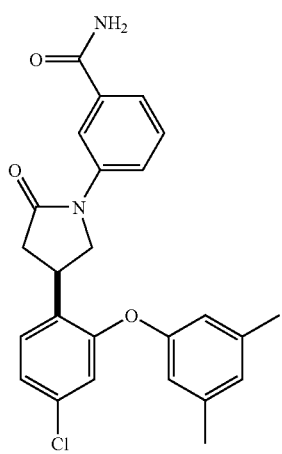
576 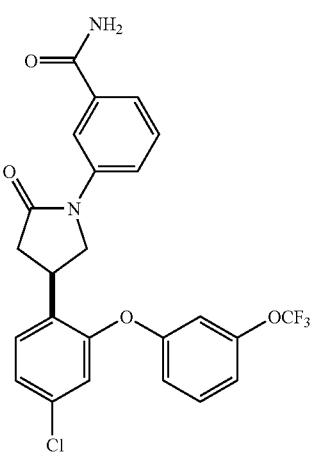
577 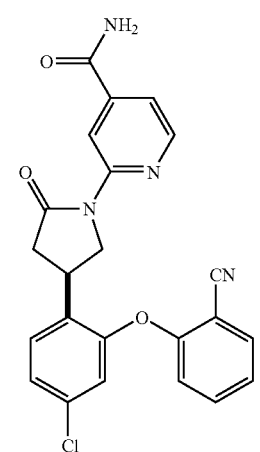

-continued
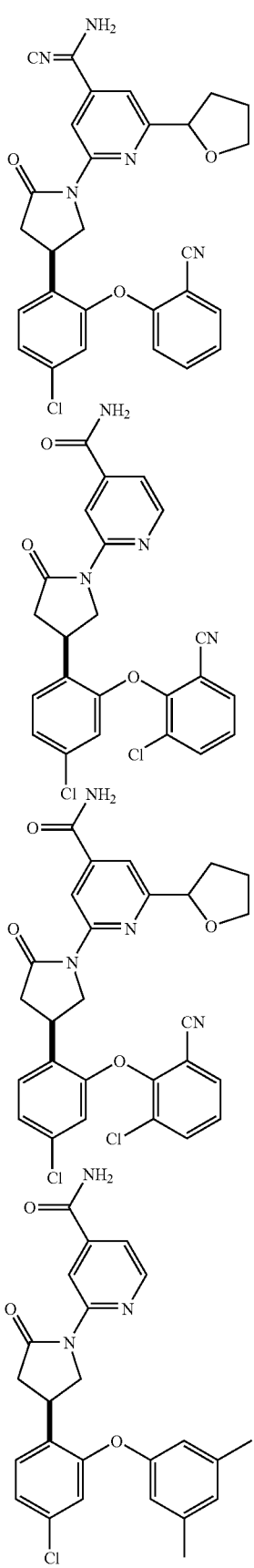
578
579
580
581
-continued
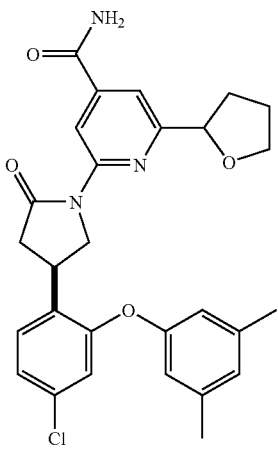
578
582
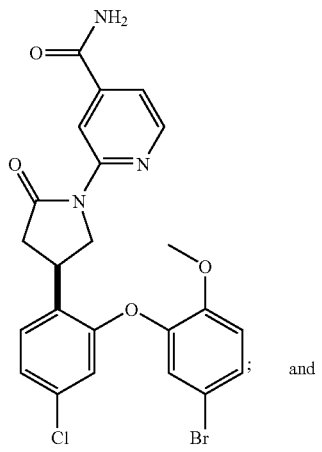
583; and
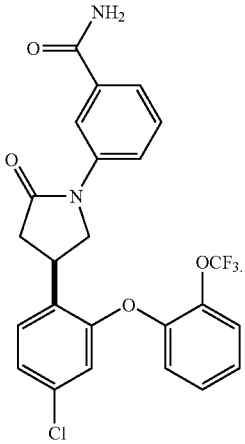
584
26. A pharmaceutical composition comprising the compound of claim 25 and a pharmaceutically acceptable excipient.
* * * * *